US007888092B2

(12) United States Patent
Madison et al.

(10) Patent No.: US 7,888,092 B2
(45) Date of Patent: Feb. 15, 2011

(54) NUCLEIC ACID MOLECULES ENCODING TRANSMEMBRANE SERINE PROTEASES, THE ENCODED PROTEINS AND METHODS BASED THEREON

(75) Inventors: Edwin L. Madison, San Diego, CA (US); Edgar O. Ong, San Diego, CA (US); Jiunn-Chern Yeh, San Diego, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 12/590,011

(22) Filed: Oct. 30, 2009

(65) Prior Publication Data

US 2010/0105121 A1     Apr. 29, 2010

Related U.S. Application Data

(60) Division of application No. 09/776,191, filed on Feb. 2, 2001, now Pat. No. 7,700,341, and a continuation-in-part of application No. 09/657,986, filed on Sep. 8, 2000, now Pat. No. 6,797,504.

(60) Provisional application No. 60/179,982, filed on Feb. 3, 2000, provisional application No. 60/183,542, filed on Feb. 18, 2000, provisional application No. 60/213,124, filed on Jun. 22, 2000, provisional application No. 60/220,970, filed on Jul. 26, 2000, provisional application No. 60/234,840, filed on Sep. 22, 2000.

(51) Int. Cl.

| C12N 9/48 | (2006.01) |
|---|---|
| C12N 1/20 | (2006.01) |
| C12N 15/00 | (2006.01) |
| C12Q 1/00 | (2006.01) |
| C12Q 1/37 | (2006.01) |
| C12Q 1/68 | (2006.01) |
| C12P 21/04 | (2006.01) |
| C07H 21/04 | (2006.01) |

(52) U.S. Cl. ............................ 435/212; 435/4; 435/6; 435/69.1; 435/71.1; 435/252.3; 435/320.1; 435/440; 435/24; 536/23.2

(58) Field of Classification Search ........................ None
See application file for complete search history.

(56) References Cited

U.S. PATENT DOCUMENTS

| 3,536,809 A | 10/1970 | Applezweig ................. 424/28 |
|---|---|---|
| 3,598,123 A | 8/1971 | Zaffaroni .................... 128/268 |
| 3,630,200 A | 12/1971 | Higuchi ...................... 128/260 |
| 3,843,443 A | 10/1974 | Fisman ......................... 195/63 |
| 3,845,770 A | 11/1974 | Theeuwes et al. ............ 128/260 |
| 3,916,899 A | 11/1975 | Theeuwes et al. ............ 128/260 |
| 3,940,475 A | 2/1976 | Gross ............................ 424/1 |
| 4,006,117 A | 2/1977 | Merrifield et al. ...... 260/45.9 NP |
| 4,008,719 A | 2/1977 | Theeuwes et al. ........... 128/260 |
| 4,179,337 A | 12/1979 | Davis et al. ................. 435/181 |
| 4,301,144 A | 11/1981 | Iwashita et al. ............... 424/78 |
| 4,496,689 A | 1/1985 | Mitra ......................... 525/54.1 |
| 4,507,230 A | 3/1985 | Tam et al. ............. 260/112.5 R |
| 4,522,811 A | 6/1985 | Eppstein et al. ................ 514/2 |
| 4,640,835 A | 2/1987 | Shimizu et al. ............... 424/94 |
| 4,670,517 A | 6/1987 | Shimizu et al. ............... 424/94 |
| 4,687,610 A | 8/1987 | Vassilatos .............. 264/211.14 |
| 4,769,027 A | 9/1988 | Baker et al. ................. 424/493 |
| 4,791,192 A | 12/1988 | Nakagawa et al. .......... 530/399 |
| 4,908,405 A | 3/1990 | Bayer et al. .................... 525/61 |
| 4,946,778 A | 8/1990 | Ladner et al. .............. 435/69.6 |
| 4,952,496 A | 8/1990 | Studier et al. ................. 435/91 |
| 4,980,286 A | 12/1990 | Morgan et al. ........... 435/172.3 |
| 5,059,595 A | 10/1991 | La Grazie ................... 424/468 |
| 5,073,543 A | 12/1991 | Marshall et al. ............... 514/21 |
| 5,120,548 A | 6/1992 | McClelland et al. ......... 424/473 |
| 5,215,899 A | 6/1993 | Dattagupta ..................... 435/6 |
| 5,225,539 A | 7/1993 | Winter .................... 530/387.3 |
| 5,270,170 A | 12/1993 | Schatz et al. ............... 435/7.37 |
| 5,292,814 A | 3/1994 | Bayer et al. ................. 525/243 |
| 5,346,823 A | 9/1994 | Estell et al. ................. 435/222 |
| 5,354,566 A | 10/1994 | Addesso et al. ................ 426/9 |
| 5,389,449 A | 2/1995 | Afeyan et al. ............... 428/523 |
| 5,436,128 A | 7/1995 | Harpold et al. ................. 435/6 |
| 5,482,848 A | 1/1996 | Dickson et al. ............. 435/219 |

(Continued)

FOREIGN PATENT DOCUMENTS

EP         0257352        3/1988

(Continued)

OTHER PUBLICATIONS

Kyrieleis et al., "Crystal structure of the catalytic domain of DESC1, a new member of the type II transmembrane serine proteinase family," FEBS J. 274(8):2148-2160 (2007). Epub Mar. 27, 2007.

(Continued)

*Primary Examiner*—Yong D Pak
(74) *Attorney, Agent, or Firm*—K & L Gates LLP; Stephanie Seidman

(57) ABSTRACT

Provided herein is are polypeptides that include the protease domain of a type II transmembrane serine protease (MTSP) as a single chain. Methods using the polypeptides to identify compounds that modulate the protease activity of an MTSP are provided. Also provided are MTSPs designated MTSP3 and MTSP4 and a form of an MTSP designated MTSP6.

21 Claims, 4 Drawing Sheets

U.S. PATENT DOCUMENTS

| | | | |
|---|---|---|---|
| 5,589,154 A | 12/1996 | Anderson | 424/1.41 |
| 5,591,767 A | 1/1997 | Mohr et al. | 514/413 |
| 5,593,990 A | 1/1997 | D'Amato | 514/235.2 |
| 5,612,474 A | 3/1997 | Patel | 536/27.14 |
| 5,629,327 A | 5/1997 | D'Amato | 514/323 |
| 5,639,476 A | 6/1997 | Olshack et al. | 424/468 |
| 5,645,833 A | 7/1997 | Dawson et al. | 424/94.64 |
| 5,674,533 A | 10/1997 | Santus et al. | 424/493 |
| 5,712,291 A | 1/1998 | D'Amato | 514/323 |
| 5,733,566 A | 3/1998 | Lewis | 424/426 |
| 5,792,616 A | 8/1998 | Persico et al. | 435/7.21 |
| 5,804,410 A | 9/1998 | Yamaoka et al. | 435/69.1 |
| 5,902,723 A | 5/1999 | Dower et al. | 435/6 |
| 5,925,525 A | 7/1999 | Fodor et al. | 435/6 |
| 5,972,616 A | 10/1999 | O'Brien et al. | 435/6 |
| 6,121,238 A | 9/2000 | Dower et al. | 514/13 |
| 6,294,663 B1 | 9/2001 | O'Brien et al. | 536/23.5 |
| 6,365,391 B1 | 4/2002 | Webster et al. | 435/219 |
| 6,638,977 B1 | 10/2003 | Madison et al. | 514/538 |
| 6,677,473 B1 | 1/2004 | Madison et al. | 560/52 |
| 7,030,231 B1 | 4/2006 | Craik et al. | 536/23.1 |
| 7,105,333 B2 | 9/2006 | Madison et al. | 435/226 |
| 7,112,430 B2 | 9/2006 | Madison et al. | 435/226 |
| 7,125,703 B2 | 10/2006 | Madison et al. | 435/226 |
| 7,172,892 B2 | 2/2007 | Madison et al. | 435/226 |
| 7,227,009 B2 | 6/2007 | Craik et al. | 536/23.1 |
| 7,572,444 B2 | 8/2009 | Foltz et al. | 424/133.1 |
| 7,700,341 B2 | 4/2010 | Madison et al. | 435/212 |
| 2001/0034437 A1 | 10/2001 | Walke et al. | 536/23.2 |
| 2002/0019006 A1 | 2/2002 | Yuan et al. | 435/6 |
| 2002/0037857 A1 | 3/2002 | Semple et al. | 514/19 |
| 2002/0064856 A1 | 5/2002 | Plowman et al. | 435/226 |
| 2002/0107266 A1 | 8/2002 | Lim-Wilby et al. | 514/339 |
| 2002/0119130 A1 | 8/2002 | Eaton et al. | 424/94.1 |
| 2002/0160962 A1 | 10/2002 | Saksena et al. | 514/19 |
| 2002/0165376 A1 | 11/2002 | Walke et al. | 536/23.2 |
| 2003/0008372 A1 | 1/2003 | Madison et al. | 435/226 |
| 2003/0050251 A1 | 3/2003 | Semple et al. | 514/19 |
| 2003/0077697 A1 | 4/2003 | Gerlack et al. | 435/69.1 |
| 2003/0119168 A1 | 6/2003 | Madison et al. | 435/226 |
| 2003/0134298 A1 | 7/2003 | Madison et al. | 435/6 |
| 2003/0134794 A1 | 7/2003 | Madison et al. | 514/2 |
| 2003/0143219 A1 | 7/2003 | Madison et al. | 424/94.67 |
| 2003/0153014 A1 | 8/2003 | Shen et al. | 435/7.9 |
| 2003/0166851 A1 | 9/2003 | Madison et al. | 530/350 |
| 2003/0170630 A1 | 9/2003 | Alsobrook et al. | 435/6 |
| 2003/0175938 A1 | 9/2003 | Shi et al. | 435/226 |
| 2003/0181658 A1 | 9/2003 | Madison et al. | 530/350 |
| 2003/0186329 A1 | 10/2003 | Madison et al. | 435/7.1 |
| 2003/0232349 A1 | 12/2003 | Delegeane et al. | 435/6 |
| 2003/0235900 A1 | 12/2003 | Madison et al. | 435/226 |
| 2004/0001801 A1 | 1/2004 | Madison et al. | 424/85.1 |
| 2005/0112579 A1 | 5/2005 | Madison et al. | 435/6 |
| 2006/0029590 A1 | 2/2006 | Thanos et al. | 424/94.63 |
| 2006/0171884 A1 | 8/2006 | Foltz et al. | 424/1.49 |
| 2007/0093443 A1 | 4/2007 | Madison et al. | 514/44 R |
| 2009/0098103 A1 | 4/2009 | Madison et al. | 424/94.64 |
| 2009/0123452 A1 | 5/2009 | Madison et al. | 424/94.64 |
| 2009/0291890 A1 | 11/2009 | Madison et al. | 514/12 |

FOREIGN PATENT DOCUMENTS

| | | |
|---|---|---|
| EP | 0613683 | 7/1994 |
| EP | 1033401 | 9/2000 |
| WO | 86/03840 | 7/1986 |
| WO | 88/09810 | 12/1988 |
| WO | 89/10134 | 11/1989 |
| WO | 90/11364 | 10/1990 |
| WO | 92/06180 | 4/1992 |
| WO | 92/06203 | 4/1992 |
| WO | 92/20316 | 11/1992 |
| WO | 92/22635 | 12/1992 |
| WO | 93/14188 | 7/1993 |
| WO | 93/20221 | 10/1993 |
| WO | 93/25221 | 12/1993 |
| WO | 94/08598 | 4/1994 |
| WO | 94/17784 | 8/1994 |
| WO | 95/23222 | 3/1995 |
| WO | 95/11755 | 5/1995 |
| WO | 95/34326 | 12/1995 |
| WO | 96/30353 | 10/1996 |
| WO | 97/21690 | 6/1997 |
| WO | 99/17790 | 4/1999 |
| WO | 99/42120 | 8/1999 |
| WO | 99/46281 | 9/1999 |
| WO | 00/12708 | 3/2000 |
| WO | 00/50061 | 3/2000 |
| WO | 00/52044 | 9/2000 |
| WO | 00/53232 | 9/2000 |
| WO | 00/55124 | 9/2000 |
| WO | 00/68247 | 11/2000 |
| WO | 00/78961 | 12/2000 |
| WO | 01/04141 | 1/2001 |
| WO | 01/23524 | 4/2001 |
| WO | 01/27624 | 4/2001 |
| WO | 01/36351 | 5/2001 |
| WO | 01/36604 | 5/2001 |
| WO | 01/36645 | 5/2001 |
| WO | 01/46407 | 6/2001 |
| WO | 01/49864 | 7/2001 |
| WO | 01/54477 | 8/2001 |
| WO | 01/55441 | 8/2001 |
| WO | 01/57194 | 8/2001 |
| WO | 01/75067 | 10/2001 |
| WO | 01/98468 | 12/2001 |
| WO | 02/00860 | 1/2002 |
| WO | 02/06453 | 1/2002 |
| WO | 02/08187 | 1/2002 |
| WO | 02/08251 | 1/2002 |
| WO | 02/95001 | 2/2002 |
| WO | 02/20475 | 3/2002 |
| WO | 02/26947 | 4/2002 |
| WO | 02/48097 | 6/2002 |
| WO | 02/072786 | 9/2002 |
| WO | 02/077263 | 10/2002 |
| WO | 02/077267 | 10/2002 |
| WO | 02/092841 | 11/2002 |
| WO | 02/095007 | 11/2002 |
| WO | 03/004681 | 1/2003 |
| WO | 03/031585 | 4/2003 |
| WO | 03/044179 | 5/2003 |
| WO | 03/104391 | 12/2003 |
| WO | 03/104394 | 12/2003 |
| WO | 2004/005471 | 1/2004 |
| WO | 2005/123119 | 12/2005 |
| WO | 2006/068975 | 8/2006 |
| WO | 2007/047995 | 4/2007 |
| WO | 2008/045148 | 4/2008 |
| WO | 2008/127702 | 10/2008 |
| WO | 99/36550 | 7/2009 |

OTHER PUBLICATIONS

Netzel-Arnett et al., "Membrane anchored serine proteases: a rapidly expanding group of cell surface proteolytic enzymes with potential roles in cancer," Cancer Metastasis Rev. 22(2-3):237-258 (2003).

Abraham et al. "Immunochemical identification of the serine protease inhibitor $\alpha_1$-antiichymotrypsin in the brain amyloid deposits of alzheimer's disease," Cell 52:487-501 (1988).

Adams et al. "The c-myc oncogene driven by immunoglobulin enhancers induces lymphoid malignancy in transgenic mice", Nature 318:533-538 (1985).

Alam et al., "Reporter genes: Application to the study of mammalian gene transcription," Anal. Biochem. 188:245-254 (1990).

Alexander et al. "Expression of the *c-myc* oncogene under control of an immunoglobulin enhancer in *Eµ-myc* transgenic mice," Mol Cell Biol 7(4):1436-1444 (1987).

Alonso et al., "Effects of synthetic urokinase inhibitors on local invasion and metastasis in a murine mammary tumor model," Breast Cancer Res. Treat., 40:209-223 (1996).

Appel et al., "The *Drosophila* stubble-stubbloid gene encodes an apparent transmembrane serine protease required for epithelial morphogenesis," Proc. Natl. Acad. Sci. USA, 90:4937-4941 (1993).

Auerbach et al. "Angiogenesis Inhibition: A review," Pharmacol. Ther. 63(3):265-311 (1994).

Avery et al., "Systemic amiloride inhibits experimentally induced neovascularization," Arch. Ophthalmol., 108:1474-1476 (1990).

Baker et al. "A scintillation proximity assay for UDP-GalNAc: Polypeptide, N-acetylgalactoseaminyltransferase," Anal. Biochem. 239:20-24 (1996).

Bannwarth et al. "Global phosphorylation of peptides containing oxidation-sensitive amino acids," Bioorganic & Medicinal Chem. Lett. 6(17):2141-2146 (1996).

Bartel et al. "Isolation of new ribozymes from a large pool of random sequences," Science 261:1411-1418 (1993).

Batra et al., "Insertion of constant region domains of human $IgG_1$ into CDR-PE40 increases its plasma half life," Molecular Immunol., 30(4):379-386 (1993).

Baum et al., "Development of a scintillation proximity assay for human cytomegalovirus protease using $^{33}$phosphorus," Anal. Biochem. 237:129-134 (1996).

Baumbach et al. "Protein purification using affinity ligands deduced from peptide libraries," BioPharm., May ed., 24-35 (1992).

Beck et al., "Identification of efficiently cleaved substrates for HIV-1 protease using a phage display library and use in inhibitor development," Virology 274(2):391-401 (2000).

Bernoist, C. and P. Chambon, "In vivo sequence requirements of the SV40 early promotor region," Nature, 290:304-310, (1981).

Benton et al. "Screening λgt recombinant clones by hybridization to single plaques in situ," Science 196:180-182 (1977).

Berg et al. "Long-chain polystyrene-grafted polyethylene film matrix: a new support for solid-phase peptide synthesis," J. Am. Chem. Soc. 111:8024-8026 (1989).

Berg et al. "Peptide synthesis on polystyrene-grafted polyethylene sheets," Pept. Proc. $20^{th}$ Eur. Pept. Symp. Jung, G et al., Eds, pp. 196-198 (1988).

Berg et al. "Polystyrene-grafted polyethylene: Design of film and felt matrices for solid-phase peptide synthesis," Innovation Perspect. Sold Phase Synth. Collect. Pap., Int. Sympl. $1^{st}$ Epton, Roger, Ed., pp. 453-459 (1990).

Berger et al., "Structure of the mouse gene for the serine protease inhibitor neuroserpin (PI12)," Gene 214:25-33 (1998).

Bergstrom et al. "Binding of nonphysiological protein and peptide substrates to proteases: differences between urokinase-type plasminogen activator and trypsin and contributions to the evolution of regulated proteolysis", Biochem. 42:5395-5402 (2003).

Billstrom et al., "The urokinase inhibitor p-aminobenzamidine inhibits growth of a human prostate tumor in SCID mice," Int. J. Cancer, 61:542-547 (1995).

Blaney et al. "Computational approaches for combinatorial library design and molecular diversity analysis," Curr. Opin. Chem. Biol., 1:54-59 (1997).

Blanton et al., "Characterization of a native and recombinant *Schistosoma haematobium* serine protease inhibitor gene product," Mol. Biochem. Parasitol., 63:1-11 (1994).

Bock et al. "Selection of single-stranded DNA molecules that bind and inhibit human thrombin," Nature, 355:564-566 (1992).

Boehm et al. "The rhombotin family of cystein-rich LIM-domain oncogenes: distinct members are involved in T-cell translocations to human chromosomes 11p15 and 11p13," Proc. Natl. Acad. Sci. USA 88:4367-4371 (1991).

Boesen et al. "Circumvention of chemotherapy-induced myelosuppression by transfer of the mdr1 gene," Biotherapy, 6:291-302 (1994).

Bork, P., "Powers and Pitfalls in Sequence Analysis: the 70% Hurdle," *Genome Research* 10: 398-400 (2000).

Borman, S., "Scientists refine understanding of protein folding and design," Chem. Eng. News, 2(12):29-35 (1996).

Boublik et al., "Eukaryotic virus display: Engineering the major surface glycoprotein of the *Autographa californica* nuclear polyhedrosis virus (AcNPV) for the presentation of foreign proteins on the virus surface," Bio/Technol., 13:1079-1084 (1995).

Bourinbaiar et al., "Effect of serine protease inhibitior, N-α-tosyl-1-lysyl-chloromethyl ketone (TLCK), on cell mediated and cell-free HIV-1 spread," Cell. Immuno., 155:230-236 (1994).

Bout et al., "Lung gene therapy: In vivo adenovirus-mediated gene transfer to rhesus monkey airway epithelium," Human Gene Therapy, 5:3-10 (1994).

Brains et al., "Effects of LEX032, a novel recombinant serine protease inhibitor, on $N^6$-nitro-L-arginine methyl ester induced leukocyte-endothelial cell," Eur. J. Pharmacol., 356:67-72 (1998).

Branden et al. "Introduction to Protein Structure," Garland Publishing Inc., New York, pp. 247-248 (1991).

Braunwalder et al., "Application of scintillating microtiter plates to measure phosphopeptide interactions with the GRB2-SH2 binding domain," J. Biomol. Screening, 1(1):23-26 (1996).

Brenner et al., "Encoded combinatorial chemistry," Proc. Natl. Acad. Sci. USA, 89:5381-5383 (1992).

Brinster, R.L., et al., "Regulation of metallothionein—thymidine kinase fusion plasmids injected into mouse eggs," Nature, 296:39-42, (1982).

Brooks et al., "Use of the 10-day-old chick embryo model for studying angiogenesis," Methods in Molecular Biology, 129:257-269 (1999).

Broun et al., "Catalytic Plasticity of Fatty Acid Modification Enzymes Underlying Chemical Diversity of Plant Lipids," Science, 282:1315-1317 (1998).

Bunin et al., "A general and expedient method for the solild-phase synthesis of 1,4-benzodiazepine derivatives," J. Am. Chem. Soc., 114:10997-10998 (1992).

Bunin et al., "The combinatorial synthesis and chemical and biological evaluation of a 1,4-benzodiazepene library," Proc. Natl. Acad. Sci. USA, 91:4708-4712 (1994).

Butz et al., "Immunization and affinity purification of antibodies using resin-immobilized lysine-branched synthetic peptides," Peptide Res. 7(1):20-23 (1994).

Caflisch et al., "Computational combinatorial chemistry for de novo ligand design: Review and Assessment," Perspectives in Drug Discovery and Design, 3:51-84 (1995).

Capecchi et al., "Altering the genome by homologous recombination," Science, 244:1288-1292 (1989).

Carter et al., "Dissecting the catalytic triad of a serine protease," Nature 332:564-568 (1988).

Chait et al., "Weighing naked proteins: Practical, high-accuracy mass measurement of peptides and proteins," Science 257:1885-1894 (1992).

Chen et al., "Analogous organic synthesis of small-compound libraries: Validation of combinatorial chemistry in small-molecule synthesis," J. Am. Chem. Soc., 116:2661-2662 (1994).

Chen et al., "IL-1β induces serine protease inhibitor 3 (SPI-3) gene expression in rat pancreatic β-cells. Detection by differential display of messenger RNA," Cytokine, 11(11):856-862 (1999).

Chen et al., "Interaction of phosphorylated FcyeR1γ immunoglobulin receptor tyrosine activation motif-based peptides with dual and single SH2 domains of $p72^{syk}$," J. Biol. Chem. 271(41):25308-25315 (1996).

Cheng et al., "Sequence-selective peptide binding with a peptido-A,B-trans-steroidal receptor selected from an encoded combinatorial receptor library," J. Am. Chem. Soc., 118:1813-1814 (1996).

Chu et al., "Using affinity capillary electrophoresis to identify the peptide in a peptide library that binds most tightly to vancomycin," J. Org. Chem., 58:648-652 (1993).

Clackson et al., "Making antibody fragments using phage display libraries," Nature, 352:624-628 (1991).

Cline et al., "Perspectives for gene therapy: inserting new genetic information into mammalian cells by physical techniques and viral vectors," Pharmac. Ther. 29:69-92 (1985).

Clowes et al., "Long-term biological response of injured rat carotid artery seeded with smooth muscle cells expressing retrovirally induced human genes," J. Clin. Invest., 93:644-651 (1994).

Cole et al., "The EBV-Hybridoma technique and its application to human lung cancer," in Monoclonal Antibodies and Cancer Therapy, Alan R. Liss, Inc., pp. 77-96 (1985).

Combs et al., "Protein structure-based combinatorial chemistry: Discovery of non-peptide binding elements to Src SH3 domain," J. Am. Chem. Soc., 118:287-288 (1996).

Coombs et al., "Directing sequence-specific proteolysis to new targets," J Biol Chem 273:4323-4328 (1998).

Coombs et al., "Distinct mechanisms contribute to stringent substrate specificity of tissue-type plasminogen activator," J. Biol. Chem. 271:4461-4467 (1996).

Coombs et al., "Revisiting catalysis by chymotrypsin family serine proteases using peptide substrates and inhibitors with unnatural main chains," J Biol Chem 274(34):24074-24079 (1999).

Coombs et al., "Substrate specificity of prostate-specific antigen (PSA)," Chem. Biol. 5(9):475-488 (1998).

Cote et al., "Generation of human monoclonal antibodies reactive with cellular antigens," Proc. Natl. Acad. Sci USA 80:2026-2030 (1983).

Cotten et al., "Receptor-mediated transport of DNA into eukaryotic cells," Meth. Enzymol. 218:619-345 (1993).

Craik et al., "The catalytic role of the active site aspartic acid in serine proteases," Science 237:909-913 (1987).

Crowley et al., "Prevention of metastasis by inhibition of the urokinase receptor," Proc Natl Acad Sci USA, 90:5021-5025 (1993).

Cumber et al., "Structural features of the antibody-A chain linkage that influences the activity and stability of ricin A chain immunotoxins," Bioconj. Chem. 3:397-401 (1992).

Cwirla et al., "Peptides on phage: a vast library of peptides for identifying ligands,", Proc Natl Acad Sci USA, 87:6378-6382 (1990).

Database EMBL, Accession No. W22987, "Human Serine Protease 67", XP002169836 abstract, Oct. 8, 1997; abstract of Japan, 1997(10), Oct. 31, 1997; abstract of Japan 09 149790, Jun. 10, 1997.

Database EMBL, Accession No. AAY41694, "Human PR0382 protein sequence", Genentech Inc., XP002175687 abstract, Dec. 7, 1999; PCT 99 46281 A, Genentech Inc., Sep. 16, 1999.

Database EMBL, Accession No. AAY41710, "Human PR0618 protein sequence", Genentech Inc., XP002175683 abstract, Dec. 7, 1999; PCT 99 46281 A, Genentech Inc., Sep. 16, 1999.

Database EMBL, Accession No. AAZ33949, "Human PR0382 nucleotide sequence", Genentech Inc., XP002175685 abstract, Dec. 7, 1999; PCT 99 46281 A, Genentech Inc., Sep. 16, 1999.

Database EMBL, Accession No. AAZ34033, "Human PR0618 nucleotide sequence", Genentech Inc., XP002175684 abstract, Dec. 7, 1999; PCT 99 46281 A, Genentech Inc., Sep. 16, 1999.

Database EMBL, Accession No. AF064819, Oct. 28, 1999, J.C. Lang and D.E. Schuller: "*Homo sapiens* serine protease DESC1 MRNA", XP002166624, abstract.

Database EMBL, Accession No. AI469095, "tm06c09.x1 *Homo sapiens* cDNA clone IMAGE:2155792", XP002175686 abstract, Mar. 17, 1999.

De Boer et al., "The tac promoter: a functional hybrid derived from teh trp and lac promoters," Proc. Natl. Acad. Sci. USA, 80:21-25 (1983).

Delaria et al., "Characterization of placental bikunin, a novel human serine protease inhibitor," J. Biol. Chem., 272(18):12209-12214 (1997).

Derwent #XP-002169836 WPI Acc. No. 1997-357902/33, for Japanese Patent Application, JP09149790-A, published Jun. 10, 1997.

Derwent #007409639, WPI Acc. No. 1988-043574/198807, for European Patent Application, EP 257352, "Determining free portion of e.g. thyroxine in presence of binder by reaction with antibody which does not effect bound-unbound equilibrium, then reacting cross reactive tracer with antibody."

Desai et al., "Tumor angiogenesis and endothelial cell modulatory factors," J. Immunol., 22(3):186-211 (1999).

Devlin et al., "Random peptide libraries: A source of specific protein binding molecules," Science, 249:404-406 (1990).

DeWitt et al., "Diversomers: An approach to nonpeptide, nonoligomeric chemical diversity," Proc. Natl. Acad. Sci. USA, 90:6909-6913 (1993).

Dexter et al., "Conditions controlling the proliferation of haemopoietic stem cells in vitro," J.C ell. Physiol., 91:335-344 (1976).

Dillon et al., "Regulating gene expression in gene therapy," TIBTECH 11(5):167-173 (1993).

Ding et al., "Origins of the specificity of tissue-type plasminogen activator," PNAS 92:7627-7631 (1995).

Dodet et al., "Commercial prospects for gene therapy—a company survey," TIBTECH 11(5):182-189 (1993).

Dower et al., "The search for molecular diversity (II): recombinant and synthetic randomized peptide libraries," An. Rep. Med. Chem., 26:271-280 (1991).

Dryjanski et al., "N-Tosyl-L-phenylalanine chloromethyl ketone, a serine protease inhibitor, identifies glutamate 398 at the coenzyme-binding site of human aldehyde dehydrogenase. Evidence for a second "Naked Anion" at the active site," Biochem., 37(40):14151-14156 (1998).

Dufer et al., "Differential effect of the serine protease inhibitor phenyl methyl sulfonyl fluoride on cytochemically detectable esterases in human leucocytes and platelets," Scand. J. Haematol., 32(1):25-32 (1984).

Eck et al., "Structure of TNF-α Implications for Receptor Binding," J. Biol. Chem., 26:17605 (1989).

Ecker et al., "Combinatorial drug discovery: Which methods will produce the greatest value?," Bio/Technol., 13:351-360 (1995).

Edwards et al., "Inhibition of elastase by a synthetic cotton-bound serine protease inhibitor: in vitro kinetics and inhibitor release," Wound Repair Regen., 7(2):106-118 (1999).

Eichler et al. "Identification of substrate-analog trypsin inhibitors through the screening of synthetic peptide combinatorial libraries," Biochem., 32:11035-11041 (1993).

Ellington et al., "In vitro selection of RNA molecules that bind specific ligands," Nature, 346:818-822 (1990).

Erickson et al., The Proteins, "Solid-Phase Peptide Synthesis," vol. II, Neurath H., Hill, R.L., Eds., Academic Press, New York, pp. 255-257 (1976).

Erickson et al, "Design, activity, and 2.8 Å crystal structure of a $C_2$ symmetric inhibitor complexed to HIV-1 protease," Science 249:527-533 (1990).

Evans et al., "Design of non-peptidal ligands for a peptide receptor: cholecystokinin antagonists," J. Med. Chem., 30:1229-1239 (1987).

Farley et al., "Cloning and sequence analysis of rat hepsin, a cell surface serine proteinase," Biochem. Biophys. Acta., 1173:350-352 (1993).

Fattom et al., "Comparative immunogenicity of conjugates composed of the *Staphylococcus aureus* type 8 capsular polysaccharide bound to carrier proteins by adipic acid dihydrazide or N-succinimidyl-3-(2-pyridyldithio)propionate," Infection and Immun., 60(1):584-589 (1992).

Fauchere et al., "Elements for the rational design of peptide drugs," Adv. Drug. Res., 15:29-69 (1986).

Fay et al., "Platelets inhibit fibrinolysis in vitro by both plasminogen activator inhibitor-1-dependent and -independent mechanisms," Blood 83:351-356 (1994).

Feinstein et al, "Thrombin, collagen and A23187 stimulated endogenous platelet arachidonate metabolism: differential inhibition by $PGE_1$, local anesthetics and a serine-protease inhibitor," Prostaglandins, 14(6):1075-1093 (1977).

Felici, F., "Selection of antibody ligands from a large library of oligopeptides expressed on a multivalent exposition vector," J. Mol. Biol. 222:301-310 (1991).

Fernandez et al., "N-Succinyl-(β-alanyl-L-alanyl-L-leucyl)doxorubicin: An extracellularly tumor-activated prodrug devoid of intravenous acute toxicity," J Med Chem, 44:3750-3753 (2001).

Findeis et al., "Targeted delivery of DNA for gene therapy via receptors," TIBTECH, 11(5):202-205 (1993).

Fodor et al., "Light-directed spatially addressable parallel chemical synthesis," Science, 251:767-773 (1991).

Forney et al., "Interaction of the human serine protease inhibitor α-1-antitrypsin with *Cryptosporidium parvum*," J. Parasitol., 82(3):496-502 (1996).

Francisco et al., "Transport and anchoring of β-lactamase to the external surface of *Esherichia coli*," Proc. Natl. Acad. Sci. USA, 89:2713-2717 (1992).

Friedman et al., "Gene therapy for disorders of the nervous system," TIBTECH, 11(5):192-197 (1993).

Friedrich et al., "Catalytic Domain Structures of MT-SP1/Matriptase, a Matrix-degrading Transmembrane Serine Proteinase", *J Bio Chem*, 277(3):2160-2168 (2002).

Fujise et al., "A tissue plasminogen activator/P-selectin fusion protein is an effective thrombolytic agent," Circulation 95(3):715-722 (1997).

Gallop et al., "Applications of combinatorial technologies to drug discovery. 1. Background and peptide combinatorial libraries," J. Med. Chem., 37(9):1233-1251 (1994).

Gante et al., "Peptidomimetics-tailored enzyme inhibitors," Angew. Chem. Int. Ed. Engl., 33:1699-1720 (1994).

Gardner et al., "The complete nucleotide sequence of an infectious clone of cauliflower mosaic virus by M13mp7 shotgun sequencing," Nucleic Acids Res., 9(12):2871-2889 (1981).

Gautier et al., "α-DNA IV: α-anomeric and β-anomeric tetrathymidylates covalently linked to intercalating oxazolopyridocarbazole. Synthesis, physicochemical properties and poly (rA) binding," Nuc. Acids Res., 15:6625-6641 (1987).

GenBank accession number for nucleotide: AI924527, Strausberg, "Airway Trypsin-like Protease," entry created Jul. 1999.

GenBank accession number for nucleotide: AI924182, Strausberg, "Airway Trypsin-like Protease," entry created Jul. 1999.

GenBank accession number for nucleotide: AI391417, Marra et al. "Plasma Kallikrein Precursor" entry created Feb. 1999.

GenBank accession number for nucleotide: AA208793, Marra et al. "Plasma Kallikrein Precursor" entry created Jan. 1997.

Genbank Accession number for nucleotide: AA883068 GenBank accession number for nucleotide: AA208793, Marra et al. "Plasma Kallikrein Precursor" entry created Jan. 1997.

GenBank accession number for nucleotide: AW591433, Strausberg, no title, entry created Mar. 2000.

GenBank accession number for nucleotide: AI978874, Strausberg, "Transmembrane Protease Serine 2" entry created Aug. 1999.

GenBank accession number for nucleotide: AI469095, Strausberg, "Serine Protease" entry created Mar. 1999.

GenBank accession number for nucleotide: AI935487, Strausberg, no title, entry created Aug. 1999.

GenBank accession number for nucleotide: AI534591, Stapleton, "*Drosphila melanogaster* Ribosomal Protein S2", entry created Mar. 1999.

GenBank accession number for nucleotide: AI758271, Strausberg, no title, entry created Jun. 1999.

GenBank accession number for nucleotide: AF133845, Yan et al., "*Homo sapiens* Corin, mRNA", submitted Mar. 1999.

GenBank accession number for nucleotide: AB013874, Tomita et al., "Low Density Lipoprotein Receptor Related Protein 4", submitted May 1998.

GenBank accession number for nucleotide: U09860, Kitamoto et al., "Human Enterokinase mRNA", submitted May 1994.

GenBank accession number for nucleotide: AB002134, Yamaoko, "*Homo sapiens* mRNA for Airway Trypsin-like Protease", submitted Mar. 1997.

GenBank accession number for nucleotide: AF118224, Lin et al., "*Homo sapiens* Matripase mRNA", submitted Jan. 1999.

GenBank accession number for nucleotide: AF133086, Takeuchi et al., "*Homo sapiens* Membrane-type Serine 1 Protease mRNA", submitted Mar. 1999.

GenBank accession number for nucleotide: AF042822, Kim et al., "*Mus musculus* Epithin mRNA", submitted Jan. 1998.

GenBank accession number for nucleotide: AF030065, Vu et al., "*Mus musculus* Serine Protease Hepsin mRNA", submitted Oct. 1997.

GenBank accession number for nucleotide: M18930, Leytus et al., "Human Hepsin mRNA", 1988.

GenBank accession number for nucleotide: X70900, Farley, "*R. norvegicus* mRNA for Hepsin", submitted Jan. 1993.

GenBank accession number for nucleotide: U75329, Paoloni-Giacobino et al., "Human Serine Protease mRNA", submitted 1996.

GenBank accession number for nucleotide: AF113596, Jacquinet et al., "*Mus musculus* Mosiac Serine Protease Epitheliasin mRNA", submitted Dec. 1998.

GenBank accession number for nucleotide: NM_016425, Wallrapp et al., "*Homo sapiens* Transmembrane Protease, Serine 4", 2000.

GenBank accession number for nucleotide: AI909842, Simpson, no title, entry created Dec. 1999.

GenBank accession number for protein: P05981, Tsuji et al., "Serine Protease Hepsin", 1991.

Georgiou et al. "Practical applications of engineering Gram-negative bacterial cell surfaces," TIBTECH 11:6-10 (1993).

Gething et al., "Variants of human tissue-type plasminogen activator that lack specific strucutal domains of the heavy chain," EMBO J., 7(9):2731-2740(1988).

Geysen et al. "Use of peptide synthesis to probe viral antigens for epitopes to a resolution of a single amino acid," Proc. Natl. Acad. Sci. USA, 81:3998-4002 (1984).

Ghendler et al., "Schistoma mansoni: isolation and characterization of Smpi56, a novel serine protease inhibitor," Exp. Parasitol., 78:121-131 (1994).

Gilbert, W. and L. Villa-Komaroff, "Useful Proteins from Recombinant Bacteria," Scientific American 242:79-94 (1980).

Glaser et al., "Antibody Engineering by Condon-Based Mutagenesis in a Filamentous Phage Vector System," J. Immunol. 149:3903-3913 (1992).

Goldmacher et al., "Photoactivation of toxin conjugates," Bioconj. Chem., 3:104-107 (1992).

Goldspiel et al., "Human gene therapy," Clinical Frontiers, Clinical Pharmacy, 12:488-505 (1993).

Gonzalez et al., "Voltage sensing by fluorescence resonance energy transfer in single cells," Biophys. J., 69:1272-1280 (1995).

Gram et al., "In vitro selection and affinity maturation of antibodies from a naive combinatorial immunoglobulin library," PNAS 89:3576-3580 (1992).

Grunstein et al., "Colony hybridization: A method for the isolation of cloned DNAs that contain a specific gene," Proc. Natl. Acad. Sci. USA, 72(10):3961-3965 (1975).

Grosschedl et al., "Introduction of a mu immunoglobulin gene into the mouse germ line: specific expression in lymphoid cells and synthesis of functional antibody," Cell 38:647-658 (1984).

Grossman et al., "Retroviruses: delivery vehicle to the liver," Curr. Opin. in Genetics and Devel., 3:110-114 (1993).

Hamdaoui et al., "Purification of a novel, heat stable serine protease inhibitor protein from ovaries of the desert locust, *Schistocerca gergaria*," Biochem. Biophys. Res. Commun., 238(2):357-360 (1997).

Hameed et al., "3,4-Dicholoroisocoumarin serine protease inhibitor induces DNA fragmentation and apoptosis in susceptible target cells," DCI and Apoptosis, Proc. Soc. Exp. Biol. Med. 219(2):132-137 (1998).

Hammer et al., "Diversity of alpha-fetoprotein gene expression in mice is generated by a combination of separate enhancer elements," Science 235:53-58 (1987).

Han et al., "Liquid-phase combinatorial synthesis," Proc. Natl. Acad. Sci. USA, 92:6419-6423 (1995).

Hanahan, D., "Heritable formation of pancreatic beta-cell tumours in transgenic mice expressing recombinant insulin/simian virus 40 oncogenes," Nature (3)15:115-122 (1985).

Harper et al., "Reaction of serine proteases with substituted isocoumarins: discovery of 3,4-dichlorisocoumarin, a new general mechanism based serine protease inhibitor," Biochem., 24:1831-1941.

Harris, J.L., et al., "Rapid and general profiling of protease specificity by using combinatorial fluorogenic substrate libraries," Proc Natl Acad Sci U S A., 97(14):7754-9, (2000).

Hazum et al., "A photocleavable protecting group for the thiol function of cysteine," Dept of Organic Chemistry, The Wizmann Institute of science Rhovet, Israel, Pept. Proc. Eur. Pept. Symp., 16$^{th}$, Brunfeldt, K (Ed)., pp. 105-110 (1981).

Herrera-Estrella et al., "Expression of chimaeric genes transferred into plant cells using a ti-plasmid-derived vector,"Nature 303:209-213 (1984).

Herrera-Estrella et al., "Light-inducible and chloroplast-associated expression of a chimaeric gene introduced into *Nicotiana tabacum* using a Ti plasmid vector," Nature 310(5973):115-120 (1984).

Hervio et al., "Negative selectivity and the evolution of protease cascades: the specificity of plasmin for peptide and protein substrates," Chem. Biol. 7(6):443-453 (2000).

Hesse et al., "Effects of the serine protease inhibitor gabexate mesilate on purified pancreatic phospholipase $A_2$," Pharmacol. Res. Commun. 16(7):637-645 (1984).

Hill et al., "A new intracellular serine protease inhibitor expressed in the rat pituitary gland complexes with granzyme B," FEBS Lett., 440:361-364 (1998).

Hiwasa et al., "Potent growth-suppressive activity of a serine protease inhibitor, ONO-3403, toward malignant human neuroblastoma cell lines," Cancer Lett. 126:221-225 (1998).

Holmes et al, "Primary structure of Human α-antiplasmin, a serine protease inhibitor (serpin)," J. Biol. Chem., 262(4):1658-1664 (1987).

Holstein et al., "The primitive metazoan Hydra expresses antistatin, a serine protease inhibitor of vertebrate blood cloagulation: cDAN cloning, cellular localization and developmental regulation," FEBS Lett., 309(3)288-292 (1992).

Hoogenboom et al., "Multi-Subunit Proteins on the Surface of Filamentous Phage: Methodologies for Displaying Antibody (Fate) Heavy and 30 Light Chains," Nucleic Acids Res., 19:4133-4137 (1991).

Hooper et al., "Localization of the mosaic transmembrane serine protease corin to heart myocytes," European Journal of Biochemistry 267:6931-6937 (2000).

Hooper et al., "Type II transmembrane serine proteases," J. Biol. Chem., 276:857-860 (2001).

Hooper et al., "Testisin, a new human serine proteinase expressed by premeiotic testicular germ cells and lost in testicular germ cell tumors," Cancer Research 59:3199-3205 (1999).

Houenou et al., "A serine protease inhibitor, protease nexin I, rescues motoneurons from naturally occurring and axotomy-induced cell death," Proc. Natl. Acad. Sci. USA., 92:895-899 (1995).

Houghten at al., "Generation and use of synthetic peptide combinatorial libraries for basic research and drug discover," Nature, 354:84-86 (1991).

Houghten at al., "General method for the rapid solid-phase synthesis of large numbers Of peptides: specificity of antigen-antibody interaction at the level of individual amino acids," Proc. Natl. Acad. Sci. USA, 82:5131-5135 (1985).

Houghten at al., "The use of synthetic peptide combinatorial libraries for the identification of bioactive peptides," BioTechniques, 313:412-421 (1992).

Houghten at al., "The use of synthetic peptide combinatorial libraries for the determination of peptide ligands in radio-receptor assays-opoid-peptides," Bioorg. Med. Chem. Lett., 3(3):405-412 (1993).

Hruby et al., "Emerging approaches in the molecular design of receptor-selective peptide ligands: conformational, topographical and dynamic considerations," Biochem. J., 268:249-262 (1990).

Huang et al., "Serine protease inhibitor TPCK prevents Taxol-induced cell death and blocks c-Raf-1 and Bcl-2 phosphorylation in human breast carcinoma cells," Oncogene, 18:3431-3439 (1999).

Huang et al., "Discovery of new ligand binding pathways in myoglobin by random mutagenesis," Nature Struct. Biol., 1(4):226-229 (1994).

Hunkapiller et al., "A microchemical facility for the analysis and synthesis of genes and proteins," Nature, 310:105-111 (1984).

Huse et al., "Generation of a large combinatorial library of the immunoglobulin repertoire in phage lambda," Science 246:1275-1281 (1989).

Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883 (1988).

Iijima et al., "Stage-specific inhibition of *Xenopus* embryogenesis by aprotinin, a serine protease inhibitor," J. Biochem. (Tokyo), 126:912-916 (1999).

Inoue et al., "Sequence-dependent hydrolysis of RNA using modified oligonucleotide splints and RNase H," FEBS Lett. 215(2):327-330 (1987).

Inoue et al., "Synthesis and hybridization studies on two complemntary nona(2'-O-methyl)ribonucleotides," Nucl. Acids Res., 15(15):6131-6148 (1987).

IUPAC-IUB, "Commission on Biochemical Nomenclature Abbreviated Nomenclature of Synthetic Polypeptides (Polymerized Amino Acids)," Biochem, 11(5):942-944 (1972).

Jackson et al., "The codependence of angiogenesis and chronic inflammation," FASEB, 11:457-465 (1997).

Jacquinet et al., "Cloning, genomic organization, chromosomal assignment and expression of a novel mosaic serine proteinase: epitheliasin," FEBS lett., 468:93-100 (2000).

Jameson et al., "Fluorescence anisotropy applied to biomolecular interactions," Methods Enzymol., 246:283-30 (1995).

Janda, K.D., "New strategies for the design of catalytic antibodies," Biotechnol. Prog., 6:178-181 (1990).

Jankun et al., "Inhibitors of urokinase reduce size of prostate cancer xenografts in sever combined immunodeficient mice," Cancer Res., 57:559-563 (1997).

Jessop et al., "Effects of serine protease inhibitor, Tame, on IL-1β in LPS-stimulated human monocytes: Relationship between synthesis and release of a 33-kDa precursor and the 17-kDa biologically active species," Inflammation, 17(5):613-631 (1993).

Ji et al., "Two-dimensional electrophoretic analysis of proteins expressed by normal and cancerous human crypts: application of mass spectrometry to peptide-mass fingerprinting," Electrophoresis, 15:391-405 (1994).

Jolley et al., "Fluorescence polarization assays for the detection of proteases and their inhibitors," J. Biomol. Screening, 1(1):33-38 (1996).

Jung et al., "Multiple peptide synthesis methods and their applications," Angew. Chem. Int. Ed. Engl., 31(4):367-486 (1992).

Kalaria et al., "Serine protease inhibitor antithrombin III and its messenger RNA in the pathogenesis of alzheimer's disease," Am. J. Pathol., 143(3):886-893 (1993).

Kaminogo et al., "Combination of serine protease inhibitor FUT-175 and thromboxane synthetase inhibitor OKY-046 decreases cerebral vasospasm in patients with subarachnoid hemorrhage," Neurol. Med. Chir. (Tokyo), 38:704-709 (1998).

Kang et al., "Antibody redesign by chain shuffling from random combinatorial immunoglobulin libraries," Proc. Natl. Acad. Sci. USA, 88:11120-11123 (1991).

Kawaguchi et al., "Purification and cloning of hepatocyte growth factor activator inhibitor type 2, a kunitz type serine protease inhibitor," J. Biol. Chem., 272(44):27558-27564 (1997).

Kay et al., "An M13 phage library displaying random 38-amino-acid-peptides as a source of novel sequences with affinity to selected target genes," Gene 128:59-65 (1993).

Ke et al., "Distinguishing the specificities of closely related proteases," J. Biol. Chem. 272:16603-16609 (1997).

Ke et al., "Identification of a hydrophobic exosite on tissue type plasminogen activator that modulates specificity for plasminogen," J Biol Chem 272:1811-1816 (1997).

Ke et al., "Optimal subsite occupancy and design of a selective inhibitor of urokinase," J Biol Chem 272:20456-20462 (1997).

Ke et al., "Rapid and efficient site-directed mutagenesis by single-tube 'megaprimer' PCR method," Nucleic Acids Res. 25(16):3371-3372 (1997).

Kelsey et al., "Species- and tissue-specific expression of human alpha 1-antitrypsin in transgenic mice," Genes and Devel. 1:161-171 (1987).

Kennedy et al., "Immobilized Enzymes". In Solid Phase Biochemistry. Analytical and Synthetic Aspects, vol. 66, Chapter 7, John Wiley & Sons, Inc., NewYork, pp. 253-391 (1993).

Kiem et al., "Retrovirus-mediated gene transduction into canine peripheral blood repopulating cells," Blood, 83(6):1467-1473 (1994).

Kim et al., "Cloning and chromosomal mapping of a gene isolated from thymic stromal cells encoding a new moue type II membrane serine protease, epithin, containing four LDL receptor modules and two CUB," Immunogenetics, 49:420-428 (1999).

Kim et al., "A cysteine-rich serine protease inhibitor (Guamerin II) from the non-blood sucking leech *Whitmania edentula*: biochemical characterization and amino acid sequence analysis," J. Enzym. Inhib., 10:81-91 (1996).

Kitamoto et al., "Enterokinase, the initiator of intestinal digestion, is a mosaic protease composed of a distinctive assortment of domains," Proc. Natl. Acad. Sci, USA, 91:7588-7592 (1994).

Kitamoto et al., "cDNA sequence and chromosomal localization of human enterokinase, the proteolytic of trypsinogen," Biochem., 34(14):4562-4568 (1998).

Kleine et al., "Lipopeptide-polyoxyethylene conjugates as mitogens and adjuvants," Immunobiol., 190:53-66 (1994).

Kobayashi et al., "Inhibition of metastasis of lewis lung carcinoma by a synthetic peptide within growth factor-like domain of urokinase in the experimental and spontaneous metastasis model," Int. J. Canc., 57:727-733 (1994).

Kodo et al., "Antibody synthesis by bone marrow cells in vitro following primary and booster tetanus toxoid immunization in humans," J. Clin. Invest. 73:1377-1384 (1984).

Kohler et al., "Continuous cultures of fused cells secreting antibody of predefined specificity," Nature, 526:495-497 (1975).

Koller et al., "Inactivating the $\beta_2$-microglobulin locus in mouse embryonic stem cells by homologous recombination," Proc. Natl. Acad. Sci USA, 86:8932-8935 (1989).

Kollias et al., "Regulated expression of human a gamma-, beta-, and hybrid gamma beta-globin genes in transgenic mice: manipulation of the developmental expression patterns," Cell 46:89-94 (1986).

Kozak et al., "Structural features in eukaryotic mRNAs that modulate the initiation of translation," J. Biol., Chem., 266(30):19867-19870 (1991).

Kozarsky et al., "Gene therapy: adenovirus vectors," Current Opinion in Genetics and Development, 3:499-503 (1993).

Kozbor et al., "The production of monoclonal antibodies from human lymphocytes," Immunology Today, 4(3):72-79 (1983).

Krumlauf et al., Developmental regulation of alpha-fetoprotein genes in transgenic mice, Mol. Cell. Biol. 5:1639-1648 (1985).

Ladurner et al., "Glutamine, alanine or glycine repeats inserted into the loop of a protein have minimal effects on stability and folding rate," J. Mol. Biol, 273:330-337 (1997).

Lam, K., "Application of combinatorial library methods in cancer research and drug discovery," Anticancer Drug Des. 12(3):145-167 (1997).

Lam et al., "A new type of synthetic peptide library for identifying ligand-binding activity," Nature, 354, 82-84 (1991).

La Vallie et al., "Cloning and Functional Expression of a cDNA Encoding the Catalytic Subunit of Bovine Enterokinase", J. Biol. Chem., 268(31):23311-23327, (1993).

Le Cam et al., "Growth hormone-mediated transcriptional activation of the rat serine protease inhibitor 2.1 gene involves both interleukin-1 β-sensitive and -insensitive pathways," Biochem. Biophys. Res. Commun., 253(2):311-314 (1998).

Lebl et al., "One bead one structure combinatorial libraries," Biopolymers (Pept. Sci.) 37:177-198 (1995).

Leder et al., "Consequences of widespread deregulation of the c-myc gene in transgenic mice: multiple neoplasms and normal development," Cell 45:485-495 (1986).

Lee, Sheau-Ling et al., "Activation of hepatocyte growth factor and urokinase/plasminogen activator by matriptase, an epithelial membrane serine protease", J. Biol. Chem., 275(47):36720-36725; (2000).

Lemaitre et al., "Specific antiviral activity of a poly(L-lysine)-conjugated oligodeoxyribonucleotide sequence complementary to vesicular stomatitis virus N protein mRNA initiation site," Proc. Natl. Acad. Sci. U.S.A. 84:648-652 (1987).

Lerner et al., "Antibodies without immunization," Science 258:1313-1314 (1992).

Lerner et al., "High throughput Screen for Inhibitors of Bacterial DNA Topoisomerase I Using the Scintillation Proximity Assay," *J. Biomol. Screening*, 1(31):135-143 (1996).

Letsinger et al., "Cholesteryl-conjugated oligonucleotides: Synthesis, properties, and activity as inhibitors of replication of human immunodeficiency virus in cell culture," *Proc. Natl. Acad. Sci. U.S.A.* 86:6553-6556 (1989).

Leytus et al., "A Novel Trypsin-like Serine Protease (Hepsin) with a Putative Transmembrane domain Expressed by Human Liver and Hepatoma Cells", *Biochem.* 27:1067-1074 (1988).

Li et al., "Minimization of a polypeptide hormone," Science 270:1657-1660 (1995).

Light et al., "Phophabs: antibody-phage alkaline phosphatase conjugates for one step ELISAs without immunization," Bioorg. Med. Chem. Lett., 2(9):1073-1078 (1992).

Lin, C., et al., "Molecular cloning of cDNA for matriptase, a matrix-degrading serine protease with tryspin-like activity," Journal of Biological Chemistry, 274:18231-18236, (1999).

Lin et al, "Purification and Characterization of a Complex Containing Matriptase and a Kunitz-type Serine Protease Inhibitor from Human Milk," *J. Biol. Chem.*, 274(26):18237-18242 (1999).

Lin et al., "Characterization of a novel, membrane-bound, 80-kDa matrix-degrading protease from human breast cancer cells. Monoclonal antibody production, isolation, and localization," *J. Biol. Chem.* 272(14):9147-9152 (1997).

Lindmark et al., "Pulmonary function in middle-aged women with heterozygous deficiency of the serine protease inhibitor alpha 1-antichymotrypsin," Am Rev Respir Dis. 141(4 Pt 1):884-888 (1990).

Little et al., "Bacterial surface presentation of proteins and peptides: an alternative to phage technology?," Trends Biotechnol., 11:3-5 (1993).

Liu et al., "Identification of a Novel Serine Protease-like Gene, the Expression of Which Is Down-Regulated during Breast Cancer Progression," *Cancer Res.* 56:3371-3379 (1996).

Liu et al., "Matrix localization of Tissue Factor Pathway Inhibitor-2/Matrix-Associated Serine Protease Inhibitor (TFPI-2/MSPII Involves Arginine-Mediated Ionic Interactions with Heparin and Dermatan Sulfate:Heparin Accelerates the Activity of TFPI-2/MSPI toward Plasmin," *Arch. Biochem. Biophys.*, 370(11):112-118 (1999).

Liu et al., "Eradication of large colon tumor xenografts by targeted delivery of maytansinoids," Proc Natl Acad Sci USA 93:8618-8623 (1996).

Loeffler et al., "Gene Transfer into Primary and Established Mammalian Cell Lines with Lipopolyamine-Coated DNA," *Meth. Enzymol* 217:599-618 (1993).

Lu et al., "Bovine Proenteropeptidase Is Activated by Trypsin, and the Specificity of Enteropeptidase Depends on the Heavy Chain", J. Biol. Chem., 272(50):31293-31300, (1997).

Lundqvist et al., "The serine protease inhibitor diisopropylfluorophosphate inhibits neutrophil NADPH-oxidase activity induced by the calcium ionophore ionomycin and serum opsonised yeast particles," *Inflamm. Res.* 44(112):510-517 (1995).

Luthman et al., "Peptides and Peptidomimetics", Book: A Textbook of Drug Design and Development, 2nd Ed., Harwood Academic Publishers, 14:386-406 (1996).

Lynch et al., "A Fluorescence Polarization Based Src-SH2 Binding Assay," *Anal. Biochem.* 247:77-82 (1997).

Maake et al., "The growth hormone dependent serine protease inhibitor, Spi 2.1 inhibits the des (1-3) insulin-like growth factor-I generating protease," *Endocrinology* 138(12):5630-5636 (1997).

Macdonald, R., "Expression of the pancreatic elastase I gene in transgenic mice," Hepatology 7:42S-51S (1987).

Madison, E., "Substrate specificity of tissue type plasminogen activator," Adv Exp Med Biol. 425:109-121 (1997).

Madison et al., "Substrate specificity of tissue type plasminogen activator. Characterization of the fibrin independent specificity of t-PA for plasminogen," J Biol. Chem. 270:7558-7562 (1995).

Madison, "Studies of serpins unfold at a feverish pace" J Clin Invest 94:2174-2175 (1994).

Madison et al., "Converting tissue plasminogen activator to a zymogen: a regulatory triad of Asp-His-Ser," Science 262:419-421 (1993).

Madison et al., "Probing structure/function relationships of tissue-type plasminogen activator by site specific mutagenesis," Fibrinolysis 81(Suppl. 1):221-236 (1994).

Madison and Sambrook, "Probing structure-function relationships of tissue-type plasminogen activator by oligonucleotide-mediated site-specific mutagenesis," *Methods Enzymol* 223:249-271 (1993).

Madison et al., "A vector, pSHT, for the expression and secretion of protein domains in mammalian cells," *Gene*, 121(1):179-180 (1992).

Madison et al., "Restoration of serine protease-inhibitor interaction by protein engineering," *J Biol. Chem.* 265:21423-21426 (1990).

Madison et al., "Amino acid residues that affect interaction of tissue-type plasminogen activator with plasminogen activator inhibitor 1," *Proc. Natl. Acad. Sci. USA* 87:3530-3533 (1990).

Madison et al., "Serpin-resistant mutants of human tissue-type plasminogen activator," *Nature* 339:721-724 (1989).

Magram et al., "Developmental regulation of a cloned adult beta-globin gene in transgenic mice," *Nature* 315(6017):338-340 (1985).

Marlor et al., "Identification and Cloning of Human Placental Bikunin, a Novel Serine Protease Inhibitor Containing Two Kunitz Domains," *J. Biol. Chem.* (272)181:12202-12208 (1997).

Marks et al., "By-passing immunization. Human antibodies from V-gene libraries displayed on phage," *J. Mol. Biol.*, 222:581-597 (1991).

Mason et al., "The hypogonadal mouse: reproductive functions restored by gene therapy," *Science* 234:1372-1378 (1986).

Mastrangeli et al., "Diversity of Airway Epithelial Cell Targets for In Vivo Recombinant Adenovirus-media ed Gene Transfer," *J. Clin. Invest.* 91:225-234 (1993).

Matsushima et al., "Structural Characterization of Porcine Enteropeptidase", *J. Biol.Chem.* 269(31):19976-19982 (1994).

Matthews et al., "Substrate phage: selection of protease substrates by monovalent phage display," *Science*, 260:1113-1117 (1993).

McCafferty et al., "Phage enzymes: Expression and affinity chromatography of functional alkaline phosphatase on the surface of bacteriophage," *Protein. Eng.*, 4(8):955-961 (1991).

McDonald, "Thrombopoietin. Its Biology, Clinical Aspects, and Possibilities," *Am. J. of Pediatric Hematology/Oncology* 14(1):8-21 (1992).

McPhalen et al., "Preliminary Crystalographic Data for the Serine Protease Inhibitor CI-2 from Barley Seeds," *J. Mol. Biol* 168:445-447 (1983).

Mellgren et al., "The Influence of a Serine Protease Inhibitor, Nafamostat Mesilate, on Plasma Coagulation, and Platelet Activation during Experimental Extracorporeal Life Support (ECLS)," *Thromb. Haemost* 79:342-347 (1998).

Menger et al., "Phosphatase catalysis developed via combinatorial organic chemistry," *J. Org. Chem.*, 60:6666-6667 (1995).

Merrifield, R.B. "Solid phase peptide synthesis. I. The synthesis of a tetrapeptide," *J. Am. Chem. Soc.*, 85:2149-2154 (1963).

Merrifield, R.B. "Solid phase peptide synthesis. III. An improved synthesis of bradykinin," *Biochemistry*, 3(9):1385-1390 (1964).

Mignatti et al., "Plasminogen activators and matrix metalloproteinases in angiogenesis," *Enzyme Protein*, 49(1-3):117-137 (1996).

Miller et al., "Use of Retroviral Vectors for Gene Transfer and Expression," *Meth.Enzymol.* 217:581-599 (1993).

Min et al., "Urokinase Receptor Antagonists Inhibit Angiogenesis and Primary Tumor Growth in Syngeneic Mice," *Canc. Res.* 56:2428-2433 (1996).

Mitani et al., "Delivering therapeutic genes—matching approach and application," *Trends Biotechnol.* 11(5):162-166 (1993).

Mitchell et al., "Preparation of aminomethyl-polystyrene resin by direct amidomethylation," Tetrahedon Letters, 42:3795-3798 (1976).

Mitchell et al., "A new synthetic route to tert-butyloxycarbonylaminoacyl-4-(oxymethyl)phenylacetamidomethyl-resin, an improved support for solid phase peptide synthesis," J. Org. Chem., 43(14):2845-2852 (1978).

Modha et al., "An association between schistosomes and contrapsin, a mouse serine protease inhibitor (serpin)," *Parasitology* 96:99-109 (1988).

Monfardini et al., "A Branched Monomethoxypoly(ethylene glycol) for Protein Modification," *Bioconjugate Chem.* 6111:62-69 (1995).

Morgan et al., "Human Gene Therapy," *Annu. Rev. Biochem.* 62:191-217 (1993).

Morgan et al., "Approaches to the Discovery of Non-Peptide Ligands for Peptide receptors and Peptidases," *Annu. Rep. Med. Chem.*, Chapter 26, Section VI, 24:243-252 (1989).

Morrison et al., "Chimeric human antibody molecules: Mouse antigen-binding domains with human constant region domains," *Proc. Natl. Acad. Sci USA*, 81:6851-6855 (1984).

Mosbach, K., "AMP and NAD as "General Ligands"," *Methods in Enzymol.*, 34:229-243, 1974.

Moser et al., "Bdellastasin, a serine protease inhibitor of the antistasin family from the medical leech (*Hirudo medicinalis*)," *Eur. J. Biochem.* 253:212-220 (1998).

Mulligan, "The Basic Science of Gene Therapy," *Science*, 260:926-932 (1993).

Nabel et al., "Direct gene transfer for immunotherapy and immunization," *TIBTECH*, 11(51):211-215 (1993).

Nakabo et al., "Lysis of leukemic cells by human macrophages: inhibition by 4-12-aminciethyl 1-benzenesulfonyl fluoride (AEBSF), a serine protease inhibitor," *J. Leukoc. Biol.* 60:328-336 (1996).

Neuberger et al., "Recombinant antibodies possessing novel effector functions," *Nature* 312:604-608 (1984).

Newton et al., "Angiogenin Single-Chain Immunofusions: Influence of Peptide Linkers and Spacers between Fusion Protein Domains," *Biochemistry* 35:545-553 (1996).

Nicolaou et al., "Radiofrequency encoded combinatorial chemistry," *Angew. Chem. Int. Ed. Engl.*, 34(20):2289-2291 (1995).

Niimi et al., "A *Drosophila* gene encoding multiple splice variants of Kazal-type serine protease inhibitor-like proteins with potential destinations of mitochondria, cytosol and the secretory pathway," *Eur. J. Biochem.*, 266:282-292 (1999).

Ngo et al. "Computational Complexity, Protein Structure Prediction, and the Levinthan Paradox," Chapter 14 in *The Protein folding problem and tertiary structure prediction* Kenneth M. Merz, Jr. and Scott M. Le Grand (Eds.) Boston: Birkhäuser pp. 433-506 (1994).

Nogrady, "Pro-Drugs and Soft Drugs," *Medicinal Chemistry A Biochemical Approach*, Oxford University Press, NY, pp. 388-392 (1985).

Nogrady, T. "Medicinal Chemistry, A Biochemical Approach," Oxford university Press, New York, pp. 388-392 (1995).

Norrby, K., "Angiogenesis: new aspects relating to its initiation and control," APMIS, 105:417-437 (1997).

Ohkoshi et al., "Effects of Serine Protease Inhibitor FOY-305 and Heparin on the Growth of Squamous Cell Carcinoma," *Anticancer Res.* 13:963-966 (1993).

Oldenburg et al., "Peptide ligands for a sugar-binding protein isolated from a random peptide library," Proc. Natl. Acad. Sci. USA, 89:5393-5397 (1992).

Ong et al., "Biosynthesis of HNK-1 Glycans on *O*-Linked Oligosaccharides Attached to the Neural Cell Adhesion Molecule (NCAM)", *J Biochem*, 277(20):18182-18190 (2002).

Ornitz et al., "Elastase I promoter directs expression of human growth hormone and SV40 T antigen genes to pancreatic acinar cells in transgenic mice," *Cold Spring Harbor Symp. Quant. Biol.* 50:399-409 (1986).

O'Reilly, "The preclinical evaluation of angiogenesis inhibitors," *Investigational New* Drugs 15:5-13 (1997).

Orth et al., "Complexes of tissue-type plasminogen activator and its serpin inhibitor plasminogen-activator inhibitor type 1 are internalized by means of the low density lipoprotein receptor-related protein/alpha 2-macroglobulin receptor," *Proc. Natl. Acad. Sci. UsSA* 89:7422-7426 (1992).

Ossowski, L., "In vivo invasion of modified chorioallantoic membrane by tumor cells: the role of cell surface-bound urokinase," *J. Cell Biol.*, 107(6.1):2437-2445 (1988).

Osterwalder et al., "Neuroserpin, an axonally secreted serine protease inhibitor," *EMBO J.* 15(12):2944-2953 (1996).

Padwa et al., "Photoelimination of a β-keto sulfide with low-lying π-π triplet state," *J. Org. Chem.*, 36(23):3550-3552 (1971).

Parks, G. and R. Lamb, "Role of NH2-terminal positively charged residues in establishing membrane protein topology," Journal of Biological Chemistry 268:19101-19109 (1993).

Palencia et al., "Determination of Activable Proacrosin/Acrosin in Bovine Sperm Using an Irreversible Isocoumarin Serine Protease Inh'b¦tor," Biol Reprod. 55:536-542 (1996).

Paoloni-Giacobino, "Cloning the TMPRSS2 Gene, Which Encodes a Novel Serine Protease with Transmembrane, LDLRA, and SRCR Domains and Maps to 21822.3," Genomics, 44:309-320 (1997).

Parmley et al, "Antibody-selectible filamentous fd phage vectors: affinity purification of target genes," Genes, 73:305-318 (1988).

Parks, G. and R. Lamb, "Topology of eukaryotic type II membrane proteins: importance of N-terminal positively charged residues flanking the hydrophobic domain," Cell 64:777-787 (1991).

Parodi et al., "Gabexate Mesilate, A New Synthetic Serine Protease Inhibitor: A Pilot Clinical Trial in Valvular Heart Surgery," *J. Cardiothorac. Vasc. Anesth.*, 10(21):235-237 (1996).

Pastan et al., "Recombinant toxins for cancer treatment," Science, 254:1173-1177 (1991).

Paul et al., "Characterization of three transcriptional repressor sites within the 3' untranslated region of the rat serine protease inhibitor 2.3 gene," Eur. J. Biochem. 254(3):538-546 (1998).

PCR protocols, Chapter 37-38 "Amplification of ribosomal RNA genes for molecular evolution studies" and "Amplification and direct sequencing of fungal ribosomal RNA genes for phylogenetics," Innis et al., Eds., Academic Press, Inc., San Diego, CA 307-322 (1990).

Pinilla et al., "Review of the utility of soluble combinatorial libraries," Biopolymers, 37:221-240 (1995).

Pinilla et al., "Synthetic peptide combinatorial libraries (SPCLs)—identification of the antigenic determinant of beta-endorphin recognized by monoclonal antibody 3E7," Gene, 128:71-76 (1993).

Pinkert et al., "An albumin enhancer located 10 kb upstream functions along with its promoter to direct efficient, liver-specific expression in transgenic mice," Genes and Devel. 1:268- 276 (1987).

Pistor et al., "Expression of viral hemagglutinin on the surface of *E. coli*," Klin. Wochenschr., 66:110-116 (1988).

Pittelkow et al., "New techniques for the in vitro culture of human skin keratinocytes and perspectives on their use for grafting of patients with extensive burns," *Mayo Clinic Proc.*, 61:771-777 (1986).

Pollack et al., "Selective chemical catalysis by an antibody," *Science*, 234:1570-1572 (1986).

Polverini, P.J., "The pathophysiology of angiogenesis," *Crit. Rev. Oral. Biol. Med.*, 6(3):230-247 (1995).

Porteous et al., "How relevant are mouse models for human diseases to somatic gene therapy," *TIBTECH* 11(5):173-181 (1993).

Powers et al., "Protein purification by affinity binding to unilamellar vesicles," *Biotechnol. Bioengineering*, 33:172-182 (1989).

Rabbani et al., "Prevention of Prostate-cancer Metastasis In Vivo by a Novel Synthetic Inhibitor of Urokinase-type Plasminogen Activator (uPA)," *Int. J. Cancer* 63:840-845 (1995).

Rao et al., "Extracellular Matrix-Associated Serine Protease Inhibitors (M, 33,000, and27,000) Are Single-Gene Products with Differential Glycosylation: cDNA Cloning of the 33-kDa Inhibitor Reveals Its Identity to Tissue Factor Pathway Inhibitor-2," *Arch. Biochem. Biophys.* 335(1):82-92; (1996).

Ravichandran et al., "Cryocrystallography of a Kunitz-type serine protease inhibitor: the 90 K structure of winged bean chymotrypsin inhibitor (WCI) at 2.13 A resolution," *Acta Cryst.* D55:1814-1821 (1999).

Readhead et al., "Expression of a myelin basic protein gene in transgenic shiverer mice: correction of the dysmyelinating phenotype," *Cell* 48:703-712 (1987).

Rheinwald, "Serial cultivation of normal human epidermal keratinocytes," Chapter 15, *Meth. Cell Biol.*, vol. 21, 21A:229-254 (1980).

Rigler et al., "Fluroescence correlations, single molecule detection and large No. screening: applications in biotechnology," J. Biotechnol., 41:177-186 (1995).

Rizo et al., "Constrained Peptides: Models of Bioactive Peptides and Protein Substructures," An. Rev. Biochem. 61:387-418 (1992).

Roberts et al., "Unusual amino acids in peptide synthesis," The Peptides. Analysis, Synthesis, Biology, Chapter 6, 5:341-449 (1983).

Robinson, "Gene therapy—proceeding from laboratory to clinic," *TIBTECH*, 11(5):155-159 (1993).

Roch et al, "Characterization of a 14 kDa Plant-related Serine Protease Inhibitor and Regulation of Cytotoxic Activity in Earthworm Coelomic Fluid," *Dev. Comp. Immunol.*, 22(11):1-12 (1998).

Rosenfeld et al., "In Vivo Transfer of the Human Cystic Fibrosis Transmembrane Conductance Regulator Gene to the Airway Epithel¦um," *Cell* 68:143-155 (1992).

Rosenfeld et al., "Adenovirus-mediated Transfer of a Recombinant al-Antirypsin Gene to the Lung Epithelium in Vivo," *Science* 252:431-434 (1991).

Rusbridge et al., "3,4-Dichloroisocoumarin, a serine protease inhibitor, inactivates glycogen phosphorylase b," *FEBS Lett.* 268(1):133-136 (1990).

Ryo et al., "Treatment of Post-Transfusion Graft-versus-Host Disease with Nafmostat Mesilate, a Serine Protease Inhibitor," *Vox Sang.* 76:241-246 (1999).

Salmons et al., "Targeting of Retroviral Vectors for Gene Therapy," *Human Gene Therapy* 4:129-141 (1993).

Sarin et al., "Inhibition of acquired immunodeficiency syndrome virus by oligodeoxynucleoside methylphosphonates," *Proc. Natl. Acad. Sci. USA*, 85:7448-7451 (1988).

Sarver et al., "Ribozymes as Potential Anti-HIV-1 Therapeutic Agents," *Science*, 247:1222-1225; (1990).

Sarvetnick et al., "Increasing the chemical potential of the germ-line antibody repertoire," *Proc. Natl. Acad. Sci. USA*, 90:4008-4011 (1993).

Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci USA* 86:5728-5732 (1989).

Sato et al., "A matrix metalloproteinase expressed on the surface of invasive tumor cells," *Nature*, 370:61-65 (1994).

Sawada et al., "Prevention of neointimal formation by a serine protease inhibitor, FUT-175, after carotid balloon injury in rats," *Stroke*, 30(31):644-650 (1999).

Scalia et al., "Beneficial Effects of LEX032, A Novel Recombinant Serine Protease Inhibitor, in Murine Traumatic Shock," *Shock* 4(41):251-256 (1995).

Scuderi, "Suppression of human leukocyte tumor necrosis factor secretion by the serine protease inhibitor $_0$-Toluenesulfonyl-L-Arginine Methyl Ester (Tame)," *J. Immunol.* 143(11):168-173 (1989).

Schmidt, M. and W. Weis, "Targeted inhibition of tumour cell growhth by a bispecific single-chain toxin containing an antibody domain and TGFα," *British Journal of Cancer* 74:853-862 (1996).

Schultz, J. and J. Schultz, "The combinatorial library: a multifunctional resource," *Biotechnol. Prog.* 12(6):729-743 (1996).

Scott et al., "Searching for peptide ligands with an epitope library," *Science*, 249:386-390 (1990).

Scott et al., "Random peptide libraries," *Curr. Opin. Biotechnol.*, 5:40-48 (1994).

Sears et al., "Engineering enzymes for bioorganic synthesis: peptide bond formation," *Biotechnol. Prog.*, 12:423-433 (1996).

Sekar et al., "Specificity of the serine protease inhibitor, Phenylmethylsulfonyli Fluoride," *Biochem. Biophys. Res. Commun.* 89(21):474-478 (1979).

Senda et al., "Treatment of ulcerative colitis with camostat mesilate, a serine protease inhibitor," *Intern. Med.*, 32(4):350-354 (1993).

Senter et al., "Novel photocleavable protein crosslinking reagents and their use in the preparation of antibody-toxin conjugates," *Photochem. Photobiol.*, 42(3):231-237 (1985).

Seto et al., "Central effect of Aprotinin, a serine protease inhibitor, on blood pressure in spontaneously hypertensive and Wistar-Kyoto Rats," *Adv. Exp. Med. Biol.* 247B:49-54 (1989).

Seto et al., "The effect of Aprotinin (a serine protease inhibitor) on renal function and renin release," *Hypertension* 5(61):893-899 (1983).

Shani, M., "Tissue-specific expression of rat myosin light-chain," *Nature* 314:283-286 (1985).

Shimomura et al., "Hepatocyte growth factor activator inhibitor, a Novel Kunitz-type serine protease inhibitor," *J. Biol Chem.* 272(101):6370-6376 (1997).

Shiozaki et al., "Effect of FUT-187, Oral Serine Protease Inhibitor, on Inflammation in the Gastric Remnant," *Jpn. J. Cancer Chemother* 23(141):1971-1979 (1996).

Shohet et al, "Inhibitor-resistant tissue-type plasminogen activator: an improved thrombolytic agent in vitro," *Thromb Haemost.* 71(1):124-128 (1994).

Sikora, "Gene therapy for cancer," *TIBTECH* 11(5):197-201 (1993).

Simon et al., "Peptides: a modular approach to drug discovery," Proc. Natl. Acad. Sci. USA, 89:9367-9371 (1992).

Silverman et al., "New assay technologies for high-throughput screening", *Curr. Opin. Chem. Biol* 2(3):397-403; (1998).

Simar-Blanchet et al., "Regulation of expression of the rat serine protease inhibitor 2.3 gene by glucocorticoids and interleukin-6. A complex and unusual interplay between positive and negative cis-acting elements," *Eur. J. Biochem.* 236(2):638-648 (1996).

Sittampalam et al., "High-throughput screening: advances in assay technologies," *Curr. Opin. Chem. Biol.* 1:384-391 (1997).

Smith, et al., "Single Step purification of polypeptides expressed in *Escherichia coli* as fusions with glutathione S-transferase," *Gene* 67:31 40 (1988).

Smith et al., "Protein loop grafting to construct a variant of tissue-type plasminogen activator that binds platelet integrin alpha IIb beta 3" *J Biol Chem.* 270(51):30486-90 (1995).

Sonatore et al., "The utility of FK506-bindign protein as a fusion partner in scintillation proximity assays: application to SH2 domains," Anal. Biochem., 240:289-297 (1996).

Sprang et al., "The three-dimensional structure of Asn102 mutant of trypsin : role of Asp102 in serine protease catalysis," Science 237:905-909 (1987).

Stankiewicz et al., "3' noncoding sequences of the CTA 1 gene enhance expression of the recombinant serine protease inhibitor, CPT1 II, in *Saccharomyces cerevisiae,*" *Acta Biochim. Pol.,* 43(3):525-529 (1996).

Steele et al., "Pigment epithelium-derived factor: Neurotropic activity and identification as a member of the serine protease inhibitor gene family," Proc. Natl. Acad. Sci. USA, 90(4):1526-1530 (1993).

Stein et al., "Physicochemical properties of polypeptides expressed in *Escherichia coli* as fusions with glutathione S-transferase," Gene, 67:31-40 (1988).

Stemple et al., Isolation of a stem cell for neurons and glia from the mammalian neural crest, Cell, 71:973-985 (1992).

Still, W.C., "Discovery of sequence-selective peptide binding by synthetic receptors using encoded combinatorial libraries," Acc. Chem. Res., 29:155-163 (1996).

Strandberg and Madison "Variants of tissue-type plasminogen activator with substantially enhanced response and selectivity toward fibrin co-factors" J Biol Chem 270:23444-23449 (1995).

Sucholeiki, I., "Solid-phase photochemical C-S bond cleavage of thioethers—A new approach to the solid phase production of non-peptide molecules," Tetrahedron Letters, 35:7307-7310 (1994).

Sullivan et al., "Development of a scintillation proximity assay for calcineurin phosphatase activity," J. Biomol. Screening, 2:19-23 (1997).

Swift et al., "Tissue-specific expression of the rat pancreatic elastase I gene in transgenic mice," Cell 38:639-646 (1984).

Tachias and Madison, "Variants of tissue-type plasminogen activator that display extraordinary resistance to inhibition by the serpin plasminogen activator inhibitor type 1," J Biol Chem 272:14580-14585 (1997).

Tachias and Madison, "Converting tissue-type plasminogen activator into a zymogen," J Biol Chem. 271(46):28749-752 (1996).

Tachias and Madison, "Converting tissue type plasminogen activator into a zymogen. Important role of Lys156," J Biol Chem 272:28-31 (1997).

Tachias et al. "Variants of tissue-type plasminogen activator which display substantially enhanced stimulation by fibrin" J Biol. Chem., 270: 18319-18322 (1995).

Takeda et al., "Construction of chimaeric processed immunoglobulin genes containing mouse variable and human constant region sequences," Nature, 314:452-454 (1985).

Takeuchi et al., "Cellular localization of membrane-type serine protease 1 and identification of protease-activated receptor-2 and single-chain urokinase-type plasminogen activator as substrates", J. Biol. Chem., 275(34):26333-26342; (2000).

Takeuchi et al., "Reverse biochemistry: Use of macromolecular protease inhibitors to dissect complex biological processes and identify a membrane-type serine protease in epithelial cancer and normal tissue", Nat'l. Acad. Sci. USA, 96(20):11054-11061; (1999).

Tanimoto et al., "Hepsin, a cell surface serine protease identified in hepatoma cells, is overexpressed in ovarian cancer," Cancer Res., 57:2884-2887 (1997).

Thompson, C.B. "Distinct roles for the costimulatory ligands B7-1 and B7-2 in T Helper Cell differentiation," Cell 81:979-982 (1995).

Thompson et al. "Synthesis and applications of small molecule libraries," Chem. Rev, 96:555-600 (1996.

Tietze, L. and M. Lieb, "Domino reactions for library synthesis of small molecules in combinatorial chemistry," Curr. Opin. Chem. Biol. 2(3):363-371 (1998).

Tolstoshev, "Gene therapy, concepts, current trials and future directions," Annu. Rev. Pharmacol. Toxicol., 32:573-596 (1993).

Tomita et al., "A novel low-density lipoprotein receptor-related protein with type II membrane protein-like structure is abundant in heart," J. Biochem., 124:784-789 (1998).

Tramontano et al., "Catalytic antibodies," Science, 234:1566-1570 (1986).

Treadwell et al., "Cartilage synthesizes the serine protease inhibitor PAI-1: support for the involvement of serine proteases in cartilage remodeling," J. Orthop. Res., 9(3):309-316 (1991).

Trouet et al., "Extracellularly Tumor-activate prodrugs for the selective chemotherapy of cancer: application to doxorubicin and preliminary in vitro and in vivo studies," Cancer Research 61:2843-2846 (2001).

Tsuji et al., "Hepsin, a cell membrane-associated protease. Characterization, tissue distribution, and gene localization," Journal of Biological Chemistry 266(25):16948-16953 (1991).

Tsutsui et al., "Cross-linking of proteins to DNA in newly synthesized chromatin by diisopropylfluorophosphate. A serine protease inhibitor," Biochem. Biophys. Res. Commun., 123(1):271-277 (1984).

Tyle et al., "Iontophoteric devices for drug discovery," Pharmaceutical Res., 3(6):318-326 (1986).

Van de Loo et al. "An oleate 12-hydroxylase from *Ricinus communis* L. is a fatty acyl desaturase homolog," *Proc. Natl. Acad. Sci. USA* 92:6743-6747 (1995).

Van der Krol et al., "Modulation of eukaryotic gene expression by complementary RNA or DNA sequences," *BioTech.*, 6(10):958-976 (1988).

Vassalli et al, "Membrane proteases in focus," Nature, 370:14-15 (1994).

Veber et al., "The design of metabolically-stable peptide analogs," TINS, 392-396 (1985).

Vedejs et al., "A method for mild photochemical oxidation; conversion of phenacyl sulfides into carbonyl compounds," J. Org. Chem., 49:573-575 (1984).

Villa-Komaroff et al., "A bacterial clone synthesizing proinsulin," Proc. Natl. Acad. Sci. USA, 75(8):3727-3731 (1978).

Vu et al., "Identification and cloning of the membrane-associated serine protease, hepsin, from mouse preimplantation embryos," J. Biol. Chem. 272(50):31315-31320 (1997).

Walter, P. and V. Lingappa, "Mechanism of protein translocation across the endoplasmic reticulum membrane," Annual Review of Cell Biology 2:499-516 (1986).

Wagner et al., "Nucleotide sequence of the thymidine kinase gene of herpes simplex virus type 1," Proc. Natl. Acad. Sci. USA 78:1441-1445 (1981).

Wallrap et al., "A novel transmembrane serine protease (TMPRSS3) overexpressed in pancreatic cancer," Cancer, 60:2602-2606 (1981).

Walsh et al., "Gene therapy for human hemoglobinopathies," Proc. Soc. Exp. Biol. Med., 204:289-300 (1993).

Wang et al., "Solid phase synthesis of protected peptides via photolytic cleavage of the α-methylphenacyl ester anchoring linkage," J. Org. Chem., 41(20):3258-3261 (1976).

Warren et al., "Spi-1: an hepatic serine protease inhibitor regulated by GH and other hormones," Mo. Cell Endocrinol., 98(1):27-32 (1993).

Watson et al., "The fine structure of bacterial and phage genes," Molecular Biology of the Gene, 4th Ed. The Bejacmin/Cummings Pub. Co., 1:224 (1987).

Weaner et al., "Tritium labeling of N-protected amino acids and peptides containing O-alkyl-tyrosyl residues," paper 22, Synthesis and Applications of Isotopically labeled compounds, Allen J. Ed., pp. 137-140 (1994).

Webber et al., "Prostate-specific antigen, a serine protease, facilitates human prostate cancer cell invasion," Clin. Cancer Res., 1:1089-1094 (1995).

Wellhoner et al., "Uptake and concentration of bioactive macromolecules by K562 cells via the transferrin cycle utilizing an acid-labile transferrin," J. Biol. Chem., 266(7):4309-4314 (1991).

Werner et al., "Identification of a protein-binidng surface by differential amide hydrogen-exchange measurements," J. Mol. Biol, 225:873-889 (1992).

Whitlock et al., "Long-term culture of B lymphocytes and their precursors from murine bone marrow," Proc. Natl. Acad. Sci. USA, 79:3608-3612 (1982).

Whitlow et al., "An improved linker for single chain Fv with reduced aggregation and enhanced proteolytic stability," Protein Engineering, 6(8):989-995 (1993).

Wikowski et al, "Conversion of a â-Ketoacyl Synthase to a Malonyl Decarboxylase by Replacement of the Active-Site Systeine with Glutamine," *Biochemistry* 38:11643-11650 (1999).

Williamson, "From genome mapping to gene therapy," TIBTECH, 11(5):159-161 (1993).

Wivel, "Regulatory considerations for gene-therapy strategies and products," TIBTECH, 11(5):189-191 (1993).

Wong, S.S., Chapter 12, "Conjugation of proteins to solid matrices," Chemistry of Protein Conjugation and Cross linking, CRC press, Inc., pp. 295-317 (1993).

Woodward et al., "Chymase-directed serine protease inhibitor that reacts with a single 30-kDa granzyme and blocks NK-mediated cytotoxicity," J. Immuno., 153:5016-5025 (1994).

Wrighton et al., "Small peptides as potent mimetics of the protein hormone erythropoietin," Science, 273:458-464 (1996).

Wu et al., "Delivery systems for gene therapy," Biotherapy, 3:87-95 (1991).

Wu et al., "Receptor-mediated in vitro gene transformation by a soluble DNA carrier system," J. Biol. Chem., 262(1):4429-4432 (1987).

Xing et al., Prevention of breast cancer growth, invasion, and metastasis by antiestrogen tamoxifen alone or in combination with urokinase inhibitor B-428,: Canc. Res., 57:3585-3593 (1997).

Xu et al., "The crystal structure of bikunin from the inter-α-inhibitor complex: a serine protease inhibitor with two kunitz domains," J. Mol. Biol., 276:955-966 (1998).

Xue et al., "Comparison of the effects of Apo(a) kringle IV-10 and plasminogen kringles on the interactions of lipoprotein(a) with regulatory molecules" Thromb Haemost. 81(3):428-35 (1999).

Xue et al. "The Kringle V-protease domain is a fibrinogen binding region within Apo(a)," *Thromb Haemost*. 86(5):1229-37 (2001).

Yahagi et al., "Complementary DNA cloning and sequencing of rat enteropeptidase and tissue distribution of its mRNA," Biochem. Biophys. Res. Commun., 219:806-812 (1996).

Yamamoto et al., "Identification of a functional promoter in the long terminal repeat of Rous sarcoma virus," Cell 22:787-797 (1980).

Yamaoka et al, "Cloning and characterization of the cDNA for human airway trypsin-like protease," J. Biol. Chem., 273(19):11895-11901 (1988).

Yamauchi et al. "Anti-carcinogenic effects of a serine protease inhibitor (FOY-305) through the suppression of neutral serine protease activity during chemical hepatocarcinogenesis in rats," Hiroshima J. Med. Sci., 36(1):81-87 No abstract available (1987).

Yan et al., "Corin, a mosaic transmembrane serine protease encoded by a novel cDNA from human heart," J. Biol. Chem., 274(21):14926-14935 (1999).

Yan et al., "Corin, a transmembrane cardiac serine protease, acts as a pro-atrial natriuretic peptideconverting enzyme," PNAS, 97(15):8525-8529 (2000).

Yanamoto et al., "Preventive effect of synthetic serine protease inhibitor, FUT-175, on cerebral vasospasm in rabbits," Neurosurgery, 30(3):351-357 (1992).

Yanamoto et al., "Therapeutic trial of cerebral vasospasm with the serine protease inhibitor, FUT-175, administered in the acute stage after subarachnoid hemorrhage," Neurosurgery, 30(3):358-363 (1992).

Yang et al., Ecotin: a serine protease inhibitor with two distinct and interacting binding sites,: J. Mol. Biol., 279:945-957 (1998).

Yen et al., "Synthesis of water-soluble copolymers containing photocleavable bonds," Makromol. Chem., 190:69-82 (1998).

Yi et al., "Bikunin, a serine protease inhibitor, is present ont eh cell boundary of epidermis," J. Invest. Dermatol., 113(2):182-188 (1999).

York et al, "Combinatorial mutagenesis of the reactive site region in plasminogen activator inhibitor I," J. Biol. Chem., 266(13):8595-8600 (1991).

Yu et al., "Message of nexin 1, a serine protease inhibitor, is accumulated in the follicular papilla during anagen of the hair cycle," J. Cell. Sci., 108:3867-3874 (1995).

Yuan et al., "Structure of murine enterokinase (enteropeptidase) and expression in small intestine during development," Am. J. Physiol. 274 G342-G349 (1998).

Zallipsky, "Functionalized poly(ethylene glycol) for preparation of biologically relevant conjucates," Bioconjugate Chem., 6:150-165 (1995).

Zebedee et al., "Human combinatorial antibody libraries to hepatitis B surface antigen," Proc. Natl. Acad. Sci. USA, 89:3175-3179 (1992).

Zhang et al., "Distinct contributions of residue 192 to the specificity of coagulation and fibrinolytic serine proteases," J Biol Chem. 274(11):7153-7156 (1999).

Zhou et al., "The vaccinia virus K2L gene encodes a serine protease inhbititor which inhibits cell-cell fusion," Virology, 189:678-686 (1992).

Ziegler et al., "Angiogenesis research enjoys growth spurt in the 1990s," J. Nat'l Cancer Institute 88(12):786-788 (1996).

Zijlstra et al., "Germ-line transmission of a disrupted $\beta_2$-microglobulin gene produced by homologous recombination in embryonic stem cells," *Nature* 342:435-438 (1989).

Zon et al., "Oligonucleotide analogs as potential chemotherapeutic agents," Pharm. Res., 5(9):539-549 (1988).

Zuckermann et al., "Efficient method for the preparation of peptides [oligo(N-substituted glycines)] by submonomer solid-phase synthesis," J. Am. Chem. Soc., 114:10646-10647 (1992).

Zuckermann et al., "Identification of highest-affinity ligands by affinity selection from equimolar peptide mixtures generated by robotic synthesis," Proc. Natl. Acad. Sci. USA, 89:4505-4509 (1992).

Office Action, issued Jun. 23, 2004, in connection with U.S. Appl. No. 09/776,191.

Office Action, issued Nov. 3, 2004, in connection with U.S. Appl. No. 09/776,191.

Office Action, issued Jul. 29, 2005, in connection with U.S. Appl. No. 09/776,191.

Office Action, issued Apr. 21, 2006, in connection with U.S. Appl. No. 09/776,191.

Office Action, issued Jan. 23, 2007, in connection with U.S. Appl. No. 09/776,191.

Office Action, issued Jun. 25, 2007, in connection with U.S. Appl. No. 09/776,191.

Office Action, issued Mar. 26, 2008, in connection with U.S. Appl. No. 09/776,191.

International Search Report, issued Sep. 11, 2001, in connection with International Patent Application No. PCT/US01/03471.

Written Opinion, issued Feb. 21, 2002, in connection with International Patent Application No. PCT/US01/03471.

International Preliminary Examination Report, issued May 14, 2002, in connection with International Patent Application No. PCT/US01/03471.

European Examination Report, issued Apr. 28, 2005, in connection with corresponding European Patent Application No. 01905377.6.

European Examination Report, issued Aug. 9, 2005, in connection with corresponding European Patent Application No. 01905377.6.

European Examination Report, issued May 3, 2006, in connection with corresponding European Patent Application No. 01905377.6.

European Examination Report, issued Apr. 26, 2007, in connection with corresponding European Patent Application No. 01905377.6.

European Examination Report, issued Oct. 14, 2009, in connection with corresponding European Patent Application No. 01905377.6.

U.S. Appl. No. 11/584,776, filed Oct. 20, 2006.

U.S. Appl. No. 11/825,627, filed Jul. 5, 2007.

U.S. Appl. No. 12/082,662, filed Apr. 11, 2008.

U.S. Appl. No. 12/384,915, filed Apr. 10, 2009.

```
                                      ▽
MTSP3     194  LACGKS---------------LKTPRVVGGEEASVDSWPWQVSIQYDKQHVCGGSILD  236
                                        205
MTSP4-S   396  PQCDGRPDCRDGSDEEHCECGLQGPSSRIVGGAVSSEGEWPWQASLQVRGRHICGGALIA  455
                                        424
MTSP4-L   540  PQCDGRPDCRDGSDEEHCECGLQGPSSRIVGGAVSSEGEWPWQASLQVRGRHICGGALIA  599
                                        568
MTSP6     205  TACGHR---------------RGYSSRIVGGNMSLLSQWPWQASLQFQGYHLCGGSVIT  248
                                        217 +

MTSP3     237  PHWVLTAAHCFRKHTDVFN--WKVRAGSDKLGS----FPSLAVAKIIIIEFNPMYPKDND  290

MTSP4-S   456  DRWVITAAHCFQEDSMASTVLWTVFLGKVWQNSRWPGEVSFKVSRLLLHPYHEEDSHDYD  515

MTSP4-L   600  DRWVITAAHCFQEDSMASTVLWTVFLGKVWQNSRWPGEVSFKVSRLLLHPYHEEDSHDYD  718

MTSP6     249  PLWIITAAHCVYDLYLPKS--WTIQVGLVSLLD--NPAPSHLVEKIVYHSKYKPKRLGND  304

MTSP3     291  IALMKLQFPLTFSGTVRPICLPFFDEELTPATPLWIIGWGFTKQNGGKMSDILLQASVQV  350
                                            *
MTSP4-S   516  VALLQLDHPVVRSAAVRPVCLPARSHFFEPGLHCWITGWGALRE-GGPISNALQKVDVQL  574
                                            *
MTSP4-L   660  VALLQLDHPVVRSAAVRPVCLPARSHFFEPGLHCWITGWGALRE-GGPISNALQKVDVQL  718
                                            *
MTSP6     305  IALMKLAGPLTFNEMIQPVCLPNSEENFPDGKVCWTSGWGATED-GGDASPVLNHAAVPL  363
                                            *

MTSP3     351  IDSTRCNADDAYQGEVTEKMMCAGIPEGGVDTCQGDSGGPLMYQSDQ--WHVVGIVSWGY  408

MTSP4-S   575  IPQDLCS--EVYRYQVTPRMLCAGYRKGKKDACQGDSGGPLVCKALSGRWFLAGLVSWGL  632

MTSP4-L   719  IPQDLCS--EVYRYQVTPRMLCAGYRKGKKDACQGDSGGPLVCKALSGRWFLAGLVSWGL  776

MTSP6     364  ISNKICNHRDVYGGIISPSMLCAGYLTGGVDSCQGDSGPLVCQERR-LWKVLVGATSFGI  442

MTSP3     409  GCGGPSTPGVYTKVSAYLNWIYNVWKAEL        437

MTSP4-S   633  GCGRPNYFGVYTRITGVISWIQQVVT           658

MTSP4-L   777  GCGRPNYFGVYTRITGVISWIQQVVT           802

MTSP6     423  GCAEVNKPGVYTRVTSFLDWIHEQMERDLKT      453
```

▽  cleavage site

+  potential glycosylation site

*  unpaired cysteine

FIG. 4

```
                           SEQUENCE LISTING

<160> NUMBER OF SEQ ID NOS: 72

<210> SEQ ID NO 1
<211> LENGTH: 3147
<212> TYPE: DNA
<213> ORGANISM: Homo Sapien
<220> FEATURE:
<221> NAME/KEY: CDS
<222> LOCATION: (23)...(2589)
<223> OTHER INFORMATION: Nucleotide encoding MTSP1
<300> PUBLICATION INFORMATION:
<301> AUTHORS: O'Brien, T.J. and Tanimoto, H.
<308> DATABASE ACCESSION NUMBER: GenBank AR081724
<309> DATABASE ENTRY DATE: 2000-08-31
<310> PATENT DOCUMENT NUMBER: US Pat 5972616
<311> PATENT FILING DATE: 1998-02-20
<312> PUBLICATION DATE: 1999-10-26

<400> SEQUENCE: 1
tcaagagcgg cctcggggta cc atg ggg agc gat cgg gcc cgc aag ggc gga      52
                         Met Gly Ser Asp Arg Ala Arg Lys Gly Gly
                          1               5                  10 ggg ggc ccg aag gac ttc ggc gcg gga ctc aag tac aac tcc cgg cac      100
Gly Gly Pro Lys Asp Phe Gly Ala Gly Leu Lys Tyr Asn Ser Arg His
             15                  20                  25 gag aaa gtg aat ggc ttg gag gaa ggc gtg gag ttc ctg cca gtc aac      148
Glu Lys Val Asn Gly Leu Glu Glu Gly Val Glu Phe Leu Pro Val Asn
         30                  35                  40 aac gtc aag aag gtg gaa aag cat ggc ccg ggg cgc tgg gtg gtg ctg      196
Asn Val Lys Lys Val Glu Lys His Gly Pro Gly Arg Trp Val Val Leu
     45                  50                  55 gca gcc gtg ctg atc ggc ctc ctc ttg gtc ttg ctg ggg atc ggc ttc      244
Ala Ala Val Leu Ile Gly Leu Leu Leu Val Leu Leu Gly Ile Gly Phe
 60                  65                  70 ctg gtg tgg cat ttg cag tac cgg gac gtc gtt cag aag gtc ttc          292
```

```
                Leu Val Trp His Leu Gln Tyr Arg Asp Val Arg Val Gln Lys Val Phe
                 75                  80                  85                  90 aat ggc tac atg agg atc aca aat gag aat ttt gtg gat gcc tac gag        340
Asn Gly Tyr Met Arg Ile Thr Asn Glu Asn Phe Val Asp Ala Tyr Glu
                 95                 100                 105 aac tcc aac tcc act gag ttt gta agc ctg gcc agc aag gtg aag gac        388
Asn Ser Asn Ser Thr Glu Phe Val Ser Leu Ala Ser Lys Val Lys Asp
                110                 115                 120 gcg ctg aag ctg ctg tac agc gga gtc cca ttc ctg ggc ccc tac cac        436
Ala Leu Lys Leu Leu Tyr Ser Gly Val Pro Phe Leu Gly Pro Tyr His
                125                 130                 135 aag gag tcg gct gtg acg gcc ttc agc gag ggc agc gtc atc gcc tac        484
Lys Glu Ser Ala Val Thr Ala Phe Ser Glu Gly Ser Val Ile Ala Tyr
                140                 145                 150 tac tgg tct gag ttc agc atc ccg cag cac ctg gtg gag gag gcc gag        532
Tyr Trp Ser Glu Phe Ser Ile Pro Gln His Leu Val Glu Glu Ala Glu
155                 160                 165                 170 cgc gtc atg gcc gag gag cgc gta gtc atg ctg ccc ccg cgg gcg cgc        580
Arg Val Met Ala Glu Glu Arg Val Val Met Leu Pro Pro Arg Ala Arg
                175                 180                 185 tcc ctg aag tcc ttt gtg gtc acc tca gtg gtg gct ttc ccc acg gac        628
Ser Leu Lys Ser Phe Val Val Thr Ser Val Val Ala Phe Pro Thr Asp
                190                 195                 200 tcc aaa aca gta cag agg acc cag gac aac agc tgc agc ttt ggc ctg        676
Ser Lys Thr Val Gln Arg Thr Gln Asp Asn Ser Cys Ser Phe Gly Leu
                205                 210                 215 cac gcc cgc ggt gtg gag ctg atg cgc ttc acc acg ccc ggc ttc cct        724
His Ala Arg Gly Val Glu Leu Met Arg Phe Thr Thr Pro Gly Phe Pro
220                 225                 230 gac agc ccc tac ccc gct cat gcc cgc tgc cag tgg gcc ctg cgg ggg        772
Asp Ser Pro Tyr Pro Ala His Ala Arg Cys Gln Trp Ala Leu Arg Gly
235                 240                 245                 250 gac gcc gac tca gtg ctg agc ctc acc ttc cgc agc ttt gac ctt gcg        820
Asp Ala Asp Ser Val Leu Ser Leu Thr Phe Arg Ser Phe Asp Leu Ala
                255                 260                 265 tcc tgc gac gag cgc ggc agc gac ctg gtg acg gtg tac aac acc ctg        868
Ser Cys Asp Glu Arg Gly Ser Asp Leu Val Thr Val Tyr Asn Thr Leu
                270                 275                 280 agc ccc atg gag ccc cac gcc ctg gtg cag ttg tgt ggc acc tac cct        916
Ser Pro Met Glu Pro His Ala Leu Val Gln Leu Cys Gly Thr Tyr Pro
                285                 290                 295 ccc tcc tac aac ctg acc ttc cac tcc tcc cag aac gtc ctg ctc atc        964
Pro Ser Tyr Asn Leu Thr Phe His Ser Ser Gln Asn Val Leu Leu Ile
                300                 305                 310 aca ctg ata acc aac act gag cgg cgg cat ccc ggc ttt gag gcc acc        1012
Thr Leu Ile Thr Asn Thr Glu Arg Arg His Pro Gly Phe Glu Ala Thr
315                 320                 325                 330 ttc ttc cag ctg cct agg atg agc agc tgt gga ggc cgc tta cgt aaa        1060
Phe Phe Gln Leu Pro Arg Met Ser Ser Cys Gly Gly Arg Leu Arg Lys
                335                 340                 345 gcc cag ggg aca ttc aac agc ccc tac tac cca ggc cac tac cca ccc        1108
Ala Gln Gly Thr Phe Asn Ser Pro Tyr Tyr Pro Gly His Tyr Pro Pro
                350                 355                 360 aac att gac tgc aca tgg aac att gag gtg ccc aac aac cag cat gtg        1156
Asn Ile Asp Cys Thr Trp Asn Ile Glu Val Pro Asn Asn Gln His Val
                365                 370                 375 aag gtg agc ttc aaa ttc ttc tac ctg ctg gag ccc ggc gtg cct gcg        1204
Lys Val Ser Phe Lys Phe Phe Tyr Leu Leu Glu Pro Gly Val Pro Ala
380                 385                 390
```

```
                                          -continued ggc acc tgc ccc aag gac tac gtg gag atc aat ggg gag aaa tac tgc      1252
Gly Thr Cys Pro Lys Asp Tyr Val Glu Ile Asn Gly Glu Lys Tyr Cys
395                 400                 405                 410 gga gag agg tcc cag ttc gtc gtc acc agc aac agc aac aag atc aca      1300
Gly Glu Arg Ser Gln Phe Val Val Thr Ser Asn Ser Asn Lys Ile Thr
            415                 420                 425 gtt cgc ttc cac tca gat cag tcc tac acc gac acc ggc ttc tta gct      1348
Val Arg Phe His Ser Asp Gln Ser Tyr Thr Asp Thr Gly Phe Leu Ala
        430                 435                 440 gaa tac ctc tcc tac gac tcc agt gac cca tgc ccg ggg cag ttc acg      1396
Glu Tyr Leu Ser Tyr Asp Ser Ser Asp Pro Cys Pro Gly Gln Phe Thr
    445                 450                 455 tgc cgc acg ggg cgg tgt atc cgg aag gag ctg cgc tgt gat ggc tgg      1444
Cys Arg Thr Gly Arg Cys Ile Arg Lys Glu Leu Arg Cys Asp Gly Trp
460                 465                 470 gcc gac tgc acc gac cac agc gat gag ctc aac tgc agt tgc gac gcc      1492
Ala Asp Cys Thr Asp His Ser Asp Glu Leu Asn Cys Ser Cys Asp Ala
475                 480                 485                 490 ggc cac cag ttc acg tgc aag aac aag ttc tgc aag ccc ctc ttc tgg      1540
Gly His Gln Phe Thr Cys Lys Asn Lys Phe Cys Lys Pro Leu Phe Trp
            495                 500                 505 gtc tgc gac agt gtg aac gac tgc gga gac aac agc gac gag cag ggg      1588
Val Cys Asp Ser Val Asn Asp Cys Gly Asp Asn Ser Asp Glu Gln Gly
        510                 515                 520 tgc agt tgt ccg gcc cag acc ttc agg tgt tcc aat ggg aag tgc ctc      1636
Cys Ser Cys Pro Ala Gln Thr Phe Arg Cys Ser Asn Gly Lys Cys Leu
    525                 530                 535 tcg aaa agc cag cag tgc aat ggg aag gac gac tgt ggg gac ggg tcc      1684
Ser Lys Ser Gln Gln Cys Asn Gly Lys Asp Asp Cys Gly Asp Gly Ser
540                 545                 550 gac gag gcc tcc tgc ccc aag gtg aac gtc gtc act tgt acc aaa cac      1732
Asp Glu Ala Ser Cys Pro Lys Val Asn Val Val Thr Cys Thr Lys His
555                 560                 565                 570 acc tac cgc tgc ctc aat ggg ctc tgc ttg agc aag ggc aac cct gag      1780
Thr Tyr Arg Cys Leu Asn Gly Leu Cys Leu Ser Lys Gly Asn Pro Glu
            575                 580                 585 tgt gac ggg aag gag gac tgt agc gac ggc tca gat gag aag gac tgc      1828
Cys Asp Gly Lys Glu Asp Cys Ser Asp Gly Ser Asp Glu Lys Asp Cys
        590                 595                 600 gac tgt ggg ctg cgg tca ttc acg aga cag gct cgt gtt gtt ggg ggc      1876
Asp Cys Gly Leu Arg Ser Phe Thr Arg Gln Ala Arg Val Val Gly Gly
    605                 610                 615 acg gat gcg gat gag ggc gag tgg ccc tgg cag gta agc ctg cat gct      1924
Thr Asp Ala Asp Glu Gly Glu Trp Pro Trp Gln Val Ser Leu His Ala
620                 625                 630 ctg ggc cag ggc cac atc tgc ggt gct tcc ctc atc tct ccc aac tgg      1972
Leu Gly Gln Gly His Ile Cys Gly Ala Ser Leu Ile Ser Pro Asn Trp
635                 640                 645                 650 ctg gtc tct gcc gca cac tgc tac atc gat gac aga gga ttc agg tac      2020
Leu Val Ser Ala Ala His Cys Tyr Ile Asp Asp Arg Gly Phe Arg Tyr
            655                 660                 665 tca gac ccc acg cag tgg acg gcc ttc ctg ggc ttg cac gac cag agc      2068
Ser Asp Pro Thr Gln Trp Thr Ala Phe Leu Gly Leu His Asp Gln Ser
        670                 675                 680 cag cgc agc gcc cct ggg gtg cag gag cgc agg ctc aag cgc atc atc      2116
Gln Arg Ser Ala Pro Gly Val Gln Glu Arg Arg Leu Lys Arg Ile Ile
    685                 690                 695 tcc cac ccc ttc ttc aat gac ttc acc ttc gac tat gac atc gcg ctg      2164
Ser His Pro Phe Phe Asn Asp Phe Thr Phe Asp Tyr Asp Ile Ala Leu
700                 705                 710
```

| | | | | | | | | | | | | | | |
|---|---|---|---|---|---|---|---|---|---|---|---|---|---|---|
| ctg | gag | ctg | gag | aaa | ccg | gca | gag | tac | agc | tcc | atg | gtg | cgg | ccc | atc | 2212 |
| Leu | Glu | Leu | Glu | Lys | Pro | Ala | Glu | Tyr | Ser | Ser | Met | Val | Arg | Pro | Ile |
| 715 | | | | 720 | | | | | 725 | | | | | 730 |

```
ctg gag ctg gag aaa ccg gca gag tac agc tcc atg gtg cgg ccc atc          2212
Leu Glu Leu Glu Lys Pro Ala Glu Tyr Ser Ser Met Val Arg Pro Ile
715                 720                 725                 730 tgc ctg ccg gac gcc tcc cat gtc ttc cct gcc ggc aag gcc atc tgg          2260
Cys Leu Pro Asp Ala Ser His Val Phe Pro Ala Gly Lys Ala Ile Trp
            735                 740                 745 gtc acg ggc tgg gga cac acc cag tat gga ggc act ggc gcg ctg atc          2308
Val Thr Gly Trp Gly His Thr Gln Tyr Gly Gly Thr Gly Ala Leu Ile
        750                 755                 760 ctg caa aag ggt gag atc cgc gtc atc aac cag acc acc tgc gag aac          2356
Leu Gln Lys Gly Glu Ile Arg Val Ile Asn Gln Thr Thr Cys Glu Asn
    765                 770                 775 ctc ctg ccg cag cag atc acg ccg cgc atg atg tgc gtg ggc ttc ctc          2404
Leu Leu Pro Gln Gln Ile Thr Pro Arg Met Met Cys Val Gly Phe Leu
780                 785                 790 agc ggc ggc gtg gac tcc tgc cag ggt gat tcc ggg gga ccc ctg tcc          2452
Ser Gly Gly Val Asp Ser Cys Gln Gly Asp Ser Gly Gly Pro Leu Ser
795                 800                 805                 810 agc gtg gag gcg gat ggg cgg atc ttc cag gcc ggt gtg gtg agc tgg          2500
Ser Val Glu Ala Asp Gly Arg Ile Phe Gln Ala Gly Val Val Ser Trp
            815                 820                 825 gga gac ggc tgc gct cag agg aac aag cca ggc gtg tac aca agg ctc          2548
Gly Asp Gly Cys Ala Gln Arg Asn Lys Pro Gly Val Tyr Thr Arg Leu
        830                 835                 840 cct ctg ttt cgg gac tgg atc aaa gag aac act ggg gta ta ggggccgggg       2599
Pro Leu Phe Arg Asp Trp Ile Lys Glu Asn Thr Gly Val
    845                 850                 855 ccacccaaat gtgtacacct gcggggccac ccatcgtcca ccccagtgtg cacgcctgca       2659
ggctggagac tggaccgctg actgcaccag cgccccaga acatacactg tgaactcaat        2719
ctccagggct ccaaatctgc ctagaaaacc tctcgcttcc tcagcctcca agtggagct        2779 gggaggtaga aggggaggac actggtggtt ctactgaccc aactggggc aaaggtttga        2839 agacacagcc tcccccgcca gccccaagct gggccgaggc gcgtttgtgt atatctgcct      2899
cccctgtctg taaggagcag cgggaacgga gcttcggagc ctcctcagtg aaggtggtgg     2959
ggctgccgga tctgggctgt ggggcccttg gccacgctc ttgaggaagc ccaggctcgg       3019
aggaccctgg aaaacagacg ggtctgagac tgaaattgtt ttaccagctc ccagggtgga     3079
cttcagtgtg tgtatttgtg taaatgggta aaacaattta tttcttttta aaaaaaaaa      3139 aaaaaaaa                                                                3147

<210> SEQ ID NO 2
<211> LENGTH: 855
<212> TYPE: PRT
<213> ORGANISM: Homo Sapien

<400> SEQUENCE: 2

Met Gly Ser Asp Arg Ala Arg Lys Gly Gly Gly Pro Lys Asp Phe
 1               5                  10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65                  70                  75                  80
```

-continued

```
Tyr Arg Asp Val Arg Val Gln Lys Val Phe Asn Gly Tyr Met Arg Ile
                 85                  90                  95
Thr Asn Glu Asn Phe Val Asp Ala Tyr Glu Asn Ser Asn Ser Thr Glu
            100                 105                 110
Phe Val Ser Leu Ala Ser Lys Val Lys Asp Ala Leu Lys Leu Leu Tyr
        115                 120                 125
Ser Gly Val Pro Phe Leu Gly Pro Tyr His Lys Glu Ser Ala Val Thr
    130                 135                 140
Ala Phe Ser Glu Gly Ser Val Ile Ala Tyr Tyr Trp Ser Glu Phe Ser
145                 150                 155                 160
Ile Pro Gln His Leu Val Glu Ala Glu Arg Val Met Ala Glu Glu
                165                 170                 175
Arg Val Val Met Leu Pro Pro Arg Ala Arg Ser Leu Lys Ser Phe Val
                180                 185                 190
Val Thr Ser Val Ala Phe Pro Thr Asp Ser Lys Thr Val Gln Arg
        195                 200                 205
Thr Gln Asp Asn Ser Cys Ser Phe Gly Leu His Ala Arg Gly Val Glu
    210                 215                 220
Leu Met Arg Phe Thr Thr Pro Gly Phe Pro Asp Ser Pro Tyr Pro Ala
225                 230                 235                 240
His Ala Arg Cys Gln Trp Ala Leu Arg Gly Asp Ala Asp Ser Val Leu
                245                 250                 255
Ser Leu Thr Phe Arg Ser Phe Asp Leu Ala Ser Cys Asp Glu Arg Gly
                260                 265                 270
Ser Asp Leu Val Thr Val Tyr Asn Thr Leu Ser Pro Met Glu Pro His
        275                 280                 285
Ala Leu Val Gln Leu Cys Gly Thr Tyr Pro Pro Ser Tyr Asn Leu Thr
    290                 295                 300
Phe His Ser Ser Gln Asn Val Leu Leu Ile Thr Leu Ile Thr Asn Thr
305                 310                 315                 320
Glu Arg Arg His Pro Gly Phe Glu Ala Thr Phe Phe Gln Leu Pro Arg
                325                 330                 335
Met Ser Ser Cys Gly Gly Arg Leu Arg Lys Ala Gln Gly Thr Phe Asn
            340                 345                 350
Ser Pro Tyr Tyr Pro Gly His Tyr Pro Pro Asn Ile Asp Cys Thr Trp
        355                 360                 365
Asn Ile Glu Val Pro Asn Asn Gln His Val Lys Val Ser Phe Lys Phe
    370                 375                 380
Phe Tyr Leu Leu Glu Pro Gly Val Pro Ala Gly Thr Cys Pro Lys Asp
385                 390                 395                 400
Tyr Val Glu Ile Asn Gly Glu Lys Tyr Cys Gly Glu Arg Ser Gln Phe
                405                 410                 415
Val Val Thr Ser Asn Ser Asn Lys Ile Thr Val Arg Phe His Ser Asp
            420                 425                 430
Gln Ser Tyr Thr Asp Thr Gly Phe Leu Ala Glu Tyr Leu Ser Tyr Asp
        435                 440                 445
Ser Ser Asp Pro Cys Pro Gly Gln Phe Thr Cys Arg Thr Gly Arg Cys
    450                 455                 460
Ile Arg Lys Glu Leu Arg Cys Asp Gly Trp Ala Asp Cys Thr Asp His
465                 470                 475                 480
Ser Asp Glu Leu Asn Cys Ser Cys Asp Ala Gly His Gln Phe Thr Cys
                485                 490                 495
```

```
Lys Asn Lys Phe Cys Lys Pro Leu Phe Trp Val Cys Asp Ser Val Asn
            500                 505                 510
Asp Cys Gly Asp Asn Ser Asp Glu Gln Gly Cys Ser Cys Pro Ala Gln
        515                 520                 525
Thr Phe Arg Cys Ser Asn Gly Lys Cys Leu Ser Lys Ser Gln Gln Cys
    530                 535                 540
Asn Gly Lys Asp Asp Cys Gly Asp Gly Ser Asp Glu Ala Ser Cys Pro
545                 550                 555                 560
Lys Val Asn Val Val Thr Cys Thr Lys His Thr Tyr Arg Cys Leu Asn
                565                 570                 575
Gly Leu Cys Leu Ser Lys Gly Asn Pro Glu Cys Asp Gly Lys Glu Asp
            580                 585                 590
Cys Ser Asp Gly Ser Asp Glu Lys Asp Cys Asp Cys Gly Leu Arg Ser
        595                 600                 605
Phe Thr Arg Gln Ala Arg Val Val Gly Gly Thr Asp Ala Asp Glu Gly
    610                 615                 620
Glu Trp Pro Trp Gln Val Ser Leu His Ala Leu Gly Gln Gly His Ile
625                 630                 635                 640
Cys Gly Ala Ser Leu Ile Ser Pro Asn Trp Leu Val Ser Ala Ala His
                645                 650                 655
Cys Tyr Ile Asp Asp Arg Gly Phe Arg Tyr Ser Asp Pro Thr Gln Trp
            660                 665                 670
Thr Ala Phe Leu Gly Leu His Asp Gln Ser Gln Arg Ser Ala Pro Gly
        675                 680                 685
Val Gln Glu Arg Arg Leu Lys Arg Ile Ile Ser His Pro Phe Phe Asn
    690                 695                 700
Asp Phe Thr Phe Asp Tyr Asp Ile Ala Leu Leu Glu Leu Glu Lys Pro
705                 710                 715                 720
Ala Glu Tyr Ser Ser Met Val Arg Pro Ile Cys Leu Pro Asp Ala Ser
                725                 730                 735
His Val Phe Pro Ala Gly Lys Ala Ile Trp Val Thr Gly Trp Gly His
            740                 745                 750
Thr Gln Tyr Gly Gly Thr Gly Ala Leu Ile Leu Gln Lys Gly Glu Ile
        755                 760                 765
Arg Val Ile Asn Gln Thr Thr Cys Glu Asn Leu Leu Pro Gln Gln Ile
    770                 775                 780
Thr Pro Arg Met Met Cys Val Gly Phe Leu Ser Gly Gly Val Asp Ser
785                 790                 795                 800
Cys Gln Gly Asp Ser Gly Gly Pro Leu Ser Ser Val Glu Ala Asp Gly
                805                 810                 815
Arg Ile Phe Gln Ala Gly Val Val Ser Trp Gly Asp Gly Cys Ala Gln
            820                 825                 830
Arg Asn Lys Pro Gly Val Tyr Thr Arg Leu Pro Leu Phe Arg Asp Trp
        835                 840                 845
Ile Lys Glu Asn Thr Gly Val
850                 855

<210> SEQ ID NO 3
<211> LENGTH: 2137
<212> TYPE: DNA
<213> ORGANISM: Homo Sapien
<220> FEATURE:
<221> NAME/KEY: CDS
<222> LOCATION: (261)...(1574)
<223> OTHER INFORMATION: DNA sequence encoding a transmembrane serine
      protease (MTSP3) protein
```

<400> SEQUENCE: 3

```
ccatcctaat acgactcact atagggctcg agcggccgcc cgggcaggtc agagagaggc    60
agcagcttgc tcagcggaca aggatgctgg gcgtgaggga ccaaggcctg ccctgcactc   120
gggcctcctc cagccagtgc tgaccaggga cttctgacct gctggccagc caggacctgt   180
gtggggaggc cctcctgctg ccttggggtg acaatctcag ctccaggcta cagggagacc   240
gggaggatca cagagccagc atg tta cag gat cct gac agt gat caa cct ctg   293
                       Met Leu Gln Asp Pro Asp Ser Asp Gln Pro Leu
                         1               5                      10 aac agc ctc gat gtc aaa ccc ctg cgc aaa ccc cgt atc ccc atg gag     341
Asn Ser Leu Asp Val Lys Pro Leu Arg Lys Pro Arg Ile Pro Met Glu
             15                  20                  25 acc ttc aga aag gtg ggg atc ccc atc atc ata gca cta ctg agc ctg     389
Thr Phe Arg Lys Val Gly Ile Pro Ile Ile Ile Ala Leu Leu Ser Leu
         30                  35                  40 gcg agt atc atc att gtg gtt gtc ctc atc aag gtg att ctg gat aaa     437
Ala Ser Ile Ile Ile Val Val Val Leu Ile Lys Val Ile Leu Asp Lys
     45                  50                  55 tac tac ttc ctc tgc ggg cag cct ctc cac ttc atc ccg agg aag cag     485
Tyr Tyr Phe Leu Cys Gly Gln Pro Leu His Phe Ile Pro Arg Lys Gln
 60                  65                  70                  75 ctg tgt gac gga gag ctg gac tgt ccc ttg ggg gag gac gag gag cac     533
Leu Cys Asp Gly Glu Leu Asp Cys Pro Leu Gly Glu Asp Glu Glu His
                 80                  85                  90 tgt gtc aag agc ttc ccc gaa ggg cct gca gtg gca gtc cgc ctc tcc     581
Cys Val Lys Ser Phe Pro Glu Gly Pro Ala Val Ala Val Arg Leu Ser
             95                 100                 105 aag gac cga tcc aca ctg cag gtg ctg gac tcg gcc aca ggg aac tgg     629
Lys Asp Arg Ser Thr Leu Gln Val Leu Asp Ser Ala Thr Gly Asn Trp
         110                 115                 120 ttc tct gcc tgt ttc gac aac ttc aca gaa gct ctc gct gag aca gcc     677
Phe Ser Ala Cys Phe Asp Asn Phe Thr Glu Ala Leu Ala Glu Thr Ala
     125                 130                 135 tgt agg cag atg ggc tac agc agc aaa ccc acc ttc aga gct gtg gag     725
Cys Arg Gln Met Gly Tyr Ser Ser Lys Pro Thr Phe Arg Ala Val Glu
140                 145                 150                 155 att ggc cca gac cag gat ctg gat gtt gtt gaa atc aca gaa aac agc     773
Ile Gly Pro Asp Gln Asp Leu Asp Val Val Glu Ile Thr Glu Asn Ser
                 160                 165                 170 cag gag ctt cgc atg cgg aac tca agt ggg ccc tgt ctc tca ggc tcc     821
Gln Glu Leu Arg Met Arg Asn Ser Ser Gly Pro Cys Leu Ser Gly Ser
             175                 180                 185 ctg gtc tcc ctg cac tgt ctt gcc tgt ggg aag agc ctg aag acc ccc     869
Leu Val Ser Leu His Cys Leu Ala Cys Gly Lys Ser Leu Lys Thr Pro
         190                 195                 200 cgt gtg gtg ggt ggg gag gag gcc tct gtg gat tct tgg cct tgg cag     917
Arg Val Val Gly Gly Glu Glu Ala Ser Val Asp Ser Trp Pro Trp Gln
     205                 210                 215 gtc agc atc cag tac gac ata cag cac gtc tgt gga ggg agc atc ctg     965
Val Ser Ile Gln Tyr Asp Ile Gln His Val Cys Gly Gly Ser Ile Leu
220                 225                 230                 235 gac ccc cac tgg gtc ctc acg gca gcc cac tgc ttc agg aaa cat acc    1013
Asp Pro His Trp Val Leu Thr Ala Ala His Cys Phe Arg Lys His Thr
                 240                 245                 250 gat gtg ttc aac tgg aag gtg cgg gca ggc tca gac aaa ctg ggc agc    1061
Asp Val Phe Asn Trp Lys Val Arg Ala Gly Ser Asp Lys Leu Gly Ser
             255                 260                 265
```

| | | | | | | | | | | | | | | | |
|---|---|---|---|---|---|---|---|---|---|---|---|---|---|---|---|
|ttc|cca|tcc|ctg|gct|gtg|gcc|aag|atc|atc|atc|att|gaa|ttc|aac|ccc|1109
|Phe|Pro|Ser|Leu|Ala|Val|Ala|Lys|Ile|Ile|Ile|Ile|Glu|Phe|Asn|Pro|
| |270| | | | |275| | | | |280| | | | |

```
ttc cca tcc ctg gct gtg gcc aag atc atc atc att gaa ttc aac ccc    1109
Phe Pro Ser Leu Ala Val Ala Lys Ile Ile Ile Ile Glu Phe Asn Pro
    270                 275                 280 atg tac ccc aaa gac aat gac atc gcc ctc atg aag ctg cag ttc cca    1157
Met Tyr Pro Lys Asp Asn Asp Ile Ala Leu Met Lys Leu Gln Phe Pro
285                 290                 295 ctc act ttc tca ggc aca gtg agg ctc atc tgt ctg ccc ttc ttt gat    1205
Leu Thr Phe Ser Gly Thr Val Arg Leu Ile Cys Leu Pro Phe Phe Asp
300                 305                 310                 315 gag gag ctc act cca gcc acc cca ctc tgg atc att gga tgg ggc ttt    1253
Glu Glu Leu Thr Pro Ala Thr Pro Leu Trp Ile Ile Gly Trp Gly Phe
                320                 325                 330 acg aag cag aat gga ggg aag atg tct gac ata ctg ctg cag gcg tca    1301
Thr Lys Gln Asn Gly Gly Lys Met Ser Asp Ile Leu Leu Gln Ala Ser
            335                 340                 345 gtc cag gtc att gac agc aca cgg tgc aat gca gac gat gcg tac cag    1349
Val Gln Val Ile Asp Ser Thr Arg Cys Asn Ala Asp Asp Ala Tyr Gln
        350                 355                 360 ggg gaa gtc acc gag aag atg atg tgt gca ggc atc ccg gaa ggg ggt    1397
Gly Glu Val Thr Glu Lys Met Met Cys Ala Gly Ile Pro Glu Gly Gly
365                 370                 375 gtg gac acc tgc cag ggt gac agt ggt ggg ccc ctg atg tac caa tct    1445
Val Asp Thr Cys Gln Gly Asp Ser Gly Gly Pro Leu Met Tyr Gln Ser
380                 385                 390                 395 gac cag tgg cat gtg gtg ggc atc gtt agc tgg ggc tat ggc tgc ggg    1493
Asp Gln Trp His Val Val Gly Ile Val Ser Trp Gly Tyr Gly Cys Gly
                400                 405                 410 ggc ccg agc acc cca gga gta tac acc aag gtc tca gcc tat ctc aac    1541
Gly Pro Ser Thr Pro Gly Val Tyr Thr Lys Val Ser Ala Tyr Leu Asn
            415                 420                 425 tgg atc tac aat gtc tgg aag gct gag ctg taa tgctgctgcc cctttgcagt  1594
Trp Ile Tyr Asn Val Trp Lys Ala Glu Leu  *
        430                 435 gctgggagcc gcttccttcc tgccctgccc acctggggat cccccaaagt cagacacaga  1654
gcaagagtcc ccttgggtac acccctctgc ccacagcctc agcatttctt ggagcagcaa  1714
agggcctcaa ttcctgtaag agaccctcgc agcccagagg cgcccagagg aagtcagcag  1774
ccctagctcg gccacacttg gtgctcccag catcccaggg agagacacag cccactgaac  1834
aaggtctcag gggtattgct aagccaagaa ggaactttcc cacactactg aatggaagca  1894
ggctgtcttg taaagcccca gatcactgtg ggctggagag gagaaggaaa gggtctgcgc  1954
cagccctgtc cgtcttcacc catccccaag cctactagag caagaaacca gttgtaatat  2014
aaaatgcact gccctactgt tggtatgact accgttacct actgttgtca ttgttattac  2074
agctatggcc actattatta aagagctgtg taacaaaaaa aaaaaaaaaa aaaaaaaaaa  2134
aaa                                                                2137

<210> SEQ ID NO 4
<211> LENGTH: 437
<212> TYPE: PRT
<213> ORGANISM: Homo Sapien

<400> SEQUENCE: 4

Met Leu Gln Asp Pro Asp Ser Asp Gln Pro Leu Asn Ser Leu Asp Val
 1               5                  10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
```

```
                35                  40                  45
Val Val Val Leu Ile Lys Val Ile Leu Asp Lys Tyr Tyr Phe Leu Cys
 50                  55                  60

Gly Gln Pro Leu His Phe Ile Pro Arg Lys Gln Leu Cys Asp Gly Glu
 65                  70                  75                  80

Leu Asp Cys Pro Leu Gly Glu Asp Glu His Cys Val Lys Ser Phe
                 85                  90                  95

Pro Glu Gly Pro Ala Val Ala Val Arg Leu Ser Lys Asp Arg Ser Thr
                100                 105                 110

Leu Gln Val Leu Asp Ser Ala Thr Gly Asn Trp Phe Ser Ala Cys Phe
                115                 120                 125

Asp Asn Phe Thr Glu Ala Leu Ala Glu Thr Ala Cys Arg Gln Met Gly
                130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
                180                 185                 190

Cys Leu Ala Cys Gly Lys Ser Leu Lys Thr Pro Arg Val Val Gly Gly
                195                 200                 205

Glu Glu Ala Ser Val Asp Ser Trp Pro Trp Gln Val Ser Ile Gln Tyr
210                 215                 220

Asp Ile Gln His Val Cys Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
                260                 265                 270

Val Ala Lys Ile Ile Ile Ile Glu Phe Asn Pro Met Tyr Pro Lys Asp
                275                 280                 285

Asn Asp Ile Ala Leu Met Lys Leu Gln Phe Pro Leu Thr Phe Ser Gly
                290                 295                 300

Thr Val Arg Leu Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
                340                 345                 350

Ser Thr Arg Cys Asn Ala Asp Asp Ala Tyr Gln Gly Glu Val Thr Glu
                355                 360                 365

Lys Met Met Cys Ala Gly Ile Pro Glu Gly Gly Val Asp Thr Cys Gln
                370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
                420                 425                 430

Trp Lys Ala Glu Leu
                435

<210> SEQ ID NO 5
```

```
<211> LENGTH: 708
<212> TYPE: DNA
<213> ORGANISM: Homo Sapien
<220> FEATURE:
<221> NAME/KEY: CDS
<222> LOCATION: (1)...(708)
<223> OTHER INFORMATION: MTSP4 protease domain cDNA

<400> SEQUENCE: 5 att gtt ggt gga gct gtg tcc tcc gag ggt gag tgg cca tgg cag gcc      48
Ile Val Gly Gly Ala Val Ser Ser Glu Gly Glu Trp Pro Trp Gln Ala
 1               5                  10                  15 agc ctc cag gtt cgg ggt cga cac atc tgt ggg ggg gcc ctc atc gct      96
Ser Leu Gln Val Arg Gly Arg His Ile Cys Gly Gly Ala Leu Ile Ala
             20                  25                  30 gac cgc tgg gtg ata aca gct gcc cac tgc ttc cag gag gac agc atg     144
Asp Arg Trp Val Ile Thr Ala Ala His Cys Phe Gln Glu Asp Ser Met
         35                  40                  45 gcc tcc acg gtg ctg tgg acc gtg ttc ctg ggc aag gtg tgg cag aac     192
Ala Ser Thr Val Leu Trp Thr Val Phe Leu Gly Lys Val Trp Gln Asn
     50                  55                  60 tcg cgc tgg cct gga gag gtg tcc ttc aag gtg agc cgc ctg ctc ctg     240
Ser Arg Trp Pro Gly Glu Val Ser Phe Lys Val Ser Arg Leu Leu Leu
 65                  70                  75                  80 cac ccg tac cac gaa gag gac agc cat gac tac gac gtg gcg ctg ctg     288
His Pro Tyr His Glu Glu Asp Ser His Asp Tyr Asp Val Ala Leu Leu
                 85                  90                  95 cag ctc gac cac ccg gtg gtg cgc tcg gcc gcc gtg cgc ccc gtc tgc     336
Gln Leu Asp His Pro Val Val Arg Ser Ala Ala Val Arg Pro Val Cys
            100                 105                 110 ctg ccc gcg cgc tcc cac ttc ttc gag ccc ggc ctg cac tgc tgg att     384
Leu Pro Ala Arg Ser His Phe Phe Glu Pro Gly Leu His Cys Trp Ile
        115                 120                 125 acg ggc tgg ggc gcc ttg cgc gag ggc ggc ccc atc agc aac gct ctg     432
Thr Gly Trp Gly Ala Leu Arg Glu Gly Gly Pro Ile Ser Asn Ala Leu
    130                 135                 140 cag aaa gtg gat gtg cag ttg atc cca cag gac ctg tgc agc gag gtc     480
Gln Lys Val Asp Val Gln Leu Ile Pro Gln Asp Leu Cys Ser Glu Val
145                 150                 155                 160 tat cgc tac cag gtg acg cca cgc atg ctg tgt gcc ggc tac cgc aag     528
Tyr Arg Tyr Gln Val Thr Pro Arg Met Leu Cys Ala Gly Tyr Arg Lys
                165                 170                 175 ggc aag aag gat gcc tgt cag ggt gac tca ggt ggt ccg ctg gtg tgc     576
Gly Lys Lys Asp Ala Cys Gln Gly Asp Ser Gly Gly Pro Leu Val Cys
            180                 185                 190 aag gca ctc agt ggc cgc tgg ttc ctg gcg ggg ctg gtc agc tgg ggc     624
Lys Ala Leu Ser Gly Arg Trp Phe Leu Ala Gly Leu Val Ser Trp Gly
        195                 200                 205 ctg ggc tgt ggc cgg cct aac tac ttc ggc gtc tac acc cgc atc aca     672
Leu Gly Cys Gly Arg Pro Asn Tyr Phe Gly Val Tyr Thr Arg Ile Thr
    210                 215                 220 ggt gtg atc agc tgg atc cag caa gtg gtg acc tga                     708
Gly Val Ile Ser Trp Ile Gln Gln Val Val Thr *
225                 230                 235

<210> SEQ ID NO 6
<211> LENGTH: 235
<212> TYPE: PRT
<213> ORGANISM: Homo Sapien

<400> SEQUENCE: 6

Ile Val Gly Gly Ala Val Ser Ser Glu Gly Glu Trp Pro Trp Gln Ala
```

```
  1               5                  10                 15
Ser Leu Gln Val Arg Gly Arg His Ile Cys Gly Gly Ala Leu Ile Ala
                20                 25                 30

Asp Arg Trp Val Ile Thr Ala Ala His Cys Phe Gln Glu Asp Ser Met
                35                 40                 45

Ala Ser Thr Val Leu Trp Thr Val Phe Leu Gly Lys Val Trp Gln Asn
 50                 55                 60

Ser Arg Trp Pro Gly Glu Val Ser Phe Lys Val Ser Arg Leu Leu Leu
 65                 70                 75                 80

His Pro Tyr His Glu Glu Asp Ser His Asp Tyr Asp Val Ala Leu Leu
                85                 90                 95

Gln Leu Asp His Pro Val Val Arg Ser Ala Ala Val Arg Pro Val Cys
                100                105                110

Leu Pro Ala Arg Ser His Phe Phe Glu Pro Gly Leu His Cys Trp Ile
                115                120                125

Thr Gly Trp Gly Ala Leu Arg Glu Gly Gly Pro Ile Ser Asn Ala Leu
                130                135                140

Gln Lys Val Asp Val Gln Leu Ile Pro Gln Asp Leu Cys Ser Glu Val
145                150                155                160

Tyr Arg Tyr Gln Val Thr Pro Arg Met Leu Cys Ala Gly Tyr Arg Lys
                165                170                175

Gly Lys Lys Asp Ala Cys Gln Gly Asp Ser Gly Gly Pro Leu Val Cys
                180                185                190

Lys Ala Leu Ser Gly Arg Trp Phe Leu Ala Gly Leu Val Ser Trp Gly
                195                200                205

Leu Gly Cys Gly Arg Pro Asn Tyr Phe Gly Val Tyr Thr Arg Ile Thr
                210                215                220

Gly Val Ile Ser Trp Ile Gln Gln Val Val Thr
225                230                235

<210> SEQ ID NO 7
<211> LENGTH: 3104
<212> TYPE: DNA
<213> ORGANISM: Homo Sapien
<220> FEATURE:
<221> NAME/KEY: CDS
<222> LOCATION: (33)...(2441)
<223> OTHER INFORMATION: cDNA encoding :MTSP4-L (long form) splice
      variant

<400> SEQUENCE: 7
tcatcggcca gagggtgatc agtgagcaga ag atg ccc gtg gcc gag gcc ccc         53
                                    Met Pro Val Ala Glu Ala Pro
                                     1               5 cag gtg gct ggc ggg cag ggg gac gga ggt gat ggc gag gaa gcg gag        101
Gln Val Ala Gly Gly Gln Gly Asp Gly Gly Asp Gly Glu Glu Ala Glu
            10                 15                  20 ccg gag ggg atg ttc aag gcc tgt gag gac tcc aag aga aaa gcc cgg        149
Pro Glu Gly Met Phe Lys Ala Cys Glu Asp Ser Lys Arg Lys Ala Arg
        25                 30                  35 ggc tac ctc cgc ctg gtg ccc ctg ttt gtg ctg ctg gcc ctg ctc gtg        197
Gly Tyr Leu Arg Leu Val Pro Leu Phe Val Leu Leu Ala Leu Leu Val
 40                 45                  50                 55 ctg gct tcg gcg ggg gtg cta ctc tgg tat ttc cta ggg tac aag gcg        245
Leu Ala Ser Ala Gly Val Leu Leu Trp Tyr Phe Leu Gly Tyr Lys Ala
            60                 65                  70 gag gtg atg gtc agc cag gtg tac tca ggc agt ctg cgt gta ctc aat        293
Glu Val Met Val Ser Gln Val Tyr Ser Gly Ser Leu Arg Val Leu Asn
```

|  |  |
|---|---:|
| cgc cac ttc tcc cag gat ctt acc cgc cgg gaa tct agt gcc ttc cgc<br>Arg His Phe Ser Gln Asp Leu Thr Arg Arg Glu Ser Ser Ala Phe Arg<br>       90                    95                100 | 341 |
| agt gaa acc gcc aaa gcc cag aag atg ctc aag gag ctc atc acc agc<br>Ser Glu Thr Ala Lys Ala Gln Lys Met Leu Lys Glu Leu Ile Thr Ser<br>105                110                  115 | 389 |
| acc cgc ctg gga act tac tac aac tcc agc tcc gtc tat tcc ttt ggg<br>Thr Arg Leu Gly Thr Tyr Tyr Asn Ser Ser Ser Val Tyr Ser Phe Gly<br>120                125                130                135 | 437 |
| gag gga ccc ctc acc tgc ttc ttc tgg ttc att ctc caa atc ccc gag<br>Glu Gly Pro Leu Thr Cys Phe Phe Trp Phe Ile Leu Gln Ile Pro Glu<br>            140                  145                150 | 485 |
| cac cgc cgg ctg atg ctg agc ccc gag gtg gtg cag gca ctg ctg gtg<br>His Arg Arg Leu Met Leu Ser Pro Glu Val Val Gln Ala Leu Leu Val<br>               155                160                165 | 533 |
| gag gag ctg ctg tcc aca gtc aac agc tcg gct gcc gtc ccc tac agg<br>Glu Glu Leu Leu Ser Thr Val Asn Ser Ser Ala Ala Val Pro Tyr Arg<br>          170                  175                180 | 581 |
| gcc gag tac gaa gtg gac ccc gag ggc cta gtg atc ctg gaa gcc agt<br>Ala Glu Tyr Glu Val Asp Pro Glu Gly Leu Val Ile Leu Glu Ala Ser<br>185                190                  195 | 629 |
| gtg aaa gac ata gct gca ttg aat tcc acg ctg ggt tgt tac cgc tac<br>Val Lys Asp Ile Ala Ala Leu Asn Ser Thr Leu Gly Cys Tyr Arg Tyr<br>200                205                210                215 | 677 |
| agc tac gtg ggc cag ggc cag gtc ctc cgg ctg aag ggg cct gac cac<br>Ser Tyr Val Gly Gln Gly Gln Val Leu Arg Leu Lys Gly Pro Asp His<br>               220                  225                230 | 725 |
| ctg gcc tcc agc tgc ctg tgg cac ctg cag ggc ccc aag gac ctc atg<br>Leu Ala Ser Ser Cys Leu Trp His Leu Gln Gly Pro Lys Asp Leu Met<br>               235                  240                245 | 773 |
| ctc aaa ctc cgg ctg gag tgg acg ctg gca gag tgc cgg gac cga ctg<br>Leu Lys Leu Arg Leu Glu Trp Thr Leu Ala Glu Cys Arg Asp Arg Leu<br>          250                  255                260 | 821 |
| gcc atg tat gac gtg gcc ggg ccc ctg gag aag agg ctc atc acc tcg<br>Ala Met Tyr Asp Val Ala Gly Pro Leu Glu Lys Arg Leu Ile Thr Ser<br>265                270                  275 | 869 |
| gtg tac ggc tgc agc cgc cag gag ccc gtg gtg gag gtt ctg gcg tcg<br>Val Tyr Gly Cys Ser Arg Gln Glu Pro Val Val Glu Val Leu Ala Ser<br>280                285                290                295 | 917 |
| ggg gcc atc atg gcg gtc gtc tgg aag aag ggc ctg cac agc tac tac<br>Gly Ala Ile Met Ala Val Val Trp Lys Lys Gly Leu His Ser Tyr Tyr<br>               300                  305                310 | 965 |
| gac ccc ttc gtg ctc tcc gtg cag ccg gtg gtc ttc cag gcc tgt gaa<br>Asp Pro Phe Val Leu Ser Val Gln Pro Val Val Phe Gln Ala Cys Glu<br>               315                  320                325 | 1013 |
| gtg aac ctg acg ctg gac aac agg ctc gac tcc cag ggc gtc ctc agc<br>Val Asn Leu Thr Leu Asp Asn Arg Leu Asp Ser Gln Gly Val Leu Ser<br>          330                  335                340 | 1061 |
| acc ccg tac ttc ccc agc tac tac tcg ccc caa acc cac tgc tcc tgg<br>Thr Pro Tyr Phe Pro Ser Tyr Tyr Ser Pro Gln Thr His Cys Ser Trp<br>345                350                  355 | 1109 |
| cac ctc acg gtg ccc tct ctg gac tac ggc ttg gcc ctc tgg ttt gat<br>His Leu Thr Val Pro Ser Leu Asp Tyr Gly Leu Ala Leu Trp Phe Asp<br>360                365                370                375 | 1157 |
| gcc tat gca ctg agg agg cag aag tat gat ttg ccg tgc acc cag ggc<br>Ala Tyr Ala Leu Arg Arg Gln Lys Tyr Asp Leu Pro Cys Thr Gln Gly<br>               380                  385                390 | 1205 |
| cag tgg acg atc cag aac agg agg ctg tgt ggc ttg cgc atc ctg cag | 1253 |

```
            Gln Trp Thr Ile Gln Asn Arg Arg Leu Cys Gly Leu Arg Ile Leu Gln
                        395                 400                 405 ccc tac gcc gag agg atc ccc gtg gtg gcc acg gcc ggg atc acc atc       1301
Pro Tyr Ala Glu Arg Ile Pro Val Val Ala Thr Ala Gly Ile Thr Ile
            410                 415                 420 aac ttc acc tcc cag atc tcc ctc acc ggg ccc ggt gtg cgg gtg cac       1349
Asn Phe Thr Ser Gln Ile Ser Leu Thr Gly Pro Gly Val Arg Val His
        425                 430                 435 tat ggc ttg tac aac cag tcg gac ccc tgc cct gga gag ttc ctc tgt       1397
Tyr Gly Leu Tyr Asn Gln Ser Asp Pro Cys Pro Gly Glu Phe Leu Cys
440                 445                 450                 455 tct gtg aat gga ctc tgt gtc cct gcc tgt gat ggg gtc aag gac tgc       1445
Ser Val Asn Gly Leu Cys Val Pro Ala Cys Asp Gly Val Lys Asp Cys
            460                 465                 470 ccc aac ggc ctg gat gag aga aac tgc gtt tgc aga gcc aca ttc cag       1493
Pro Asn Gly Leu Asp Glu Arg Asn Cys Val Cys Arg Ala Thr Phe Gln
        475                 480                 485 tgc aaa gag gac agc aca tgc atc tca ctg ccc aag gtc tgt gat ggg       1541
Cys Lys Glu Asp Ser Thr Cys Ile Ser Leu Pro Lys Val Cys Asp Gly
    490                 495                 500 cag cct gat tgt ctc aac ggc agc gac gaa gag cag tgc cag gaa ggg       1589
Gln Pro Asp Cys Leu Asn Gly Ser Asp Glu Glu Gln Cys Gln Glu Gly
505                 510                 515 gtg cca tgt ggg aca ttc acc ttc cag tgt gag gac cgg agc tgc gtg       1637
Val Pro Cys Gly Thr Phe Thr Phe Gln Cys Glu Asp Arg Ser Cys Val
520                 525                 530                 535 aag aag ccc aac ccg cag tgt gat ggg cgg ccc gac tgc agg gac ggc       1685
Lys Lys Pro Asn Pro Gln Cys Asp Gly Arg Pro Asp Cys Arg Asp Gly
            540                 545                 550 tcg gat gag gag cac tgt gaa tgt ggc ctc cag ggc ccc tcc agc cgc       1733
Ser Asp Glu Glu His Cys Glu Cys Gly Leu Gln Gly Pro Ser Ser Arg
        555                 560                 565 att gtt ggt gga gct gtg tcc tcc gag ggt gag tgg cca tgg cag gcc       1781
Ile Val Gly Gly Ala Val Ser Ser Glu Gly Glu Trp Pro Trp Gln Ala
        570                 575                 580 agc ctc cag gtt cgg ggt cga cac atc tgt ggg ggg gcc ctc atc gct       1829
Ser Leu Gln Val Arg Gly Arg His Ile Cys Gly Gly Ala Leu Ile Ala
585                 590                 595 gac cgc tgg gtt ata aca gct gcc cac tgc ttc cag gag gac agc atg       1877
Asp Arg Trp Val Ile Thr Ala Ala His Cys Phe Gln Glu Asp Ser Met
600                 605                 610                 615 gcc tcc acg gtg ctg tgg acc gtg ttc ctg ggc aag gtg tgg cag aac       1925
Ala Ser Thr Val Leu Trp Thr Val Phe Leu Gly Lys Val Trp Gln Asn
            620                 625                 630 tcg cgc tgg cct gga gag gtg tcc ttc aag gtg agc cgc ctg ctc ctg       1973
Ser Arg Trp Pro Gly Glu Val Ser Phe Lys Val Ser Arg Leu Leu Leu
        635                 640                 645 cac ccg tac cac gaa gag gac agc cat gac tac gac gtg gcg ctg ctg       2021
His Pro Tyr His Glu Glu Asp Ser His Asp Tyr Asp Val Ala Leu Leu
        650                 655                 660 cag ctc gac cac ccg gtg gtg cgc tcg gcc gcc gtg cgc ccc gtc tgc       2069
Gln Leu Asp His Pro Val Val Arg Ser Ala Ala Val Arg Pro Val Cys
665                 670                 675 ctg ccc gcg cgc tcc cac ttc ttc gag ccc ggc ctg cac tgc tgg att       2117
Leu Pro Ala Arg Ser His Phe Phe Glu Pro Gly Leu His Cys Trp Ile
680                 685                 690                 695 acg ggc tgg ggc gcc ttg cgc gag ggc ggc ccc atc agc aac gct ctg       2165
Thr Gly Trp Gly Ala Leu Arg Glu Gly Gly Pro Ile Ser Asn Ala Leu
            700                 705                 710
```

```
cag aaa gtg gat gtg cag ttg atc cca cag gac ctg tgc agc gag gtc        2213
Gln Lys Val Asp Val Gln Leu Ile Pro Gln Asp Leu Cys Ser Glu Val
        715                 720                 725 tat cgc tac cag gtg acg cca cgc atg ctg tgt gcc ggc tac cgc aag        2261
Tyr Arg Tyr Gln Val Thr Pro Arg Met Leu Cys Ala Gly Tyr Arg Lys
    730                 735                 740 ggc aag aag gat gcc tgt cag ggt gac tca ggt ggt ccg ctg gtg tgc        2309
Gly Lys Lys Asp Ala Cys Gln Gly Asp Ser Gly Gly Pro Leu Val Cys
745                 750                 755 aag gca ctc agt ggc cgc tgg ttc ctg gcg ggg ctg gtc agc tgg ggc        2357
Lys Ala Leu Ser Gly Arg Trp Phe Leu Ala Gly Leu Val Ser Trp Gly
760                 765                 770                 775 ctg ggc tgt ggc cgg cct aac tac ttc ggc gtc tac acc cgc atc aca        2405
Leu Gly Cys Gly Arg Pro Asn Tyr Phe Gly Val Tyr Thr Arg Ile Thr
                780                 785                 790 ggt gtg atc agc tgg atc cag caa gtg gtg acc tga ggaactgccc            2451
Gly Val Ile Ser Trp Ile Gln Gln Val Val Thr *
            795                 800 ccctgcaaag cagggcccac ctcctggact cagagagccc agggcaactg ccaagcaggg      2511
ggacaagtat tctggcgggg ggtgggggag agagcaggcc ctgtggtggc aggaggggca      2571
tcttgtttcg tccctgatgt ctgtccagta tggcaggagg atgagaagtg ccagcagttg      2631
ggggtcaaga cgtcccttga ggacccaggc ccacacccag ccctttgcc tcccaattct       2691 ctctcctccg tccccttcct ccactgctgc ctaatgcaag gcagtggctc agcagcaaga      2751
atgctggttc tacatcccga ggagtgtctg aggtgcgccc cactctgtac agaggctgtt     2811
tgggcagcct tgcctccaga gagcagattc cagcttcgga agccctggt ctaacttggg      2871 atctgggaat ggaaggtgct cccatcggag gggaccctca gagccctgga gactgccagg    2931
tgggcctgct gccactgtaa gccaaaaggt ggggaagtcc tgactccagg gtccttgccc    2991 caccctgcc tgccacctgg gccctcacag cccagaccct cactgggagg tgagctcagc      3051
tgccctttgg aataaagctg cctgatgcaa aaaaaaaaaa aaaaaaaaaa aaa             3104

<210> SEQ ID NO 8
<211> LENGTH: 802
<212> TYPE: PRT
<213> ORGANISM: Homo Sapien

<400> SEQUENCE: 8

Met Pro Val Ala Glu Ala Pro Gln Val Ala Gly Gly Gln Gly Asp Gly
1               5                   10                  15

Gly Asp Gly Glu Glu Ala Glu Pro Glu Gly Met Phe Lys Ala Cys Glu
            20                  25                  30

Asp Ser Lys Arg Lys Ala Arg Gly Tyr Leu Arg Leu Val Pro Leu Phe
        35                  40                  45

Val Leu Leu Ala Leu Leu Val Leu Ala Ser Ala Gly Val Leu Leu Trp
    50                  55                  60

Tyr Phe Leu Gly Tyr Lys Ala Glu Val Met Val Ser Gln Val Tyr Ser
65                  70                  75                  80

Gly Ser Leu Arg Val Leu Asn Arg His Phe Ser Gln Asp Leu Thr Arg
                85                  90                  95

Arg Glu Ser Ser Ala Phe Arg Ser Glu Thr Ala Lys Ala Gln Lys Met
            100                 105                 110

Leu Lys Glu Leu Ile Thr Ser Thr Arg Leu Gly Thr Tyr Tyr Asn Ser
        115                 120                 125

Ser Ser Val Tyr Ser Phe Gly Glu Gly Pro Leu Thr Cys Phe Phe Trp
```

-continued

```
            130                 135                 140
Phe Ile Leu Gln Ile Pro Glu His Arg Arg Leu Met Leu Ser Pro Glu
145                 150                 155                 160

Val Val Gln Ala Leu Leu Val Glu Glu Leu Leu Ser Thr Val Asn Ser
                    165                 170                 175

Ser Ala Ala Val Pro Tyr Arg Ala Glu Tyr Glu Val Asp Pro Glu Gly
                180                 185                 190

Leu Val Ile Leu Glu Ala Ser Val Lys Asp Ile Ala Ala Leu Asn Ser
                195                 200                 205

Thr Leu Gly Cys Tyr Arg Tyr Ser Tyr Val Gly Gln Gly Gln Val Leu
                210                 215                 220

Arg Leu Lys Gly Pro Asp His Leu Ala Ser Ser Cys Leu Trp His Leu
225                 230                 235                 240

Gln Gly Pro Lys Asp Leu Met Leu Lys Leu Arg Leu Glu Trp Thr Leu
                245                 250                 255

Ala Glu Cys Arg Asp Arg Leu Ala Met Tyr Asp Val Ala Gly Pro Leu
                260                 265                 270

Glu Lys Arg Leu Ile Thr Ser Val Tyr Gly Cys Ser Arg Gln Glu Pro
                275                 280                 285

Val Val Glu Val Leu Ala Ser Gly Ala Ile Met Ala Val Val Trp Lys
                290                 295                 300

Lys Gly Leu His Ser Tyr Tyr Asp Pro Phe Val Leu Ser Val Gln Pro
305                 310                 315                 320

Val Val Phe Gln Ala Cys Glu Val Asn Leu Thr Leu Asp Asn Arg Leu
                325                 330                 335

Asp Ser Gln Gly Val Leu Ser Thr Pro Tyr Phe Pro Ser Tyr Tyr Ser
                340                 345                 350

Pro Gln Thr His Cys Ser Trp His Leu Thr Val Pro Ser Leu Asp Tyr
                355                 360                 365

Gly Leu Ala Leu Trp Phe Asp Ala Tyr Ala Leu Arg Arg Gln Lys Tyr
                370                 375                 380

Asp Leu Pro Cys Thr Gln Gly Gln Trp Thr Ile Gln Asn Arg Arg Leu
385                 390                 395                 400

Cys Gly Leu Arg Ile Leu Gln Pro Tyr Ala Glu Arg Ile Pro Val Val
                405                 410                 415

Ala Thr Ala Gly Ile Thr Ile Asn Phe Thr Ser Gln Ile Ser Leu Thr
                420                 425                 430

Gly Pro Gly Val Arg Val His Tyr Gly Leu Tyr Asn Gln Ser Asp Pro
                435                 440                 445

Cys Pro Gly Glu Phe Leu Cys Ser Val Asn Gly Leu Cys Val Pro Ala
450                 455                 460

Cys Asp Gly Val Lys Asp Cys Pro Asn Gly Leu Asp Glu Arg Asn Cys
465                 470                 475                 480

Val Cys Arg Ala Thr Phe Gln Cys Lys Glu Asp Ser Thr Cys Ile Ser
                485                 490                 495

Leu Pro Lys Val Cys Asp Gly Gln Pro Asp Cys Leu Asn Gly Ser Asp
                500                 505                 510

Glu Glu Gln Cys Gln Glu Gly Val Pro Cys Gly Thr Phe Thr Phe Gln
                515                 520                 525

Cys Glu Asp Arg Ser Cys Val Lys Lys Pro Asn Pro Gln Cys Asp Gly
                530                 535                 540

Arg Pro Asp Cys Arg Asp Gly Ser Asp Glu Glu His Cys Glu Cys Gly
545                 550                 555                 560
```

```
Leu Gln Gly Pro Ser Ser Arg Ile Val Gly Ala Val Ser Glu
                565                 570                 575
Gly Glu Trp Pro Trp Gln Ala Ser Leu Gln Val Arg Gly Arg His Ile
            580                 585                 590
Cys Gly Gly Ala Leu Ile Ala Asp Arg Trp Val Ile Thr Ala Ala His
            595                 600                 605
Cys Phe Gln Glu Asp Ser Met Ala Ser Thr Val Leu Trp Thr Val Phe
        610                 615                 620
Leu Gly Lys Val Trp Gln Asn Ser Arg Trp Pro Gly Glu Val Ser Phe
625                 630                 635                 640
Lys Val Ser Arg Leu Leu Leu His Pro Tyr His Glu Asp Ser His
                645                 650                 655
Asp Tyr Asp Val Ala Leu Leu Gln Leu Asp His Pro Val Val Arg Ser
            660                 665                 670
Ala Ala Val Arg Pro Val Cys Leu Pro Ala Arg Ser His Phe Phe Glu
            675                 680                 685
Pro Gly Leu His Cys Trp Ile Thr Gly Trp Gly Ala Leu Arg Glu Gly
        690                 695                 700
Gly Pro Ile Ser Asn Ala Leu Gln Lys Val Asp Val Gln Leu Ile Pro
705                 710                 715                 720
Gln Asp Leu Cys Ser Glu Val Tyr Arg Tyr Gln Val Thr Pro Arg Met
                725                 730                 735
Leu Cys Ala Gly Tyr Arg Lys Gly Lys Lys Asp Ala Cys Gln Gly Asp
            740                 745                 750
Ser Gly Gly Pro Leu Val Cys Lys Ala Leu Ser Gly Arg Trp Phe Leu
        755                 760                 765
Ala Gly Leu Val Ser Trp Gly Leu Gly Cys Gly Arg Pro Asn Tyr Phe
            770                 775                 780
Gly Val Tyr Thr Arg Ile Thr Gly Val Ile Ser Trp Ile Gln Gln Val
785                 790                 795                 800
Val Thr

<210> SEQ ID NO 9
<211> LENGTH: 2672
<212> TYPE: DNA
<213> ORGANISM: Homo Sapien
<220> FEATURE:
<221> NAME/KEY: CDS
<222> LOCATION: (33)...(2009)
<223> OTHER INFORMATION: cDNA encoding: MTSP4-S (short form) splice
      variant

<400> SEQUENCE: 9
tcatcggcca gagggtgatc agtgagcaga ag atg ccc gtg gcc gag gcc ccc        53
                                    Met Pro Val Ala Glu Ala Pro
                                    1               5 cag gtg gct ggc ggg cag ggg gac gga ggt gat ggc gag gaa gcg gag       101
Gln Val Ala Gly Gly Gln Gly Asp Gly Gly Asp Gly Glu Glu Ala Glu
        10                  15                  20 ccg gag ggg atg ttc aag gcc tgt gag gac tcc aag aga aaa gcc cgg       149
Pro Glu Gly Met Phe Lys Ala Cys Glu Asp Ser Lys Arg Lys Ala Arg
25                  30                  35 ggc tac ctc cgc ctg gtg ccc ctg ttt gtg ctg ctg gcc ctc gtg           197
Gly Tyr Leu Arg Leu Val Pro Leu Phe Val Leu Leu Ala Leu Leu Val
40                  45                  50                  55 ctg gct tcg gcg ggg gtg cta ctc tgg tat ttc cta ggg tac aag gcg       245
Leu Ala Ser Ala Gly Val Leu Leu Trp Tyr Phe Leu Gly Tyr Lys Ala
```

```
                  60                  65                  70
gag gtg atg gtc agc cag gtg tac tca ggc agt ctg cgt gta ctc aat     293
Glu Val Met Val Ser Gln Val Tyr Ser Gly Ser Leu Arg Val Leu Asn
             75                  80                  85 cgc cac ttc tcc cag gat ctt acc cgc cgg gaa tct agt gcc ttc cgc     341
Arg His Phe Ser Gln Asp Leu Thr Arg Arg Glu Ser Ser Ala Phe Arg
         90                  95                 100 agt gaa acc gcc aaa gcc cag aag atg ctc aag gag ctc atc acc agc     389
Ser Glu Thr Ala Lys Ala Gln Lys Met Leu Lys Glu Leu Ile Thr Ser
        105                 110                 115 acc cgc ctg gga act tac tac aac tcc agc tcc gtc tat tcc ttt ggg     437
Thr Arg Leu Gly Thr Tyr Tyr Asn Ser Ser Ser Val Tyr Ser Phe Gly
120                 125                 130                 135 gtg tac ggc tgc agc cgc cag gag ccc gtg gtg gag gtt ctg gcg tcg     485
Val Tyr Gly Cys Ser Arg Gln Glu Pro Val Val Glu Val Leu Ala Ser
                140                 145                 150 ggg gcc atc atg gcg gtc gtc tgg aag aag ggc ctg cac agc tac tac     533
Gly Ala Ile Met Ala Val Val Trp Lys Lys Gly Leu His Ser Tyr Tyr
            155                 160                 165 gac ccc ttc gtg ctc tcc gtg cag ccg gtg gtc ttc cag gcc tgt gaa     581
Asp Pro Phe Val Leu Ser Val Gln Pro Val Val Phe Gln Ala Cys Glu
        170                 175                 180 gtg aac ctg acg ctg gac aac agg ctc gac tcc cag ggc gtc ctc agc     629
Val Asn Leu Thr Leu Asp Asn Arg Leu Asp Ser Gln Gly Val Leu Ser
        185                 190                 195 acc ccg tac ttc ccc agc tac tac tcg ccc caa acc cac tgc tcc tgg     677
Thr Pro Tyr Phe Pro Ser Tyr Tyr Ser Pro Gln Thr His Cys Ser Trp
200                 205                 210                 215 cac ctc acg gtg ccc tct ctg gac tac ggc ttg gcc ctc tgg ttt gat     725
His Leu Thr Val Pro Ser Leu Asp Tyr Gly Leu Ala Leu Trp Phe Asp
                220                 225                 230 gcc tat gca ctg agg agg cag aag tat gat ttg ccg tgc acc cag ggc     773
Ala Tyr Ala Leu Arg Arg Gln Lys Tyr Asp Leu Pro Cys Thr Gln Gly
            235                 240                 245 cag tgg acg atc cag aac agg agg ctg tgt ggc ttg cgc atc ctg cag     821
Gln Trp Thr Ile Gln Asn Arg Arg Leu Cys Gly Leu Arg Ile Leu Gln
        250                 255                 260 ccc tac gcc gag agg atc ccc gtg gtg gcc acg gcc ggg atc acc atc     869
Pro Tyr Ala Glu Arg Ile Pro Val Val Ala Thr Ala Gly Ile Thr Ile
265                 270                 275 aac ttc acc tcc cag atc tcc ctc acc ggg ccc ggt gtg cgg gtg cac     917
Asn Phe Thr Ser Gln Ile Ser Leu Thr Gly Pro Gly Val Arg Val His
280                 285                 290                 295 tat ggc ttg tac aac cag tcg gac ccc tgc cct gga gag ttc ctc tgt     965
Tyr Gly Leu Tyr Asn Gln Ser Asp Pro Cys Pro Gly Glu Phe Leu Cys
                300                 305                 310 tct gtg aat gga ctc tgt gtc cct gcc tgt gat ggg gtc aag gac tgc    1013
Ser Val Asn Gly Leu Cys Val Pro Ala Cys Asp Gly Val Lys Asp Cys
            315                 320                 325 ccc aac ggc ctg gat gag aga aac tgc gtt tgc aga gcc aca ttc cag    1061
Pro Asn Gly Leu Asp Glu Arg Asn Cys Val Cys Arg Ala Thr Phe Gln
        330                 335                 340 tgc aaa gag gac agc aca tgc atc tca ctg ccc aag gtc tgt gat ggg    1109
Cys Lys Glu Asp Ser Thr Cys Ile Ser Leu Pro Lys Val Cys Asp Gly
        345                 350                 355 cag cct gat tgt ctc aac ggc agc gac gaa gag cag tgc cag gaa ggg    1157
Gln Pro Asp Cys Leu Asn Gly Ser Asp Glu Glu Gln Cys Gln Glu Gly
360                 365                 370                 375 gtg cca tgt ggg aca ttc acc ttc cag tgt gag gac cgg agc tgc gtg    1205
```

```
                Val Pro Cys Gly Thr Phe Thr Phe Gln Cys Glu Asp Arg Ser Cys Val
                            380                 385                 390 aag aag ccc aac ccg cag tgt gat ggg cgg ccc gac tgc agg gac ggc          1253
Lys Lys Pro Asn Pro Gln Cys Asp Gly Arg Pro Asp Cys Arg Asp Gly
                395                 400                 405 tcg gat gag gag cac tgt gaa tgt ggc ctc cag ggc ccc tcc agc cgc          1301
Ser Asp Glu Glu His Cys Glu Cys Gly Leu Gln Gly Pro Ser Ser Arg
            410                 415                 420 att gtt ggt gga gct gtg tcc tcc gag ggt gag tgg cca tgg cag gcc          1349
Ile Val Gly Gly Ala Val Ser Ser Glu Gly Glu Trp Pro Trp Gln Ala
        425                 430                 435 agc ctc cag gtt cgg ggt cga cac atc tgt ggg ggg gcc ctc atc gct          1397
Ser Leu Gln Val Arg Gly Arg His Ile Cys Gly Gly Ala Leu Ile Ala
440                 445                 450                 455 gac cgc tgg gtg ata aca gct gcc cac tgc ttc cag gag gac agc atg          1445
Asp Arg Trp Val Ile Thr Ala Ala His Cys Phe Gln Glu Asp Ser Met
                460                 465                 470 gcc tcc acg gtg ctg tgg acc gtg ttc ctg ggc aag gtg tgg cag aac          1493
Ala Ser Thr Val Leu Trp Thr Val Phe Leu Gly Lys Val Trp Gln Asn
            475                 480                 485 tcg cgc tgg cct gga gag gtg tcc ttc aag gtg agc cgc ctg ctc ctg          1541
Ser Arg Trp Pro Gly Glu Val Ser Phe Lys Val Ser Arg Leu Leu Leu
        490                 495                 500 cac ccg tac cac gaa gag gac agc cat gac tac gac gtg gcg ctg ctg          1589
His Pro Tyr His Glu Glu Asp Ser His Asp Tyr Asp Val Ala Leu Leu
    505                 510                 515 cag ctc gac cac ccg gtg gtg cgc tcg gcc gcc gtg cgc ccc gtc tgc          1637
Gln Leu Asp His Pro Val Val Arg Ser Ala Ala Val Arg Pro Val Cys
520                 525                 530                 535 ctg ccc gcg cgc tcc cac ttc ttc gag ccc ggc ctg cac tgc tgg att          1685
Leu Pro Ala Arg Ser His Phe Phe Glu Pro Gly Leu His Cys Trp Ile
                540                 545                 550 acg ggc tgg ggc gcc ttg cgc gag ggc ggc ccc atc agc aac gct ctg          1733
Thr Gly Trp Gly Ala Leu Arg Glu Gly Gly Pro Ile Ser Asn Ala Leu
            555                 560                 565 cag aaa gtg gat gtg cag ttg atc cca cag gac ctg tgc agc gag gtc          1781
Gln Lys Val Asp Val Gln Leu Ile Pro Gln Asp Leu Cys Ser Glu Val
        570                 575                 580 tat cgc tac cag gtg acg cca cgc atg ctg tgt gcc ggc tac cgc aag          1829
Tyr Arg Tyr Gln Val Thr Pro Arg Met Leu Cys Ala Gly Tyr Arg Lys
    585                 590                 595 ggc aag aag gat gcc tgt cag ggt gac tca ggt ggt ccg ctg gtg tgc          1877
Gly Lys Lys Asp Ala Cys Gln Gly Asp Ser Gly Gly Pro Leu Val Cys
600                 605                 610                 615 aag gca ctc agt ggc cgc tgg ttc ctg gcg ggg ctg gtc agc tgg ggc          1925
Lys Ala Leu Ser Gly Arg Trp Phe Leu Ala Gly Leu Val Ser Trp Gly
                620                 625                 630 ctg ggc tgt ggc cgg cct aac tac ttc ggc gtc tac acc cgc atc aca          1973
Leu Gly Cys Gly Arg Pro Asn Tyr Phe Gly Val Tyr Thr Arg Ile Thr
            635                 640                 645 ggt gtg atc agc tgg atc cag caa gtg gtg acc tga ggaactgccc              2019
Gly Val Ile Ser Trp Ile Gln Gln Val Val Thr *
        650                 655 ccctgcaaag cagggcccac ctcctggact cagagagccc aggcaactg  ccaagcaggg        2079 ggacaagtat tctggcgggg ggtggggag  agagcaggcc ctgtggtggc aggaggggca        2139
tcttgtttcg tccctgatgt ctgtccagta tggcaggagg atgagaagtg ccagcagttg        2199
ggggtcaaga cgtcccttga ggacccaggc ccacacccag cccttttgcc tcccaattct        2259
```

```
ctctcctccg tcccttcct ccactgctgc ctaatgcaag gcagtggctc agcagcaaga   2319
atgctggttc tacatcccga ggagtgtctg aggtgcgccc cactctgtac agaggctgtt   2379
tgggcagcct tgcctccaga gagcagattc cagcttcgga agcccctggt ctaacttggg   2439
atctgggaat ggaaggtgct cccatcggag gggaccctca gagccctgga gactgccagg   2499
tgggcctgct gccactgtaa gccaaaaggt ggggaagtcc tgactccagg gtccttgccc   2559 caccctgcc tgccacctgg gccctcacag cccagaccct cactgggagg tgagctcagc   2619 tgcccttttgg aataaagctg cctgatgcaa aaaaaaaaa aaaaaaaaaa aaa           2672
```

<210> SEQ ID NO 10
<211> LENGTH: 658
<212> TYPE: PRT
<213> ORGANISM: Homo Sapien

<400> SEQUENCE: 10

```
Met Pro Val Ala Glu Ala Pro Gln Val Ala Gly Gly Gln Gly Asp Gly
  1               5                  10                  15

Gly Asp Gly Glu Glu Ala Glu Pro Glu Gly Met Phe Lys Ala Cys Glu
                 20                  25                  30

Asp Ser Lys Arg Lys Ala Arg Gly Tyr Leu Arg Leu Val Pro Leu Phe
             35                  40                  45

Val Leu Leu Ala Leu Leu Val Leu Ala Ser Ala Gly Val Leu Leu Trp
         50                  55                  60

Tyr Phe Leu Gly Tyr Lys Ala Glu Val Met Val Ser Gln Val Tyr Ser
 65                  70                  75                  80

Gly Ser Leu Arg Val Leu Asn Arg His Phe Ser Gln Asp Leu Thr Arg
                 85                  90                  95

Arg Glu Ser Ser Ala Phe Arg Ser Glu Thr Ala Lys Ala Gln Lys Met
            100                 105                 110

Leu Lys Glu Leu Ile Thr Ser Thr Arg Leu Gly Thr Tyr Tyr Asn Ser
        115                 120                 125

Ser Ser Val Tyr Ser Phe Gly Val Tyr Gly Cys Ser Arg Gln Glu Pro
    130                 135                 140

Val Val Glu Val Leu Ala Ser Gly Ala Ile Met Ala Val Val Trp Lys
145                 150                 155                 160

Lys Gly Leu His Ser Tyr Tyr Asp Pro Phe Val Leu Ser Val Gln Pro
                165                 170                 175

Val Val Phe Gln Ala Cys Glu Val Asn Leu Thr Leu Asp Asn Arg Leu
            180                 185                 190

Asp Ser Gln Gly Val Leu Ser Thr Pro Tyr Phe Pro Ser Tyr Tyr Ser
        195                 200                 205

Pro Gln Thr His Cys Ser Trp His Leu Thr Val Pro Ser Leu Asp Tyr
    210                 215                 220

Gly Leu Ala Leu Trp Phe Asp Ala Tyr Ala Leu Arg Arg Gln Lys Tyr
225                 230                 235                 240

Asp Leu Pro Cys Thr Gln Gly Gln Trp Thr Ile Gln Asn Arg Arg Leu
                245                 250                 255

Cys Gly Leu Arg Ile Leu Gln Pro Tyr Ala Glu Arg Ile Pro Val Val
            260                 265                 270

Ala Thr Ala Gly Ile Thr Ile Asn Phe Thr Ser Gln Ile Ser Leu Thr
        275                 280                 285

Gly Pro Gly Val Arg Val His Tyr Gly Leu Tyr Asn Gln Ser Asp Pro
    290                 295                 300
```

```
Cys Pro Gly Glu Phe Leu Cys Ser Val Asn Gly Leu Cys Val Pro Ala
305                 310                 315                 320

Cys Asp Gly Val Lys Asp Cys Pro Asn Gly Leu Asp Glu Arg Asn Cys
            325                 330                 335

Val Cys Arg Ala Thr Phe Gln Cys Lys Glu Asp Ser Thr Cys Ile Ser
            340                 345                 350

Leu Pro Lys Val Cys Asp Gly Gln Pro Asp Cys Leu Asn Gly Ser Asp
        355                 360                 365

Glu Glu Gln Cys Gln Glu Gly Val Pro Cys Gly Thr Phe Thr Phe Gln
    370                 375                 380

Cys Glu Asp Arg Ser Cys Val Lys Lys Pro Asn Pro Gln Cys Asp Gly
385                 390                 395                 400

Arg Pro Asp Cys Arg Asp Gly Ser Asp Glu Glu His Cys Glu Cys Gly
            405                 410                 415

Leu Gln Gly Pro Ser Ser Arg Ile Val Gly Ala Val Ser Ser Glu
        420                 425                 430

Gly Glu Trp Pro Trp Gln Ala Ser Leu Gln Val Arg Gly Arg His Ile
    435                 440                 445

Cys Gly Gly Ala Leu Ile Ala Asp Arg Trp Val Ile Thr Ala Ala His
450                 455                 460

Cys Phe Gln Glu Asp Ser Met Ala Ser Thr Val Leu Trp Thr Val Phe
465                 470                 475                 480

Leu Gly Lys Val Trp Gln Asn Ser Arg Trp Pro Gly Glu Val Ser Phe
            485                 490                 495

Lys Val Ser Arg Leu Leu Leu His Pro Tyr His Glu Asp Ser His
        500                 505                 510

Asp Tyr Asp Val Ala Leu Leu Gln Leu Asp His Pro Val Val Arg Ser
    515                 520                 525

Ala Ala Val Arg Pro Val Cys Leu Pro Ala Arg Ser His Phe Phe Glu
530                 535                 540

Pro Gly Leu His Cys Trp Ile Thr Gly Trp Gly Ala Leu Arg Glu Gly
545                 550                 555                 560

Gly Pro Ile Ser Asn Ala Leu Gln Lys Val Asp Val Gln Leu Ile Pro
            565                 570                 575

Gln Asp Leu Cys Ser Glu Val Tyr Arg Tyr Gln Val Thr Pro Arg Met
        580                 585                 590

Leu Cys Ala Gly Tyr Arg Lys Gly Lys Lys Asp Ala Cys Gln Gly Asp
    595                 600                 605

Ser Gly Gly Pro Leu Val Cys Lys Ala Leu Ser Gly Arg Trp Phe Leu
610                 615                 620

Ala Gly Leu Val Ser Trp Gly Leu Gly Cys Gly Arg Pro Asn Tyr Phe
625                 630                 635                 640

Gly Val Tyr Thr Arg Ile Thr Gly Val Ile Ser Trp Ile Gln Gln Val
            645                 650                 655

Val Thr

<210> SEQ ID NO 11
<211> LENGTH: 1656
<212> TYPE: DNA
<213> ORGANISM: Homo Sapien
<220> FEATURE:
<221> NAME/KEY: CDS
<222> LOCATION: (268)...(1629)
<223> OTHER INFORMATION: DNA sequence encoding a transmembrane serine
      protease (MTSP-6) protein
```

-continued

```
<400> SEQUENCE: 11
cgcccgggca ggtcagtaac actgtggcct actatctctt ccgtggtgcc atctacattt      60
ttgggactcg ggaattatga ctgttttggg ttaatcgata ctgaatgcgc tttgtgtgga     120
ctgtcgaatt tcaaagattt accgtatgac caagatgcac ctgatgctac aagtataaat     180 agggggaacaa atgctttctg ttcttcctcg gctaaggagg tagaggtgga ggcggagccg    240
gatgtcagag gtcctgaaat agtcacc atg ggg gaa aat gat ccg cct gct gtt     294
                                Met Gly Glu Asn Asp Pro Pro Ala Val
                                  1               5 gaa gcc ccc ttc tca ttc cga tcg ctt ttt ggc ctt gat gat ttg aaa       342
Glu Ala Pro Phe Ser Phe Arg Ser Leu Phe Gly Leu Asp Asp Leu Lys
 10              15                  20                  25 ata agt cct gtt gca cca gat gca gat gct gtt gct gca cag atc ctg       390
Ile Ser Pro Val Ala Pro Asp Ala Asp Ala Val Ala Ala Gln Ile Leu
                 30                  35                  40 tca ctg ctg cca ttg aag ttt ttt cca atc atc gtc att ggg atc att       438
Ser Leu Leu Pro Leu Lys Phe Phe Pro Ile Ile Val Ile Gly Ile Ile
             45                  50                  55 gca ttg ata tta gca ctg gcc att ggt ctg ggc atc cac ttc gac tgc       486
Ala Leu Ile Leu Ala Leu Ala Ile Gly Leu Gly Ile His Phe Asp Cys
         60                  65                  70 tca ggg aag tac aga tgt cgc tca tcc ttt aag tgt atc gag ctg ata       534
Ser Gly Lys Tyr Arg Cys Arg Ser Ser Phe Lys Cys Ile Glu Leu Ile
     75                  80                  85 gct cga tgt gac gga gtc tcg gat tgc aaa gac ggg gag gac gag tac       582
Ala Arg Cys Asp Gly Val Ser Asp Cys Lys Asp Gly Glu Asp Glu Tyr
 90                  95                 100                 105 cgc tgt gtc cgg gtg ggt ggt cag aat gcc gtg ctc cag gtg ttc aca       630
Arg Cys Val Arg Val Gly Gly Gln Asn Ala Val Leu Gln Val Phe Thr
                110                 115                 120 gct gct tcg tgg aag acc atg tgc tcc gat gac tgg aag ggt cac tac       678
Ala Ala Ser Trp Lys Thr Met Cys Ser Asp Asp Trp Lys Gly His Tyr
            125                 130                 135 gca aat gtt gcc tgt gcc caa ctg ggt ttc cca agc tat gta agt tca       726
Ala Asn Val Ala Cys Ala Gln Leu Gly Phe Pro Ser Tyr Val Ser Ser
        140                 145                 150 gat aac ctc aga gtg agc tcg cta gag ggg cag ttc cgg gag gag ttt       774
Asp Asn Leu Arg Val Ser Ser Leu Glu Gly Gln Phe Arg Glu Glu Phe
    155                 160                 165 gtg tcc atc gat cac ctc ttg cca gat gac aag gtg act gca tta cac       822
Val Ser Ile Asp His Leu Leu Pro Asp Asp Lys Val Thr Ala Leu His
170                 175                 180                 185 cac tca gta tat gtg agg gag gga tgt gcc tct ggc cac gtg gtt acc       870
His Ser Val Tyr Val Arg Glu Gly Cys Ala Ser Gly His Val Val Thr
                190                 195                 200 ttg cag tgc aca gcc tgt ggt cat aga agg ggc tac agc tca cgc atc       918
Leu Gln Cys Thr Ala Cys Gly His Arg Arg Gly Tyr Ser Ser Arg Ile
            205                 210                 215 gtg ggt gga aac atg tcc ttg ctc tcg cag tgg ccc tgg cag gcc agc       966
Val Gly Gly Asn Met Ser Leu Leu Ser Gln Trp Pro Trp Gln Ala Ser
        220                 225                 230 ctt cag ttc cag ggc tac cac ctg tgc ggg ggc tct gtc atc acg ccc      1014
Leu Gln Phe Gln Gly Tyr His Leu Cys Gly Gly Ser Val Ile Thr Pro
    235                 240                 245 ctg tgg atc atc act gct gca cac tgt gtt tat gac ttg tac ctc ccc      1062
Leu Trp Ile Ile Thr Ala Ala His Cys Val Tyr Asp Leu Tyr Leu Pro
250                 255                 260                 265 aag tca tgg acc atc cag gtg ggt cta gtt tcc ctg ttg gac aat cca      1110
```

-continued

```
Lys Ser Trp Thr Ile Gln Val Gly Leu Val Ser Leu Leu Asp Asn Pro
                270                 275                 280 gcc cca tcc cac ttg gtg gag aag att gtc tac cac agc aag tac aag      1158
Ala Pro Ser His Leu Val Glu Lys Ile Val Tyr His Ser Lys Tyr Lys
                285                 290                 295 cca aag agg ctg ggc aat gac atc gcc ctt atg aag ctg gcc ggg cca      1206
Pro Lys Arg Leu Gly Asn Asp Ile Ala Leu Met Lys Leu Ala Gly Pro
                300                 305                 310 ctc acg ttc aat gaa atg atc cag cct gtg tgc ctg ccc aac tct gaa      1254
Leu Thr Phe Asn Glu Met Ile Gln Pro Val Cys Leu Pro Asn Ser Glu
            315                 320                 325 gag aac ttc ccc gat gga aaa gtg tgc tgg acg tca gga tgg ggg gcc      1302
Glu Asn Phe Pro Asp Gly Lys Val Cys Trp Thr Ser Gly Trp Gly Ala
330                 335                 340                 345 aca gag gat gga ggt gac gcc tcc cct gtc ctg aac cac gcg gcc gtc      1350
Thr Glu Asp Gly Gly Asp Ala Ser Pro Val Leu Asn His Ala Ala Val
                350                 355                 360 cct ttg att tcc aac aag atc tgc aac cac agg gac gtg tac ggt ggc      1398
Pro Leu Ile Ser Asn Lys Ile Cys Asn His Arg Asp Val Tyr Gly Gly
                365                 370                 375 atc atc tcc ccc tcc atg ctc tgc gcg ggc tac ctg acg ggt ggc gtg      1446
Ile Ile Ser Pro Ser Met Leu Cys Ala Gly Tyr Leu Thr Gly Gly Val
                380                 385                 390 gac agc tgc cag ggg gac agc ggg ggg ccc ctg gtg tgt caa gag agg      1494
Asp Ser Cys Gln Gly Asp Ser Gly Gly Pro Leu Val Cys Gln Glu Arg
            395                 400                 405 agg ctg tgg aag tta gtg gga gcg acc agc ttt ggc atc ggc tgc gca      1542
Arg Leu Trp Lys Leu Val Gly Ala Thr Ser Phe Gly Ile Gly Cys Ala
410                 415                 420                 425 gag gtg aac aag cct ggg gtg tac acc cgt gtc acc tcc ttc ctg gac      1590
Glu Val Asn Lys Pro Gly Val Tyr Thr Arg Val Thr Ser Phe Leu Asp
                430                 435                 440 tgg atc cac gag cag atg gag aga gac cta aaa acc tga agaggaaggg      1639
Trp Ile His Glu Gln Met Glu Arg Asp Leu Lys Thr *
                445                 450 gataagtagc cacctga                                                    1656

<210> SEQ ID NO 12
<211> LENGTH: 453
<212> TYPE: PRT
<213> ORGANISM: Homo Sapien

<400> SEQUENCE: 12

Met Gly Glu Asn Asp Pro Pro Ala Val Glu Ala Pro Phe Ser Phe Arg
1               5                   10                  15

Ser Leu Phe Gly Leu Asp Asp Leu Lys Ile Ser Pro Val Ala Pro Asp
                20                  25                  30

Ala Asp Ala Val Ala Ala Gln Ile Leu Ser Leu Leu Pro Leu Lys Phe
            35                  40                  45

Phe Pro Ile Ile Val Gly Ile Ile Ala Leu Ile Leu Ala Leu Ala
        50                  55                  60

Ile Gly Leu Gly Ile His Phe Asp Cys Ser Lys Tyr Arg Cys Arg
65                  70                  75                  80

Ser Ser Phe Lys Cys Ile Glu Leu Ile Ala Arg Cys Asp Gly Val Ser
                85                  90                  95

Asp Cys Lys Asp Gly Glu Asp Glu Tyr Arg Cys Val Arg Val Gly Gly
                100                 105                 110

Gln Asn Ala Val Leu Gln Val Phe Thr Ala Ala Ser Trp Lys Thr Met
```

```
            115                 120                 125
Cys Ser Asp Asp Trp Lys Gly His Tyr Ala Asn Val Ala Cys Ala Gln
130                 135                 140

Leu Gly Phe Pro Ser Tyr Val Ser Ser Asp Asn Leu Arg Val Ser Ser
145                 150                 155                 160

Leu Glu Gly Gln Phe Arg Glu Phe Val Ser Ile Asp His Leu Leu
            165                 170                 175

Pro Asp Asp Lys Val Thr Ala Leu His His Ser Val Tyr Val Arg Glu
            180                 185                 190

Gly Cys Ala Ser Gly His Val Val Thr Leu Gln Cys Thr Ala Cys Gly
            195                 200                 205

His Arg Arg Gly Tyr Ser Ser Arg Ile Val Gly Gly Asn Met Ser Leu
210                 215                 220

Leu Ser Gln Trp Pro Trp Gln Ala Ser Leu Gln Phe Gln Gly Tyr His
225                 230                 235                 240

Leu Cys Gly Gly Ser Val Ile Thr Pro Leu Trp Ile Ile Thr Ala Ala
                245                 250                 255

His Cys Val Tyr Asp Leu Tyr Leu Pro Lys Ser Trp Thr Ile Gln Val
            260                 265                 270

Gly Leu Val Ser Leu Leu Asp Asn Pro Ala Pro Ser His Leu Val Glu
            275                 280                 285

Lys Ile Val Tyr His Ser Lys Tyr Lys Pro Lys Arg Leu Gly Asn Asp
            290                 295                 300

Ile Ala Leu Met Lys Leu Ala Gly Pro Leu Thr Phe Asn Glu Met Ile
305                 310                 315                 320

Gln Pro Val Cys Leu Pro Asn Ser Glu Glu Asn Phe Pro Asp Gly Lys
                325                 330                 335

Val Cys Trp Thr Ser Gly Trp Gly Ala Thr Glu Asp Gly Gly Asp Ala
            340                 345                 350

Ser Pro Val Leu Asn His Ala Ala Val Pro Leu Ile Ser Asn Lys Ile
            355                 360                 365

Cys Asn His Arg Asp Val Tyr Gly Gly Ile Ile Ser Pro Ser Met Leu
370                 375                 380

Cys Ala Gly Tyr Leu Thr Gly Gly Val Asp Ser Cys Gln Gly Asp Ser
385                 390                 395                 400

Gly Gly Pro Leu Val Cys Gln Glu Arg Arg Leu Trp Lys Leu Val Gly
                405                 410                 415

Ala Thr Ser Phe Gly Ile Gly Cys Ala Glu Val Asn Lys Pro Gly Val
            420                 425                 430

Tyr Thr Arg Val Thr Ser Phe Leu Asp Trp Ile His Glu Gln Met Glu
            435                 440                 445

Arg Asp Leu Lys Thr
450

<210> SEQ ID NO 13
<211> LENGTH: 23
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: N= Inosine
<220> FEATURE:
<223> OTHER INFORMATION: Oligonucleotide Primer

<400> SEQUENCE: 13
```

| | |
|---|---|
| tggrtnvtnw sngcnrcnca ytg | 23 |

<210> SEQ ID NO 14
<211> LENGTH: 30
<212> TYPE: DNA
<213> ORGANISM: Artificial Sequence
<220> FEATURE:
<221> NAME/KEY: misc_feature
<222> LOCATION: (0)...(0)
<223> OTHER INFORMATION: N= Inosine
<220> FEATURE:
<223> OTHER INFORMATION: Oligonucleotide Primer

<400> SEQUENCE: 14

| | |
|---|---|
| nggnccnccn swrtcnccyt nrcanghrtc | 30 |

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 15

| | |
|---|---|
| tcaccgagaa gatgatgtgt gcaggcatcc | 30 |

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 16

| | |
|---|---|
| gggacagggg ctgtaaggca gggaatgag | 29 |

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 17

| | |
|---|---|
| cccgcagcca tagccccagc taacg | 25 |

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 18

| | |
|---|---|
| gcagacgatg cgtaccaggg ggaagtc | 27 |

<210> SEQ ID NO 19
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 19

| | |
|---|---|
| ctcgagaaaa gagtggtggg tggggaggag gcctctgtg | 39 |

```
<210> SEQ ID NO 20
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 20
gcggccgcat tacagctcag ccttccagac                                      30

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 21
cctccacggt gctgtggacc gtgttcc                                         27

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 22
cctcgcgcaa ggcgccccag cccg                                            24

<210> SEQ ID NO 23
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 23
gcgtggcgtc acctggtagc gatagacctc gc                                   32

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 24
cctccacggt gctgtggacc gtgttcc                                         27

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 25
cctcgcgcaa ggcgccccag cccg                                            24

<210> SEQ ID NO 26
<211> LENGTH: 26
<212> TYPE: DNA
<213> ORGANISM: Artificial Sequence
<220> FEATURE:
<223> OTHER INFORMATION: Oligonucleotide Primer
```

<400> SEQUENCE: 26
tcatcggcca gagggtgatc agtgag                                            26

<210> SEQ ID NO 27
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 27
cctcctcagt gcataggcat caaaccag                                          28

<210> SEQ ID NO 28
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 28
tctctcgaga aagaattgt tggtggagct gtgtcctccg ag                           42

<210> SEQ ID NO 29
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 29
aggtgggcct tgctttgcag gggggcagtt c                                      31

<210> SEQ ID NO 30
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 30
tcacgcatcg tgggtggaac atgtcc                                            26

<210> SEQ ID NO 31
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 31
acccacctcc atctgctcgt ggatcc                                            26

<210> SEQ ID NO 32
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 32
ccacagcctc ctctcttgac acaccag                                           27

<210> SEQ ID NO 33
<211> LENGTH: 26

-continued

```
<212> TYPE: DNA
<213> ORGANISM: Artificial Sequence
<220> FEATURE:
<223> OTHER INFORMATION: Oligonucleotide primer

<400> SEQUENCE: 33
acgcccctgt ggatcatcac tgctgc                                          26

<210> SEQ ID NO 34
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 34
tccctccctc acatatactg agtggtg                                         27

<210> SEQ ID NO 35
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 35
cgactgctca gggaagtcag atgtcg                                          26

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 36
gcggccgcac tatacccag tgttctcttt gatcca                                36

<210> SEQ ID NO 37
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 37
ctggtgtgtc aagagaggag gctgtgg                                         27

<210> SEQ ID NO 38
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 38
actcaggtgg ctacttatcc ccttcctc                                        28

<210> SEQ ID NO 39
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 39
```

-continued

```
tctctcgaga aaagagtggt gggtggggag gaggcctctg tg                    42
```

<210> SEQ ID NO 40
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 40

```
attcgcggcc gcattacagc tcagccttcc agac                             34
```

<210> SEQ ID NO 41
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 41

```
tctctcgaga aaagaattgt tggtggagct gtgtcctccg ag                    42
```

<210> SEQ ID NO 42
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 42

```
attcgcggcc gctcaggtca ccacttgctg gatccag                          37
```

<210> SEQ ID NO 43
<211> LENGTH: 36
<212> TYPE: DNA
<213> ORGANISM: Artificial Sequence
<220> FEATURE:
<223> OTHER INFORMATION: Oligonucleotide Primer

<400> SEQUENCE: 43

```
ctcgagaaac gcatcgtggg tggaaacatg tccttg                           36
```

<210> SEQ ID NO 44
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 44

```
actcaggtgg ctacttatcc ccttcctc                                    28
```

<210> SEQ ID NO 45
<211> LENGTH: 9276
<212> TYPE: DNA
<213> ORGANISM: Pichia pastoris

<400> SEQUENCE: 45

```
agatctaaca tccaaagacg aaaggttgaa tgaaaccttt ttgccatccg acatccacag   60
gtccattctc acacataagt gccaaacgca acaggagggg atacactagc agcagaccgt  120
tgcaaacgca ggacctccac tcctcttctc ctcaacaccc acttttgcca tcgaaaaacc  180
agcccagtta ttgggcttga ttggagctcg ctcattccaa ttccttctat taggctacta  240
acaccatgac tttattagcc tgtctatcct ggccccctg gcgaggttca tgtttgttta  300
```

```
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcgcca taccgtttgt    540
cttgtttggt attgattgac gaatgctcaa aaataatctc attaatgctt agcgcagtct    600
ctctatcgct tctgaacccc ggtgcacctg tgccgaaacg caaatgggga acacccgct    660
ttttggatga ttatgcattg tctccacatt gtatgcttcc aagattctgg tgggaatact    720
gctgatagcc taacgttcat gatcaaaatt taactgttct aacccctact tgacagcaat    780
atataaacag aaggaagctg ccctgtctta aaccttttt tttatcatca ttattagctt    840
actttcataa ttgcgactgg ttccaattga caagcttttg attttaacga cttttaacga    900
caacttgaga agatcaaaaa acaactaatt attcgaagga tccaaacgat gagatttcct    960
tcaattttta ctgcagtttt attcgcagca tcctccgcat tagctgctcc agtcaacact   1020
acaacagaag atgaaacggc acaaattccg gctgaagctg tcatcggtta ctcagattta   1080
gaagggatt tcgatgttgc tgttttgcca ttttccaaca gcacaaataa cgggttattg   1140
tttataaata ctactattgc cagcattgct gctaaagaag aagggggtatc tctcgagaaa   1200
agagaggctg aagcttacgt agaattccct agggcggccg cgaattaatt cgccttagac   1260
atgactgttc ctcagttcaa gttgggcact tacgagaaga ccggtcttgc tagattctaa   1320
tcaagaggat gtcagaatgc catttgcctg agagatgcag gcttcatttt tgatactttt   1380
ttatttgtaa cctatatagt ataggatttt ttttgtcatt ttgtttcttc tcgtacgagc   1440
ttgctcctga tcagcctatc tcgcagctga tgaatatctt gtggtagggg tttgggaaaa   1500
tcattcgagt ttgatgtttt tcttggtatt tcccactcct cttcagagta cagaagatta   1560
agtgagaagt tcgtttgtgc aagcttatcg ataagcttta atgcggtagt ttatcacagt   1620
taaattgcta acgcagtcag gcaccgtgta tgaaatctaa caatgcgctc atcgtcatcc   1680
tcggcaccgt caccctggat gctgtaggca taggcttggt tatgccggta ctgccgggcc   1740
tcttgcggga tatcgtccat tccgacagca tcgccagtca ctatggcgtg ctgctagcgc   1800
tatatgcgtt gatgcaattt ctatgcgcac ccgttctcgg agcactgtcc gaccgctttg   1860
gccgccgccc agtcctgctc gcttcgctac ttggagccac tatcgactac gcgatcatgg   1920
cgaccacacc cgtcctgtgg atctatcgaa tctaaatgta agttaaaatc tctaaataat   1980
taaataagtc ccagtttctc catacgaacc ttaacagcat gcggtgagc atctagacct   2040
tcaacagcag ccagatccat cactgcttgg ccaatatgtt tcagtccctc aggagttacg   2100
tcttgtgaag tgatgaactt ctggaaggtt gcagtgttaa ctccgctgta ttgacgggca   2160
tatccgtacg ttggcaaagt gtggttggta ccggaggagt aatctccaca actctctgga   2220
gagtaggcac caacaaacac agatccagcg tgttgtactt gatcaacata agaagaagca   2280
ttctcgattt gcaggatcaa gtgttcagga gcgtactgat tggacatttc caaagcctgc   2340
tcgtaggttg caaccgatag ggttgtagag tgtgcaatac acttgcgtac aatttcaacc   2400
cttggcaact gcacagcttg gttgtgaaca gcatcttcaa ttctggcaag ctccttgtct   2460
gtcatatcga cagccaacag aatcacctgg gaatcaatac catgttcagc ttgagacaga   2520
aggtctgagg caacgaaatc tggatcagcg tatttatcag caataactag aacttcagaa   2580
ggcccagcag gcatgtcaat actacacagg gctgatgtgt cattttgaac catcatcttg   2640
```

```
gcagcagtaa cgaactggtt tcctggacca aatattttgt cacacttagg aacagtttct   2700
gttccgtaag ccatagcagc tactgcctgg gcgcctcctg ctagcacgat acacttagca   2760
ccaaccttgt gggcaacgta gatgacttct ggggtaaggg taccatcctt cttaggtgga   2820
gatgcaaaaa caatttcttt gcaaccagca actttggcag gaacacccag catcagggaa   2880
gtggaaggca gaattgcggt tccaccagga atatagaggc caactttctc aataggtctt   2940
gcaaaacgag agcagactac accagggcaa gtctcaactt gcaacgtctc cgttagttga   3000
gcttcatgga atttcctgac gttatctata gagagatcaa tggctctctt aacgttatct   3060
ggcaattgca taagttcctc tgggaaagga gcttctaaca caggtgtctt caaagcgact   3120
ccatcaaact tggcagttag ttctaaaagg gctttgtcac cattttgacg aacattgtcg   3180
acaattggtt tgactaattc cataatctgt tccgttttct ggataggacg acgaagggca   3240
tcttcaattt cttgtgagga ggccttagaa acgtcaattt gcacaattc aatacgacct   3300 tcagaaggga cttctttagg tttggattct tctttaggtt gttccttggt gtatcctggc   3360
ttggcatctc ctttccttct agtgaccttt agggacttca tatccaggtt tctctccacc   3420
tcgtccaacg tcacaccgta cttggcacat ctaactaatg caaaataaaa taagtcagca   3480
cattcccagg ctatatcttc cttggattta gcttctgcaa gttcatcagc ttcctcccta   3540
attttagcgt tcaacaaaac ttcgtcgtca aataaccgtt tggtataaga accttctgga   3600
gcattgctct tacgatccca caaggtggct tccatggctc taagacccctt tgattggcca   3660 aaacaggaag tgcgttccaa gtgacagaaa ccaacacctg tttgttcaac cacaaatttc   3720
aagcagtctc catcacaatc caattcgata cccagcaact tttgagttgc tccagatgta   3780
gcacctttat accacaaacc gtgacgacga gattggtaga ctccagtttg tgtccttata   3840
gcctccggaa tagacttttt ggacgagtac accaggccca acgagtaatt agaagagtca   3900
gccaccaaag tagtgaatag accatcgggg cggtcagtag tcaaagacgc caacaaaatt   3960
tcactgacag ggaaactttt gacatcttca gaaagttcgt attcagtagt caattgccga   4020
gcatcaataa tgggggattat accagaagca acagtggaag tcacatctac caactttgcg   4080
gtctcagaaa aagcataaac agttctacta ccgccattag tgaaactttt caaatcgccc   4140
agtggagaag aaaaaggcac agcgatacta gcattagcgg gcaaggatgc aactttatca   4200
accagggtcc tatagataac cctagcgcct gggatcatcc tttggacaac tctttctgcc   4260
aaatctaggt ccaaaatcac ttcattgata ccattattgt acaacttgag caagttgtcg   4320
atcagctcct caaattggtc ctctgtaacg gatgactcaa cttgcacatt aacttgaagc   4380
tcagtcgatt gagtgaactt gatcaggttg tgcagctggt cagcagcata gggaaacacg   4440
gcttttccta ccaaactcaa ggaattatca aactctgcaa cacttgcgta tgcaggtagc   4500
aagggaaatg tcatacttga agtcggacag tgagtgtagt cttgagaaat tctgaagccg   4560
tatttttatt atcagtgagt cagtcatcag gagatcctct acgccggacg catcgtggcc   4620
gacctgcagg ggggggggggg gcgctgaggt ctgcctcgtg aagaaggtgt tgctgactca   4680
taccaggcct gaatcgcccc atcatccagc cagaaagtga gggagccacg gttgatgaga   4740
gctttgttgt aggtggacca gttggtgatt ttgaacttt gctttgccac ggaacggtct   4800
gcgttgtcgg gaagatgcgt gatctgatcc ttcaactcag caaagttcg atttattcaa   4860 caaagccgcc gtcccgtcaa gtcagcgtaa tgctctgcca gtgttacaac caattaacca   4920
attctgatta gaaaaactca tcgagcatca aatgaaactg caatttattc atatcaggat   4980
tatcaatacc atattttga aaaagccgtt tctgtaatga aggagaaaac tcaccgaggc   5040
```

```
agttccatag gatggcaaga tcctggtatc ggtctgcgat tccgactcgt ccaacatcaa    5100
tacaacctat taatttcccc tcgtcaaaaa taaggttatc aagtgagaaa tcaccatgag    5160
tgacgactga atccggtgag aatggcaaaa gcttatgcat ttctttccag acttgttcaa    5220
caggccagcc attacgctcg tcatcaaaat cactcgcatc aaccaaaccg ttattcattc    5280
gtgattgcgc ctgagcgaga cgaaatacgc gatcgctgtt aaaaggacaa ttacaaacag    5340
gaatcgaatg caaccggcgc aggaacactg ccagcgcatc aacaatattt tcacctgaat    5400
caggatattc ttctaatacc tggaatgctg ttttcccggg gatcgcagtg gtgagtaacc    5460
atgcatcatc aggagtacgg ataaaatgct tgatggtcgg aagaggcata aattccgtca    5520
gccagtttag tctgaccatc tcatctgtaa catcattggc aacgctacct ttgccatgtt    5580
tcagaaacaa ctctggcgca tcgggcttcc catacaatcg atagattgtc gcacctgatt    5640
gcccgacatt atcgcgagcc catttatacc catataaatc agcatccatg ttggaattta    5700
atcgcggcct cgagcaagac gtttcccgtt gaatatggct cataacaccc cttgtattac    5760
tgtttatgta agcagacagt tttattgttc atgatgatat atttttatct tgtgcaatgt    5820
aacatcagag attttgagac acaacgtggc tttccccccc cccctgcag gtcggcatca    5880 ccggcgccac aggtgcggtt gctggcgcct atatcgccga catcaccgat ggggaagatc    5940
gggctcgcca cttcgggctc atgagcgctt gtttcggcgt gggtatggtg gcaggccccg    6000
tggccggggg actgttgggc gccatctcct tgcatgcacc attccttgcg gcggcggtgc    6060
tcaacggcct caacctacta ctgggctgct tcctaatgca ggagtcgcat aagggagagc    6120
gtcgagtatc tatgattgga agtatgggaa tggtgatacc cgcattcttc agtgtcttga    6180
ggtctcctat cagattatgc ccaactaaag caaccgagg aggagatttc atggtaaatt    6240
tctctgactt ttggtcatca gtagactcga actgtgagac tatctcggtt atgacagcag    6300
aaatgtcctt cttggagaca gtaaatgaag tcccaccaat aaagaaatcc ttgttatcag    6360
gaacaaactt cttgtttcga acttttcgg tgccttgaac tataaaatgt agagtggata    6420
tgtcgggtag gaatggagcg ggcaaatgct taccttctgg accttcaaga ggtatgtagg    6480
gtttgtagat actgatgcca acttcagtga caacgttgct atttcgttca aaccattccg    6540
aatccagaga aatcaaagtt gtttgtctac tattgatcca agccagtgcg gtcttgaaac    6600
tgacaatagt gtgctcgtgt tttgaggtca tctttgtatg aataaatcta gtctttgatc    6660
taaataatct tgacgagcca aggcgataaa tacccaaatc taaaactctt ttaaaacgtt    6720
aaaaggacaa gtatgtctgc ctgtattaaa ccccaaatca gctcgtagtc tgatcctcat    6780
caacttgagg ggcactatct tgttttagag aaatttgcgg agatgcgata tcgagaaaaa    6840
ggtacgctga ttttaaacgt gaaatttatc tcaagatctc tgcctcgcgc gtttcggtga    6900
tgacggtgaa aacctctgac acatgcagct cccggagacg tcacagctt gtctgtaagc     6960 ggatgccggg agcagacaag cccgtcaggg cgcgtcagcg ggtgttggcg ggtgtcgggg    7020
cgcagccatg acccagtcac gtagcgatag cggagtgtat actggcttaa ctatgcggca    7080
tcagagcaga ttgtactgag agtgcaccat atgcggtgtg aaataccgca cagatgcgta    7140
aggagaaaat accgcatcag cgctcttccg cttcctcgc tcactgactc gctgcgctcg     7200
gtcgttcggc tgcggcgagc ggtatcagct cactcaaagg cggtaatacg ttatccaca    7260 gaatcagggg ataacgcagg aaagaacatg tgagcaaaag ccagcaaaa ggccaggaac     7320 cgtaaaaagg ccgcgttgct ggcgtttttc cataggctcc gcccccctga cgagcatcac    7380
```

| | |
|---|---:|
| aaaaatcgac gctcaagtca gaggtggcga aacccgacag gactataaag ataccaggcg | 7440 |
| tttccccctg gaagctccct cgtgcgctct cctgttccga ccctgccgct taccggatac | 7500 |
| ctgtccgcct ttctcccttc gggaagcgtg gcgctttctc aatgctcacg ctgtaggtat | 7560 |
| ctcagttcgg tgtaggtcgt tcgctccaag ctgggctgtg tgcacgaacc ccccgttcag | 7620 |
| cccgaccgct gcgccttatc cggtaactat cgtcttgagt ccaacccggt aagacacgac | 7680 |
| ttatcgccac tggcagcagc cactggtaac aggattagca gagcgaggta tgtaggcggt | 7740 |
| gctacagagt tcttgaagtg gtggcctaac tacggctaca ctagaaggac agtatttggt | 7800 |
| atctgcgctc tgctgaagcc agttaccttc ggaaaaagag ttggtagctc ttgatccggc | 7860 |
| aaacaaacca ccgctggtag cggtggtttt tttgtttgca agcagcagat tacgcgcaga | 7920 |
| aaaaaaggat ctcaagaaga tcctttgatc ttttctacgg ggtctgacgc tcagtggaac | 7980 |
| gaaaactcac gttaagggat tttggtcatg agattatcaa aaaggatctt cacctagatc | 8040 |
| cttttaaatt aaaaatgaag ttttaaatca atctaaagta tatatgagta aacttggtct | 8100 |
| gacagttacc aatgcttaat cagtgaggca cctatctcag cgatctgtct atttcgttca | 8160 |
| tccatagttg cctgactccc cgtcgtgtag ataactacga tacgggaggg cttaccatct | 8220 |
| ggccccagtg ctgcaatgat accgcgagac ccacgctcac cggctccaga tttatcagca | 8280 |
| ataaaccagc cagccggaag ggccgagcgc agaagtggtc ctgcaacttt atccgcctcc | 8340 |
| atccagtcta ttaattgttg ccgggaagct agagtaagta gttcgccagt taatagtttg | 8400 |
| cgcaacgttg ttgccattgc tgcaggcatc gtggtgtcac gctcgtcgtt tggtatggct | 8460 |
| tcattcagct ccggttccca acgatcaagg cgagttacat gatcccccat gttgtgcaaa | 8520 |
| aaagcggtta gctccttcgg tcctccgatc gttgtcagaa gtaagttggc cgcagtgtta | 8580 |
| tcactcatgg ttatggcagc actgcataat tctcttactg tcatgccatc cgtaagatgc | 8640 |
| ttttctgtga ctggtgagta ctcaaccaag tcattctgag aatagtgtat gcggcgaccg | 8700 |
| agttgctctt gcccggcgtc aacacgggat aataccgcgc cacatagcag aactttaaaa | 8760 |
| gtgctcatca ttggaaaacg ttcttcgggg cgaaaactct caaggatctt accgctgttg | 8820 |
| agatccagtt cgatgtaacc cactcgtgca cccaactgat cttcagcatc ttttactttc | 8880 |
| accagcgttt ctgggtgagc aaaaacagga aggcaaaatg ccgcaaaaaa gggaataagg | 8940 |
| gcgacacgga aatgttgaat actcatactc ttcctttttc aatattattg aagcatttat | 9000 |
| cagggttatt gtctcatgag cggatacata tttgaatgta tttagaaaaa taaacaaata | 9060 |
| ggggttccgc gcacatttcc ccgaaaagtg ccacctgacg tctaagaaac cattattatc | 9120 |
| atgacattaa cctataaaaa taggcgtatc acgaggccct ttcgtcttca agaattaatt | 9180 |
| ctcatgtttg acagcttatc atcgataagc tgactcatgt tggtattgtg aaatagacgc | 9240 |
| agatcgggaa cactgaaaaa taacagttat tattcg | 9276 |

<210> SEQ ID NO 46
<211> LENGTH: 3908
<212> TYPE: DNA
<213> ORGANISM: Escherichia coli

<400> SEQUENCE: 46

| | |
|---|---:|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |

```
gtaccgagct cggatccact agtaacggcc gccagtgtgc tggaattcgc ccttaagggc    300
gaattctgca gatatccatc acactggcgg ccgctcgagc atgcatctag agggcccaat    360
tcgccctata gtgagtcgta ttacaattca ctggccgtcg ttttacaacg tcgtgactgg    420
gaaaaccctg gcgttaccca acttaatcgc cttgcagcac atccccettt cgccagctgg    480
cgtaatagcg aagaggcccg caccgatcgc ccttcccaac agttgcgcag cctgaatggc    540
gaatgggacg cgccctgtag cggcgcatta agcgcggcgg gtgtggtggt tacgcgcagc    600
gtgaccgcta cacttgccag cgccctagcg cccgctcctt cgctttctt cccttccttt    660
ctcgccacgt tcgccggctt tccccgtcaa gctctaaatc gggggctccc tttagggttc    720
cgatttagag ctttacggca cctcgaccgc aaaaaacttg atttgggtga tggttcacgt    780
agtgggccat cgccctgata acggttttt cgcccttga cgttggagtc cacgttcttt    840
aatagtggac tcttgttcca aactggaaca acactcaacc ctatcgcggt ctattctttt    900
gatttataag ggattttgcc gatttcggcc tattggttaa aaaatgagct gatttaacaa    960
attcagggcg caagggctgc taaaggaacc ggaacacgta aaagccagt ccgcagaaac   1020
ggtgctgacc ccggatgaat gtcagctact gggctatctg acaagggaa aacgcaagcg   1080
caaagagaaa gcaggtagct tgcagtgggc ttacatggcg atagctagac tgggcggttt   1140
tatgacagc aagcgaaccg gaattgccag ctggggcgcc ctctggtaag gttgggaagc   1200
cctgcaaagt aaactggatg ctttcttgc cgccaaggat ctgatggcgc aggggatcaa   1260
gatctgatca agagacagga tgaggatcgt ttcgcatgat tgaacaagat ggattgcacg   1320
caggttctcc ggccgcttgg gtggagaggc tattcggcta tgactgggca aacagacaa   1380
tcggctgctc tgatgccgcc gtgttccggc tgtcagcgca ggggcgcccg gttcttttg   1440
tcaagaccga cctgtccggt gccctgaatg aactgcagga cgaggcagcg cggctatcgt   1500
ggctggccac gacgggcgtt ccttgcgcag ctgtgctcga cgttgtcact gaagcgggaa   1560
gggactggct gctattgggc gaagtgccgg ggcaggatct cctgtcatct cgccttgctc   1620
ctgccgagaa agtatccatc atggctgatg caatgcggcg gctgcatacg cttgatccgg   1680
ctacctgccc attcgaccac caagcgaaac atcgcatcga gcgagcacgt actcggatgg   1740
aagccggtct tgtcgatcag gatgatctgg acgaagagca tcaggggctc gcgccagccg   1800
aactgttcgc caggctcaag gcgcgcatgc ccgacggcga ggatctcgtc gtgatccatg   1860
gcgatgcctg cttgccgaat atcatggtgg aaaatggccg cttttctgga ttcaacgact   1920
gtggccggct gggtgtggcg gaccgctatc aggacatagc gttggatacc cgtgatattg   1980
ctgaagagct tggcggcgaa tgggctgacc gcttcctcgt gctttacggt atcgccgctc   2040
ccgattcgca gcgcatcgcc ttctatcgcc ttcttgacga gttcttctga attgaaaaag   2100
gaagagtatg agtattcaac atttccgtgt cgcccttatt ccctttttg cggcattttg   2160
ccttcctgtt tttgctcacc cagaaacgct ggtgaaagta aaagatgctg aagatcagtt   2220
gggtgcacga gtgggttaca tcgaactgga tctcaacagc ggtaagatcc ttgagagttt   2280
tcgccccgaa gaacgttttc caatgatgag cacttttaaa gttctgctat gtcatacact   2340
attatcccgt attgacgccg ggcaagagca actcggtcgc cgggcgcggt attctcagaa   2400
tgacttggtt gagtactcac cagtcacaga aaagcatctt acggatggca tgacagtaag   2460
agaattatgc agtgctgcca taaccatgag tgataacact gcggccaact tacttctgac   2520
aacgatcgga ggaccgaagg agctaaccgc ttttttgcac aacatggggg atcatgtaac   2580
```

-continued

```
tcgccttgat cgttgggaac cggagctgaa tgaagccata ccaaacgacg agagtgacac    2640
cacgatgcct gtagcaatgc caacaacgtt gcgcaaacta ttaactggcg aactacttac    2700
tctagcttcc cggcaacaat taatagactg gatggaggcg gataaagttg caggaccact    2760
tctgcgctcg gcccttccgg ctggctggtt tattgctgat aaatctggag ccggtgagcg    2820
tgggtctcgc ggtatcattg cagcactggg gccagatggt aagccctccc gtatcgtagt    2880
tatctacacg acggggagtc aggcaactat ggatgaacga aatagacaga tcgctgagat    2940
aggtgcctca ctgattaagc attggtaact gtcagaccaa gtttactcat atatacttta    3000
gattgattta aaacttcatt tttaatttaa aaggatctag gtgaagatcc ttttttgataa    3060 tctcatgacc aaaatccctt aacgtgagtt ttcgttccac tgagcgtcag accccgtaga    3120
aaagatcaaa ggatcttctt gagatccttt ttttctgcgc gtaatctgct gcttgcaaac    3180
aaaaaaacca ccgctaccag cggtggtttg tttgccggat caagagctac caactctttt    3240
tccgaaggta actggcttca gcagagcgca gataccaaat actgtccttc tagtgtagcc    3300
gtagttaggc caccacttca gaactctgt agcaccgcct acatacctcg ctctgctaat    3360
cctgttacca gtggctgctg ccagtggcga taagtcgtgt cttaccgggt tggactcaag    3420
acgatagtta ccggataagg cgcagcggtc gggctgaacg gggggttcgt gcacacagcc    3480
cagcttggag cgaacgacct acaccgaact gagatacctta cagcgtgagc attgagaaag    3540
cgccacgctt cccgaaggga gaaaggcgga caggtatccg gtaagcggca gggtcggaac    3600
aggagagcgc acgagggagc ttccaggggg aaacgcctgg tatctttata gtcctgtcgg    3660
gtttcgccac ctctgacttg agcgtcgatt tttgtgatgc tcgtcagggg gcggagcct    3720 atggaaaaac gccagcaacg cggccttttt acggttcctg gccttttgct ggccttttgc    3780
tcacatgttc tttcctgcgt tatcccctga ttctgtggat aaccgtatta ccgcctttga    3840
gtgagctgat accgctcgcc gcagccgaac gaccgagcgc agcgagtcag tgagcgagga    3900
agcggaag                                                             3908
```

<210> SEQ ID NO 47
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 47

```
ggaattccat atgccgcgct ttaaagtggt gggtggggag gaggcc              46
```

<210> SEQ ID NO 48
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 48

```
cgcgataccc gttacagctc agccttccag ac                            32
```

<210> SEQ ID NO 49
<211> LENGTH: 3147
<212> TYPE: DNA
<213> ORGANISM: Homo Sapien
<220> FEATURE:
<221> NAME/KEY: CDS
<222> LOCATION: (1865)...(2590)
<223> OTHER INFORMATION: Nucleic acid sequence of protease domain of

MTSP1

<400> SEQUENCE: 49

| | |
|---|---:|
| tcaagagcgg cctcggggta ccatggggag cgatcgggcc cgcaagggcg gagggggccc | 60 |
| gaaggacttc ggcgcgggac tcaagtacaa ctcccggcac gagaaagtga atggcttgga | 120 |
| ggaaggcgtg gagttcctgc cagtcaacaa cgtcaagaag gtggaaaagc atggcccggg | 180 |
| gcgctgggtg gtgctggcag ccgtgctgat cggcctcctc ttggtcttgc tggggatcgg | 240 |
| cttcctggtg tggcatttgc agtaccggga cgtgcgtgtc cagaaggtct tcaatggcta | 300 |
| catgaggatc acaaatgaga attttgtgga tgcctacgag aactccaact ccactgagtt | 360 |
| tgtaagcctg ccagcaagg tgaaggacgc gctgaagctg ctgtacagcg gagtcccatt | 420 |
| cctgggcccc taccacaagg agtcggctgt gacggccttc agcgagggca gcgtcatcgc | 480 |
| ctactactgg tctgagttca gcatcccgca gcacctggtg gaggaggccg agcgcgtcat | 540 |
| ggccgaggag cgcgtagtca tgctgccccc gcgggcgcgc tccctgaagt cctttgtggt | 600 |
| cacctcagtg gtggctttcc ccacggactc caaaacagta cagaggaccc aggacaacag | 660 |
| ctgcagcttt ggcctgcacg cccgcggtgt ggagctgatg cgcttcacca cgcccggctt | 720 |
| ccctgacagc ccctaccccg ctcatgcccg ctgccagtgg gccctgcggg gggacgccga | 780 |
| ctcagtgctg agcctcacct tccgcagctt tgaccttgcg tcctgcgacg agcgcggcag | 840 |
| cgacctggtg acggtgtaca caccctgag ccccatggag ccccacgccc tggtgcagtt | 900 |
| gtgtggcacc tacctcccct cctacaacct gaccttccac tcctcccaga acgtcctgct | 960 |
| catcacactg ataaccaaca ctgagcggcg gcatcccggc tttgaggcca ccttcttcca | 1020 |
| gctgcctagg atgagcagct gtggaggccg cttacgtaaa gcccagggga cattcaacag | 1080 |
| ccctactac ccaggccact acccacccaa cattgactgc acatggaaca ttgaggtgcc | 1140 |
| caacaaccag catgtgaagg tgagcttcaa attcttctac ctgctggagc ccggcgtgcc | 1200 |
| tgcgggcacc tgccccaagg actacgtgga gatcaatggg gagaaatact gcggagagag | 1260 |
| gtcccagttc gtcgtcacca gcaacagcaa caagatcaca gttcgcttcc actcagatca | 1320 |
| gtcctacacc gacaccggct tcttagctga atacctctcc tacgactcca gtgacccatg | 1380 |
| cccgggggcag ttcacgtgcc gcacggggcg gtgtatccgg aaggagctgc gctgtgatgg | 1440 |
| ctgggccgac tgcaccgacc acagcgatga gctcaactgc agttgcgacg ccggccacca | 1500 |
| gttcacgtgc aagaacaagt ctgcaagcc cctcttctgg gtctgcgaca gtgtgaacga | 1560 |
| ctgcggagac aacagcgacg agcaggggtg cagttgtccg gcccagacct tcaggtgttc | 1620 |
| caatgggaag tgcctctcga aaagccagca gtgcaatggg aaggacgact gtggggacgg | 1680 |
| gtccgacgag gcctcctgcc ccaaggtgaa cgtcgtcact tgtaccaaac acacctaccg | 1740 |
| ctgcctcaat gggctctgct tgagcaaggg caaccctgag tgtgacggga aggaggactg | 1800 |
| tagcgacggc tcagatgaga aggactgcga ctgtgggctg cggtcattca cgagacaggc | 1860 |

| | | | | | | | | | | | | | | | | |
|---|---|---|---|---|---|---|---|---|---|---|---|---|---|---|---|---:|
| tcgt | gtt | gtt | ggg | ggc | acg | gat | gcg | gat | gag | ggc | gag | tgg | ccc | tgg | cag | 1909 |
| | Val | Val | Gly | Gly | Thr | Asp | Ala | Asp | Glu | Gly | Glu | Trp | Pro | Trp | Gln | |
| | 1 | | | 5 | | | | | 10 | | | | | 15 | | |
| gta | agc | ctg | cat | gct | ctg | ggc | cag | ggc | cac | atc | tgc | ggt | gct | tcc | ctc | 1957 |
| Val | Ser | Leu | His | Ala | Leu | Gly | Gln | Gly | His | Ile | Cys | Gly | Ala | Ser | Leu | |
| | 20 | | | | 25 | | | | | 30 | | | | | | |
| atc | tct | ccc | aac | tgg | ctg | gtc | tct | gcc | gca | cac | tgc | tac | atc | gat | gac | 2005 |
| Ile | Ser | Pro | Asn | Trp | Leu | Val | Ser | Ala | Ala | His | Cys | Tyr | Ile | Asp | Asp | |
| | 35 | | | | 40 | | | | | 45 | | | | | | |
| aga | gga | ttc | agg | tac | tca | gac | ccc | acg | cag | tgg | acg | gcc | ttc | ctg | ggc | 2053 |

```
                Arg Gly Phe Arg Tyr Ser Asp Pro Thr Gln Trp Thr Ala Phe Leu Gly
                         50                  55                  60 ttg cac gac cag agc cag cgc agc gcc cct ggg gtg cag gag cgc agg           2101
Leu His Asp Gln Ser Gln Arg Ser Ala Pro Gly Val Gln Glu Arg Arg
 65                  70                  75 ctc aag cgc atc atc tcc cac ccc ttc ttc aat gac ttc acc ttc gac           2149
Leu Lys Arg Ile Ile Ser His Pro Phe Phe Asn Asp Phe Thr Phe Asp
 80                  85                  90                  95 tat gac atc gcg ctg ctg gag ctg gag aaa ccg gca gag tac agc tcc           2197
Tyr Asp Ile Ala Leu Leu Glu Leu Glu Lys Pro Ala Glu Tyr Ser Ser
                100                 105                 110 atg gtg cgg ccc atc tgc ctg ccg gac gcc tcc cat gtc ttc cct gcc           2245
Met Val Arg Pro Ile Cys Leu Pro Asp Ala Ser His Val Phe Pro Ala
                115                 120                 125 ggc aag gcc atc tgg gtc acg ggc tgg gga cac acc cag tat gga ggc           2293
Gly Lys Ala Ile Trp Val Thr Gly Trp Gly His Thr Gln Tyr Gly Gly
                130                 135                 140 act ggc gcg ctg atc ctg caa aag ggt gag atc cgc gtc atc aac cag           2341
Thr Gly Ala Leu Ile Leu Gln Lys Gly Glu Ile Arg Val Ile Asn Gln
145                 150                 155 acc acc tgc gag aac ctc ctg ccg cag cag atc acg ccg cgc atg atg           2389
Thr Thr Cys Glu Asn Leu Leu Pro Gln Gln Ile Thr Pro Arg Met Met
160                 165                 170                 175 tgc gtg ggc ttc ctc agc ggc ggc gtg gac tcc tgc cag ggt gat tcc           2437
Cys Val Gly Phe Leu Ser Gly Gly Val Asp Ser Cys Gln Gly Asp Ser
                180                 185                 190 ggg gga ccc ctg tcc agc gtg gag gcg gat ggg cgg atc ttc cag gcc           2485
Gly Gly Pro Leu Ser Ser Val Glu Ala Asp Gly Arg Ile Phe Gln Ala
                195                 200                 205 ggt gtg gtg agc tgg gga gac ggc tgc gct cag agg aac aag cca ggc           2533
Gly Val Val Ser Trp Gly Asp Gly Cys Ala Gln Arg Asn Lys Pro Gly
                210                 215                 220 gtg tac aca agg ctc cct ctg ttt cgg gac tgg atc aaa gag aac act           2581
Val Tyr Thr Arg Leu Pro Leu Phe Arg Asp Trp Ile Lys Glu Asn Thr
225                 230                 235 ggg gta tag gggccggggc cacccaaatg tgtacacctg cggggccacc                   2630
Gly Val *
240 catcgtccac cccagtgtgc acgcctgcag gctggagact ggaccgctga ctgcaccagc         2690 gcccccagaa catacactgt gaactcaatc tccagggctc caaatctgcc tagaaaacct         2750 ctcgcttcct cagcctccaa agtggagctg ggaggtagaa ggggaggaca ctggtggttc         2810 tactgaccca actgggggca aaggtttgaa gacacagcct cccccgccag ccccaagctg         2870 ggccgaggcg cgtttgtgta tatctgcctc ccctgtctgt aaggagcagc gggaacggag         2930 cttcggagcc tcctcagtga aggtggtggg gctgccggat ctgggctgtg gggcccttgg         2990 gccacgctct tgaggaagcc caggctcgga ggaccctgga aaacagacgg gtctgagact         3050 gaaattgttt taccagctcc cagggtggac ttcagtgtgt gtatttgtgt aaatgggtaa         3110 aacaatttat ttcttttta aaaaaaaaa aaaaaa                                    3147

<210> SEQ ID NO 50
<211> LENGTH: 241
<212> TYPE: PRT
<213> ORGANISM: Homo Sapien

<400> SEQUENCE: 50

Val Val Gly Gly Thr Asp Ala Asp Glu Gly Glu Trp Pro Trp Gln Val
 1               5                  10                  15
```

-continued

```
Ser Leu His Ala Leu Gly Gln Gly His Ile Cys Gly Ala Ser Leu Ile
             20                  25                  30

Ser Pro Asn Trp Leu Val Ser Ala Ala His Cys Tyr Ile Asp Asp Arg
         35                  40                  45

Gly Phe Arg Tyr Ser Asp Pro Thr Gln Trp Thr Ala Phe Leu Gly Leu
     50                  55                  60

His Asp Gln Ser Gln Arg Ser Ala Pro Gly Val Gln Glu Arg Arg Leu
 65                  70                  75                  80

Lys Arg Ile Ile Ser His Pro Phe Phe Asn Asp Phe Thr Phe Asp Tyr
                 85                  90                  95

Asp Ile Ala Leu Leu Glu Leu Glu Lys Pro Ala Glu Tyr Ser Ser Met
            100                 105                 110

Val Arg Pro Ile Cys Leu Pro Asp Ala Ser His Val Phe Pro Ala Gly
        115                 120                 125

Lys Ala Ile Trp Val Thr Gly Trp Gly His Thr Gln Tyr Gly Gly Thr
    130                 135                 140

Gly Ala Leu Ile Leu Gln Lys Gly Glu Ile Arg Val Ile Asn Gln Thr
145                 150                 155                 160

Thr Cys Glu Asn Leu Leu Pro Gln Gln Ile Thr Pro Arg Met Met Cys
                165                 170                 175

Val Gly Phe Leu Ser Gly Gly Val Asp Ser Cys Gln Gly Asp Ser Gly
            180                 185                 190

Gly Pro Leu Ser Ser Val Glu Ala Asp Gly Arg Ile Phe Gln Ala Gly
        195                 200                 205

Val Val Ser Trp Gly Asp Gly Cys Ala Gln Arg Asn Lys Pro Gly Val
    210                 215                 220

Tyr Thr Arg Leu Pro Leu Phe Arg Asp Trp Ile Lys Glu Asn Thr Gly
225                 230                 235                 240

Val

<210> SEQ ID NO 51
<211> LENGTH: 46
<212> TYPE: DNA
<213> ORGANISM: Artificial Sequence
<220> FEATURE:
<223> OTHER INFORMATION: Oligonucleoide Primer

<400> SEQUENCE: 51
tctctcgaga aaagagtggt gggtgggtgg ggaggaggcc tctgtg           46

<210> SEQ ID NO 52
<211> LENGTH: 43
<212> TYPE: DNA
<213> ORGANISM: Artificial sequence
<220> FEATURE:
<223> OTHER INFORMATION: Oligonucleotide primer

<400> SEQUENCE: 52
gctcctcatc aaagaagggc agagagatgg gcctgactgt gcc              43

<210> SEQ ID NO 53
<211> LENGTH: 34
<212> TYPE: DNA
<213> ORGANISM: Artificial Sequence
<220> FEATURE:
<223> OTHER INFORMATION: Oligonucleoide Primer

<400> SEQUENCE: 53
```
attcgcggcc gcattacagc tcagccttcc agac 34

<210> SEQ ID NO 54
<211> LENGTH: 43
<212> TYPE: DNA
<213> ORGANISM: Artificial Sequence
<220> FEATURE:
<223> OTHER INFORMATION: Oligonucleoide Primer

<400> SEQUENCE: 54
ggcacagtca ggcccatctc tctgcccttc tttgatgagg agc 43

<210> SEQ ID NO 55
<211> LENGTH: 28
<212> TYPE: DNA
<213> ORGANISM: Artificial Sequence
<220> FEATURE:
<223> OTHER INFORMATION: Oligonucleoide Primer

<400> SEQUENCE: 55
caccccttct tcaatgactt caccttcg 28

<210> SEQ ID NO 56
<211> LENGTH: 18
<212> TYPE: DNA
<213> ORGANISM: Artificial Sequence
<220> FEATURE:
<223> OTHER INFORMATION: Oligonucleoide Primer

<400> SEQUENCE: 56
tacctctcct acgactcc 18

<210> SEQ ID NO 57
<211> LENGTH: 25
<212> TYPE: DNA
<213> ORGANISM: Artificial Sequence
<220> FEATURE:
<223> OTHER INFORMATION: Oligonucleoide Primer

<400> SEQUENCE: 57
gaggttctcg caggtggtct ggttg 25

<210> SEQ ID NO 58
<211> LENGTH: 39
<212> TYPE: DNA
<213> ORGANISM: Artificial Sequence
<220> FEATURE:
<223> OTHER INFORMATION: Oligonucleoide Primer

<400> SEQUENCE: 58
ctcgagaaaa gagttgttgg gggcacggat gcggatgag 39

<210> SEQ ID NO 59
<211> LENGTH: 11
<212> TYPE: PRT
<213> ORGANISM: Homo Sapien

<400> SEQUENCE: 59

Phe Glu Val Phe Ser Gln Ser Ser Ser Leu Gly
 1               5                  10

<210> SEQ ID NO 60
<211> LENGTH: 32
<212> TYPE: PRT
<213> ORGANISM: Homo Sapien

```
<400> SEQUENCE: 60

Glu Ile Val Ala Pro Arg Glu Arg Ala Asp Arg Arg Gly Arg Lys Leu
 1               5                  10                  15

Leu Cys Trp Arg Lys Pro Thr Lys Met Lys Gly Pro Arg Pro Ser His
            20                  25                  30

<210> SEQ ID NO 61
<211> LENGTH: 4933
<212> TYPE: DNA
<213> ORGANISM: Homo Sapien
<220> FEATURE:
<221> NAME/KEY: CDS
<222> LOCATION: (94)...(3222)
<223> OTHER INFORMATION: Nucleotide sequence encoding corin
<300> PUBLICATION INFORMATION:
<308> DATABASE ACCESSION NUMBER: GenBank AF133845
<309> DATABASE ENTRY DATE: 1999-05-24

<400> SEQUENCE: 61
aaatcatccg tagtgcctcc ccgggggaca cgtagaggag agaaaagcga ccaagataaa      60
agtggacaga agaataagcg agacttttta tcc atg aaa cag tct cct gcc ctc     114
                                    Met Lys Gln Ser Pro Ala Leu
                                     1               5 gct ccg gaa gag cgc tac cgc aga gcc ggg tcc cca aag ccg gtc ttg     162
Ala Pro Glu Glu Arg Tyr Arg Arg Ala Gly Ser Pro Lys Pro Val Leu
        10                  15                  20 aga gct gat gac aat aac atg ggc aat ggc tgc tct cag aag ctg gcg     210
Arg Ala Asp Asp Asn Asn Met Gly Asn Gly Cys Ser Gln Lys Leu Ala
 25                  30                  35 act gct aac ctc ctc cgg ttc cta ttg ctg gtc ctg att cca tgt atc     258
Thr Ala Asn Leu Leu Arg Phe Leu Leu Leu Val Leu Ile Pro Cys Ile
 40                  45                  50                  55 tgt gct ctc gtt ctc ttg ctg gtg atc ctg ctt tcc tat gtt gga aca     306
Cys Ala Leu Val Leu Leu Leu Val Ile Leu Leu Ser Tyr Val Gly Thr
                60                  65                  70 tta caa aag gtc tat ttt aaa tca aat ggg agt gaa cct ttg gtc act     354
Leu Gln Lys Val Tyr Phe Lys Ser Asn Gly Ser Glu Pro Leu Val Thr
            75                  80                  85 gat ggt gaa atc caa ggg tcc gat gtt att ctt aca aat aca att tat     402
Asp Gly Glu Ile Gln Gly Ser Asp Val Ile Leu Thr Asn Thr Ile Tyr
        90                  95                  100 aac cag agc act gtg gtg tct act gca cat ccc gac caa cac gtt cca     450
Asn Gln Ser Thr Val Val Ser Thr Ala His Pro Asp Gln His Val Pro
    105                 110                 115 gcc tgg act acg gat gct tct ctc cca ggg gac caa agt cac agg aat     498
Ala Trp Thr Thr Asp Ala Ser Leu Pro Gly Asp Gln Ser His Arg Asn
120                 125                 130                 135 aca agt gcc tgt atg aac atc acc cac agc cag tgt cag atg ctg ccc     546
Thr Ser Ala Cys Met Asn Ile Thr His Ser Gln Cys Gln Met Leu Pro
                140                 145                 150 tac cac gcc acg ctg aca cct ctc ctc tca gtt gtc aga aac atg gaa     594
Tyr His Ala Thr Leu Thr Pro Leu Leu Ser Val Val Arg Asn Met Glu
            155                 160                 165 atg gaa aag ttc ctc aag ttt ttc aca tat ctc cat cgc ctc agt tgc     642
Met Glu Lys Phe Leu Lys Phe Phe Thr Tyr Leu His Arg Leu Ser Cys
        170                 175                 180 tat caa cat atc atg ctg ttt ggc tgt acc ctc gcc ttc cct gag tgc     690
Tyr Gln His Ile Met Leu Phe Gly Cys Thr Leu Ala Phe Pro Glu Cys
    185                 190                 195 atc att gat ggc gat gac agt cat gga ctc ctg ccc tgt agg tcc ttc     738
Ile Ile Asp Gly Asp Asp Ser His Gly Leu Leu Pro Cys Arg Ser Phe
```

-continued

| | | | | |
|---|---|---|---|---|
| 200 | 205 | 210 | 215 | |

```
tgt gag gct gca aaa gaa ggc tgt gaa tca gtc ctg ggg atg gtg aat    786
Cys Glu Ala Ala Lys Glu Gly Cys Glu Ser Val Leu Gly Met Val Asn
                220             225             230 tac tcc tgg ccg gat ttc ctc aga tgc tcc cag ttt aga aac caa act    834
Tyr Ser Trp Pro Asp Phe Leu Arg Cys Ser Gln Phe Arg Asn Gln Thr
        235             240             245 gaa agc agc aat gtc agc aga att tgc ttc tca cct cag cag gaa aac    882
Glu Ser Ser Asn Val Ser Arg Ile Cys Phe Ser Pro Gln Gln Glu Asn
            250             255             260 gga aag caa ttg ctc tgt gga agg ggt gag aac ttt ctg tgt gcc agt    930
Gly Lys Gln Leu Leu Cys Gly Arg Gly Glu Asn Phe Leu Cys Ala Ser
        265             270             275 gga atc tgc atc ccc ggg aaa ctg caa tgt aat ggc tac aac gac tgt    978
Gly Ile Cys Ile Pro Gly Lys Leu Gln Cys Asn Gly Tyr Asn Asp Cys
280             285             290             295 gac gac tgg agt gac gag gct cat tgc aac tgc agc gag aat ctg ttt   1026
Asp Asp Trp Ser Asp Glu Ala His Cys Asn Cys Ser Glu Asn Leu Phe
            300             305             310 cac tgt cac aca ggc aag tgc ctt aat tac agc ctt gtg tgt gat gga   1074
His Cys His Thr Gly Lys Cys Leu Asn Tyr Ser Leu Val Cys Asp Gly
        315             320             325 tat gat gac tgt ggg gat ttg agt gat gag caa aac tgt gat tgc aat   1122
Tyr Asp Asp Cys Gly Asp Leu Ser Asp Glu Gln Asn Cys Asp Cys Asn
        330             335             340 ccc aca aca gag cat cgc tgc ggg gac ggg cgc tgc atc gcc atg gag   1170
Pro Thr Thr Glu His Arg Cys Gly Asp Gly Arg Cys Ile Ala Met Glu
345             350             355 tgg gtg tgt gat ggt gac cac gac tgt gtg gat aag tcc gac gag gtc   1218
Trp Val Cys Asp Gly Asp His Asp Cys Val Asp Lys Ser Asp Glu Val
360             365             370             375 aac tgc tcc tgt cac agc cag ggt ctg gtg gaa tgc aga aat gga caa   1266
Asn Cys Ser Cys His Ser Gln Gly Leu Val Glu Cys Arg Asn Gly Gln
            380             385             390 tgt atc ccc agc acg ttt caa tgt gat ggt gac gag gac tgc aag gat   1314
Cys Ile Pro Ser Thr Phe Gln Cys Asp Gly Asp Glu Asp Cys Lys Asp
        395             400             405 ggg agt gat gag gag aac tgc agc gtc att cag act tca tgt caa gaa   1362
Gly Ser Asp Glu Glu Asn Cys Ser Val Ile Gln Thr Ser Cys Gln Glu
        410             415             420 gga gac caa aga tgc ctc tac aat ccc tgc ctt gat tca tgt ggt ggt   1410
Gly Asp Gln Arg Cys Leu Tyr Asn Pro Cys Leu Asp Ser Cys Gly Gly
        425             430             435 agc tct ctc tgt gac ccg aac aac agt ctg aat aac tgt agt caa tgt   1458
Ser Ser Leu Cys Asp Pro Asn Asn Ser Leu Asn Asn Cys Ser Gln Cys
440             445             450             455 gaa cca att aca ttg gaa ctc tgc atg aat ttg ccc tac aac agt aca   1506
Glu Pro Ile Thr Leu Glu Leu Cys Met Asn Leu Pro Tyr Asn Ser Thr
            460             465             470 agt tat cca aat tat ttt ggc cac agg act caa aag gaa gca tcc atc   1554
Ser Tyr Pro Asn Tyr Phe Gly His Arg Thr Gln Lys Glu Ala Ser Ile
        475             480             485 agc tgg gag tct tct ctt ttc cct gca ctt gtt caa acc aac tgt tat   1602
Ser Trp Glu Ser Ser Leu Phe Pro Ala Leu Val Gln Thr Asn Cys Tyr
        490             495             500 aaa tac ctc atg ttc ttt tct tgc acc att ttg gta cca aaa tgt gat   1650
Lys Tyr Leu Met Phe Phe Ser Cys Thr Ile Leu Val Pro Lys Cys Asp
        505             510             515 gtg aat aca ggc gag cgt atc cct cct tgc agg gca ttg tgt gaa cac   1698
```

```
Val Asn Thr Gly Glu Arg Ile Pro Pro Cys Arg Ala Leu Cys Glu His
520                 525                 530                 535 tct aaa gaa cgc tgt gag tct gtt ctt ggg att gtg ggc cta cag tgg        1746
Ser Lys Glu Arg Cys Glu Ser Val Leu Gly Ile Val Gly Leu Gln Trp
                540                 545                 550 cct gaa gac aca gat tgc agt caa ttt cca gag gaa aat tca gac aat        1794
Pro Glu Asp Thr Asp Cys Ser Gln Phe Pro Glu Glu Asn Ser Asp Asn
            555                 560                 565 caa acc tgc ctg atg cct gat gaa tat gtg gaa gaa tgc tca cct agt        1842
Gln Thr Cys Leu Met Pro Asp Glu Tyr Val Glu Glu Cys Ser Pro Ser
        570                 575                 580 cat ttc aag tgc cgc tca gga cag tgt gtt ctg gct tcc aga aga tgt        1890
His Phe Lys Cys Arg Ser Gly Gln Cys Val Leu Ala Ser Arg Arg Cys
    585                 590                 595 gat ggc cag gcc gac tgt gac gat gac agt gat gag gaa aac tgt ggt        1938
Asp Gly Gln Ala Asp Cys Asp Asp Asp Ser Asp Glu Glu Asn Cys Gly
600                 605                 610                 615 tgt aaa gag aga gat ctt tgg gaa tgt cca tcc aat aaa caa tgt ttg        1986
Cys Lys Glu Arg Asp Leu Trp Glu Cys Pro Ser Asn Lys Gln Cys Leu
                620                 625                 630 aag cac aca gtg atc tgc gat ggg ttc cca gac tgc cct gat tac atg        2034
Lys His Thr Val Ile Cys Asp Gly Phe Pro Asp Cys Pro Asp Tyr Met
            635                 640                 645 gac gag aaa aac tgc tca ttt tgc caa gat gat gag ctg gaa tgt gca        2082
Asp Glu Lys Asn Cys Ser Phe Cys Gln Asp Asp Glu Leu Glu Cys Ala
        650                 655                 660 aac cat gcg tgt gtg tca cgt gac ctg tgg tgt gat ggt gaa gcc gac        2130
Asn His Ala Cys Val Ser Arg Asp Leu Trp Cys Asp Gly Glu Ala Asp
    665                 670                 675 tgc tca gac agt tca gat gaa tgg gac tgt gtg acc ctc tct ata aat        2178
Cys Ser Asp Ser Ser Asp Glu Trp Asp Cys Val Thr Leu Ser Ile Asn
680                 685                 690                 695 gtg aac tcc tct tcc ttt ctg atg gtt cac aga gct gcc aca gaa cac        2226
Val Asn Ser Ser Ser Phe Leu Met Val His Arg Ala Ala Thr Glu His
                700                 705                 710 cat gtg tgt gca gat ggc tgg cag gag ata ttg agt cag ctg gcc tgc        2274
His Val Cys Ala Asp Gly Trp Gln Glu Ile Leu Ser Gln Leu Ala Cys
            715                 720                 725 aag cag atg ggt tta gga gaa cca tct gtg acc aaa ttg ata cag gaa        2322
Lys Gln Met Gly Leu Gly Glu Pro Ser Val Thr Lys Leu Ile Gln Glu
        730                 735                 740 cag gag aaa gag ccg cgg tgg ctg aca tta cac tcc aac tgg gag agc        2370
Gln Glu Lys Glu Pro Arg Trp Leu Thr Leu His Ser Asn Trp Glu Ser
    745                 750                 755 ctc aat ggg acc act tta cat gaa ctt cta gta aat ggg cag tct tgt        2418
Leu Asn Gly Thr Thr Leu His Glu Leu Leu Val Asn Gly Gln Ser Cys
760                 765                 770                 775 gag agc aga agt aaa att tct ctt ctg tgt act aaa caa gac tgt ggg        2466
Glu Ser Arg Ser Lys Ile Ser Leu Leu Cys Thr Lys Gln Asp Cys Gly
                780                 785                 790 cgc cgc cct gct gcc cga atg aac aaa agg atc ctt gga ggt cgg acg        2514
Arg Arg Pro Ala Ala Arg Met Asn Lys Arg Ile Leu Gly Gly Arg Thr
            795                 800                 805 agt cgc cct gga agg tgg cca tgg cag tgt tct ctg cag agt gaa ccc        2562
Ser Arg Pro Gly Arg Trp Pro Trp Gln Cys Ser Leu Gln Ser Glu Pro
        810                 815                 820 agt gga cat atc tgt ggc tgt gtc ctc att gcc aag aag tgg gtt ctg        2610
Ser Gly His Ile Cys Gly Cys Val Leu Ile Ala Lys Lys Trp Val Leu
    825                 830                 835
```

```
aca gtt gcc cac tgc ttc gag ggg aga gag aat gct gca gtt tgg aaa      2658
Thr Val Ala His Cys Phe Glu Gly Arg Glu Asn Ala Ala Val Trp Lys
840                 845                 850                 855 gtg gtg ctt ggc atc aac aat cta gac cat cca tca gtg ttc atg cag      2706
Val Val Leu Gly Ile Asn Asn Leu Asp His Pro Ser Val Phe Met Gln
                860                 865                 870 aca cgc ttt gtg aag acc atc atc ctg cat ccc cgc tac agt cga gca      2754
Thr Arg Phe Val Lys Thr Ile Ile Leu His Pro Arg Tyr Ser Arg Ala
        875                 880                 885 gtg gtg gac tat gac atc agc atc gtt gag ctg agt gaa gac atc agt      2802
Val Val Asp Tyr Asp Ile Ser Ile Val Glu Leu Ser Glu Asp Ile Ser
    890                 895                 900 gag act ggc tac gtc cgg cct gtc tgc ttg ccc aac ccg gag cag tgg      2850
Glu Thr Gly Tyr Val Arg Pro Val Cys Leu Pro Asn Pro Glu Gln Trp
905                 910                 915 cta gag cct gac acg tac tgc tat atc aca ggc tgg ggc cac atg ggc      2898
Leu Glu Pro Asp Thr Tyr Cys Tyr Ile Thr Gly Trp Gly His Met Gly
920                 925                 930                 935 aat aaa atg cca ttt aag ctg caa gag gga gag gtc cgc att att tct      2946
Asn Lys Met Pro Phe Lys Leu Gln Glu Gly Glu Val Arg Ile Ile Ser
                940                 945                 950 ctg gaa cat tgt cag tcc tac ttt gac atg aag acc atc acc act cgg      2994
Leu Glu His Cys Gln Ser Tyr Phe Asp Met Lys Thr Ile Thr Thr Arg
        955                 960                 965 atg ata tgt gct ggc tat gag tct ggc aca gtt gat tca tgc atg ggt      3042
Met Ile Cys Ala Gly Tyr Glu Ser Gly Thr Val Asp Ser Cys Met Gly
    970                 975                 980 gac agc ggt ggg cct ctt gtt tgt gag aag cct gga gga cgg tgg aca      3090
Asp Ser Gly Gly Pro Leu Val Cys Glu Lys Pro Gly Gly Arg Trp Thr
985                 990                 995 tta ttt gga tta act tca tgg ggc tcc gtc tgc ttt tcc aaa gtc ctg      3138
Leu Phe Gly Leu Thr Ser Trp Gly Ser Val Cys Phe Ser Lys Val Leu
1000                1005                1010                1015 ggg cct ggc gtt tat agt aat gtg tca tat ttc gtc gaa tgg att aaa      3186
Gly Pro Gly Val Tyr Ser Asn Val Ser Tyr Phe Val Glu Trp Ile Lys
                1020                1025                1030 aga cag att tac atc cag acc ttt ctc cta aac taa ttataaggat           3232
Arg Gln Ile Tyr Ile Gln Thr Phe Leu Leu Asn *
        1035                1040 gatcagagac ttttgccagc tacactaaaa gaaaatggcc ttcttgactg tgaagagctg    3292
cctgcagaga gctgtacaga agcactttc atggacagaa atgctcaatc gtgcactgca     3352
aatttgcatg tttgttttgg actaattttt ttcaatttat ttttcacct tcatttttct     3412 cttatttcaa gttcaatgaa agactttaca aaagcaaaca aagcagactt tgtccttttg    3472
ccaggcctaa ccatgactgc agcacaaaat tatcgactct ggcgagattt aaaatcaggt    3532
gctacagtaa caggttatgg aatggtctct tttatcctat cacaaaaaaa gacatagata    3592
tttaggctga ttaattatct ctaccagttt ttgtttctca agctcagtgc atagtggtaa    3652
atttcagtgt taacattgga gacttgcttt tctttttctt tttttatacc ccacaattct    3712
tttttattac acttcgaatt ttagggtaca cgagcacaac gtgcaggtta gttacatatg    3772
tatacatgtg ccatgttggt gtgctgaacc cagtaactcg tcatttgatt tattaaaagc    3832
caagataatt tacatgttta aagtatttac tattaccccc ttctaatgtt tgcataattc    3892
tgagaactga taaaagacag caataaaaga ccagtgtcat ccatttaggt agcaagacat    3952
attgaatgca aagttcttta gatatcaata ttaacacttg acattattgg accccccatt    4012
ctggatgtat atcaagatca taatttttata gaagagtctc tatagaactg tcctcatagc   4072
```

-continued

```
tgggtttgtt caggatatat gagttggctg attgagactg caacaactac atctatattt    4132
atgggcaata ttttgtttta cttatgtggc aaagaactgg atattaaact ttgcaaaaga    4192
gaatttagat gagagatgca atttttaaa aagaaaatta atttgcatcc ctcgtttaat     4252
taaatttatt tttcagtttt cttgcgttca tccataccaa caaagtcata agagcatat     4312
tttagagcac agtaagactt tgcatggagt aaaacatttt gtaattttcc tcaaaagatg    4372
tttaatatct ggtttcttct cattggtaat taaaatttta gaaatgattt ttagctctag    4432
gccactttac gcaactcaat ttctgaagca attagtggta aaaagtattt ttccccacta    4492
aaaaacttta aaacacaaat cttcatatat acttaattta attagtcagg catccatttt    4552
gcctttttaaa caactaggat tccctactaa cctccaccag caacctggac tgcctcagca   4612
ttccaaatag atactacctg caatttttata catgtatttt tgtatctttt ctgtgtgtaa   4672
acatagttga aattcaaaaa gttgtagcaa tttctatact attcatctcc tgtccttcag    4732
tttgtataaa cctaaggaga gtgtgaaatc cagcaactga attgtggtca cgattgtatg    4792
aaagttcaag aacatatgtc agttttgtta cagttgtagc tacatactca atgtatcaac    4852
ttttagcctg ctcaacttag gctcagtgaa atatatatat tatacttatt ttaaataatt    4912
cttaatacaa ataaaatggt a                                               4933
```

<210> SEQ ID NO 62
<211> LENGTH: 1042
<212> TYPE: PRT
<213> ORGANISM: Homo Sapien

<400> SEQUENCE: 62

```
Met Lys Gln Ser Pro Ala Leu Ala Pro Glu Glu Arg Tyr Arg Arg Ala
 1               5                  10                  15

Gly Ser Pro Lys Pro Val Leu Arg Ala Asp Asp Asn Asn Met Gly Asn
            20                  25                  30

Gly Cys Ser Gln Lys Leu Ala Thr Ala Asn Leu Leu Arg Phe Leu Leu
        35                  40                  45

Leu Val Leu Ile Pro Cys Ile Cys Ala Leu Val Leu Leu Leu Val Ile
    50                  55                  60

Leu Leu Ser Tyr Val Gly Thr Leu Gln Lys Val Tyr Phe Lys Ser Asn
65                  70                  75                  80

Gly Ser Glu Pro Leu Val Thr Asp Gly Glu Ile Gln Gly Ser Asp Val
                85                  90                  95

Ile Leu Thr Asn Thr Ile Tyr Asn Gln Ser Thr Val Val Ser Thr Ala
           100                 105                 110

His Pro Asp Gln His Val Pro Ala Trp Thr Thr Asp Ala Ser Leu Pro
       115                 120                 125

Gly Asp Gln Ser His Arg Asn Thr Ser Ala Cys Met Asn Ile Thr His
   130                 135                 140

Ser Gln Cys Gln Met Leu Pro Tyr His Ala Thr Leu Thr Pro Leu Leu
145                 150                 155                 160

Ser Val Val Arg Asn Met Glu Met Glu Lys Phe Leu Lys Phe Phe Thr
               165                 170                 175

Tyr Leu His Arg Leu Ser Cys Tyr Gln His Ile Met Leu Phe Gly Cys
           180                 185                 190

Thr Leu Ala Phe Pro Glu Cys Ile Ile Asp Gly Asp Asp Ser His Gly
       195                 200                 205

Leu Leu Pro Cys Arg Ser Phe Cys Glu Ala Ala Lys Glu Gly Cys Glu
```

-continued

```
            210                 215                 220
Ser Val Leu Gly Met Val Asn Tyr Ser Trp Pro Asp Phe Leu Arg Cys
225                 230                 235                 240

Ser Gln Phe Arg Asn Gln Thr Glu Ser Ser Asn Val Ser Arg Ile Cys
                245                 250                 255

Phe Ser Pro Gln Gln Glu Asn Gly Lys Gln Leu Leu Cys Gly Arg Gly
            260                 265                 270

Glu Asn Phe Leu Cys Ala Ser Gly Ile Cys Ile Pro Gly Lys Leu Gln
            275                 280                 285

Cys Asn Gly Tyr Asn Asp Cys Asp Asp Trp Ser Asp Glu Ala His Cys
            290                 295                 300

Asn Cys Ser Glu Asn Leu Phe His Cys His Thr Gly Lys Cys Leu Asn
305                 310                 315                 320

Tyr Ser Leu Val Cys Asp Gly Tyr Asp Asp Cys Gly Asp Leu Ser Asp
                325                 330                 335

Glu Gln Asn Cys Asp Cys Asn Pro Thr Thr Glu His Arg Cys Gly Asp
            340                 345                 350

Gly Arg Cys Ile Ala Met Glu Trp Val Cys Asp Gly Asp His Asp Cys
            355                 360                 365

Val Asp Lys Ser Asp Glu Val Asn Cys Ser Cys His Ser Gln Gly Leu
            370                 375                 380

Val Glu Cys Arg Asn Gly Gln Cys Ile Pro Ser Thr Phe Gln Cys Asp
385                 390                 395                 400

Gly Asp Glu Asp Cys Lys Asp Gly Ser Asp Glu Glu Asn Cys Ser Val
                405                 410                 415

Ile Gln Thr Ser Cys Gln Glu Gly Asp Gln Arg Cys Leu Tyr Asn Pro
            420                 425                 430

Cys Leu Asp Ser Cys Gly Gly Ser Leu Cys Asp Pro Asn Asn Ser
            435                 440                 445

Leu Asn Asn Cys Ser Gln Cys Glu Pro Ile Thr Leu Glu Leu Cys Met
450                 455                 460

Asn Leu Pro Tyr Asn Ser Thr Ser Tyr Pro Asn Tyr Phe Gly His Arg
465                 470                 475                 480

Thr Gln Lys Glu Ala Ser Ile Ser Trp Glu Ser Ser Leu Phe Pro Ala
                485                 490                 495

Leu Val Gln Thr Asn Cys Tyr Lys Tyr Leu Met Phe Phe Ser Cys Thr
            500                 505                 510

Ile Leu Val Pro Lys Cys Asp Val Asn Thr Gly Glu Arg Ile Pro Pro
            515                 520                 525

Cys Arg Ala Leu Cys Glu His Ser Lys Glu Arg Cys Glu Ser Val Leu
530                 535                 540

Gly Ile Val Gly Leu Gln Trp Pro Glu Asp Thr Asp Cys Ser Gln Phe
545                 550                 555                 560

Pro Glu Glu Asn Ser Asp Asn Gln Thr Cys Leu Met Pro Asp Glu Tyr
                565                 570                 575

Val Glu Glu Cys Ser Pro Ser His Phe Lys Cys Arg Ser Gly Gln Cys
            580                 585                 590

Val Leu Ala Ser Arg Arg Cys Asp Gly Gln Ala Asp Cys Asp Asp Asp
            595                 600                 605

Ser Asp Glu Glu Asn Cys Gly Cys Lys Glu Arg Asp Leu Trp Glu Cys
            610                 615                 620

Pro Ser Asn Lys Gln Cys Leu Lys His Thr Val Ile Cys Asp Gly Phe
625                 630                 635                 640
```

```
Pro Asp Cys Pro Asp Tyr Met Asp Glu Lys Asn Cys Ser Phe Cys Gln
            645                 650                 655
Asp Asp Glu Leu Glu Cys Ala Asn His Ala Cys Val Ser Arg Asp Leu
            660                 665                 670
Trp Cys Asp Gly Glu Ala Asp Cys Ser Asp Ser Ser Asp Glu Trp Asp
            675                 680                 685
Cys Val Thr Leu Ser Ile Asn Val Asn Ser Ser Phe Leu Met Val
690                 695                 700
His Arg Ala Ala Thr Glu His His Val Cys Ala Asp Gly Trp Gln Glu
705                 710                 715                 720
Ile Leu Ser Gln Leu Ala Cys Lys Gln Met Gly Leu Gly Glu Pro Ser
            725                 730                 735
Val Thr Lys Leu Ile Gln Glu Gln Glu Lys Glu Pro Arg Trp Leu Thr
            740                 745                 750
Leu His Ser Asn Trp Glu Ser Leu Asn Gly Thr Thr Leu His Glu Leu
            755                 760                 765
Leu Val Asn Gly Gln Ser Cys Glu Ser Arg Ser Lys Ile Ser Leu Leu
770                 775                 780
Cys Thr Lys Gln Asp Cys Gly Arg Arg Pro Ala Ala Arg Met Asn Lys
785                 790                 795                 800
Arg Ile Leu Gly Gly Arg Thr Ser Arg Pro Gly Arg Trp Pro Trp Gln
            805                 810                 815
Cys Ser Leu Gln Ser Glu Pro Ser Gly His Ile Cys Gly Cys Val Leu
            820                 825                 830
Ile Ala Lys Lys Trp Val Leu Thr Val Ala His Cys Phe Glu Gly Arg
            835                 840                 845
Glu Asn Ala Ala Val Trp Lys Val Val Leu Gly Ile Asn Asn Leu Asp
            850                 855                 860
His Pro Ser Val Phe Met Gln Thr Arg Phe Val Lys Thr Ile Ile Leu
865                 870                 875                 880
His Pro Arg Tyr Ser Arg Ala Val Val Asp Tyr Asp Ile Ser Ile Val
            885                 890                 895
Glu Leu Ser Glu Asp Ile Ser Glu Thr Gly Tyr Val Arg Pro Val Cys
            900                 905                 910
Leu Pro Asn Pro Glu Gln Trp Leu Glu Pro Asp Thr Tyr Cys Tyr Ile
            915                 920                 925
Thr Gly Trp Gly His Met Gly Asn Lys Met Pro Phe Lys Leu Gln Glu
            930                 935                 940
Gly Glu Val Arg Ile Ile Ser Leu Glu His Cys Gln Ser Tyr Phe Asp
945                 950                 955                 960
Met Lys Thr Ile Thr Thr Arg Met Ile Cys Ala Gly Tyr Glu Ser Gly
            965                 970                 975
Thr Val Asp Ser Cys Met Gly Asp Ser Gly Gly Pro Leu Val Cys Glu
            980                 985                 990
Lys Pro Gly Gly Arg Trp Thr Leu Phe Gly Leu Thr Ser Trp Gly Ser
            995                 1000                1005
Val Cys Phe Ser Lys Val Leu Gly Pro Gly Val Tyr Ser Asn Val Ser
      1010                1015                1020
Tyr Phe Val Glu Trp Ile Lys Arg Gln Ile Tyr Ile Gln Thr Phe Leu
1025                1030                1035                1040
Leu Asn
```

```
<210> SEQ ID NO 63
<211> LENGTH: 3696
<212> TYPE: DNA
<213> ORGANISM: Homo Sapien
<220> FEATURE:
<221> NAME/KEY: CDS
<222> LOCATION: (41)...(3100)
<223> OTHER INFORMATION: Nucleotide sequence encoding human
      entorkinase
<300> PUBLICATION INFORMATION:
<308> DATABASE ACCESSION NUMBER: GenBank HSU09860
<309> DATABASE ENTRY DATE: 1995-06-03

<400> SEQUENCE: 63
accagacagt tcttaaatta gcaagccttc aaaaccaaaa atg ggg tcg aaa aga        55
                                              Met Gly Ser Lys Arg
                                              1               5 ggc ata tct tct agg cat cat tct ctc agc tcc tat gaa atc atg ttt       103
Gly Ile Ser Ser Arg His His Ser Leu Ser Ser Tyr Glu Ile Met Phe
         10                  15                  20 gca gct ctc ttt gcc ata ttg gta gtg ctc tgt gct gga tta att gca       151
Ala Ala Leu Phe Ala Ile Leu Val Val Leu Cys Ala Gly Leu Ile Ala
             25                  30                  35 gta tcc tgc ctg aca atc aag gaa tcc caa cga ggt gca gca ctt gga       199
Val Ser Cys Leu Thr Ile Lys Glu Ser Gln Arg Gly Ala Ala Leu Gly
 40                  45                  50 cag agt cat gaa gcc aga gcg aca ttt aaa ata aca tcc gga gtt aca       247
Gln Ser His Glu Ala Arg Ala Thr Phe Lys Ile Thr Ser Gly Val Thr
 55                  60                  65 tat aat cct aat ttg caa gac aaa ctc tca gtg gat ttc aaa gtt ctt       295
Tyr Asn Pro Asn Leu Gln Asp Lys Leu Ser Val Asp Phe Lys Val Leu
 70                  75                  80                  85 gct ttt gac ctt cag caa atg ata gat gag atc ttt cta tca agc aat       343
Ala Phe Asp Leu Gln Gln Met Ile Asp Glu Ile Phe Leu Ser Ser Asn
                 90                  95                 100 ctg aag aat gaa tat aag aac tca aga gtt tta caa ttt gaa aat ggc       391
Leu Lys Asn Glu Tyr Lys Asn Ser Arg Val Leu Gln Phe Glu Asn Gly
             105                 110                 115 agc att ata gtc gta ttt gac ctt ttc ttt gcc cag tgg gtg tca gat       439
Ser Ile Ile Val Val Phe Asp Leu Phe Phe Ala Gln Trp Val Ser Asp
         120                 125                 130 caa aat gta aaa gaa gaa ctg att caa ggc ctt gaa gca aat aaa tcc       487
Gln Asn Val Lys Glu Glu Leu Ile Gln Gly Leu Glu Ala Asn Lys Ser
     135                 140                 145 agc caa ctg gtc act ttc cat att gat ttg aac agc gtt gat atc cta       535
Ser Gln Leu Val Thr Phe His Ile Asp Leu Asn Ser Val Asp Ile Leu
150                 155                 160                 165 gac aag cta aca acc acc agt cat ctg gca act cca gga aat gtc tca       583
Asp Lys Leu Thr Thr Thr Ser His Leu Ala Thr Pro Gly Asn Val Ser
                 170                 175                 180 ata gag tgc ctg cct ggt tca agt cct tgt act gat gct cta acg tgt       631
Ile Glu Cys Leu Pro Gly Ser Ser Pro Cys Thr Asp Ala Leu Thr Cys
             185                 190                 195 ata aaa gct gat tta ttt tgt gat gga gaa gta aac tgt cca gat ggt       679
Ile Lys Ala Asp Leu Phe Cys Asp Gly Glu Val Asn Cys Pro Asp Gly
         200                 205                 210 tct gac gaa gac aat aaa atg tgt gcc aca gtt tgt gat gga aga ttt       727
Ser Asp Glu Asp Asn Lys Met Cys Ala Thr Val Cys Asp Gly Arg Phe
     215                 220                 225 ttg tta act gga tca tct ggg tct ttc cag gct act cat tat cca aaa       775
Leu Leu Thr Gly Ser Ser Gly Ser Phe Gln Ala Thr His Tyr Pro Lys
230                 235                 240                 245
```

```
cct tct gaa aca agt gtt gtc tgc cag tgg atc ata cgt gta aac caa      823
Pro Ser Glu Thr Ser Val Val Cys Gln Trp Ile Ile Arg Val Asn Gln
            250                 255                 260 gga ctt tcc att aaa ctg agc ttc gat gat ttt aat aca tat tat aca      871
Gly Leu Ser Ile Lys Leu Ser Phe Asp Asp Phe Asn Thr Tyr Tyr Thr
        265                 270                 275 gat ata tta gat att tat gaa ggt gta gga tca agc aag att tta aga      919
Asp Ile Leu Asp Ile Tyr Glu Gly Val Gly Ser Ser Lys Ile Leu Arg
    280                 285                 290 gct tct att tgg gaa act aat cct ggc aca ata aga att ttt tcc aac      967
Ala Ser Ile Trp Glu Thr Asn Pro Gly Thr Ile Arg Ile Phe Ser Asn
295                 300                 305 caa gtt act gcc acc ttt ctt ata gaa tct gat gaa agt gat tat gtt     1015
Gln Val Thr Ala Thr Phe Leu Ile Glu Ser Asp Glu Ser Asp Tyr Val
310                 315                 320                 325 ggc ttt aat gca aca tat act gca ttt aac agc agt gag ctt aat aat     1063
Gly Phe Asn Ala Thr Tyr Thr Ala Phe Asn Ser Ser Glu Leu Asn Asn
            330                 335                 340 tat gag aaa att aat tgt aac ttt gag gat ggc ttt tgt ttc tgg gtc     1111
Tyr Glu Lys Ile Asn Cys Asn Phe Glu Asp Gly Phe Cys Phe Trp Val
        345                 350                 355 cag gat cta aat gat gat aat gaa tgg gaa agg att cag gga agc acc     1159
Gln Asp Leu Asn Asp Asp Asn Glu Trp Glu Arg Ile Gln Gly Ser Thr
    360                 365                 370 ttt tct cct ttt act gga ccc aat ttt gac cac act ttt ggc aat gct     1207
Phe Ser Pro Phe Thr Gly Pro Asn Phe Asp His Thr Phe Gly Asn Ala
375                 380                 385 tca gga ttt tac att tct acc cca act gga cca gga ggg aga caa gaa     1255
Ser Gly Phe Tyr Ile Ser Thr Pro Thr Gly Pro Gly Gly Arg Gln Glu
390                 395                 400                 405 cga gtg ggg ctt tta agc ctc cct ttg gac ccc act ttg gag cca gct     1303
Arg Val Gly Leu Leu Ser Leu Pro Leu Asp Pro Thr Leu Glu Pro Ala
            410                 415                 420 tgc ctt agt ttc tgg tat cat atg tat ggt gaa aat gtc cat aaa tta     1351
Cys Leu Ser Phe Trp Tyr His Met Tyr Gly Glu Asn Val His Lys Leu
        425                 430                 435 agc att aat atc agc aat gac caa aat atg gag aag aca gtt ttc caa     1399
Ser Ile Asn Ile Ser Asn Asp Gln Asn Met Glu Lys Thr Val Phe Gln
    440                 445                 450 aag gaa gga aat tat gga gac aat tgg aat tat gga caa gta acc cta     1447
Lys Glu Gly Asn Tyr Gly Asp Asn Trp Asn Tyr Gly Gln Val Thr Leu
455                 460                 465 aat gaa aca gtt aaa ttt aag gtt gct ttt aat gct ttt aaa aac aag     1495
Asn Glu Thr Val Lys Phe Lys Val Ala Phe Asn Ala Phe Lys Asn Lys
470                 475                 480                 485 atc ctg agt gat att gcg ttg gat gac att agc cta aca tat ggg att     1543
Ile Leu Ser Asp Ile Ala Leu Asp Asp Ile Ser Leu Thr Tyr Gly Ile
            490                 495                 500 tgc aat ggg agt ctt tat cca gaa cca act ttg gtg cca act cct cca     1591
Cys Asn Gly Ser Leu Tyr Pro Glu Pro Thr Leu Val Pro Thr Pro Pro
        505                 510                 515 cca gaa ctt cct acg gac tgt gga gga cct ttt gag ctg tgg gag cca     1639
Pro Glu Leu Pro Thr Asp Cys Gly Gly Pro Phe Glu Leu Trp Glu Pro
    520                 525                 530 aat aca aca ttc agt tct acg aac ttt cca aac agc tac cct aat ctg     1687
Asn Thr Thr Phe Ser Ser Thr Asn Phe Pro Asn Ser Tyr Pro Asn Leu
535                 540                 545 gct ttc tgt gtt tgg att tta aat gca caa aaa gga aag aat ata caa     1735
Ala Phe Cys Val Trp Ile Leu Asn Ala Gln Lys Gly Lys Asn Ile Gln
550                 555                 560                 565
```

```
ctt cat ttt caa gaa ttt gac tta gaa aat att aac gat gta gtt gaa      1783
Leu His Phe Gln Glu Phe Asp Leu Glu Asn Ile Asn Asp Val Val Glu
            570                 575                 580 ata aga gat ggt gaa gaa gct gat tcc ttg ctc tta gct gtg tac aca      1831
Ile Arg Asp Gly Glu Glu Ala Asp Ser Leu Leu Leu Ala Val Tyr Thr
            585                 590                 595 ggg cct ggc cca gta aag gat gtg ttc tct acc acc aac aga atg act      1879
Gly Pro Gly Pro Val Lys Asp Val Phe Ser Thr Thr Asn Arg Met Thr
            600                 605                 610 gtg ctt ctc atc act aac gat gtg ttg gca aga gga ggg ttt aaa gca      1927
Val Leu Leu Ile Thr Asn Asp Val Leu Ala Arg Gly Gly Phe Lys Ala
615                 620                 625 aac ttt act act ggc tat cac ttg ggg att cca gag cca tgc aag gca      1975
Asn Phe Thr Thr Gly Tyr His Leu Gly Ile Pro Glu Pro Cys Lys Ala
630                 635                 640                 645 gac cat ttt caa tgt aaa aat gga gag tgt gtt cca ctg gtg aat ctc      2023
Asp His Phe Gln Cys Lys Asn Gly Glu Cys Val Pro Leu Val Asn Leu
            650                 655                 660 tgt gac ggt cat ctg cac tgt gag gat ggc tca gat gaa gca gat tgt      2071
Cys Asp Gly His Leu His Cys Glu Asp Gly Ser Asp Glu Ala Asp Cys
            665                 670                 675 gtg cgt ttt ttc aat ggc aca acg aac aac aat ggt tta gtg cgg ttc      2119
Val Arg Phe Phe Asn Gly Thr Thr Asn Asn Asn Gly Leu Val Arg Phe
            680                 685                 690 aga atc cag agc ata tgg cat aca gct tgt gct gag aac tgg acc acc      2167
Arg Ile Gln Ser Ile Trp His Thr Ala Cys Ala Glu Asn Trp Thr Thr
695                 700                 705 cag att tca aat gat gtt tgt caa ctg ctg gga cta ggg agt gga aac      2215
Gln Ile Ser Asn Asp Val Cys Gln Leu Leu Gly Leu Gly Ser Gly Asn
710                 715                 720                 725 tca tca aag cca atc ttc tct acc gat ggt gga cca ttt gtc aaa tta      2263
Ser Ser Lys Pro Ile Phe Ser Thr Asp Gly Gly Pro Phe Val Lys Leu
            730                 735                 740 aac aca gca cct gat ggc cac tta ata cta aca ccc agt caa cag tgt      2311
Asn Thr Ala Pro Asp Gly His Leu Ile Leu Thr Pro Ser Gln Gln Cys
            745                 750                 755 tta cag gat tcc ttg att cgg tta cag tgt aac cat aaa tct tgt gga      2359
Leu Gln Asp Ser Leu Ile Arg Leu Gln Cys Asn His Lys Ser Cys Gly
            760                 765                 770 aaa aaa ctg gca gct caa gac atc acc cca aag att gtt gga gga agt      2407
Lys Lys Leu Ala Ala Gln Asp Ile Thr Pro Lys Ile Val Gly Gly Ser
775                 780                 785 aat gcc aaa gaa ggg gcc tgg ccc tgg gtt gtg ggt ctg tat tat ggc      2455
Asn Ala Lys Glu Gly Ala Trp Pro Trp Val Val Gly Leu Tyr Tyr Gly
790                 795                 800                 805 ggc cga ctg ctc tgc ggc gca tct ctc gtc agc agt gac tgg ctg gtg      2503
Gly Arg Leu Leu Cys Gly Ala Ser Leu Val Ser Ser Asp Trp Leu Val
            810                 815                 820 tcc gcc gca cac tgc gtg tat ggg aga aac tta gag cca tcc aag tgg      2551
Ser Ala Ala His Cys Val Tyr Gly Arg Asn Leu Glu Pro Ser Lys Trp
            825                 830                 835 aca gca atc cta ggc ctg cat atg aaa tca aat ctg acc tct cct caa      2599
Thr Ala Ile Leu Gly Leu His Met Lys Ser Asn Leu Thr Ser Pro Gln
            840                 845                 850 aca gtc cct cga tta ata gat gaa att gtc ata aac cct cat tac aat      2647
Thr Val Pro Arg Leu Ile Asp Glu Ile Val Ile Asn Pro His Tyr Asn
855                 860                 865 agg cga aga aag gac aac gac att gcc atg atg cat ctg gaa ttt aaa      2695
Arg Arg Arg Lys Asp Asn Asp Ile Ala Met Met His Leu Glu Phe Lys
```

```
                    870              875              880              885
gtg aat tac aca gat tac ata caa cct att tgt tta ccg gaa gaa aat      2743
Val Asn Tyr Thr Asp Tyr Ile Gln Pro Ile Cys Leu Pro Glu Glu Asn
                890              895              900 caa gtt ttt cct cca gga aga aat tgt tct att gct ggt tgg ggg acg      2791
Gln Val Phe Pro Pro Gly Arg Asn Cys Ser Ile Ala Gly Trp Gly Thr
            905              910              915 gtt gta tat caa ggt act act gca aac ata ttg caa gaa gct gat gtt      2839
Val Val Tyr Gln Gly Thr Thr Ala Asn Ile Leu Gln Glu Ala Asp Val
        920              925              930 cct ctt cta tca aat gag aga tgc caa cag cag atg cca gaa tat aac      2887
Pro Leu Leu Ser Asn Glu Arg Cys Gln Gln Gln Met Pro Glu Tyr Asn
    935              940              945 att act gaa aat atg ata tgt gca ggc tat gaa gaa gga gga ata gat      2935
Ile Thr Glu Asn Met Ile Cys Ala Gly Tyr Glu Glu Gly Gly Ile Asp
950              955              960              965 tct tgt cag ggg gat tca gga gga cca tta atg tgc caa gaa aac aac      2983
Ser Cys Gln Gly Asp Ser Gly Gly Pro Leu Met Cys Gln Glu Asn Asn
            970              975              980 agg tgg ttc ctt gct ggt gtg acc tca ttt gga tac aag tgt gcc ctg      3031
Arg Trp Phe Leu Ala Gly Val Thr Ser Phe Gly Tyr Lys Cys Ala Leu
        985              990              995 cct aat cgc ccc gga gtg tat gcc agg gtc tca agg ttt acc gaa tgg      3079
Pro Asn Arg Pro Gly Val Tyr Ala Arg Val Ser Arg Phe Thr Glu Trp
    1000             1005             1010 ata caa agt ttt cta cat tag cgcatttctt aaactaaaca ggaaagtcgc         3130
Ile Gln Ser Phe Leu His  *
    1015 attattttcc cattctactc tagaaagcat ggaaattaag tgtttcgtac aaaaatttta    3190 aaaagttacc aaaggttttt attcttacct atgtcaatga aatgctaggg ggccagggaa    3250 acaaaatttt aaaataata aaattcacca tagcaataca gaataacttt aaaataccat     3310 taaatacatt tgtatttcat tgtgaacagg tatttcttca cagatctcat ttttaaaatt    3370 cttaatgatt attttttatta cttactgttg tttaaaggga tgttatttta aagcatatac   3430 catacactta agaaatttga gcagaattta aaaagaaag aaaataaatt gttttttccca    3490 aagtatgtca ctgttggaaa taaactgcca taaattttct agttccagtt tagtttgctg    3550 ctattagcag aaactcaatt gtttctctgt cttttctatc aaaattttca acatatgcat    3610 aaccttagta ttttcccaac caatagaaac tatttattgt aagcttatgt cacaggcctg    3670 gactaaattg attttacgtt cctctt                                         3696

<210> SEQ ID NO 64
<211> LENGTH: 1019
<212> TYPE: PRT
<213> ORGANISM: Homo Sapien

<400> SEQUENCE: 64

Met Gly Ser Lys Arg Gly Ile Ser Ser Arg His His Ser Leu Ser Ser
 1               5                   10                  15

Tyr Glu Ile Met Phe Ala Ala Leu Phe Ala Ile Leu Val Val Leu Cys
                20                  25                  30

Ala Gly Leu Ile Ala Val Ser Cys Leu Thr Ile Lys Glu Ser Gln Arg
            35                  40                  45

Gly Ala Ala Leu Gly Gln Ser His Glu Ala Arg Ala Thr Phe Lys Ile
        50                  55                  60

Thr Ser Gly Val Thr Tyr Asn Pro Asn Leu Gln Asp Lys Leu Ser Val
```

-continued

```
                65                  70                  75                  80
Asp Phe Lys Val Leu Ala Phe Asp Leu Gln Gln Met Ile Asp Glu Ile
                    85                  90                  95
Phe Leu Ser Ser Asn Leu Lys Asn Glu Tyr Lys Asn Ser Arg Val Leu
                    100                 105                 110
Gln Phe Glu Asn Gly Ser Ile Ile Val Val Phe Asp Leu Phe Phe Ala
                    115                 120                 125
Gln Trp Val Ser Asp Gln Asn Val Lys Glu Glu Leu Ile Gln Gly Leu
                    130                 135                 140
Glu Ala Asn Lys Ser Ser Gln Leu Val Thr Phe His Ile Asp Leu Asn
145                 150                 155                 160
Ser Val Asp Ile Leu Asp Lys Leu Thr Thr Thr Ser His Leu Ala Thr
                    165                 170                 175
Pro Gly Asn Val Ser Ile Glu Cys Leu Pro Gly Ser Ser Pro Cys Thr
                    180                 185                 190
Asp Ala Leu Thr Cys Ile Lys Ala Asp Leu Phe Cys Asp Gly Glu Val
                    195                 200                 205
Asn Cys Pro Asp Gly Ser Asp Glu Asp Asn Lys Met Cys Ala Thr Val
                    210                 215                 220
Cys Asp Gly Arg Phe Leu Leu Thr Gly Ser Ser Gly Ser Phe Gln Ala
225                 230                 235                 240
Thr His Tyr Pro Lys Pro Ser Glu Thr Ser Val Val Cys Gln Trp Ile
                    245                 250                 255
Ile Arg Val Asn Gln Gly Leu Ser Ile Lys Leu Ser Phe Asp Asp Phe
                    260                 265                 270
Asn Thr Tyr Tyr Thr Asp Ile Leu Asp Ile Tyr Glu Gly Val Gly Ser
                    275                 280                 285
Ser Lys Ile Leu Arg Ala Ser Ile Trp Glu Thr Asn Pro Gly Thr Ile
                    290                 295                 300
Arg Ile Phe Ser Asn Gln Val Thr Ala Thr Phe Leu Ile Glu Ser Asp
305                 310                 315                 320
Glu Ser Asp Tyr Val Gly Phe Asn Ala Thr Tyr Thr Ala Phe Asn Ser
                    325                 330                 335
Ser Glu Leu Asn Asn Tyr Glu Lys Ile Asn Cys Asn Phe Glu Asp Gly
                    340                 345                 350
Phe Cys Phe Trp Val Gln Asp Leu Asn Asp Asp Asn Glu Trp Glu Arg
                    355                 360                 365
Ile Gln Gly Ser Thr Phe Ser Pro Phe Thr Gly Pro Asn Phe Asp His
                    370                 375                 380
Thr Phe Gly Asn Ala Ser Gly Phe Tyr Ile Ser Thr Pro Thr Gly Pro
385                 390                 395                 400
Gly Gly Arg Gln Glu Arg Val Gly Leu Leu Ser Leu Pro Leu Asp Pro
                    405                 410                 415
Thr Leu Glu Pro Ala Cys Leu Ser Phe Trp Tyr His Met Tyr Gly Glu
                    420                 425                 430
Asn Val His Lys Leu Ser Ile Asn Ile Ser Asn Asp Gln Asn Met Glu
                    435                 440                 445
Lys Thr Val Phe Gln Lys Glu Gly Asn Tyr Gly Asp Asn Trp Asn Tyr
                    450                 455                 460
Gly Gln Val Thr Leu Asn Glu Thr Val Lys Phe Lys Val Ala Phe Asn
465                 470                 475                 480
Ala Phe Lys Asn Lys Ile Leu Ser Asp Ile Ala Leu Asp Asp Ile Ser
                    485                 490                 495
```

```
Leu Thr Tyr Gly Ile Cys Asn Gly Ser Leu Tyr Pro Glu Pro Thr Leu
            500                 505                 510

Val Pro Thr Pro Pro Glu Leu Pro Thr Asp Cys Gly Gly Pro Phe
        515                 520                 525

Glu Leu Trp Glu Pro Asn Thr Thr Phe Ser Ser Thr Asn Phe Pro Asn
        530                 535                 540

Ser Tyr Pro Asn Leu Ala Phe Cys Val Trp Ile Leu Asn Ala Gln Lys
545                 550                 555                 560

Gly Lys Asn Ile Gln Leu His Phe Gln Glu Phe Asp Leu Glu Asn Ile
                565                 570                 575

Asn Asp Val Val Glu Ile Arg Asp Gly Glu Glu Ala Asp Ser Leu Leu
            580                 585                 590

Leu Ala Val Tyr Thr Gly Pro Gly Pro Val Lys Asp Val Phe Ser Thr
            595                 600                 605

Thr Asn Arg Met Thr Val Leu Leu Ile Thr Asn Asp Val Leu Ala Arg
        610                 615                 620

Gly Gly Phe Lys Ala Asn Phe Thr Thr Gly Tyr His Leu Gly Ile Pro
625                 630                 635                 640

Glu Pro Cys Lys Ala Asp His Phe Gln Cys Lys Asn Gly Glu Cys Val
                645                 650                 655

Pro Leu Val Asn Leu Cys Asp Gly His Leu His Cys Glu Asp Gly Ser
                660                 665                 670

Asp Glu Ala Asp Cys Val Arg Phe Phe Asn Gly Thr Thr Asn Asn Asn
                675                 680                 685

Gly Leu Val Arg Phe Arg Ile Gln Ser Ile Trp His Thr Ala Cys Ala
        690                 695                 700

Glu Asn Trp Thr Thr Gln Ile Ser Asn Asp Val Cys Gln Leu Leu Gly
705                 710                 715                 720

Leu Gly Ser Gly Asn Ser Ser Lys Pro Ile Phe Ser Thr Asp Gly Gly
                725                 730                 735

Pro Phe Val Lys Leu Asn Thr Ala Pro Asp Gly His Leu Ile Leu Thr
        740                 745                 750

Pro Ser Gln Gln Cys Leu Gln Asp Ser Leu Ile Arg Leu Gln Cys Asn
        755                 760                 765

His Lys Ser Cys Gly Lys Lys Leu Ala Ala Gln Asp Ile Thr Pro Lys
        770                 775                 780

Ile Val Gly Gly Ser Asn Ala Lys Glu Gly Ala Trp Pro Trp Val Val
785                 790                 795                 800

Gly Leu Tyr Tyr Gly Gly Arg Leu Leu Cys Gly Ala Ser Leu Val Ser
                805                 810                 815

Ser Asp Trp Leu Val Ser Ala Ala His Cys Val Tyr Gly Arg Asn Leu
        820                 825                 830

Glu Pro Ser Lys Trp Thr Ala Ile Leu Gly Leu His Met Lys Ser Asn
        835                 840                 845

Leu Thr Ser Pro Gln Thr Val Pro Arg Leu Ile Asp Glu Ile Val Ile
        850                 855                 860

Asn Pro His Tyr Asn Arg Arg Arg Lys Asp Asn Asp Ile Ala Met Met
865                 870                 875                 880

His Leu Glu Phe Lys Val Asn Tyr Thr Asp Tyr Ile Gln Pro Ile Cys
                885                 890                 895

Leu Pro Glu Glu Asn Gln Val Phe Pro Pro Gly Arg Asn Cys Ser Ile
        900                 905                 910
```

```
Ala Gly Trp Gly Thr Val Val Tyr Gln Gly Thr Thr Ala Asn Ile Leu
        915                 920                 925

Gln Glu Ala Asp Val Pro Leu Leu Ser Asn Glu Arg Cys Gln Gln Gln
        930                 935                 940

Met Pro Glu Tyr Asn Ile Thr Glu Asn Met Ile Cys Ala Gly Tyr Glu
945                 950                 955                 960

Glu Gly Gly Ile Asp Ser Cys Gln Gly Asp Ser Gly Gly Pro Leu Met
                965                 970                 975

Cys Gln Glu Asn Asn Arg Trp Phe Leu Ala Gly Val Thr Ser Phe Gly
        980                 985                 990

Tyr Lys Cys Ala Leu Pro Asn Arg Pro Gly Val Tyr Ala Arg Val Ser
        995                 1000                1005

Arg Phe Thr Glu Trp Ile Gln Ser Phe Leu His
        1010                1015
```

<210> SEQ ID NO 65
<211> LENGTH: 1500
<212> TYPE: DNA
<213> ORGANISM: Homo Sapien
<220> FEATURE:
<221> NAME/KEY: CDS
<222> LOCATION: (62)...(1318)
<223> OTHER INFORMATION: Nucleotide sequence encoding human airway
      trypsin-like protease
<300> PUBLICATION INFORMATION:
<308> DATABASE ACCESSION NUMBER: GenBank AB002134
<309> DATABASE ENTRY DATE: 1998-06-04

<400> SEQUENCE: 65

```
gagtgggaat ctcaaagcag ttgagtaggc agaaaaaaga acctcttcat taaggattaa       60 a atg tat agg cca gca cgt gta act tcg act tca aga ttt ctg aat cca      109
  Met Tyr Arg Pro Ala Arg Val Thr Ser Thr Ser Arg Phe Leu Asn Pro
  1               5                  10                  15 tat gta gta tgt ttc att gtc gtc gca ggg gta gtg atc ctg gca gtc      157
Tyr Val Val Cys Phe Ile Val Val Ala Gly Val Val Ile Leu Ala Val
                20                  25                  30 acc ata gct cta ctt gtt tac ttt tta gct ttt gat caa aaa tct tac      205
Thr Ile Ala Leu Leu Val Tyr Phe Leu Ala Phe Asp Gln Lys Ser Tyr
            35                  40                  45 ttt tat agg agc agt ttt caa ctc cta aat gtt gaa tat aat agt cag      253
Phe Tyr Arg Ser Ser Phe Gln Leu Leu Asn Val Glu Tyr Asn Ser Gln
        50                  55                  60 tta aat tca cca gct aca cag gaa tac agg act ttg agt gga aga att      301
Leu Asn Ser Pro Ala Thr Gln Glu Tyr Arg Thr Leu Ser Gly Arg Ile
65                  70                  75                  80 gaa tct ctg att act aaa aca ttc aaa gaa tca aat tta aga aat cag      349
Glu Ser Leu Ile Thr Lys Thr Phe Lys Glu Ser Asn Leu Arg Asn Gln
                85                  90                  95 ttc atc aga gct cat gtt gcc aaa ctg agg caa gat ggt agt ggt gtg      397
Phe Ile Arg Ala His Val Ala Lys Leu Arg Gln Asp Gly Ser Gly Val
                100                 105                 110 aga gcg gat gtt gtc atg aaa ttt caa ttc act aga aat aac aat gga      445
Arg Ala Asp Val Val Met Lys Phe Gln Phe Thr Arg Asn Asn Asn Gly
            115                 120                 125 gca tca atg aaa agc aga att gag tct gtt tta cga caa atg ctg aat      493
Ala Ser Met Lys Ser Arg Ile Glu Ser Val Leu Arg Gln Met Leu Asn
        130                 135                 140 aac tct gga aac ctg gaa ata aac cct tca act gag ata aca tca ctt      541
Asn Ser Gly Asn Leu Glu Ile Asn Pro Ser Thr Glu Ile Thr Ser Leu
145                 150                 155                 160
```

```
act gac cag gct gca gca aat tgg ctt att aat gaa tgt ggg gcc ggt      589
Thr Asp Gln Ala Ala Ala Asn Trp Leu Ile Asn Glu Cys Gly Ala Gly
            165                 170                 175 cca gac cta ata aca ttg tct gag cag aga atc ctt gga ggc act gag      637
Pro Asp Leu Ile Thr Leu Ser Glu Gln Arg Ile Leu Gly Gly Thr Glu
            180                 185                 190 gct gag gag gga agc tgg ccg tgg caa gtc agt ctg cgg ctc aat aat      685
Ala Glu Glu Gly Ser Trp Pro Trp Gln Val Ser Leu Arg Leu Asn Asn
        195                 200                 205 gcc cac cac tgt gga ggc agc ctg atc aat aac atg tgg atc ctg aca      733
Ala His His Cys Gly Gly Ser Leu Ile Asn Asn Met Trp Ile Leu Thr
    210                 215                 220 gca gct cac tgc ttc aga agc aac tct aat cct cgt gac tgg att gcc      781
Ala Ala His Cys Phe Arg Ser Asn Ser Asn Pro Arg Asp Trp Ile Ala
225                 230                 235                 240 acg tct ggt att tcc aca aca ttt cct aaa cta aga atg aga gta aga      829
Thr Ser Gly Ile Ser Thr Thr Phe Pro Lys Leu Arg Met Arg Val Arg
                245                 250                 255 aat att tta att cat aac aat tat aaa tct gca act cat gaa aat gac      877
Asn Ile Leu Ile His Asn Asn Tyr Lys Ser Ala Thr His Glu Asn Asp
            260                 265                 270 att gca ctt gtg aga ctt gag aac agt gtc acc ttt acc aaa gat atc      925
Ile Ala Leu Val Arg Leu Glu Asn Ser Val Thr Phe Thr Lys Asp Ile
            275                 280                 285 cat agt gtg tgt ctc cca gct gct acc cag aat att cca cct ggc tct      973
His Ser Val Cys Leu Pro Ala Ala Thr Gln Asn Ile Pro Pro Gly Ser
        290                 295                 300 act gct tat gta aca gga tgg ggc gct caa gaa tat gct ggc cac aca     1021
Thr Ala Tyr Val Thr Gly Trp Gly Ala Gln Glu Tyr Ala Gly His Thr
305                 310                 315                 320 gtt cca gag cta agg caa gga cag gtc aga ata ata agt aat gat gta     1069
Val Pro Glu Leu Arg Gln Gly Gln Val Arg Ile Ile Ser Asn Asp Val
                325                 330                 335 tgt aat gca cca cat agt tat aat gga gcc atc ttg tct gga atg ctg     1117
Cys Asn Ala Pro His Ser Tyr Asn Gly Ala Ile Leu Ser Gly Met Leu
            340                 345                 350 tgt gct gga gta cct caa ggt gga gtg gac gca tgt cag ggt gac tct     1165
Cys Ala Gly Val Pro Gln Gly Gly Val Asp Ala Cys Gln Gly Asp Ser
        355                 360                 365 ggt ggc cca cta gta caa gaa gac tca cgg cgg ctt tgg ttt att gtg     1213
Gly Gly Pro Leu Val Gln Glu Asp Ser Arg Arg Leu Trp Phe Ile Val
    370                 375                 380 ggg ata gta agc tgg gga gat cag tgt ggc ctg ccg gat aag cca gga     1261
Gly Ile Val Ser Trp Gly Asp Gln Cys Gly Leu Pro Asp Lys Pro Gly
385                 390                 395                 400 gtg tat act cga gtg aca gcc tac ctt gac tgg att agg caa caa act     1309
Val Tyr Thr Arg Val Thr Ala Tyr Leu Asp Trp Ile Arg Gln Gln Thr
                405                 410                 415 ggg atc tag tgcaacaagt gcatccctgt tgcaaagtct gtatgcaggt             1358
Gly Ile * gtgcctgtct taaattccaa agctttacat ttcaactgaa aaagaaacta gaaatgtcct   1418
aatttaacat cttgttacat aaatatggtt taacaaacac tgtttaacct ttctttatta  1478
ttaaaggttt tctattttct cc                                            1500

<210> SEQ ID NO 66
<211> LENGTH: 418
<212> TYPE: PRT
<213> ORGANISM: Homo Sapien
```

<400> SEQUENCE: 66

```
Met Tyr Arg Pro Ala Arg Val Thr Ser Thr Ser Arg Phe Leu Asn Pro
1               5                   10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Gly Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415
```

Gly Ile

```
<210> SEQ ID NO 67
<211> LENGTH: 1783
<212> TYPE: DNA
<213> ORGANISM: Homo Sapien
<220> FEATURE:
<221> NAME/KEY: CDS
<222> LOCATION: (246)...(1499)
<223> OTHER INFORMATION: Nucleotide sequence encoding human hepsin
<300> PUBLICATION INFORMATION:
<308> DATABASE ACCESSION NUMBER: GenBank M18930
<309> DATABASE ENTRY DATE: 1993-06-11

<400> SEQUENCE: 67
```

| | | |
|---|---|---|
| tcgagcccgc tttccaggga ccctacctga gggcccacag gtgaggcagc ctggcctagc | | 60 |
| aggccccacg ccaccgcctc tgcctccagg ccgcccgctg ctgcggggcc accatgctcc | | 120 |
| tgcccaggcc tggagactga cccgaccccg cactacctc gaggctccgc ccccaccctgc | | 180 |
| tggaccccag gtcccaccc tgcccagga ggtcagccag ggaatcatta acaagaggca | | 240 |

| | |  |
|---|---|---|
| gtgac atg gcg cag aag gag ggt ggc cgg act gtg cca tgc tgc tcc aga<br>     Met Ala Gln Lys Glu Gly Gly Arg Thr Val Pro Cys Cys Ser Arg<br>      1            5                10              15 | 290 |
| ccc aag gtg gca gct ctc act gcg ggg acc ctg cta ctt ctg aca gcc<br>Pro Lys Val Ala Ala Leu Thr Ala Gly Thr Leu Leu Leu Leu Thr Ala<br>             20                     25                     30 | 338 |
| atc ggg gcg gca tcc tgg gcc att gtg gct gtt ctc ctc agg agt gac<br>Ile Gly Ala Ala Ser Trp Ala Ile Val Ala Val Leu Leu Arg Ser Asp<br>           35                    40                   45 | 386 |
| cag gag ccg ctg tac cca gtg cag gtc agc tct gcg gac gct cgg ctc<br>Gln Glu Pro Leu Tyr Pro Val Gln Val Ser Ser Ala Asp Ala Arg Leu<br>      50                     55                     60 | 434 |
| atg gtc ttt gac aag acg gaa ggg acg tgg cgg ctg ctg tgc tcc tcg<br>Met Val Phe Asp Lys Thr Glu Gly Thr Trp Arg Leu Leu Cys Ser Ser<br>65                     70                     75 | 482 |
| cgc tcc aac gcc agg gta gcc gga ctc agc tgc gag gag atg ggc ttc<br>Arg Ser Asn Ala Arg Val Ala Gly Leu Ser Cys Glu Glu Met Gly Phe<br> 80                     85                     90              95 | 530 |
| ctc agg gca ctg acc cac tcc gag ctg gac gtg cga acg gcg ggc gcc<br>Leu Arg Ala Leu Thr His Ser Glu Leu Asp Val Arg Thr Ala Gly Ala<br>           100                   105                 110 | 578 |
| aat ggc acg tcg ggc ttc ttc tgt gtg gac gag ggg agg ctg ccc cac<br>Asn Gly Thr Ser Gly Phe Phe Cys Val Asp Glu Gly Arg Leu Pro His<br>        115                  120                  125 | 626 |
| acc cag agg ctg ctg gag gtc atc tcc gtg tgt gat tgc ccc aga ggc<br>Thr Gln Arg Leu Leu Glu Val Ile Ser Val Cys Asp Cys Pro Arg Gly<br>       130                  135                  140 | 674 |
| cgt ttc ttg gcc gcc atc tgc caa gac tgt ggc cgc agg aag ctg ccc<br>Arg Phe Leu Ala Ala Ile Cys Gln Asp Cys Gly Arg Arg Lys Leu Pro<br>145                  150                   155 | 722 |
| gtg gac cgc atc gtg gga ggc cgg gac acc agc ttg ggc cgg tgg ccg<br>Val Asp Arg Ile Val Gly Gly Arg Asp Thr Ser Leu Gly Arg Trp Pro<br>160                   165                   170               175 | 770 |
| tgg caa gtc agc ctt cgc tat gat gga gca cac ctc tgt ggg gga tcc<br>Trp Gln Val Ser Leu Arg Tyr Asp Gly Ala His Leu Cys Gly Gly Ser<br>              180                   185                  190 | 818 |
| ctg ctc tcc ggg gac tgg gtg ctg aca gcc gcc cac tgc ttc ccg gag<br>Leu Leu Ser Gly Asp Trp Val Leu Thr Ala Ala His Cys Phe Pro Glu<br>        195                  200                  205 | 866 |
| cgg aac cgg gtc ctg tcc cga tgg cga gtg ttt gcc ggt gcc gtg gcc | 914 |

| | | |
|---|---|---|
| Arg Asn Arg Val Leu Ser Arg Trp Arg Val Phe Ala Gly Ala Val Ala<br>        210                          215                      220 | | |
| cag gcc tct ccc cac ggt ctg cag ctg ggg gtg cag gct gtg gtc tac<br>Gln Ala Ser Pro His Gly Leu Gln Leu Gly Val Gln Ala Val Val Tyr<br>225                     230                     235 | 962 | |
| cac ggg ggc tat ctt ccc ttt cgg gac ccc aac agc gag gag aac agc<br>His Gly Gly Tyr Leu Pro Phe Arg Asp Pro Asn Ser Glu Glu Asn Ser<br>240                   245                   250                   255 | 1010 | |
| aac gat att gcc ctg gtc cac ctc tcc agt ccc ctg ccc ctc aca gaa<br>Asn Asp Ile Ala Leu Val His Leu Ser Ser Pro Leu Pro Leu Thr Glu<br>                   260                   265                   270 | 1058 | |
| tac atc cag cct gtg tgc ctc cca gct gcc ggc cag gcc ctg gtg gat<br>Tyr Ile Gln Pro Val Cys Leu Pro Ala Ala Gly Gln Ala Leu Val Asp<br>                   275                   280                   285 | 1106 | |
| ggc aag atc tgt acc gtg acg ggc tgg ggc aac acg cag tac tat ggc<br>Gly Lys Ile Cys Thr Val Thr Gly Trp Gly Asn Thr Gln Tyr Tyr Gly<br>                   290                   295                   300 | 1154 | |
| caa cag gcc ggg gta ctc cag gag gct cga gtc ccc ata atc agc aat<br>Gln Gln Ala Gly Val Leu Gln Glu Ala Arg Val Pro Ile Ile Ser Asn<br>305                     310                     315 | 1202 | |
| gat gtc tgc aat ggc gct gac ttc tat gga aac cag atc aag ccc aag<br>Asp Val Cys Asn Gly Ala Asp Phe Tyr Gly Asn Gln Ile Lys Pro Lys<br>320                     325                     330                   335 | 1250 | |
| atg ttc tgt gct ggc tac ccc gag ggt ggc att gat gcc tgc cag ggc<br>Met Phe Cys Ala Gly Tyr Pro Glu Gly Gly Ile Asp Ala Cys Gln Gly<br>                   340                   345                   350 | 1298 | |
| gac agc ggt ggt ccc ttt gtg tgt gag gac agc atc tct cgg acg cca<br>Asp Ser Gly Gly Pro Phe Val Cys Glu Asp Ser Ile Ser Arg Thr Pro<br>               355                     360                   365 | 1346 | |
| cgt tgg cgg ctg tgt ggc att gtg agt tgg ggc act ggc tgt gcc ctg<br>Arg Trp Arg Leu Cys Gly Ile Val Ser Trp Gly Thr Gly Cys Ala Leu<br>                   370                   375                   380 | 1394 | |
| gcc cag aag cca ggc gtc tac acc aaa gtc agt gac ttc cgg gag tgg<br>Ala Gln Lys Pro Gly Val Tyr Thr Lys Val Ser Asp Phe Arg Glu Trp<br>385                     390                     395 | 1442 | |
| atc ttc cag gcc ata aag act cac tcc gaa gcc agc ggc atg gtg acc<br>Ile Phe Gln Ala Ile Lys Thr His Ser Glu Ala Ser Gly Met Val Thr<br>400                     405                   410                   415 | 1490 | |
| cag ctc tga ccggtggctt ctcgctgcgc agcctccagg gcccgaggtg<br>Gln Leu * | 1539 | |
| atcccggtgg tgggatccac gctgggccga ggatgggacg ttttctttct tgggcccggt | 1599 | |
| ccacaggtcc aaggacaccc tccctccagg gtcctctctt ccacagtggc gggcccactc | 1659 | |
| agccccgaga ccacccaacc tcaccctcct gaccccatg taaatattgt tctgctgtct | 1719 | |
| gggactcctg tctaggtgcc cctgatgatg ggatgctctt taaataataa agatggtttt | 1779 | |
| gatt | 1783 | |

<210> SEQ ID NO 68
<211> LENGTH: 417
<212> TYPE: PRT
<213> ORGANISM: Homo Sapien

<400> SEQUENCE: 68

Met Ala Gln Lys Glu Gly Gly Arg Thr Val Pro Cys Cys Ser Arg Pro
1                 5                   10                  15

Lys Val Ala Ala Leu Thr Ala Gly Thr Leu Leu Leu Leu Thr Ala Ile
                   20                   25                   30

Gly Ala Ala Ser Trp Ala Ile Val Ala Val Leu Leu Arg Ser Asp Gln

-continued

```
              35                  40                  45
Glu Pro Leu Tyr Pro Val Gln Val Ser Ser Ala Asp Ala Arg Leu Met
 50                  55                  60

Val Phe Asp Lys Thr Glu Gly Thr Trp Arg Leu Leu Cys Ser Ser Arg
 65                  70                  75                  80

Ser Asn Ala Arg Val Ala Gly Leu Ser Cys Glu Glu Met Gly Phe Leu
                 85                  90                  95

Arg Ala Leu Thr His Ser Glu Leu Asp Val Arg Thr Ala Gly Ala Asn
                100                 105                 110

Gly Thr Ser Gly Phe Phe Cys Val Asp Glu Gly Arg Leu Pro His Thr
            115                 120                 125

Gln Arg Leu Leu Glu Val Ile Ser Val Cys Asp Cys Pro Arg Gly Arg
130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
        195                 200                 205

Asn Arg Val Leu Ser Arg Trp Arg Val Phe Ala Gly Ala Val Ala Gln
210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
        275                 280                 285

Lys Ile Cys Thr Val Thr Gly Trp Gly Asn Thr Gln Tyr Tyr Gly Gln
290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
            340                 345                 350

Ser Gly Gly Pro Phe Val Cys Glu Asp Ser Ile Ser Arg Thr Pro Arg
        355                 360                 365

Trp Arg Leu Cys Gly Ile Val Ser Trp Gly Thr Gly Cys Ala Leu Ala
370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu

<210> SEQ ID NO 69
<211> LENGTH: 2479
<212> TYPE: DNA
<213> ORGANISM: Homo sapien
<220> FEATURE:
```

-continued

```
<221> NAME/KEY: CDS
<222> LOCATION: (57)...(1535)
<223> OTHER INFORMATION: Nucleotide sequence encoding human serine
      protease
<300> PUBLICATION INFORMATION:
<308> DATABASE ACCESSION NUMBER: GenBank U75329
<309> DATABASE ENTRY DATE: 1997-10-10

<400> SEQUENCE: 69
gtcatattga acattccaga tacctatcat tactcgatgc tgttgataac agcaag atg        59
                                                              Met
                                                                1 gct ttg aac tca ggg tca cca cca gct att gga cct tac tat gaa aac       107
Ala Leu Asn Ser Gly Ser Pro Pro Ala Ile Gly Pro Tyr Tyr Glu Asn
          5                  10                  15 cat gga tac caa ccg gaa aac ccc tat ccc gca cag ccc act gtg gtc       155
His Gly Tyr Gln Pro Glu Asn Pro Tyr Pro Ala Gln Pro Thr Val Val
 20                  25                  30 ccc act gtc tac gag gtg cat ccg gct cag tac tac ccg tcc ccc gtg       203
Pro Thr Val Tyr Glu Val His Pro Ala Gln Tyr Tyr Pro Ser Pro Val
         35                  40                  45 ccc cag tac gcc ccg agg gtc ctg acg cag gct tcc aac ccc gtc gtc       251
Pro Gln Tyr Ala Pro Arg Val Leu Thr Gln Ala Ser Asn Pro Val Val
 50                  55                  60                  65 tgc acg cag ccc aaa tcc cca tcc ggg aca gtg tgc acc tca aag act       299
Cys Thr Gln Pro Lys Ser Pro Ser Gly Thr Val Cys Thr Ser Lys Thr
                 70                  75                  80 aag aaa gca ctg tgc atc acc ttg acc ctg ggg acc ttc ctc gtg gga       347
Lys Lys Ala Leu Cys Ile Thr Leu Thr Leu Gly Thr Phe Leu Val Gly
             85                  90                  95 gct gcg ctg gcc gct ggc cta ctc tgg aag ttc atg ggc agc aag tgc       395
Ala Ala Leu Ala Ala Gly Leu Leu Trp Lys Phe Met Gly Ser Lys Cys
        100                 105                 110 tcc aac tct ggg ata gag tgc gac tcc tca ggt acc tgc atc aac ccc       443
Ser Asn Ser Gly Ile Glu Cys Asp Ser Ser Gly Thr Cys Ile Asn Pro
    115                 120                 125 tct aac tgg tgt gat ggc gtg tca cac tgc ccc ggc ggg gag gac gag       491
Ser Asn Trp Cys Asp Gly Val Ser His Cys Pro Gly Gly Glu Asp Glu
130                 135                 140                 145 aat cgg tgt gtt cgc ctc tac gga cca aac ttc atc ctt cag atg tac       539
Asn Arg Cys Val Arg Leu Tyr Gly Pro Asn Phe Ile Leu Gln Met Tyr
                150                 155                 160 tca tct cag agg aag tcc tgg cac cct gtg tgc caa gac gac tgg aac       587
Ser Ser Gln Arg Lys Ser Trp His Pro Val Cys Gln Asp Asp Trp Asn
            165                 170                 175 gag aac tac ggg cgg gcg gcc tgc agg gac atg ggc tat aag aat aat       635
Glu Asn Tyr Gly Arg Ala Ala Cys Arg Asp Met Gly Tyr Lys Asn Asn
        180                 185                 190 ttt tac tct agc caa gga ata gtg gat gac agc gga tcc acc agc ttt       683
Phe Tyr Ser Ser Gln Gly Ile Val Asp Asp Ser Gly Ser Thr Ser Phe
    195                 200                 205 atg aaa ctg aac aca agt gcc ggc aat gtc gat atc tat aaa aaa ctg       731
Met Lys Leu Asn Thr Ser Ala Gly Asn Val Asp Ile Tyr Lys Lys Leu
210                 215                 220                 225 tac cac agt gat gcc tgt tct tca aaa gca gtg gtt tct tta cgc tgt       779
Tyr His Ser Asp Ala Cys Ser Ser Lys Ala Val Val Ser Leu Arg Cys
                230                 235                 240 tta gcc tgc ggg gtc aac ttg aac tca agc cgc cag agc agg atc gtg       827
Leu Ala Cys Gly Val Asn Leu Asn Ser Ser Arg Gln Ser Arg Ile Val
            245                 250                 255 ggc ggt gag agc gcg ctc ccg ggg gcc tgg ccc tgg cag gtc agc ctg       875
```

```
Gly Gly Glu Ser Ala Leu Pro Gly Ala Trp Pro Trp Gln Val Ser Leu
            260                 265                 270 cac gtc cag aac gtc cac gtg tgc gga ggc tcc atc atc acc ccc gag      923
His Val Gln Asn Val His Val Cys Gly Gly Ser Ile Ile Thr Pro Glu
275                 280                 285 tgg atc gtg aca gcc gcc cac tgc gtg gaa aaa cct ctt aac aat cca      971
Trp Ile Val Thr Ala Ala His Cys Val Glu Lys Pro Leu Asn Asn Pro
290                 295                 300                 305 tgg cat tgg acg gca ttt gcg ggg att ttg aga caa tct ttc atg ttc     1019
Trp His Trp Thr Ala Phe Ala Gly Ile Leu Arg Gln Ser Phe Met Phe
            310                 315                 320 tat gga gcc gga tac caa gta caa aaa gtg att tct cat cca aat tat     1067
Tyr Gly Ala Gly Tyr Gln Val Gln Lys Val Ile Ser His Pro Asn Tyr
            325                 330                 335 gac tcc aag acc aag aac aat gac att gcg ctg atg aag ctg cag aag     1115
Asp Ser Lys Thr Lys Asn Asn Asp Ile Ala Leu Met Lys Leu Gln Lys
            340                 345                 350 cct ctg act ttc aac gac cta gtg aaa cca gtg tgt ctg ccc aac cca     1163
Pro Leu Thr Phe Asn Asp Leu Val Lys Pro Val Cys Leu Pro Asn Pro
355                 360                 365 ggc atg atg ctg cag cca gaa cag ctc tgc tgg att tcc ggg tgg ggg     1211
Gly Met Met Leu Gln Pro Glu Gln Leu Cys Trp Ile Ser Gly Trp Gly
370                 375                 380                 385 gcc acc gag gag aaa ggg aag acc tca gaa gtg ctg aac gct gcc aag     1259
Ala Thr Glu Glu Lys Gly Lys Thr Ser Glu Val Leu Asn Ala Ala Lys
            390                 395                 400 gtg ctt ctc att gag aca cag aga tgc aac agc aga tat gtc tat gac     1307
Val Leu Leu Ile Glu Thr Gln Arg Cys Asn Ser Arg Tyr Val Tyr Asp
            405                 410                 415 aac ctg atc aca cca gcc atg atc tgt gcc ggc ttc ctg cag ggg aac     1355
Asn Leu Ile Thr Pro Ala Met Ile Cys Ala Gly Phe Leu Gln Gly Asn
            420                 425                 430 gtc gat tct tgc cag ggt gac agt gga ggg cct ctg gtc act tcg aac     1403
Val Asp Ser Cys Gln Gly Asp Ser Gly Gly Pro Leu Val Thr Ser Asn
435                 440                 445 aac aat atc tgg tgg ctg ata ggg gat aca agc tgg ggt tct ggc tgt     1451
Asn Asn Ile Trp Trp Leu Ile Gly Asp Thr Ser Trp Gly Ser Gly Cys
450                 455                 460                 465 gcc aaa gct tac aga cca gga gtg tac ggg aat gtg atg gta ttc acg     1499
Ala Lys Ala Tyr Arg Pro Gly Val Tyr Gly Asn Val Met Val Phe Thr
            470                 475                 480 gac tgg att tat cga caa atg aag gca aac ggc taa tccacatggt          1545
Asp Trp Ile Tyr Arg Gln Met Lys Ala Asn Gly  *
            485                 490 cttcgtcctt gacgtcgttt tacaagaaaa caatggggct ggttttgctt ccccgtgcat  1605
gatttactct tagagatgat tcagaggtca cttcattttt attaaacagt gaacttgtct  1665
ggctttggca ctctctgcca tactgtgcag gctgcagtgg ctcccctgcc cagcctgctc  1725
tccctaaccc cttgtccgca agggtgatg gccggctggt tgtgggcact ggcggtcaat   1785
tgtggaagga agagggttgg aggctgcccc cattgagatc ttcctgctga gtcctttcca  1845
ggggccaatt ttggatgagc atggagctgt cacttctcag ctgctggatg acttgagatg  1905
aaaaaggaga gacatggaaa gggagacagc caggtggcac ctgcagcggc tgccctctgg  1965
ggccacttgg tagtgtcccc agcctacttc acaagggat tttgctgatg ggttcttaga   2025
gccttagcag ccctggatgg tggccagaaa taaaggggacc agcccttcat gggtggtgac  2085
gtggtagtca cttgtaaggg gaacagaaac attttttgttc ttatggggtg agaatataga  2145
```

```
cagtgccctt ggtgcgaggg aagcaattga aaaggaactt gccctgagca ctcctggtgc    2205
aggtctccac ctgcacattg gtggggctc ctgggaggga gactcagcct tcctcctcat     2265
cctccctgac cctgctccta gcaccctgga gagtgaatgc ccttggtcc ctggcagggc    2325 gccaagtttg gcaccatgtc ggcctcttca ggcctgatag tcattggaaa ttgaggtcca    2385
tgggggaaat caaggatgct cagtttaagg tacactgttt ccatgttatg tttctacaca    2445
ttgatggtgg tgaccctgag ttcaaagcca tctt                                 2479

<210> SEQ ID NO 70
<211> LENGTH: 492
<212> TYPE: PRT
<213> ORGANISM: Homo sapien

<400> SEQUENCE: 70

Met Ala Leu Asn Ser Gly Ser Pro Ala Ile Gly Pro Tyr Tyr Glu
 1               5                  10                  15

Asn His Gly Tyr Gln Pro Glu Asn Pro Tyr Pro Ala Gln Pro Thr Val
                20                  25                  30

Val Pro Thr Val Tyr Glu Val His Pro Ala Gln Tyr Tyr Pro Ser Pro
            35                  40                  45

Val Pro Gln Tyr Ala Pro Arg Val Leu Thr Gln Ala Ser Asn Pro Val
        50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Leu Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320
```

```
Phe Tyr Gly Ala Gly Tyr Gln Val Gln Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
        435                 440                 445

Asn Asn Asn Ile Trp Trp Leu Ile Gly Asp Thr Ser Trp Gly Ser Gly
    450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Lys Ala Asn Gly
                485                 490

<210> SEQ ID NO 71
<211> LENGTH: 2079
<212> TYPE: DNA
<213> ORGANISM: Homo sapien
<220> FEATURE:
<221> NAME/KEY: CDS
<222> LOCATION: (251)...(1522)
<223> OTHER INFORMATION: Nucleotide sequence encoding transmembrane
      protease, serine 4 (TMPRSS4)
<300> PUBLICATION INFORMATION:
<308> DATABASE ACCESSION NUMBER: GenBank NM016425
<309> DATABASE ENTRY DATE: 2000-11-06

<400> SEQUENCE: 71
gagaggcagc agcttgttca gcggacaagg atgctgggcg tgagggacca aggcctgccc     60
tgcactcggg cctcctccag ccagtgctga ccagggactt ctgacctgct ggccagccag    120
gacctgtgtg gggaggccct cctgctgcct tggggtgaca atctcagctc caggctacag    180
ggagaccggg aggatcacag agccagcatg gtacaggatc tgacagtga tcaacctctg    240 aacagcctcg atg tca aac ccc tgc gca aac ccc gta tcc cca tgg aga      289
            Met Ser Asn Pro Cys Ala Asn Pro Val Ser Pro Trp Arg
            1               5                   10 cct tca gaa agt gtg ggg atc ccc atc atc ata gca cta ctg agc ctg      337
Pro Ser Glu Ser Val Gly Ile Pro Ile Ile Ile Ala Leu Leu Ser Leu
    15                  20                  25 gcg agt atc atc att gtg gtt gtc ctc atc aag gtg att ctg gat aaa      385
Ala Ser Ile Ile Ile Val Val Val Leu Ile Lys Val Ile Leu Asp Lys
30                  35                  40                  45 tac tac ttc ctc tgc ggg cag cct ctc cac ttc atc ccg agg aag cag      433
Tyr Tyr Phe Leu Cys Gly Gln Pro Leu His Phe Ile Pro Arg Lys Gln
                50                  55                  60 ctg tgt gac gga gag ctg gac tgt ccc ttg ggg gag gac gag gag cac      481
Leu Cys Asp Gly Glu Leu Asp Cys Pro Leu Gly Glu Asp Glu Glu His
            65                  70                  75 tgt gtc aag agc ttc ccc gaa ggg cct gca gtg gca gtc cgc ctc tcc      529
```

```
            Cys Val Lys Ser Phe Pro Glu Gly Pro Ala Val Ala Val Arg Leu Ser
                    80                  85                  90 aag gac cga tcc aca ctg cag gtg ctg gac tcg gcc aca ggg aac tgg        577
Lys Asp Arg Ser Thr Leu Gln Val Leu Asp Ser Ala Thr Gly Asn Trp
 95                 100                 105 ttc tct gcc tgt ttc gac aac ttc aca gaa gct ctc gct gag aca gcc        625
Phe Ser Ala Cys Phe Asp Asn Phe Thr Glu Ala Leu Ala Glu Thr Ala
110                 115                 120                 125 tgt agg cag atg ggc tac agc agc aaa ccc act ttc aga gct gtg gag        673
Cys Arg Gln Met Gly Tyr Ser Ser Lys Pro Thr Phe Arg Ala Val Glu
                130                 135                 140 att ggc cca gac cag gat ctg gat gtt gtt gaa atc aca gaa aac agc        721
Ile Gly Pro Asp Gln Asp Leu Asp Val Val Glu Ile Thr Glu Asn Ser
            145                 150                 155 cag gag ctt cgc atg cgg aac tca agt ggg ccc tgt ctc tca ggc tcc        769
Gln Glu Leu Arg Met Arg Asn Ser Ser Gly Pro Cys Leu Ser Gly Ser
        160                 165                 170 ctg gtc tcc ctg cac tgt ctt gcc tgt ggg aag agc ctg aag acc ccc        817
Leu Val Ser Leu His Cys Leu Ala Cys Gly Lys Ser Leu Lys Thr Pro
    175                 180                 185 cgt gtg gtg ggt ggg gag gag gcc tct gtg gat tct tgg cct tgg cag        865
Arg Val Val Gly Gly Glu Glu Ala Ser Val Asp Ser Trp Pro Trp Gln
190                 195                 200                 205 gtc agc atc cag tac gac aaa cag cac gtc tgt gga ggg agc atc ctg        913
Val Ser Ile Gln Tyr Asp Lys Gln His Val Cys Gly Gly Ser Ile Leu
                210                 215                 220 gac ccc cac tgg gtc ctc acg gca gcc cac tgc ttc agg aaa cat acc        961
Asp Pro His Trp Val Leu Thr Ala Ala His Cys Phe Arg Lys His Thr
            225                 230                 235 gat gtg ttc aac tgg aag gtg cgg gca ggc tca gac aaa ctg ggc agc       1009
Asp Val Phe Asn Trp Lys Val Arg Ala Gly Ser Asp Lys Leu Gly Ser
        240                 245                 250 ttc cca tcc ctg gct gtg gcc aag atc atc atc att gaa ttc aac ccc       1057
Phe Pro Ser Leu Ala Val Ala Lys Ile Ile Ile Ile Glu Phe Asn Pro
    255                 260                 265 atg tac ccc aaa gac aat gac atc gcc ctc atg aag ctg cag ttc cca       1105
Met Tyr Pro Lys Asp Asn Asp Ile Ala Leu Met Lys Leu Gln Phe Pro
270                 275                 280                 285 ctc act ttc tca ggc aca gtc agg ccc atc tgt ctg ccc ttc ttt gat       1153
Leu Thr Phe Ser Gly Thr Val Arg Pro Ile Cys Leu Pro Phe Phe Asp
                290                 295                 300 gag gag ctc act cca gcc acc cca ctc tgg atc att gga tgg ggc ttt       1201
Glu Glu Leu Thr Pro Ala Thr Pro Leu Trp Ile Ile Gly Trp Gly Phe
            305                 310                 315 acg aag cag aat gga ggg aag atg tct gac ata ctg ctg cag gcg tca       1249
Thr Lys Gln Asn Gly Gly Lys Met Ser Asp Ile Leu Leu Gln Ala Ser
        320                 325                 330 gtc cag gtc att gac agc aca cgg tgc aat gca gac gat gcg tac cag       1297
Val Gln Val Ile Asp Ser Thr Arg Cys Asn Ala Asp Asp Ala Tyr Gln
    335                 340                 345 ggg gaa gtc acc gag aag atg atg tgt gca ggc atc ccg gaa ggg ggt       1345
Gly Glu Val Thr Glu Lys Met Met Cys Ala Gly Ile Pro Glu Gly Gly
350                 355                 360                 365 gtg gac acc tgc cag ggt gac agt ggt ggg ccc ctg atg tac caa tct       1393
Val Asp Thr Cys Gln Gly Asp Ser Gly Gly Pro Leu Met Tyr Gln Ser
                370                 375                 380 gac cag tgg cat gtg gtg ggc atc gtt agc tgg ggc tat ggc tgc ggg       1441
Asp Gln Trp His Val Val Gly Ile Val Ser Trp Gly Tyr Gly Cys Gly
            385                 390                 395
```

-continued

```
ggc ccg agc acc cca gga gta tac acc aag gtc tca gcc tat ctc aac       1489
Gly Pro Ser Thr Pro Gly Val Tyr Thr Lys Val Ser Ala Tyr Leu Asn
        400                 405                 410 tgg atc tac aat gtc tgg aag gct gag ctg taa tgctgctgcc cctttgcagt     1542
Trp Ile Tyr Asn Val Trp Lys Ala Glu Leu *
    415                 420 gctgggagcc gcttccttcc tgccctgccc acctggggat ccccaaagt cagacacaga      1602 gcaagagtcc cctgggtac accccctctgc ccacagcctc agcatttctt ggagcagcaa     1662
agggcctcaa ttcctgtaag accctcgc agcccagagg cgcccagagg aagtcagcag       1722
ccctagctcg gccacacttg gtgctcccag catcccaggg agagacacag cccactgaac     1782
aaggtctcag gggtattgct aagccaagaa ggaactttcc cacactactg aatggaagca     1842
ggctgtcttg taaaagccca gatcactgtg gctggagag gagaaggaaa gggtctgcgc      1902
cagccctgtc cgtcttcacc catccccaag cctactagag caagaaacca gttgtaatat     1962
aaaatgcact gccctactgt tggtatgact accgttacct actgttgtca ttgttattac     2022
agctatggcc actattatta aagagctgtg taacatcaaa aaaaaaaaaa aaaaaaa       2079
```

<210> SEQ ID NO 72
<211> LENGTH: 423
<212> TYPE: PRT
<213> ORGANISM: Homo sapien

<400> SEQUENCE: 72

```
Met Ser Asn Pro Cys Ala Asn Pro Val Ser Pro Trp Arg Pro Ser Glu
 1               5                  10                  15

Ser Val Gly Ile Pro Ile Ile Ala Leu Leu Ser Leu Ala Ser Ile
            20                  25                  30

Ile Ile Val Val Leu Ile Lys Val Ile Leu Asp Lys Tyr Tyr Phe
        35                  40                  45

Leu Cys Gly Gln Pro Leu His Phe Ile Pro Arg Lys Gln Leu Cys Asp
 50                  55                  60

Gly Glu Leu Asp Cys Pro Leu Gly Glu Asp Glu His Cys Val Lys
 65                  70                  75                  80

Ser Phe Pro Glu Gly Pro Ala Val Ala Val Arg Leu Ser Lys Asp Arg
                85                  90                  95

Ser Thr Leu Gln Val Leu Asp Ser Ala Thr Gly Asn Trp Phe Ser Ala
            100                 105                 110

Cys Phe Asp Asn Phe Thr Glu Ala Leu Ala Glu Thr Ala Cys Arg Gln
        115                 120                 125

Met Gly Tyr Ser Ser Lys Pro Thr Phe Arg Ala Val Glu Ile Gly Pro
    130                 135                 140

Asp Gln Asp Leu Asp Val Val Glu Ile Thr Glu Asn Ser Gln Glu Leu
145                 150                 155                 160

Arg Met Arg Asn Ser Ser Gly Pro Cys Leu Ser Gly Ser Leu Val Ser
                165                 170                 175

Leu His Cys Leu Ala Cys Gly Lys Ser Leu Lys Thr Pro Arg Val Val
            180                 185                 190

Gly Gly Glu Glu Ala Ser Val Asp Ser Trp Pro Trp Gln Val Ser Ile
        195                 200                 205

Gln Tyr Asp Lys Gln His Val Cys Gly Gly Ser Ile Leu Asp Pro His
    210                 215                 220

Trp Val Leu Thr Ala Ala His Cys Phe Arg Lys His Thr Asp Val Phe
225                 230                 235                 240
```

-continued

```
Asn Trp Lys Val Arg Ala Gly Ser Asp Lys Leu Gly Ser Phe Pro Ser
            245                 250                 255

Leu Ala Val Ala Lys Ile Ile Ile Ile Glu Phe Asn Pro Met Tyr Pro
            260             265                 270

Lys Asp Asn Asp Ile Ala Leu Met Lys Leu Gln Phe Pro Leu Thr Phe
        275                 280                 285

Ser Gly Thr Val Arg Pro Ile Cys Leu Pro Phe Phe Asp Glu Glu Leu
    290                 295             300

Thr Pro Ala Thr Pro Leu Trp Ile Ile Gly Trp Gly Phe Thr Lys Gln
305                 310                 315                 320

Asn Gly Gly Lys Met Ser Asp Ile Leu Leu Gln Ala Ser Val Gln Val
                325             330                 335

Ile Asp Ser Thr Arg Cys Asn Ala Asp Asp Ala Tyr Gln Gly Glu Val
            340             345                 350

Thr Glu Lys Met Met Cys Ala Gly Ile Pro Glu Gly Gly Val Asp Thr
            355                 360                 365

Cys Gln Gly Asp Ser Gly Gly Pro Leu Met Tyr Gln Ser Asp Gln Trp
    370                 375                 380

His Val Val Gly Ile Val Ser Trp Gly Tyr Gly Cys Gly Gly Pro Ser
385                 390                 395                 400

Thr Pro Gly Val Tyr Thr Lys Val Ser Ala Tyr Leu Asn Trp Ile Tyr
                405                 410                 415

Asn Val Trp Lys Ala Glu Leu
                420
```

NUCLEIC ACID MOLECULES ENCODING TRANSMEMBRANE SERINE PROTEASES, THE ENCODED PROTEINS AND METHODS BASED THEREON

RELATED APPLICATIONS

This application is a divisional of U.S. application Ser. No. 09/776,191, to Edwin L. Madison, Edgar O. Ong and Jiunn-Chern Yeh, filed on Feb. 2, 2001, entitled "NUCLEIC ACID MOLECULES ENCODING TRANSMEMBRANE SERINE PROTEASES, THE ENCODED PROTEINS AND METHODS BASED THEREON," now U.S. Pat. No. 7,700,341, which claims the benefit of priority under 35 U.S.C. §119(e) to U.S. provisional application Ser. No. 60/179,982, to Edwin L. Madison and Edgar O. Ong, filed Feb. 3, 2000, entitled "NUCLEOTIDE AND PROTEIN SEQUENCES OF A TRANSMEMBRANE SERINE PROTEASE AND METHODS BASED THEREOF"; to U.S. provisional application Ser. No. 60/183,542, to Edwin L. Madison and Edgar O. Ong, filed Feb. 18, 2000, entitled "NUCLEOTIDE AND PROTEIN SEQUENCES OF A TRANSMEMBRANE SERINE PROTEASE AND METHODS BASED THEREOF"; to U.S. provisional application Ser. No. 60/213,124, to Edwin L. Madison and Edgar O. Ong, filed Jun. 22, 2000, entitled "NUCLEOTIDE AND PROTEIN SEQUENCES OF A TRANSMEMBRANE SERINE PROTEASE AND METHODS BASED THEREOF"; to U.S. provisional application Ser. No. 60/220,970, to Edwin L. Madison and Edgar O. Ong, filed Jul. 26, 2000, entitled "NUCLEOTIDE AND PROTEIN SEQUENCES OF A TRANSMEMBRANE SERINE PROTEASE AND METHODS BASED THEREOF"; and to U.S. provisional application Ser. No. 60/234,840 to Edwin L. Madison, Edgar O. Ong and Jiunn-Chern Yeh, filed Sep. 22, 2000, entitled "NUCLEIC ACID MOLECULES ENCODING TRANSMEMBRANE SERINE PROTEASES, THE ENCODED PROTEINS AND METHODS BASED THEREON" is claimed herein. Benefit of priority under 35 U.S.C. §120 to U.S. application Ser. No. 09/657,986, to Edwin L. Madison, Joseph Edward Semple, Gary Samuel Coombs, John Eugene Reiner, Edgar O. Ong, Gian Luca Araldi, filed Sep. 8, 2000, entitled "INHIBITORS OF SERINE PROTEASE ACTIVITY OF MATRIPTASE OR MTSP1," now U.S. Pat. No. 6,797,504, is also claimed herein. This application is a continuation-in-part of application Ser. No. 09/657,986, filed Sep. 8, 2000, now U.S. Pat. No. 6,797,504. For international purposes, benefit of priority to each of the above-noted applications is claimed herein.

This application is related to U.S. provisional application Ser. No. 60/166,391 to Edwin L. Madison and Edgar O. Ong, filed Nov. 18, 1999 entitled "NUCLEOTIDE AND PROTEIN SEQUENCES OF PROTEASE DOMAINS OF ENDOTHELIASE AND METHODS BASED THEREON". This application is also related to International PCT application No. PCT/US00/31803, filed Nov. 17, 2000.

The above-noted provisional applications, patent applications and International PCT application are incorporated by reference in their entirety. All patents, applications, published applications and other publications and sequences from GenBank and other data bases referred to herein are incorporated by reference in their entirety.

FIELD OF INVENTION

Nucleic acid molecules that encode proteases and portions thereof, particularly protease domains are provided. Also provided are prognostic, diagnostic and therapeutic methods using the proteases and domains thereof and the encoding nucleic acid molecules.

BACKGROUND OF THE INVENTION AND OBJECTS THEREOF

Cancer a leading cause of death in the United States, developing in one in three Americans; one of every four Americans dies of cancer. Cancer is characterized by an increase in the number of abnormal neoplastic cells, which proliferate to form a tumor mass, the invasion of adjacent tissues by these neoplastic tumor cells, and the generation of malignant cells that metastasize via the blood or lymphatic system to regional lymph nodes and to distant sites.

Among the hallmarks of cancer is a breakdown in the communication among tumor cells and their environment. Normal cells do not divide in the absence of stimulatory signals, cease dividing in the presence of inhibitory signals. Growth-stimulatory and growth-inhibitory signals, are routinely exchanged between cells within a tissue. In a cancerous, or neoplastic, state, a cell acquires the ability to "override" these signals and to proliferate under conditions in which normal cells do not grow.

In order to proliferate tumor cells acquire a number of distinct aberrant traits reflecting genetic alterations. The genomes of certain well-studied tumors carry several different independently altered genes, including activated oncogenes and inactivated tumor suppressor genes. Each of these genetic changes appears to be responsible for imparting some of the traits that, in the aggregate, represent the full neoplastic phenotype.

A variety of biochemical factors have been associated with different phases of metastasis. Cell surface receptors for collagen, glycoproteins such as laminin, and proteoglycans, facilitate tumor cell attachment, an important step in invasion and metastases. Attachment triggers the release of degradative enzymes which facilitate the penetration of tumor cells through tissue barriers. Once the tumor cells have entered the target tissue, specific growth factors are required for further proliferation. Tumor invasion (or progression) involves a complex series of events, in which tumor cells detach from the primary tumor, break down the normal tissue surrounding it, and migrate into a blood or lymphatic vessel to be carried to a distant site. The breaking down of normal tissue barriers is accomplished by the elaboration of specific enzymes that degrade the proteins of the extracellular matrix that make up basement membranes and stromal components of tissues.

A class of extracellular matrix degrading enzymes have been implicated in tumor invasion. Among these are the matrix metalloproteinases (MMP). For example, the production of the matrix metalloproteinase stromelysin is associated with malignant tumors with metastatic potential (see, e.g., Matrisian et al. (1990) *Smnrs. in Cancer Biology* 1:107-115; McDonnell et al. (1990) *Cancer and Metastasis Reviews* 9:309-319).

The capacity of cancer cells to metastasize and invade tissue is facilitated by degradation of the basement membrane. Several proteinase enzymes, including the MMPs, have been reported to facilitate the process of invasion of tumor cells. MMPs are reported to enhance degradation of the basement membrane, which thereby permits tumorous cells to invade tissues. For example, two major metalloproteinases having molecular weights of about 70 kDa and 92 kDa appear to enhance ability of tumor cells to metastasize.

Type II Transmembrane Serine Proteases (TTSPs)

In addition to the MMPs, serine proteases have been implicated in neoplastic disease progression. Most serine proteases, which are either secreted enzymes or are sequestered in cytoplasmic storage organelles, have roles in blood coagulation, wound healing, digestion, immune responses and tumor invasion and metastasis. A class cell surface proteins designated type II transmembrane serine proteases, which are membrane-anchored proteins with N-terminal extracellular domains, has been identified. As cell surface proteins, they are positioned to play a role in intracellular signal transduction and in mediating cell surface proteolytic events.

Cell surface proteolysis is a mechanism for the generation of biologically active proteins that mediate a variety of cellular functions. These membrane-anchored proteins, include a disintegrin-like and metalloproteinase (ADAM) and membrane-type matrix metalloproteinase (MT-MMP). In mammals, at least 17 members of the family are known, including seven in humans (see, Hooper et al. (2001) *J. Biol. Chem.* 276:857-860). These include: corin (accession nos. AF133845 and AB013874; see, Yan et al. (1999) *J. Biol. Chem.* 274:14926-14938; Tomia et at (1998) *J. Biochem.* 124:784-789; Yan et at (2000) *Proc. Natl. Acad. Sci. U.S.A.* 97:8525-8529); enterpeptidase (also designated enterokinase; accession no. U09860 for the human protein; see, Kitamoto et al. (1995) *Biochem.* 27:4562-4568; Yahagi et al. (1996) *Biochem. Biophys. Res. Commun.* 219:806-812; Kitamoto et al. (1994) *Proc. Natl. Acad. Sci. U.S.A.* 91:7588-7592; Matsushima et at (1994) *J. Biol. Chem.* 269:19976-19982); human airway trypsin-like protease (HAT; accession no. A80021 34; see Yamaoka et al. *J. Biol. Chem.* 273:11894-11901); MTSP1 and matriptase (also called TADG-15; see SEQ ID Nos. 1 and 2; accession nos. AFI 33086/AF118224, AF04280022; Takeuchi et at (1999) *Proc. Natl. Acad. Sci. U.S.A.* 96:11054-1161; Lin et al. (1999) *J. Biol. Chem.* 274: 18231-18236; Takeuchi et at (2000) *J. Biol. Chem.* 275: 26333-26342; and Kim et al. (1999) *Immunogenetics* 49:420-429); hepsin (see, accession nos. M18930, AF030065, X70900; Leytus et al. (1988) *Biochem.* 27:11895-11901; Vu et al. (1997) *J. Biol. Chem.* 272:31315-31320; and Farley et al. (1993) *Biochem. Biophys. Acta* 1173:350-352; and see, U.S. Pat. No. 5,972,616); TMPRS2 (see, Accession Nos. U75329 and AF113596; Paoloni-Giacobino et al. (1997) *Genomics* 44:309-320; and Jacquinet et al. (2000) *FEBS Lett.* 468:93-100); and TMPRSS4 (see, Accession No. NM 016425; Wallrapp et al. (2000) *Cancer* 60: 2602-2606).

Serine proteases, including transmembrane serine proteases, have been implicated in processes involved in neoplastic development and progression. While the precise role of these proteases has not been elaborated, serine proteases and inhibitors thereof are involved in the control of many intra- and extracellular physiological processes, including degradative actions in cancer cell invasion, metastatic spread, and neovascularization of tumors, that are involved in tumor progression. It is believed that proteases are involved in the degradation of extracellular matrix (ECM) and contribute to tissue remodeling, and are necessary for cancer invasion and metastasis. The activity and/or expression of some proteases have been shown to correlate with tumor progression and development.

For example, a membrane-type serine protease MTSP1 (also called matriptase; see SEQ ID Nos. 1 and 2 from U.S. Pat. No. 5,972,616; and GenBank Accession No. AF118224; (1999) *J. Biol. Chem.* 274:18231-18236; U.S. Pat. No. 5,792, 616; see, also Takeuchi (1999) *Proc. Natl. Acad. Sci. U.S.A.* 96:11054-1161) that is expressed in epithelial cancer and normal tissue (Takeucuhi et al. (1999) *Proc. Natl. Acad. Sci. USA,* 96(20):11054-61) has been identified. Matriptase was originally identified in human breast cancer cells as a major gelatinase (see, U.S. Pat. No. 5,482,848), a type of matrix metalloprotease (MMP). It has been proposed that it plays a role in the metastasis of breast cancer. Its primary cleavage specificity is Arg-Lys residues. Matriptase also is expressed in a variety of epithelial tissues with high levels of activity and/or expression in the human gastrointestinal tract and the prostate.

Prostate-specific antigen (PSA), a kallikrein-like serine protease, degrades extracellular matrix glycoproteins fibronectin and laminin, and, has been postulated to facilitate invasion by prostate cancer cells (Webber et al. (1995) *Clin. Cancer Res.,* 1(10):1089-94). Blocking PSA proteolytic activity with PSA-specific monoclonal antibodies results in a dose-dependent decrease in vitro in the invasion of the reconstituted basement membrane Matrigel by LNCaP human prostate carcinoma cells which secrete high levels of PSA.

Hepsin, a cell surface serine protease identified in hepatoma cells, is overexpressed in ovarian cancer (Tanimoto et al. (1997) *Cancer Res.,* 57(14):2884-7). The hepsin transcript appears to be abundant in carcinoma tissue and is almost never expressed in normal adult tissue, including normal ovary. It has been suggested that hepsin is frequently overexpressed in ovarian tumors and therefore may be a candidate protease in the invasive process and growth capacity of ovarian tumor cells.

A serine protease-like gene, designated normal epithelial cell-specific 1 (NES1) (Liu et al., *Cancer Res.,* 56(14):3371-9 (1996)) has been identified. Although expression of the NES1 mRNA is observed in all normal and immortalized nontumorigenic epithelial cell lines, the majority of human breast cancer cell lines show a drastic reduction or a complete lack of its expression. The structural similarity of NES1 to polypeptides known to regulate growth factor activity and a negative correlation of NES1 expression with breast oncogenesis suggest a direct or indirect role for this protease-like gene product in the suppression of tumorigenesis.

Hence transmembrane serine proteases appear to be involved in the etiology and pathogenesis of tumors. There is a need to further elucidate their role in these processes and to identify additional transmembrane proteases. Therefore, it is an object herein to provide transmembrane serine protease (MTSP) proteins and nucleic acids encoding such MTSP proteases that are involved in the regulation of or participate in tumorigenesis and/or carcinogenesis. It is also an object herein to provide prognostic, diagnostic, therapeutic screening methods using the such proteases and the nucleic acids encoding such proteases.

SUMMARY OF THE INVENTION

Provided herein are isolated protease domains of the Transmembrane Serine Protease family, particularly the Type II Transmembrane Serine Protease (TTSP) family (also referred to herein as MTSPs), and more particularly TTSP family members whose functional activity differs in tumor cells from non-tumor cells in the same tissue. For example, the MTSPs include those that are activated and/or expressed in tumor cells at different levels, typically higher, from non-tumor cells; and those from cells in which substrates therefor differ in tumor cells from non-tumor cells or otherwise alter the specificity of the MTSP.

The MTSP family as intended herein does not include any membrane anchored or spanning proteases that are expressed on endothelial cells. Included among the MTSPs are several heretofore unidentified MTSP family members, designated herein as MTSP3 and MTSP4 and a new form of a protein designated herein as MTSP6. In addition to the protease domains of each of MTSP3 and MTSP4, the full-length proteins, including those that results from splice variants, zymogens and activated forms, and uses thereof, are also provided.

The protease domains as provided herein are single-chain polypeptides, with an N-terminus (such as IV, VV, IL and II) generated at the cleavage site (generally having the consensus sequence R↓VVGG, R↓IVGG, R↓IVNG, R↓ILGG, R↓VGLL, R↓ILGG or a variation thereof; an N-terminus R↓V or R↓I, where the arrow represents the cleavage point) when the zymogen is activated. To identify the protease domain an RI should be identified, and then the following amino acids compared to the above noted motif.

The protease domains generated herein, however, do not result from activation, which produces a two chain activated product, but rather are single chain polypeptides with the N-terminus include the consensus sequence ↓VVGG, ↓IVGG, ↓VGLL, ↓ILGG or ↓IVNG or other such motif at the N-terminus. As shown herein, such polypeptides, although not the result of activation and not double-chain forms, exhibit proteolytic (catalytic) activity. These protease domain polypeptides are used in assays to screen for agents that modulate the activity of the MTSP. Such assays are also provided herein. In exemplary assays, the affects of test compounds in the ability of a protease domains to proteolytically cleave a known substrate, typically a fluorescently, chromogenically or otherwise detectably labeled substrate, are assessed. Agents, generally compounds, particularly small molecules, that modulate the activity of the protease domain are candidate compounds for modulating the activity of the MTSP. The protease domains can also be used to produce single-chain protease-specific antibodies. The protease domains provided herein include, but are not limited to, the single chain region having an N-terminus at the cleavage site for activation of the zymogen, through the C-terminus, or C-terminal truncated portions thereof that exhibit proteolytic activity as a single-chain polypeptide in in vitro proteolysis assays, of any MTSP family member, preferably from a mammal, including and most preferably human, that, for example, is expressed in tumor cells at different levels from non-tumor cells, and that is not expressed on an endothelial cell. These include, but are not limited to: MTSP1 (or matriptase), MTSP3, MTSP4 and MTSP6. Other MTSP protease domains of interest herein, particularly for use in in vitro drug screening proteolytic assays, include, but are not limited to: corin (accession nos. AF133845 and AB013874; see, Yan et al (1999) *J. Biol. Chem.* 274:14926-14938; Tomia et al. (1998) *J. Biochem.* 124:784-789; Yan et al. (2000) *Proc. Natl. Acad. Sci. U.S.A.* 97:8525-8529; SEQ ID Nos. 61 and 62 for the human protein); enterpeptidase (also designated enterokinase; accession no. U09860 for the human protein; see, Kitamoto et al. (1995) *Biochem.* 27:4562-4568; Yahagi et al. (1996) *Biochem. Biophys. Res. Commun.* 219:806-812; Kitamoto et al. (1994) *Proc. Natl. Acad. Sci. U.S.A.* 91:7588-7592; Matsushima et al. (1994) *J. Biol. Chem.* 269:19976-19982; see SEQ ID Nos. 63 and 64 for the human protein); human airway trypsin-like protease (HAT; accession no. AB002134; see Yamaoka et al. *J. Biol. Chem.* 273:11894-11901; SEQ ID Nos. 65 and 66 for the human protein); hepsin (see, accession nos. M18930, AF030065, X70900; Leytus et al. (1988) *Biochem.* 27:11895-11901; Vu et al. (1997) *J. Biol. Chem.* 272:31315-31320; and Farley et al. (1993) *Biochem. Biophys. Acta* 1173:350-352; SEQ ID Nos. 67 and 68 for the human protein); TMPRS2 (see, Accession Nos. U75329 and AF113596; Paoloni-Giacobino et al. (1997) *Genomics* 44:309-320; and Jacquinet et al. (2000) *FEBS Lett.* 468:93-100; SEQ ID Nos. 69 and 70 for the human protein) TMPRSS4 (see, Accession No. NM 016425; Wallrapp et al. (2000) *Cancer* 60:2602-2606; SEQ ID Nos. 71 and 72 for the human protein); and TADG-12 (also designated MTSP6, see SEQ ID Nos. 11 and 12; see International PCT application No. WO 00/52044, which claims priority to U.S. application Ser. No. 09/261,416).

Also provided are muteins of the single chain protease domains and MTSPs, particularly muteins in which the Cys residue in the protease domain that is free (i.e., does not form disulfide linkages with any other Cys residue in the protein) is substituted with another amino acid substitution, preferably with a conservative amino acid substitution or a substitution that does not eliminate the activity, and muteins in which a glycosylation site(s) is eliminated. Muteins in which other conservative amino acid substitutions in which catalytic activity is retained are also contemplated (see, e.g., Table 1, for exemplary amino acid substitutions). See, also, FIG. 4, which identifies the free Cys residues in MTSP3, MTSP4 and MTSP6.

Hence, provided herein are members of a family of transmembrane serine protease (MTSP) proteins, and functional domains, especially protease (or catalytic) domains thereof, muteins and other derivatives and analogs thereof. Also provided herein are nucleic acids encoding the MTSPs.

Exemplary MTSPs (see, e.g., SEQ ID No. 1-12, 49 and 50) are provided herein, as are the single chain protease domains thereof as follows: SEQ ID Nos. 1, 2, 49 and 50 set forth amino acid and nucleic acid sequences of MTSP1 and the protease domain thereof; SEQ ID No. 3 sets forth the MTSP3 nucleic acid sequence and SEQ ID No. 4 the encoded MTSP3 amino acids; SEQ ID No. 5 MTSP4 a nucleic acid sequence of the protease domain and SEQ ID No. 6 the encoded MTSP4 amino acid protease domain; SEQ ID No. 7 MTSP4-L a nucleic acid sequence and SEQ ID No. 8 the encoded MTSP4-L amino acid sequence; SEQ ID No. 9 an MTSP4-S encoding nucleic acid sequence and SEQ ID No. 10 the encoded MTSP4-S amino acid sequence; and SEQ ID No. 11 an MTSP6 encoding nucleic acid sequence and SEQ ID No. 12 the encoded MTSP6 amino acid sequence. The single chain protease domains of each are delineated below.

Nucleic acid molecules that encode a single-chain protease domain or catalytically active portion thereof are provided. Also provided are nucleic acid molecules that hybridize to such MTSP encoding nucleic acid along their full length and encode the protease domain or portion thereof are provided. Hybridization is preferably effected under conditions of at least low, generally at least moderate, and often high stringency.

Additionally provided herein are antibodies that specifically bind to the MTSPs, cells, combinations, kits and articles of manufacture that contain the nucleic acid encoding the MTSP and/or the MTSP. Further provided herein are prognostic, diagnostic, therapeutic screening methods using MTSPs and the nucleic acids encoding MTSP. Also provided are transgenic non-human animals bearing inactivated genes encoding the MTSP and bearing the genes encoding the MTSP under non-native promoter control. Such animals are useful in animal models of tumor initiation, growth and/or progression models.

Provided herein are members of a family of membrane serine proteases (MTSP) that are expressed in certain tumor or cancer cells such lung, prostate, colon and breast cancers. In particular, it is shown herein, that MTSPs, particularly, MTSP3, MTSP4 and MTSP6 are expressed in lung carcinoma, breast carcinoma, colon adenocarcinoma and/or ovarian carcinomas as well as in certain normal cells and tissues (see e.g., EXAMPLES for tissue-specific expression profiles of each protein exemplified herein). The MTSPs that are of particular interest herein, are those that are expressed in tumor cells, for example, those that appear to be expressed at different levels in tumor cells from normal cells, or whose functional activity is different in tumor cells from normal cells, such as by an alteration in a substrate therefor, or a cofactor. Hence the MTSP provided herein can serve as diagnostic markers for certain tumors. The level of activated MTSP3, MTSP4 and MTSP6 can be diagnostic of prostate cancer. In addition, MTSP4 is expressed and/or activated in lymphomas, leukemias, lung cancer, breast, prostrate and colon cancers. MTSP6 is activated and/or expressed in breast, lung, prostate, colon and ovarian cancers. Furthermore, compounds that modulate the activity of these MTSPs, as assessed by the assays provided herein, particularly the in vitro proteolytic assays that use the single chain protease domains, are potential therapeutic candidates for treatment of various malignancies and neoplastic disease.

Also provided herein are methods of modulating the activity of the MTSPs and screening for compounds that modulate, including inhibit, antagonize, agonize or otherwise alter the activity of the MTSPs. Of particular interest is the extracellular domain of these MTSPs that includes the proteolytic (catalytic) portion of the protein.

MTSP proteins, including, but not limited to, MTSP3, MTSP4, and MTSP6, including splice variants thereof, and nucleic acids encoding MTSPs, and domains, derivatives and analogs thereof are provided herein. Single chain protease domains, in the N-terminal is that which would be generated by activation of the zymogen, from any MTSP, particularly those that are not expressed in endothelial cells and that are expressed in tumor cells are also provided.

Antibodies that specifically bind to the MTSP, particularly the single chain protease domain, and any and all forms of MTSP3 and MTSP4, and cells, combinations, kits and articles of manufacture containing the MTSP proteins, domains thereof, or encoding nucleic acids are also provided herein. Transgenic non-human animals bearing inactivated genes encoding the MTSP and bearing the genes encoding the MTSP under a non-native promoter control are additionally provided herein. Also provided are nucleic acid molecules encoding each of the MTSPs and domains thereof.

Also provided are plasmids containing any of the nucleic acid molecules provided herein. Cells containing the plasmids are also provided. Such cells include, but are not limited to, bacterial cells, yeast cells, fungal cells, plant cells, insect cells and animal cells.

Also provided is a method of producing a MTSP by growing the above-described cells under conditions whereby the MTSP is expressed by the cells, and recovering the expressed MTSP protein. Methods for isolating nucleic acid encoding other MTSPs are also provided.

Also provided are cells, preferably eukaryotic cells, such as mammalian cells and yeast cells, in which the MTSP protein, preferably MTSP3 and MTSP4, is expressed in the surface of the cells. Such cells are used in drug screening assays to identify compounds that modulate the activity of the MTSP protein. These assays including in vitro binding assays, and transcription based assays in which signal transduction mediated by the MTSP is assessed.

Further provided herein are prognostic, diagnostic and therapeutic screening methods using the MTSP and the nucleic acids encoding MTSP. In particular, the prognostic, diagnostic and therapeutic screening methods are used for preventing, treating, or for finding agents useful in preventing or treating, tumors or cancers such as lung carcinoma, colon adenocarcinoma and ovarian carcinoma.

Also provided are methods for screening for compounds that modulate the activity of any MTSP. The compounds are identified by contacting them with the MTSP and a substrate for the MTSP. A change in the amount of substrate cleaved in the presence of the compounds compared to that in the absence of the compound indicates that the compound modulates the activity of the MTSP. Such compounds are selected for further analyses or for use to modulate the activity of the MTSP, such as inhibitors or agonists. The compounds can also be identified by contacting the substrates with a cell that expresses the MTSP or the extracellular domain or proteolytically active portion thereof. For assays in which the extracellular domain or a proteolytically active portion thereof is employed, the MTSP is any MTSP that is expressed on cells, other than endothelial cells, including, but not limited to MTSP1, MTSP3, MTSP4 and MTSP6.

Also provided herein are modulators of the activity of the MTSP, especially the modulators obtained according to the screening methods provide herein. Such modulators may have use in treating cancerous conditions, and other neoplastic conditions.

Pharmaceutical composition containing the protease domains of an MTSP protein, and the MTSP proteins, MTSP3, MTSP4 and MTSP6 are provided herein in a pharmaceutically acceptable carrier or excipient are provided herein.

Also provided are articles of manufacture that contain the MTSP proteins and protease domains of MTSPs in single chain form. The articles contain a) packaging material; b) the polypeptide (or encoding nucleic acid), particularly the single chain protease domain thereof; and c) a label indicating that the article is for using ins assays for identifying modulators of the activities of an MTSP protein is provided herein.

Conjugates containing a) a MTSP protease domain in single chain from; and b) a targeting agent linked to the MTSP directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can contain a plurality of agents linked thereto. The conjugate can be a chemical conjugate; and it can be a fusion protein.

In yet another embodiment, the targeting agent is a protein or peptide fragment. The protein or peptide fragment can include a protein binding sequence, a nucleic acid binding sequence, a lipid binding sequence, a polysaccharide binding sequence, or a metal binding sequence.

Method of diagnosing a disease or disorder characterized by detecting an aberrant level of an MTSP, particularly an MTSP3, MTSP4 or MTSP6, in a subject is provided. The method can be practiced by measuring the level of the DNA, RNA, protein or functional activity of the MTSP. An increase or decrease in the level of the DNA, RNA, protein or functional activity of the MTSP, relative to the level of the DNA, RNA, protein or functional activity found in an analogous sample not having the disease or disorder (or other suitable control) is indicative of the presence of the disease or disorder in the subject or other relative any other suitable control.

Combinations are provided herein. The combination can include: a) an inhibitor of the activity of an MTSP; and b) an anti-cancer treatment or agent. The MTSP inhibitor and the anti-cancer agent can be formulated in a single pharmaceutical composition or each is formulated in a separate pharmaceutical composition. The MTSP inhibitor can be an antibody or a fragment or binding portion thereof against the MTSP, such as an antibody that specifically binds to the protease domain, an inhibitor of the MTSP production, or an inhibitor of the MTSP membrane-localization or an inhibitor of MTSP activation. Other MTSP inhibitors include, but are not limited to, an antisense nucleic acid encoding the MTSP, particularly a portion of the protease domain; a nucleic acid encoding at least a portion of a gene encoding the MTSP with a heterologous nucleotide sequence inserted therein such that the heterologous sequence inactivates the biological activity encoded MTSP or the gene encoding it. The portion of the gene encoding the MTSP preferably flanks the heterologous sequence to promote homologous recombination with a genomic gene encoding the MTSP.

Also, provided are methods for treating or preventing a tumor or cancer in a mammal by administering to a mammal an effective amount of an inhibitor of an MTSP3, MTSP4 or MTSP6, whereby the tumor or cancer is treated or prevented. The MTSP inhibitor used in the treatment or for prophylaxis is administered with a pharmaceutically acceptable carrier or excipient. The mammal treated can be a human. The treatment or prevention method can additionally include administering an anti-cancer treatment or agent simultaneously with or subsequently or before administration of the MTSP inhibitor.

Also provided is a recombinant non-human animal in which an endogenous gene of an MTSP has been deleted or inactivated by homologous recombination or insertional mutagenesis of the animal or an ancestor thereof. A recombinant non-human animal is provided herein, where the gene of an MTSP is under control of a promoter that is not the native promoter of the gene or that is not the native promoter of the gene in the non-human animal or where the nucleic acid encoding the MTSP is heterologous to the non-human animal and the promoter is the native or a non-native promoter.

Also provided are methods of treatments of tumors by administering a prodrug that is activated by an MTSP that is expressed or active in tumor cells, particularly those in which its functional activity in tumor cells is greater than in nonetumor cells. The prodrug is administered and, upon administration, active MTSP expressed on cells cleaves the prodrug and releases active drug in the vicinity of these cells. The active anti-cancer drug accumulates in the vicinity of the tumor. This is particularly useful in instances in which an MTSP is expressed or active in greater quantity, higher level or predominantly in tumor cells compared to other cells.

BRIEF DESCRIPTION OF DRAWINGS

FIG. 4 provides an alignment of the C-terminal portions of MTSP3 (set forth herein as SEQ ID No. 4), the two splice variant-encoded forms of MTSP4 (MTSP4-L and MTSP4-S set forth herein as SEQ ID Nos. 8 and 10, respectively), and MTSP6 (set forth herein as SEQ ID No. 12), that encompasses the protease domains thereof; the figure shows the cleavage sites, which form the N-terminus of the protease domain of each protein; a potential glycosylation site is noted and the free Cys residues in the protease domain of each are noted (*). Muteins of each protein may be prepared by replacing the residues in the glycosylation site, particularly the N residue, and the free Cys residues, with preferably conservative amino acid residues. Such muteins are also provided herein.

DETAILED DESCRIPTION OF THE INVENTION

A. Definitions

Figure 1:
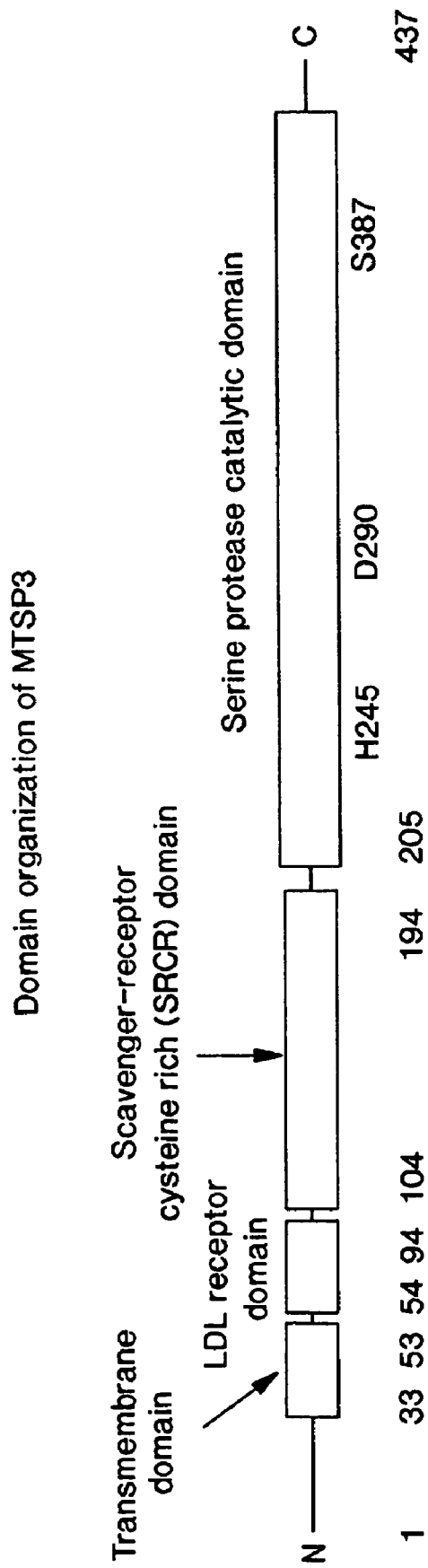
FIG. 1 illustrates the domain organization of the MTSP3.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, serine protease refers to a diverse family of proteases wherein a serine residue is involved in the hydrolysis of proteins or peptides. The serine residue can be part of the catalytic triad mechanism, which includes a serine, a histidine and an aspartic acid in the catalysis, or be part of the hydroxyl/ε-amine or hydroxyl/α-amine catalytic dyad mechanism, which involves a serine and a lysine in the catalysis.

As used herein, "transmembrane serine protease (MTSP)" refers to a family of transmembrane serine proteases that share common structural features as described herein (see, also Hooper et al. (2001) *J. Biol. Chem.* 276:857-860). Thus, reference, for example, to "MTSP" encompasses all proteins encoded by the MTSP gene family, including but are not limited to: MTSP1, MTSP3, MTSP4 and MTSP6, or an equivalent molecule obtained from any other source or that has been prepared synthetically or that exhibits the same activity. Other MTSPs include, but are not limited to, corin, enterpeptidase, human airway trypsin-like protease (HAT), MTSP1, TMPRSS2, and TMPRSS4. Sequences of encoding nucleic molecules and the encoded amino acid sequences of exemplary MTSPs and/or domains thereof are set forth in SEQ ID Nos. 1-12, 49, 50 and 61-72. The term also encompass MTSPs with conservative amino acid substitutions that do not substantially alter activity of each member, and also encompasses splice variants thereof. Suitable conservative substitutions of amino acids are known to those of skill in this art and may be made generally without altering the biological activity of the resulting molecule. Of particular interest are MTSPs of mammalian, including human, origin. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Bejacmin/Cummings Pub. co., p. 224).

As used herein, a "protease domain of an MTSP" refers to the protease domain of MTSP that is located within the extracellular domain of a MTSP and exhibits serine proteolytic activity. It includes at least the smallest fragment thereof that acts catalytically as a single chain form. Hence it is at least the minimal portion of the extracellular domain that exhibits proteolytic activity as assessed by standard assays in vitro assays. Those of skill in this art recognize that such protease domain is the portion of the protease that is structurally equivalent to the trypsin or chymotrypsin fold.

Figure 2:
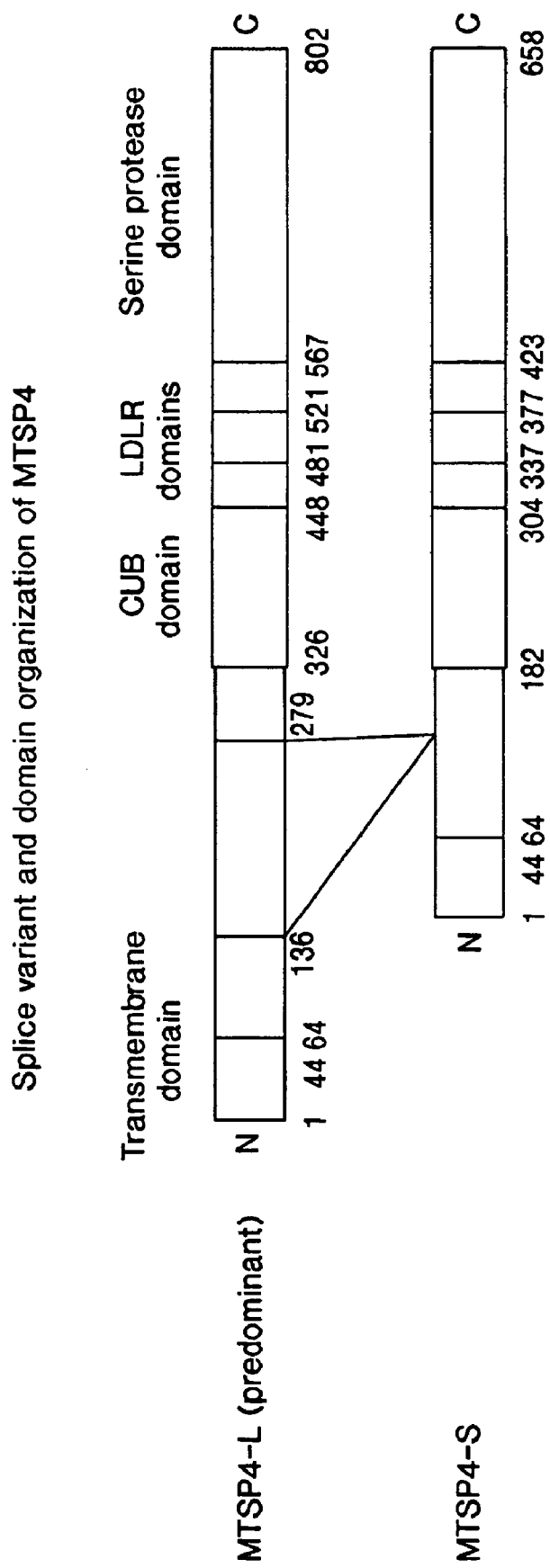
FIG. 2 illustrates the domain organization of the MTSP4 splice variants and domains thereof; MTSP4-L includes a transmembrane domain, a CUB domain, a low density lipoprotein receptor (LDLR) domains, and a serine protease catalytic domain; MTSP4-S lacking the portion between amino acids 136-279.
Figure 3:
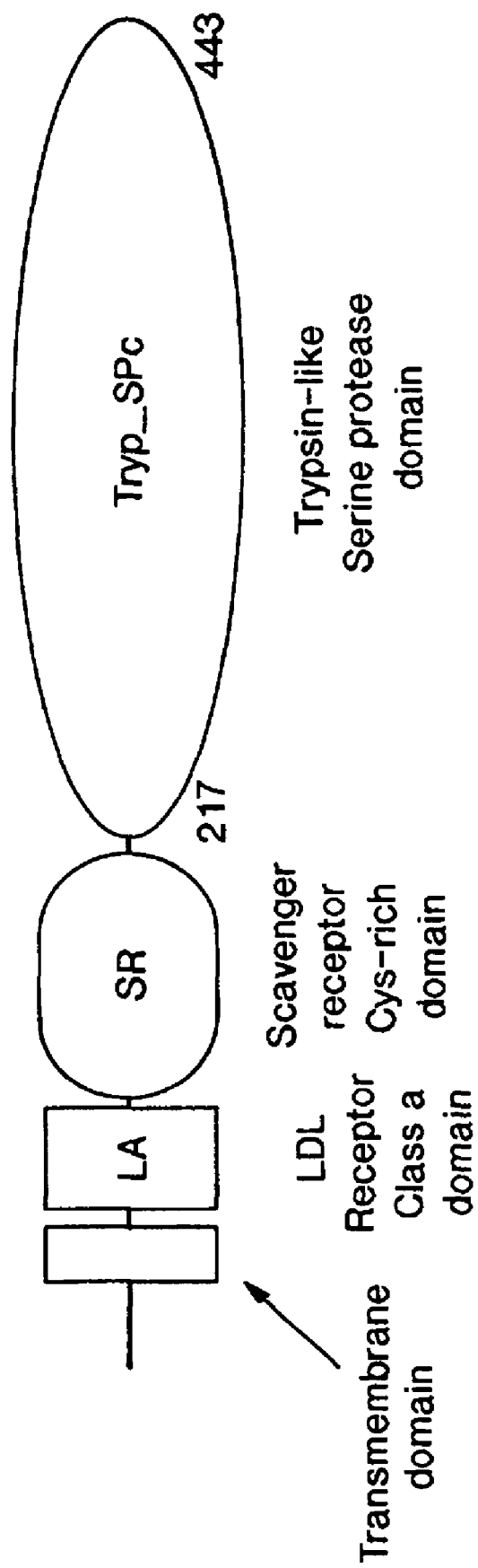
FIG. 3 depicts the domain organization of MTSP6.

Exemplary MTSP proteins, with the protease domains indicated, are illustrated in FIGS. 1-3, Smaller portions thereof that retain protease activity are contemplated. The protease domains vary in size and constitution, including insertions and deletions in surface loops. They retain conserved structure, including at least one of the active site triad, primary specificity pocket, oxyanion hole and/or other features of serine protease domains of proteases. Thus, for purposes herein, the protease domain is a portion of a MTSP, as defined herein, and is homologous to a domain of other MTSPs, such as corin, enterpeptidase, human airway trypsin-like protease (HAT), MTSP1, TMPRSS2, and TMPRSS4, which have been previously identified; it was not recognized, however, that an isolated single chain form of the protease domain could function proteolytically in in vitro assays. As with the larger class of enzymes of the chymotrypsin (S1) fold (see, e.g., Internet accessible MEROPS data base), the MTSPs protease domains share a high degree of amino acid sequence identity. The His, Asp and Ser residues necessary for activity are present in conserved motifs. The activation site, which results in the N-terminus of second chain in the two chain forms is has a conserved motif and readily can be identified (see, e.g., amino acids 801-806, SEQ ID No. 62, amino acids 406-410, SEQ ID No. 64; amino acids 186-190, SEQ ID No. 66; amino acids 161-166, SEQ ID No. 68; amino acids 255-259, SEQ ID No. 70; amino acids 190-194, SEQ ID No. 72).

As used herein, the catalytically active domain of an MTSP refers to the protease domain. Reference to the protease domain of an MTSP refers includes the single and double-chain forms of any of these proteins. The zymogen form of each protein is single chain form, which can be converted to the active two chain form by cleavage. The protease domain may also be converted to a two chain form. By active form is meant a form active in vivo.

Significantly, it is shown herein, that, at least in vitro, the single chain forms of the MTSPs and the catalytic domains or proteolytically active portions thereof (typically C-terminal truncation) thereof exhibit protease activity. Hence provided herein are isolated single chain forms of the protease domains of MTSPs and their use in in vitro drug screening assays for identification of agents that modulate the activity thereof.

As used herein an MTSP3, whenever referenced herein, includes at least one or all of or any combination of:
a polypeptide encoded by the sequence of nucleotides set forth in SEQ ID No. 3;
a polypeptide encoded by a sequence of nucleotides that hybridizes under conditions of low, moderate or high stringency to the sequence of nucleotides set forth in SEQ ID No. 3;
a polypeptide that comprises the sequence of amino acids set forth as amino acids 205-437 of SEQ ID No. 4;
a polypeptide that comprises a sequence of amino acids having at least about 85% or 90% sequence identity with the sequence of amino acids set forth in SEQ ID No. 4; and/or
a splice variant of the MTSP3 set forth in SEQ ID Nos. 3 and 4.

The MTSP3 may be from any animal, particularly a mammal, and includes but are not limited to, humans, rodents, fowl, ruminants and other animals. The full length zymogen or double chain activated form is contemplated or any domain thereof, including the protease domain, which can be a double chain activated form, or a single chain form.

As used herein an MTSP4, whenever referenced herein, includes at least one or all of or any combination of: a polypeptide encoded by a sequence of nucleotides set forth in any of SEQ ID No. 5, 7 or 9;
a polypeptide encoded by a sequence of nucleotides that hybridizes under conditions of low, moderate or high stringency to the sequence of nucleotides set forth in any of SEQ ID Nos. 5, 7 or 9;
a polypeptide that comprises the sequence of amino acids set forth in any of SEQ ID Nos. 6, 8 or 10;
a polypeptide that comprises a sequence of amino acids having at least about 85% or 90% or 95% sequence identity with the sequence of amino acids set forth in SEQ ID No. 6, 8 or 10; and/or
a splice variant of the MTSP4s set forth in SEQ ID Nos. 7-10.

The MTSP4 may be from any animal, particularly a mammal, and includes but are not limited to, humans, rodents, fowl, ruminants and other animals. The full length zymogen or double chain activated form is contemplated or any domain thereof, including the protease domain, which can be a double chain activated form, or a single chain form.

As used herein an MTSP6, whenever referenced herein, includes at least one or all of or any combination of:
a polypeptide encoded by the sequence of nucleotides set forth in any of SEQ ID No. 11;
a polypeptide encoded by a sequence of nucleotides that hybridizes under conditions of low, moderate or high stringency to the sequence of nucleotides set forth in any of SEQ ID Nos. 11;
a polypeptide that comprises the sequence of amino acids set forth in any of SEQ ID Nos. 12;
a polypeptide that comprises a sequence of amino acids having at least about 90% or 95% or 98% sequence identity with the sequence of aminoacids set forth in SEQ ID No. 12; and/or
a splice variant of the MTSP4s set forth in SEQ ID No. 12.

The MTSP6 may be from any animal, particularly a mammal, and includes but are not limited to, humans, rodents, fowl, ruminants and other animals. The full length zymogen or double chain activated form is contemplated or any domain thereof, including the protease domain, which can be a double chain activated form, or a single chain form. Of particular interest herein is the MTSP6 of SEQ ID No. 12.

As used herein, a human protein is one encoded by DNA present in the genome of a human, including all allelic variants and conservative variations as long as they are not variants found in other mammals.

As used herein, a "nucleic acid encoding a protease domain or catalytically active portion of a MTSP" shall be construed as referring to a nucleic acid encoding only the recited single chain protease domain or active portion thereof, and not the other contiguous portions of the MTSP as a continuous sequence.

As used herein, a CUB domain is a motif that mediates protein-protein interactions in complement components C1r/C1s and has also been identified in various proteins involved in developmental processes.

As used herein, catalytic activity refers to the activity of the MTSP as a serine proteases. Function of the MTSP refers to its function in tumor biology, including promotion of or involvement in tumorigenesis, metastasis or carcinogenesis, and also roles in signal transduction.

As used herein, a "propeptide" or "pro sequence" is sequence of amino acids positioned at the amino terminus of a mature biologically active polypeptide. When so-positioned, the resulting polypeptide is called a zymogen. Zymogens, generally, are biologically inactive and can be converted to mature active polypeptides by catalytic or autocatalytic cleavage of the propeptide from the zymogen. A zymogen is an enzymatically inactive protein that is converted to a proteolytic enzyme by the action of an activator. Cleavage may be effected autocatalytically.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, neoplastic disease refers to any disorder involving cancer, including tumor development, growth, metastasis and progression.

As used herein, cancer refers to a general term for diseases caused by any type of malignant tumor.

As used herein, malignant, as applies to tumors, refers to primary tumors that have the capacity of metastasis with loss of growth control and positional control.

As used herein, an anti-cancer agent (used interchangeable with "anti-tumor or anti-neoplastic agent") refers to any agents used in the anti-cancer treatment. These include any agents, when used alone or in combination with other compounds, that can alleviate, reduce, ameliorate, prevent, or place or maintain in a state of remission of clinical symptoms or diagnostic markers associated with neoplastic disease, tumor and cancer, and can be used in methods, combinations and compositions provided herein. Non-limiting examples of anti-neoplastic agents include anti-angiogenic agents, alkylating agents, antimetabolite, certain natural products, platinum coordination complexes, anthracenediones, substituted ureas, methylhydrazine derivatives, adrenocortical suppressants, certain hormones, antagonists and anti-cancer polysaccharides.

As used herein, a splice variant refers to a variant produced by differential processing of a primary transcript of genomic DNA that results in more than one type of mRNA. Splice variants of MTSPs are provided herein.

As used herein, angiogenesis is intended to broadly encompass the totality of processes directly or indirectly involved in the establishment and maintenance of new vasculature (neovascularization), including, but not limited to, neovascularization associated with tumors.

As used herein, anti-angiogenic treatment or agent refers to any therapeutic regimen and compound, when used alone or in combination with other treatment or compounds, that can alleviate, reduce, ameliorate, prevent, or place or maintain in a state of remission of clinical symptoms or diagnostic markers associated with undesired and/or uncontrolled angiogenesis. Thus, for purposes herein an anti-angiogenic agent refers to an agent that inhibits the establishment or maintenance of vasculature. Such agents include, but are not limited to, anti-tumor agents, and agents for treatments of other disorders associated with undesirable angiogenesis, such as diabetic retinopathies, restenosis, hyperproliferative disorders and others.

As used herein, non-anti-angiogenic anti-tumor agents refer to anti-tumor agents that do not act primarily by inhibiting angiogenesis.

As used herein, pro-angiogenic agents are agents that promote the establishment or maintenance of the vasculature. Such agents include agents for treating cardiovascular disorders, including heart attacks and strokes.

As used herein, undesired and/or uncontrolled angiogenesis refers to pathological angiogenesis wherein the influence of angiogenesis stimulators outweighs the influence of angiogenesis inhibitors. As used herein, deficient angiogenesis refers to pathological angiogenesis associated with disorders where there is a defect in normal angiogenesis resulting in aberrant angiogenesis or an absence or substantial reduction in angiogenesis.

As used herein, endotheliase refers to a mammalian protein, including humans, that has a transmembrane domain and is expressed on the surface of endothelial cells and includes a protease domain, particularly an extracellular protease domain, and is preferably a serine protease. Thus, reference, for example, to endotheliase encompasses all proteins encoded by the endotheliase gene family, or an equivalent molecule obtained from any other source or that has been prepared synthetically or that exhibits the same activity. The endotheliase gene family are transmembrane proteases expressed in endothelial cells. Endotheliases are excluded from the MTSPs contemplated herein.

As used herein, the protease domain of an endotheliase refers to the polypeptide portion of the endotheliase that is the extracellular portion that exhibits protease activity. The protease domain is a polypeptide that includes at least the minimum number of amino acids, generally more than 50 or 100, required for protease activity. Protease activity may be assessed empirically, such as by testing the polypeptide for its ability to act as a protease. Assays, such as the assays described in the EXAMPLES, employing a known substrate in place of the test compounds may be used. Furthermore, since proteases, particularly serine proteases, have characteristic structures and sequences or motifs, the protease domain may be readily identified by such structure and sequence or motif.

As used herein, the protease domain of an MTSP protein refers to the protease domain of an MTSP that is located within or is the extracellular domain of an MTSP and exhibits serine proteolytic activity. Hence it is at least the minimal portion of the extracellular domain that exhibits proteolytic activity as assessed by standard assays in vitro. It refers, herein, to a single chain form heretofore thought to be inactive. Exemplary protease domains include at least a sufficient portion of sequences of amino acids set forth as amino acids 615-855 in SEQ ID No. 2 (encoded by nucleotides 1865-2587 in SEQ ID No. 1; see also SEQ ID Nos. 49 and 50) from MTSP1, amino acids 205-437 of SEQ ID NO. 4 from MTSP3, SEQ ID No. 6, which sets forth the protease domain of MTSP4, and amino acids 217-443 of SEQ ID No. 11 from MTSP6. Also contemplated are nucleic acid molecules that encode polypeptide that has proteolytic activity in an in vitro proteolysis assay and that have at least 80%, 85%, 90% or 95% sequence identity with the full length of a protease domain of an MTSP protein, or that hybridize along their full length to a nucleic acids that encode a protease domain, particularly under conditions of moderate, generally high, stringency.

For each of these protease domains, residues at the N-terminus can be critical for activity, since it has been shown that an Asp in the N-terminus of such proteases is essential for formation of the catalytically active conformation upon activation cleavage of the zymogen form of the protease. It is shown herein that the protease domain of the singles chain form of the protease is catalytically active. Hence the protease domain will require the N-terminal amino acids; the c-terminus portion may be truncated. The amount that can be removed can be determined empirically by testing the protein for protease activity in an in vitro assays that assesses catalytic cleavage.

Hence smaller portions of the protease domains, particularly the single chain domains, thereof that retain protease activity are contemplated. Such smaller versions will generally be C-terminal truncated versions of the protease domains. The protease domains vary in size and constitution, including insertions and deletions in surface loops. Such domains exhibit conserved structure, including at least one structural feature, such as the active site triad, primary specificity pocket, oxyanion hole and/or other features of serine protease domains of proteases. Thus, for purposes herein, the protease domain is a single chain portion of an MTSP, as defined herein, but is homologous in its structural features and retention of sequence of similarity or homology the protease domain of chymotrypsin or trypsin. Most significantly, the polypeptide will exhibit proteolytic activity as a single chain.

As used herein, by homologous means about greater than 25% nucleic acid sequence identity, preferably 25% 40%, 60%, 80%, 90% or 95%. The terms "homology" and "identity" are often used interchangeably. In general, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073).

By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two nucleic acid molecules have nucleotide sequences that are at least 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Atschul, S. F., et al., *J Molec Biol* 215:403 (1990); Guide to Huge Computers, Martin J. Bishop, ed., Academic Press, San Diego, 1994, and Carillo et al. (1988) *SIAM J Applied Math* 48:1073). For example, the BLAST function of the National Center for Biotechnology Information database may be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules may be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids) which are similar, divided by the total number of symbols in the shorter of the two sequences. Default parameters for the GAP program may include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" represents a comparison between a test and a reference polypeptide or polynucleotide. For example, a test polypeptide may be defined as any polypeptide that is 90% or more identical to a reference polypeptide. As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions. At level of homologies or identities above about 85-90%, the result should be independent of the program and gap parameters set; such high levels of identity readily can be assess, often without relying on software.

As used herein, primer refers to an oligonucleotide containing two or more deoxyribonucleotides or ribonucleotides, preferably more than three, from which synthesis of a primer extension product can be initiated. Experimental conditions conducive to synthesis include the presence of nucleoside triphosphates and an agent for polymerization and extension, such as DNA polymerase, and a suitable buffer, temperature and pH.

As used herein, animals include any animal, such as, but are not limited to, goats, cows, deer, sheep, rodents, pigs and humans. Non-human animals, exclude humans as the contemplated animal. The MTSPs provided herein are from any source, animal, plant, prokaryotic and fungal. Preferred MTSPs are of animal origin, preferably mammalian origin.

As used herein, genetic therapy involves the transfer of heterologous DNA to the certain cells, target cells, of a mammal, particularly a human, with a disorder or conditions for which such therapy is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor inhibitor thereof, or a tumor necrosis factor or inhibitor thereof, such as a receptor therefor, that is not normally produced in the mammalian host or that is not produced in therapeutically effective amounts or at a therapeutically useful time. The heterologous DNA encoding the therapeutic product may be modified prior to introduction into the cells of the afflicted host in order to enhance or otherwise alter the product or expression thereof Genetic therapy may also involve delivery of an inhibitor or repressor or other modulator of gene expression.

As used herein, heterologous DNA is DNA that encodes RNA and proteins that are not normally produced in vivo by the cell in which it is expressed or that mediates or encodes mediators that alter expression of endogenous DNA by affecting transcription, translation, or other regulatable biochemical processes. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anti-cancer agents, enzymes and hormones, and DNA that encodes other types of proteins, such as antibodies. Antibodies that are encoded by heterologous DNA may be secreted or expressed on the surface of the cell in which the heterologous DNA has been introduced.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

As used herein, recitation that a polypeptide consists essentially of the protease domain means that the only MTSP portion of the polypeptide is a protease domain or a catalytically active portion thereof. The polypeptide may optionally, and generally will, include additional non-MTSP-derived sequences of amino acids.

As used herein, cancer or tumor treatment or agent refers to any therapeutic regimen and/or compound that, when used alone or in combination with other treatments or compounds, can alleviate, reduce, ameliorate, prevent, or place or maintain in a state of remission of clinical symptoms or diagnostic markers associated with deficient angiogenesis.

As used herein, domain refers to a portion of a molecule, e.g., proteins or nucleic acids, that is structurally and/or functionally distinct from other portions of the molecule.

As used herein, protease refers to an enzyme catalyzing hydrolysis of proteins or peptides. For purposes herein, the protease domain is a single chain form of an MTSP protein. For MTSP3 and MTSP4 the protease domain also includes two chain forms.

As used herein, catalytic activity refers to the activity of the MTSP as a protease as assessed in in vitro proteolytic assays that detect proteolysis of a selected substrate.

As used herein, nucleic acids include DNA, RNA and analogs thereof, including protein nucleic acids (PNA) and mixture thereof. Nucleic acids can be single or double stranded. When referring to probes or primers, optionally labeled, with a detectable label, such as a fluorescent or radiolabel, single-stranded molecules are contemplated. Such molecules are typically of a length such that they are statistically unique of low copy number (typically less than 5, preferably less than 3) for probing or priming a library. Generally a probe or primer contains at least 14, 16 or 30 contiguous of sequence complementary to or identical to a gene of interest. Probes and primers can be 10, 20, 30, 50, 100 or more nucleic acids long.

As used herein, nucleic acid encoding a fragment or portion of an MTSP refers to a nucleic acid encoding only the recited fragment or portion of MTSP, and not the other contiguous portions of the MTSP.

As used herein, heterologous or foreign DNA and RNA are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Heterologous DNA and RNA may also encode RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, a sequence complementary to at least a portion of an RNA, with reference to antisense oligonucleotides, means a sequence having sufficient complementarily to be able to hybridize with the RNA, preferably under moderate or high stringency conditions, forming a stable duplex; in the case of double-stranded MTSP antisense nucleic acids, a single strand of the duplex DNA may thus be tested, or triplex formation may be assayed. The ability to hybridize depends on the degree of complementarily and the length of the antisense nucleic acid. Generally, the longer the hybridizing nucleic acid, the more base mismatches with a MTSP encoding RNA it can contain and still form a stable duplex (or triplex, as the case may be). One skilled in the art can ascertain a tolerable degree of mismatch by use of standard procedures to determine the melting point of the hybridized complex.

For purposes herein, conservative amino acid substitutions may be made in any of MTSPs and protease domains thereof provided that the resulting protein exhibits protease activity. Conservative amino acid substitutions, such as those set forth in Table 1, are those that do not eliminate proteolytic activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Bejacmin/Cummings Pub. co., p. 224). Also included within the definition, is the catalytically active fragment of an MTSP, particularly a single chain protease portion. Conservative amino acid substitutions are made, for example, in accordance with those set forth in TABLE 1 as follows:

TABLE 1

| Original residue | Conservative substitution |
| --- | --- |
| Ala (A) | Gly; Ser, Abu |
| Arg (R) | Lys, orn |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val; Met; Nle; Nva |
| Leu (L) | Ile; Val; Met; Nle; Nv |
| Lys (K) | Arg; Gln; Glu |
| Met (M) | Leu; Tyr; Ile; NLe Val |
| Ornitine | Lys; Arg |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met; Nle; Nv |

Other substitutions are also permissible and may be determined empirically or in accord with known conservative substitutions.

As used herein, Abu is 2-aminobutyric acid; Orn is ornithine.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a splice variant refers to a variant produced by differential processing of a primary transcript of genomic DNA that results in more than one type of mRNA.

As used herein, a probe or primer based on a nucleotide sequence disclosed herein, includes at least 10, 14, preferably at least 16 or 30 or 100 contiguous sequence of nucleotides of SEQ ID Nos. 1, 3, 5, 7, 9 or 11.

As used herein, amelioration of the symptoms of a particular disorder by administration of a particular pharmaceutical composition refers to any lessening, whether permanent or temporary, lasting or transient that can be attributed to or associated with administration of the composition.

As used herein, antisense polynucleotides refer to synthetic sequences of nucleotide bases complementary to mRNA or the sense strand of double stranded DNA. Admixture of sense and antisense polynucleotides under appropriate conditions leads to the binding of the two molecules, or hybridization. When these polynucleotides bind to (hybridize with) mRNA, inhibition of protein synthesis (translation) occurs. When these polynucleotides bind to double stranded DNA, inhibition of RNA synthesis (transcription) occurs. The resulting inhibition of translation and/or transcription leads to an inhibition of the synthesis of the protein encoded by the sense strand. Antisense nucleic acid molecule typically contain a sufficient number of nucleotides to specifically bind to a target nucleic acid, generally at least 5 contiguous nucleotides, often at least 14 or 16 or 30 contiguous nucleotides or modified nucleotides complementary to the coding portion of a nucleic acid molecule that encodes a gene of interest, for example, nucleic acid encoding a single chain protease domain of an MTSP.

As used herein, an array refers to a collection of elements, such as antibodies, containing three or more members. An addressable array is one in which the members of the array are identifiable, typically by position on a solid phase support. Hence, in general the members of the array will be immobilized to discrete identifiable loci on the surface of a solid phase.

As used herein, antibody refers to an immunoglobulin, whether natural or partially or wholly synthetically produced, including any derivative thereof that retains the specific binding ability the antibody. Hence antibody includes any protein having a binding domain that is homologous or substantially homologous to an immunoglobulin binding domain. Antibodies include members of any immunoglobulin claims, including IgG, IgM, IgA, IgD and IgE.

As used herein, antibody fragment refers to any derivative of an antibody that is less then full length, retaining at least a portion of the full-length antibody's specific binding ability. Examples of antibody fragments include, but are not limited to, Fab, Fab', F(ab)$_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain ($V_H$) and one variable light domain linked by noncovalent interactions.

As used herein, a dsFV refers to an Fv with an engineered intermolecular disulfide bond, which stabilizes the $V_H$—$V_L$ pair.

As used herein, an F(ab)$_2$ fragment is an antibody fragment that results from digestion of an immunoglobulin with pepsin at pH 4.0-4.5; it may be recombinantly produced.

As used herein, Fab fragments is an antibody fragment that results from digestion of an immunoglobulin with papain; it may be recombinantly produced.

As used herein, scFVs refer to antibody fragments that contain a variable light chain (VL) and variable heavy chain (VH) covalently connected by a polypeptide linker in any order. The linker is of a length such that the two variable domains are bridged without substantial interference. Preferred linkers are (Gly-Ser)n residues with some Glu or Lys residues dispersed throughout to increase solubility.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, diabodies are dimeric scFV; diabodies typically have shorter peptide linkers than scFvs, and they preferentially dimerize.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, production by recombinant means by using recombinant DNA methods means the use of the well known methods of molecular biology for expressing proteins encoded by cloned DNA.

As used herein the term assessing is intended to include quantitative and qualitative determination in the sense of obtaining an absolute value for the activity of an MTSP, or a domain thereof, present in the sample, and also of obtaining an index, ratio, percentage, visual or other value indicative of the level of the activity. Assessment may be direct or indirect and the chemical species actually detected need not of course be the proteolysis product itself but may for example be a derivative thereof or some further substance.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in in vitro systems designed to test or use such activities. Thus, for purposes herein the biological activity of a luciferase is its oxygenase activity whereby, upon oxidation of a substrate, light is produced.

As used herein, a combination refers to any association between two or among more items.

As used herein, a combination refers to any association between two or among more items. As used herein, a composition refers to any mixture. It may be a solution, a suspension, liquid, powder, a paste, aqueous, non-aqueous or any combination thereof.

As used herein, a conjugate refers to the compounds provided herein that include one or more MTSPs, particularly single chain protease domains thereof, and one or more targeting agents. These conjugates include those produced by recombinant means as fusion proteins, those produced by chemical means, such as by chemical coupling, through, for example, coupling to sulfhydryl groups, and those produced by any other method whereby at least one MTSP, or a domain thereof, is linked, directly or indirectly via linker(s) to a targeting agent.

As used herein, a targeting agent, is any moiety, such as a protein or effective portion thereof, that provides specific binding of the conjugate to a cell surface receptor, which, preferably, internalizes the conjugate or MTSP portion thereof. A targeting agent may also be one that promotes or facilitates, for example, affinity isolation or purification of the conjugate; attachment of the conjugate to a surface; or detection of the conjugate or complexes containing the conjugate.

As used herein, an antibody conjugate refers to a conjugate in which the targeting agent is an antibody.

As used herein, humanized antibodies refer to antibodies that are modified to include human sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, derivative or analog of a molecule refers to a portion derived from or a modified version of the molecule.

As used herein, fluid refers to any composition that can flow. Fluids thus encompass compositions that are in the form of semi-solids, pastes, solutions, aqueous mixtures, gels, lotions, creams and other such compositions.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein equivalent, when referring to two sequences of nucleic acids means that the two sequences in question encode the same sequence of amino acids or equivalent proteins. When equivalent is used in referring to two proteins or peptides, it means that the two proteins or peptides have substantially the same amino acid sequence with only conservative amino acid substitutions (see, e.g., Table 1, above) that do not substantially alter the activity or function of the protein or peptide. When equivalent refers to a property, the property does not need to be present to the same extent [e.g., two peptides can exhibit different rates of the same type of enzymatic activity], but the activities are preferably substantially the same. Complementary, when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, an agent that modulates the activity of a protein or expression of a gene or nucleic acid either decreases or increases or otherwise alters the activity of the protein or, in some manner up- or down-regulates or otherwise alters expression of the nucleic acid in a cell.

As used herein, inhibitor of an the activity of an MTSP encompasses any substances that prohibit or decrease production, post-translational modification(s), maturation, or membrane localization of the MTSP or any substances that interfere with or decrease the proteolytic efficacy of thereof, particular of a single chain form in vitro.

As used herein, a method for treating or preventing neoplastic disease means that any of the symptoms, such as the tumor, metastasis thereof, the vascularization of the tumors or other parameters by which the disease is characterized are reduced, ameliorated, prevented, placed in a state of remission, or maintained in a state of remission. It also means that the hallmarks of neoplastic disease and metastasis may be eliminated, reduced or prevented by the treatment. Non-limiting examples of the hallmarks include uncontrolled degradation of the basement membrane and proximal extracellular matrix, migration, division, and organization of the endothelial cells into new functioning capillaries, and the persistence of such functioning capillaries.

As used herein, operatively linked or operationally associated refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak *J. Biol. Chem.* 266:19867-19870 (1991)) can be inserted immediately 5' of the start codon and may enhance expression. The desirability of (or need for) such modification may be empirically determined.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, a drug identified by the screening methods provided herein refers to any compound that is a candidate for use as a therapeutic or as lead compound for designed a therapeutic. Such compounds can be small molecules, including small organic molecules, peptides, peptide mimetics, antisense molecules, antibodies, fragments of antibodies, recombinant antibodies and other such compound which can serve as drug candidate or lead compound.

As used herein, production by recombinant means by using recombinant DNA methods means the use of the well known methods of molecular biology for expressing proteins encoded by cloned DNA.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters.

As used herein, a receptor refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, sample refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein: stringency of hybridization in determining percentage mismatch is as follows:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: *Molecular Cloning, A Laboratory Manual*, Cold Spring Harbor Laboratory Press (1989), vol. 3, p. B.13, see, also, numerous catalogs that describe commonly used laboratory solutions). SSPE is pH 7.4 phosphate-buffered 0.18 NaCl. Further, those of skill in the art recognize that the stability of hybrids is determined by Tm, which is a function of the sodium ion concentration and temperature ($Tm=81.5°$ C.$-16.6(\log_{10}[Na^+])+0.41(\%$ G+C$)-600/1$)), so that the only parameters in the wash conditions critical to hybrid stability are sodium ion concentration in the SSPE (or SSC) and temperature.

It is understood that equivalent stringencies may be achieved using alternative buffers, salts and temperatures. By way of example and not limitation, procedures using conditions of low stringency are as follows (see also Shilo and Weinberg, *Proc. Natl. Acad. Sci. USA*, 78:6789-6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65-68° C. and reexposed to film. Other conditions of low stringency which may be used are well known in the art (e.g., as employed for cross-species hybridizations).

By way of example and not way of limitation, procedures using conditions of moderate stringency is provided. For example, but not limited to, procedures using such conditions of moderate stringency are as follows: Filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 5-20×10$^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS.

By way of example and not way of limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which may be used are well known in the art.

The term substantially identical or homologous or similar varies with the context as understood by those skilled in the relevant art and generally means at least 70%, preferably means at least 80%, more preferably at least 90%, and most preferably at least 95% identity.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, target cell refers to a cell that expresses an MTSP in vivo.

As used herein, test substance refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an MTSP, particularly a single chain form that includes the protease domain or a sufficient portion thereof for activity, as determined by in vitro method, such as the assays provided herein.

As used herein, the terms a therapeutic agent, therapeutic regimen, radioprotectant, chemotherapeutic mean conventional drugs and drug therapies, including vaccines, which are known to those skilled in the art. Radiotherapeutic agents are well known in the art.

As used herein, treatment means any manner in which the symptoms of a conditions, disorder or disease are ameliorated or otherwise beneficially altered. Treatment also encompasses any pharmaceutical use of the compositions herein.

As used herein, vector (or plasmid) refers to discrete elements that are used to introduce heterologous DNA into cells for either expression or replication thereof. The vectors typically remain episomal, but may be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein binding sequence refers to a protein or peptide sequence that is capable of specific binding to other protein or peptide sequences generally, to a set of protein or peptide sequences or to a particular protein or peptide sequence.

As used herein, epitope tag refers to a short stretch of amino acid residues corresponding to an epitope to facilitate subsequent biochemical and immunological analysis of the epitope tagged protein or peptide. Epitope tagging is achieved by appending the sequence of the epitope tag to the protein-encoding sequence in an appropriate expression vector. Epitope tagged proteins can be affinity purified using highly specific antibodies raised against the tags.

As used herein, metal binding sequence refers to a protein or peptide sequence that is capable of specific binding to metal ions generally, to a set of metal ions or to a particular metal ion.

As used herein, a composition refers to a any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction which is made from a lysed or disrupted cell.

As used herein, an agent is said to be randomly selected when the agent is chosen randomly without considering the specific sequences involved in the association of a protein alone or with its associated substrates, binding partners, etc. An example of randomly selected agents is the use a chemical library or a peptide combinatorial library, or a growth broth of an organism.

As used herein, an agent is the to be rationally selected or designed when the agent is chosen on a non-random basis which takes into account the sequence of the target site and/or its conformation in connection with the agent's action. As described in the Examples, there are proposed binding sites for serine protease and (catalytic) sites in the protein having SEQ ID NO:3 or SEQ ID NO:4. Agents can be rationally selected or rationally designed by utilizing the peptide sequences that make up these sites. For example, a rationally selected peptide agent can be a peptide whose amino acid sequence is identical to the ATP or calmodulin binding sites or domains.

For clarity of disclosure, and not by way of limitation, the detailed description is divided into the subsections that follow.

B. MTSP Proteins, Muteins, Derivatives and Analogs Thereof MTSPs

The MTSPs are a family of transmembrane serine proteases that are found in mammals and also other species that share a number of common structural features including: a proteolytic extracellular C-terminal domain; a transmembrane domain, with a hydrophobic domain near the N-terminus; a short cytoplasmic domain; and a variable length stem region containing modular domains. The proteolytic domains share sequence homology including conserved his, asp, and ser residues necessary for catalytic activity that are present in conserved motifs. The MTSPs are synthesized as zymogens, and activated to double chain forms by cleavage. It is shown herein that the single chain proteolytic domain can function in vitro and, hence is useful in in vitro assays for identifying agents that modulate the activity of members of this family. Also provided are family members designated MTSP3, MTSP4 and an MTSP6 variant.

The MTSP family is a target for therapeutic intervention and also some, may serve as diagnostic markers for tumor development, growth and/or progression. As discussed, the members of this family are involved in proteolytic processes that are implicated in tumor development, growth and/or progression. This implication is based upon their functions as proteolytic enzymes in processes related to ECM degradative pathways. In addition, their levels of expression or level of activation or their apparent activity resulting from substrate levels or alterations in substrates and levels thereof differs in tumor cells and non-tumor cells in the same tissue. Hence, protocols and treatments that alter their activity, such as their proteolytic activities and roles in signal transduction, and/or their expression, such as by contacting them with a compound that modulates their activity and/or expression, could impact tumor development, growth and/or progression. Also, in some instances, the level of activation and/or expression may be altered in tumors, such as lung carcinoma, colon adenocarcinoma and ovarian carcinoma.

The MTSP may serve as a diagnostic marker for tumors. It is shown herein, that MTSP3 and MTSP4 and the MTSP6 variant provided herein are expressed and/or activated in certain tumors; hence their activation or expression may serve as a diagnostic marker for tumor development, growth and/or progression. In other instances the MTSP protein can exhibit altered activity by virtue of a change in activity or expression of a co-factor therefor or a substrate therefor. In addition, in some instances, these MTSPS and/or variants thereof may be shed from cell surfaces. Detection of the shed MTSPS, particularly the extracellular domains, in body fluids, such as serum, blood, saliva, cerebral spinal fluid, synovial fluid and interstitial fluids, urine, sweat and other such fluids and secretions, may serve as a diagnostic tumor marker. In particular, detection of higher levels of such shed polypeptides in a subject compared to a subject known not to have any neoplastic disease or compared to earlier samples from the same subject, can be indicative of neoplastic disease in the subject.

Provided herein are isolated substantially pure single polypeptides that contain the protease domain of an MTSP as a single chain. The MTSPs contemplated herein are not expressed on endothelial cells, and, preferably, are expressed on tumor cells, typically at a level that differs from the level in which they are expressed in the non-tumor cell of the same type. Hence, for example, if the MTSP is expressed in an ovarian tumor cell, to be of interest herein with respect to ovarian cancer, it is expressed at the same level in non-tumor ovarian cells. MTSP protease domains include the single chain protease domains of MTSP1, MTSP3, MTSP4, MTSP6 and other such proteases, including, but are not limited to, corin, enterpeptidase, human airway trypsin-like protease (HAT), MTSP1, TMPRS2, and TMPRSS4.

Provided are the protease domains or proteins that include a portion of an MTSP that is the protease domain of any MTSP, particularly an MTSP1, MTSP3, MTSP4 and MTSP6. The protein can also include other non-MTSP sequences of amino acids, but will include the protease domain or a sufficient portion thereof to exhibit catalytic activity in any in vitro assay that assess such protease activity, such as any provided herein.

Also provided herein are nucleic acid molecules that encode MTSP proteins and the encoded proteins. In particular, nucleic acid molecules encoding MTSP-3 and MTSP-4 from animals, including splice variants thereof are provided. The encoded proteins are also provided. Also provided are functional domains thereof.

In specific aspects, the MTSP protease domains, portions thereof, and muteins thereof are from or based on animal MTSPS, including, but are not limited to, rodent, such as mouse and rat; fowl, such as chicken; ruminants, such as goats, cows, deer, sheep; ovine, such as pigs; and humans.

In particular, MTSP derivatives can be made by altering their sequences by substitutions, additions or deletions that provide for functionally equivalent molecules. Due to the degeneracy of nucleotide coding sequences, other nucleic sequences which encode substantially the same amino acid sequence as a MTSP gene can be used. These include but are not limited to nucleotide sequences comprising all or portions of MTSP genes that are altered by the substitution of different codons that encode the amino acid residue within the sequence, thus producing a silent change. Likewise, the MTSP derivatives include, but are not limited to, those containing, as a primary amino acid sequence, all or part of the amino acid sequence of MTSP, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid (see, e.g., Table 1).

In a preferred embodiment, the substantially purified MTSP protease is encoded by a nucleic acid that hybridizes to the a nucleic acid molecule containing the protease domain encoded by the nucleotide sequence set forth in any of SEQ. ID Nos. 1, 3, 5, 7, 9 or 11 under at least moderate, generally high, stringency conditions, such that the protease domain encoding nucleic acid thereof hybridizes along its full length. In preferred embodiments the substantially purified MTSP protease is a single chain polypeptide that includes substantially the sequence of amino acids set forth in any SEQ ID Nos. 2, 4, 6, 8, 10 and 12 that encodes the protease domain. Specific sequences for the following human MTSPs and domains thereof are provided as follows: SEQ ID No. 3 MTSP3 nucleic acid sequence; SEQ ID No. 4 MTSP3 amino acid sequence; SEQ ID No. 5 MTSP4 nucleic acid encoding the protease domain; SEQ ID No. 6 MTSP4 amino acid sequence of the protease domain; SEQ ID No. 7 MTSP4-L nucleic acid sequence; SEQ ID No. 8 MTSP4-L amino acid sequence; SEQ ID No. 9 MTSP4-S nucleic acid sequence; SEQ ID No. 10 MTSP4-S amino acid sequence; SEQ ID No. 11 MTSP6 nucleic acid sequence; SEQ ID No. 12 MTSP6 amino acid sequence. SEQ ID No. 1 sets forth the nucleic acid sequence of the long form of MTSP1; SEQ ID No. 2 the encoded amino acid sequence; SEQ ID No. 49 sets forth the sequence of a protease domain of an MTSP1, and SEQ ID No. 50 the sequence of the encoded single chain protease domain thereof. FIGS. 1-3 depict the structural organization of the MTSP3, MTSP4 and MTSP6, respectively.

In particular, exemplary protease domains include at least a sufficient portion of sequences of amino acids set forth as amino acids 615-855 in SEQ ID No. 2 (encoded by nucleotides 1865-2587 in SEQ ID No. 1; see also SEQ ID Nos. 49 and 50) from MTSP1 (matriptase), amino acids 205-437 of SEQ ID NO. 4 from MTSP3, SEQ ID No. 6, which sets forth the protease domain of MTSP4, and amino acids 217-443 of SEQ ID No. 11 from MTSP6.

Also contemplated are nucleic acid molecules that encode a single chain MTSP protease that have proteolytic activity in an in vitro proteolysis assay and that have at least 60%, 70%, 80%, 85%, 90% or 95% sequence identity with the full length of a protease domain of an MTSP protein, or that hybridize along their full length to a nucleic acids that encode a protease domain, particularly under conditions of moderate, generally high, stringency. As above, the encoded polypeptides contain the protease as a single chain.

The isolated nucleic acids may include of at least 8 nucleotides of an MTSP sequence. In other embodiments, the nucleic acids may contain least 25 (continuous) nucleotides, 50 nucleotides, 100 nucleotides, 150 nucleotides, or 200 nucleotides of a MTSP sequence, or a full-length MTSP coding sequence. In another embodiment, the nucleic acids are smaller than 35, 200 or 500 nucleotides in length. Nucleic acids can be single or double stranded. Nucleic acids that hybridizes to or complementary to the foregoing sequences, in particular the inverse complement to nucleic acids that hybridizes to the foregoing sequences (i.e., the inverse complement of a nucleic acid strand has the complementary sequence running in reverse orientation to the strand so that the inverse complement would hybridize without mismatches to the nucleic acid strand; thus, for example, where the coding strand is that hybridizes to a nucleic acid with no mismatches between the coding strand and the that hybridizes strand, then the inverse complement of the that hybridizes strand is identical to the coding strand) are also provided. In specific aspects, nucleic acids are provided that include a sequence complementary to (specifically are the inverse complement of) at least 10, 25, 50, 100, or 200 nucleotides or the entire coding region of an MTSP encoding nucleic acid, particularly the protease domain thereof. For MTSP3 and MTSP4 the full-length protein or domain or active fragment thereof.

For each of the nucleic acid molecules, the nucleic acid can be DNA or RNA or PNA or other nucleic acid analogs or may include non-natural nucleotide bases.

Also provided are isolated nucleic acid molecules that include a sequence of nucleotides complementary to the nucleotide sequence encoding an MTSP.

Probes and primers derived from the nucleic acid molecules are provided, Such probes and primers contain at least 8, 14, 16, 30, 100 or more contiguous nucleotides with identity to contiguous nucleotides of an MTSP, including, but are not limited to, MTSP1, MTSP3, MTSP4 and MTSP6. The probes and primers are optionally labelled with a detectable label, such as a radiolabel or a fluorescent tag, or can be mass differentiated for detection by mass spectrometry or other means.

Plasmids and vectors containing the nucleic acid molecules are also provided. Cells containing the vectors, including cells that express the encoded proteins are provided. The cell can be a bacterial cell, a yeast cell, a fungal cell, a plant cell, an insect cell or an animal cell. Methods for producing an MTSP or single chain form of the protease domain thereof by, for example, growing the cell under conditions whereby the encoded MTSP is expressed by the cell, and recovering the expressed protein, are provided herein. As noted, for MTSP3 and MTSP4, the full-length zymogens and activated proteins and activated (two strand) protease and single chain protease domains are provided.

Except for the MTSP proteins (MTSP3 and MTSP4) heretofore unidentified and provided herein, the isolated polypeptides contain the MTSP protease domain or a catalytically active portion thereof and, generally, do not contain additional MTSP. Hence isolated, substantially pure proteases, protease domains or catalytically active portion thereof in single chain form of MTSPs are provided. The protease domains may be included in a longer protein, but such longer protein is not the MTSP zymogen.

Thus, MTSP3 and MTSP4 proteins are provided. For these proteins, the domains, fragments, derivatives or analogs that are functionally active, i.e., capable of exhibiting one or more functional activities associated with the MTSP protein, e.g., serine protease activity, immunogenicity and antigenicity, are provided. As discussed above, the protease domains thereof are also provided. For MTSP3 and MTSP4, the zymogens and activated forms, and also, the single chain and double chain, activated protease domains are provided.

Also provided are nucleic acid molecules that hybridize to the above-noted sequences of nucleotides encoding MTSP3 and MTSP4 (SEQ ID Nos. 3, 5, 7 and 9) at least at low stringency, more preferably at moderate stringency, and most preferably at high stringency, and that encode the protease domain and/or the full length protein or other domains of an MTSP family member, such as MTSP3, MTSP4, MTSP6 or a splice variant or allelic variant thereof, or MTSP6 or a splice variant or allelic variant thereof. Preferably the molecules hybridize under such conditions along their full length for at least one domain and encode at least one domain, such as the protease or extracellular domain, of the polypeptide. In particular, such nucleic acid molecules include any isolated nucleic fragment that encodes at least one domain of a membrane serine protease, that (1) contains a sequence of nucleotides that encodes the protease or a domain thereof, and (2) is selected from among:

(a) a sequence of nucleotides that encodes the protease or a domain thereof includes a sequence of nucleotides set forth above;

(b) a sequence of nucleotides that encodes such portion or the full length protease and hybridizes under conditions of high stringency, preferably to nucleic acid that is complementary to a mRNA transcript present in a mammalian cell that encodes such protein or fragment thereof;

(c) a sequence of nucleotides that encodes a transmembrane protease or domain thereof that includes a sequence of amino acids encoded by such portion or the full length open reading frame; and (d) a sequence of nucleotides that encodes the transmembrane protease that includes a sequence of amino acids encoded by a sequence of nucleotides that encodes such subunit and hybridizes under conditions of high stringency to DNA that is complementary to the mRNA transcript.

Exemplary MTSPs

The above discussion provides an overview and some details of the exemplified MTSPs. The following discussion provides additional details (see, also, EXAMPLES).

MTSP1 (Matriptase)

Matriptase is a trypsin-like serine protease with broad spectrum cleavage activity and two potential regulatory modules. It was named "matriptase" because its ability to degrade the extra-cellular matrix and its trypsin-like activity. When isolated from breast cancer cells (or T-47D cell conditioned medium), matriptase has been reported to be primarily in an uncomplexed form. Matriptase has been isolated from human milk; when isolated from human milk, matriptase was reported to be in one of two complexed forms, 95 kDa (the predominant form) and 110 kDa; uncomplexed matriptase was not detected. (Liu, et al., *J. Biol. Chem.* 274(26):18237-18242 (1999).) It has been proposed that matriptase exists as an uncomplexed protease when in its active state. In breast milk, matriptase has been reported to exist in complex with a fragment of hepatocyte growth factor inhibitor-1 (HAI-1), a Kuntz-type serine protease inhibitor having activity against trypsin-like serine proteases.

Ecotin and Ecotin M84R/M85R are macromolecular inhibitors of serine proteases of the chymotrypsin fold and inhibit ductal branching, morphogenesis and differentiation of the explanted ductal prostate. PC-3 is a cell line derived from prostate cancer epithelial cells. Ecotin and M84R/M85R ecotin were found to decrease tumor size and metastasis in PC-3 implanted nude mice.

Matriptase has been isolated and its encoding nucleic acids cloned from T-47D human breast cancer cell-conditioned medium (Lin et al. (1999) *J. Biol. Chem.* 274:18231-18236). Upon analysis of the cDNA, it was determined that the full length protease has 683 amino acids and contains three main structural regions: a serine protease domain near the carboxyl-terminal region, four tandem low-density lipoprotein receptor domains, and two tandem complement subcomponents C1r and C1s.

Studies to identify additional serine proteases made by cancer cells were done using PC-3 cells. A serine protease termed "MT-SP1", reported to be a transmembrane protease was cloned (Takeuchi et al. (1999) *Proc. Natl. Acad. Sci. U.S.A.* 96:11054-11061). It was subsequently found the originally identified matriptase sequence is included in the translated sequence of the cDNA that encodes MT-SP1. The matriptase cDNA was reported to be a partial MT-SP1 cDNA and to lack 516 of the coding nucleotides (Takeuchi, et al., *J. Biol. Chem* 275:26333-26342 (2000).) Since the reported matriptase encoding cDNA sequence encoded a possible initiating methionine, it was proposed that alternative splicing could yield a protein lacking the N-terminal region of MTSP1.

Matriptase and MT-SP1 demonstrate trypsin-like protease activity and are Type II transmembrane proteins with a common extracellular protease domain. Studies of substrate specificity of MT-SP1 reveal that protease-activated receptor 2 (PAR2) and single-chain urokinase-type plasminogen activator (sc-uPA) are macromolecular substrates of MT-SP1. PAR2 is functions in inflammation, cytoprotection and/or cell adhesion, while sc-uPa is functions in tumor cell invasion and metastasis.

An exemplary nucleotide sequences encoding a human MTSP1 is set forth in SEQ ID Nos 1 and 2 (see also SEQ ID Nos. 49 and 50 for the protease domain thereof). As previously noted SEQ ID No. 1 sets for an MTSP1-encoding nucleic acid sequence. This sequence is the longer version and includes the protease domain, which is common to both variants Nucleic acids encoding the MTSP that hybridizes to the nucleotide sequence set forth in SEQ ID No. 1 can be obtained by any method known in the art, e.g, by PCR amplification using synthetic primers that hybridizes to the 3' and 5' ends of the sequence and/or by cloning from a cDNA or genomic library using a PCR amplification product or an oligonucleotide specific for the gene sequence (e.g., as described in Section C herein). Homologs (e.g., nucleic acids of the above-listed genes of species other than human) or other related sequences (e.g., paralogs) and muteins can be obtained by low, moderate or high stringency hybridization with all or a portion of the particular sequence provided as a probe using methods well known in the art for nucleic acid hybridization and cloning.

Isolated single chain protease domains of MTSP1 proteins from animals are provided herein. As shown herein, the single chain protease domain is catalytically active and can be used in a variety of drug screening assays, particularly in vitro proteolytic assays. Exemplary MTSP protease domains are set forth as the amino acids (615-855 of SEQ ID No. 2) encoded by nucleotides 1865-2587 of SEQ ID No. 1 (see, also, SEQ ID Nos. 49 and 50). The MTSP1 single chain protease domain is catalytically active Muteins of the MTSP1 proteins are provided. In the activated double chain molecule, residue 731 forms a disulfide bond with the Cys at residue 604. In the single chain form, the residue at 731 in the protease domain is free. Muteins in which Cys residues, particularly the free Cys residue (amino acid 731 in SEQ ID No. 2) in the single chain protease domain are provided. Other muteins in which conservative amino acids replacements are effected and that retain proteolytic activity as a single chain are also provided. Such changes may be systematically introduced and tested for activity in in vitro assays, such as those provided herein.

MTSP3

In a specific embodiment, a nucleic acid that encodes a MTSP, designated MTSP3 is provided. In particular, the nucleic acid includes an open reading frame within the following sequence of nucleotides set forth in SEQ ID No. 3. In particular the protein is encoded by the open reading frame that begins at nucleotide 261 and ends at 1574.

Also provided are nucleic acid molecules that hybridize under conditions of at least low stringency, preferably moderate stringency, more preferably high stringency to the following sequence of nucleic acids (SEQ ID No. 3), particularly to the open reading frame encompassed by nucleotides that encode a single protease domain thereof, or any domain of MTSP3

Also included are substantially purified MTSP3 zymogen, activated double chains, single chain protease domains and double chain protease domains. These are encoded by a nucleic acid that includes sequence encoding a protease domain that exhibits proteolytic activity and that hybridizes to a nucleic acid molecule having a nucleotide sequence set forth in SEQ ID No. 3, typically under moderate, generally under high stringency, conditions and most preferably along the full length of the protease domain. Splice variants are also contemplated herein.

In a preferred embodiment, the isolated nucleic acid fragment hybridizes to the nucleic acid having the nucleotide sequence set forth in SEQ ID No: 3 under high stringency conditions, and preferably comprises the sequence of nucleotides set forth in any of SEQ ID Nos. 3 or comprises a portion thereof that encodes a transmembrane domain and may additionally include a LDLR domain, a scavenger-receptor cysteine rich (SRCR) domain and a serine protease catalytic domain or any other identified domain (see FIGURES) or comprises nucleic acid molecule that encodes the protein encoded by SEQ ID NO. 4.

The isolated nucleic acid fragment is DNA, including genomic or cDNA, or is RNA, or can include other components, such as protein nucleic acid. The isolated nucleic acid may include additional components, such as heterologous or native promoters, and other transcriptional and translational regulatory sequences, these genes may be linked to other genes, such as reporter genes or other indicator genes or genes that encode indicators.

Also provided is an isolated nucleic acid molecule that includes the sequence of molecules that is complementary to the nucleotide sequence encoding the MTSP or the portion thereof.

Also provided are fragments thereof that can be used as probes or primers and that contain at least about 10 nucleotides, more preferably 14 nucleotides, more preferably at least about 16 nucleotides, most preferably at least about 30 nucleotides.

Hence provided herein are polypeptides that are encoded by such nucleic acid molecules. Included among those polypeptides are the MTSP3 protease domain or a polypeptide with conservative amino acid changes such that the specificity and protease activity remains substantially unchanged. In particular, a substantially purified mammalian MTSP protein is provided that has a transmembrane domain and may additionally include a CUB domain, one or more of an LDLR domain(s), a scavenger-receptor cysteine rich (SRCR) domain and a serine protease catalytic domain is provided.

Also provided is a substantially purified protein comprising a sequence of amino acids that has at least 60%, more preferably at least about 90%, most preferably at least about 95%, identity to the MTSP3, wherein the percentage identity is determined using standard algorithms and gap penalties that maximize the percentage identity. The human MTSP3 protein is most preferred, although other mammalian MTSP3 proteins are contemplated.

Muteins of MTSP3, particularly those in which Cys residues, such as the Cys310 in the single chain protease domain, is replaced with another amino acid that does not eliminate the activity, are provided.

MTSP4

Among the proteins provided herein is MTSP4. MTSP4 is highly expressed in the liver, and is expressed in substantially lower levels in other tissues (see, EXAMPLES). It is also expressed in non-liver-derived tumors (see EXAMPLES), including Burkitt's lymphoma, colorectal adenocarcinoma (SW480), lung carcinoma (A549), and in leukemic cells, indicating a role in one or more of tumor progression, tumor invasion, tumor growth and tumor metastases.

Also provided are nucleic acid molecules that hybridize under conditions of at least low stringency, preferably moderate stringency, more preferably high stringency to the sequence of nucleic acids set forth in SEQ ID Nos. 5, 7 or 9), particularly to the open reading frame encompassed by nucleotides that encode a single protease domain thereof, or any domain of an MTSP4.

Also included are substantially purified MTSP4 zymogens, activated double chains, single chain protease domains and double chain protease domains. These are encoded by a nucleic acid that includes sequence encoding a protease domain that exhibits proteolytic activity and that hybridizes to a nucleic acid molecule having a nucleotide sequence set forth in SEQ ID Nos. 5, 7 and 9, typically under moderate, generally under high stringency, conditions and most preferably along the full length of the protease domain.

In a preferred embodiment, the isolated nucleic acid fragment hybridizes to the nucleic acid having the nucleotide sequence set forth in SEQ ID No: 5, 7 or 9 under high stringency conditions, and preferably comprises the sequence of nucleotides set forth in any of SEQ ID Nos. 5, 7 or 9 comprises a portion thereof that encodes a transmembrane domain and may additionally include a LDLR domain, a scavenger-receptor cysteine rich (SRCR) domain and a serine protease catalytic domain or any other identified domain (see FIGURES) or comprises nucleic acid molecule that encodes the protein encoded by SEQ ID NO. 6, 9 or 10.

The isolated nucleic acid fragment is DNA, including genomic or cDNA, or is RNA, or can include other components, such as protein nucleic acid. The isolated nucleic acid may include additional components, such as heterologous or native promoters, and other transcriptional and translational regulatory sequences, these genes may be linked to other genes, such as reporter genes or other indicator genes or genes that encode indicators.

Also provided is an isolated nucleic acid molecule that includes the sequence of molecules that is complementary to the nucleotide sequence encoding and MTSP4 or the portion thereof.

Also provided are fragments thereof that can be used as probes or primers and that contain at least about 10 nucleotides, more preferably 14 nucleotides, more preferably at least about 16 nucleotides, most preferably at least about 30 nucleotides.

In particular nucleic acid molecules encoding two forms of MTSP4 are provide. The encoded proteins are multi-domain, type II membrane-type serine proteases and include a transmembrane domain at the N terminus followed by a CUB domain, 3 LDLR domains and a trypsin-like serine protease domain at the C terminus. The difference between the two forms, which are splice variants, is the absence in MTSP4-S of a 432-bp nucleotide sequence between the transmembrane and the CUB domains (see FIG. 2; see, also SEQ ID Nos. 5-10).

Also provided is a nucleic acid that encodes the extracellular protease domain of an MTSP4 is provided. Both forms of MTSP4 exemplified herein include a protease domain in common (see SEQ ID Nos. 5 and 6).

In particular, the extracellular protease domain of the MTSP4 proteins is encoded by the open reading frame that begins at nucleotide 1 and ends at 708 (TGA) (SEQ ID No. 5. This open reading frame encodes a portion of the MSTP4 protein and includes the protease domain. Full length MSTP4 proteins (SEQ ID Nos. 7 and 9) include the above domain. The extracellular protease domain, as a single chain, and also an activated double chain, exhibit protease activity. The disulfide bonds that form that two chain form of MTSP forms are likely between Cys415 and Cys535 for MTSP4-S, and between Cys559 and Cys679 for MTSP4-L.

For use of the single chain protease domain thereof, it is of interest to replace the free Cys (i.e. Cys535 (Cys679)) in the protease domain with another amino acid, such as any amino acid that does not alter the function (such change is likely to be any amino acid). Thus, muteins of MTSP4, particularly those in which Cys residues, such as the Cys535 and Cys679 in the single chain protease domains of MTSP4-S and MTSP4-L, respectively, are provided.

MTSP6

Nucleic acid and the encoded MTSP6 protein of an exemplary MTSP6 are also provided. The respective sequences are set forth in SEQ ID Nos. 11 and 12. The MTSP6 DNA and protein sequences were analyzed using DNA Strider (version 1.2). The ORF encoding the MTSP6 variant provided herein is composed of 1,362 bp, which translate into a 453-amino acid protein. MTSP6 is a multi-domain, type-II membrane-type serine protease containing a transmembrane domain (amino acids 48-68) at the N-terminus followed by a LDLRa domain (LDL receptor domain class a) (amino acids 72-108), a SR domain (Scavenger receptor Cys-rich domain)(amino acids 109-205), and a trypsin-like serine protease domain (amino acids 216-443) (see FIG. 3). Muteins of MTSP6, particularly those in which Cys residues, such as the Cys324 in the single chain protease domain of MTSP6 are provided.

International PCT application No. WO 00/52044 describes MTSPs that resemble the MTSP6 provided herein. The polypeptide provided therein differs at single amino acid positions, such as 90 in SEQ ID No. 12 (Ala is replaced with a Thr), and significantly from the instant MTSP6 in that ten amino acids (amino acid nos. 46-55 in SEQ ID No. 12) are replaced with the eleven amino acids: phe glu val phe ser gln ser ser ser leu gly (SEQ ID No. 59) resulting in a protein that is one 454 amino acids long.

There are a few other amino acid sequence differences and a number of nucleic acid sequence differences. Significantly, there are substantial differences in the protease domain at amino acids 368-394 (368 ICNHRDVYGGIISPSML-CAGYLTGGVD—394; SEQ ID No. 12) are replaced at position 369-396 with amino acids: 369 DLQPQ—GRVR-WHHHLPLHALRGLPDGWRWN 396, where the differences from 368-394 (Seq ID No. 12) are indicated.

In addition, a second C-terminus truncated variant with an altered protease domain is identified in the PCT application. The variant is the same as the 454 variant through amino acid 261 thereof (corresponding to 160 of SEQ ID No. 12 herein), followed by 33 amino acids (see SEQ ID No. 60 herein) that differ by virtue of a frame shift.

C. Tumor Specificity and Tissue Expression Profiles

Each MTSP has a characteristic tissue expression profile; the MTSPs in particular, although not exclusively expressed or activated in tumors, exhibit characteristic tumor tissue expression or activation profiles. In some instances, MTSPs may have different activity in a tumor cell from a non-tumor cell by virtue of a change in a substrate or cofactor thereof or other factor that would alter the apparent functional activity of the MTSP. Hence each can serve as a diagnostic marker for particular tumors, by virtue of a level of activity and/or expression or function in a subject (i.e. a mammal, particularly a human) with neoplastic disease, compared to a subject or subjects that do not have the neoplastic disease. In addition, detection of activity (and/or expression) in a particular tissue can be indicative of neoplastic disease. Shed MTSPs in body fluids can be indicative of neoplastic disease. Also, by virtue of the activity and/or expression profiles of each, they can serve as therapeutic targets, such as by administration of modulators of the activity thereof, or, as by administration of a prodrug specifically activated by one of the MTSPs.

Tissue Expression Profiles

MTSP3

The MTSP3 transcript was detected in lung carcinoma (LX-1), colon adenocarcinoma (CX-1), colon adenocarcinoma (GI-112) and ovarian carcinoma (GI-102). No apparent signal was detected in another form of lung carcinoma (GI-117), breast carcinoma (GI-101), pancreatic adenocarcinoma (GI-103) and prostatic adenocarcinoma (PC3).

MTSP1 is expressed in breast cancers.

MTSP4

The MTSP4 transcript, a DNA fragment encoding part of the LDL receptor domain and the protease domain was used to probe an RNA blot composed of 76 different human tissues (catalog number 7775-1; human multiple tissue expression (MTE) array; CLONTECH). As in the northern analysis of gel blot, a very strong signal was observed in the liver. Signals in other tissues were observed in (decreasing signal level): fetal liver>heart=kidney=adrenal gland=testis=fetal heart and kidney=skeletal muscle=bladder=placenta>brain=spinal cord=colon=stomach=spleen=lymph node=bone marrow=trachea=uterus=pancreas=salivary gland=mammary gland=lung. MTSP4 is also expressed less abundantly in several tumor cell lines including HeLa S3=leukemia K-562=Burkitt's lymphomas (Raji and Daudi) =colorectal adenocarcinoma (SW480)>lung carcinoma (A549)=leukemia MOLT-4=leukemia HL-60. PCR of the MTSP4 transcript from cDNA libraries made from several human primary tumors xenografted in nude mice (human tumor multiple tissue cDNA panel, catalog number K1522-1, CLONTECH) was performed using MTSP4-specific primers. The MTSP4 transcript was detected in breast carcinoma (GI-101), lung carcinoma (LX-1), colon adenocarcinoma (GI-112) and pancreatic adenocarcinoma (GI-103). No apparent signal was detected in another form of lung carcinoma (GI-117), colon adenocarcinoma (CX-1), ovarian carcinoma (GI-102), and prostatic adenocarcinoma (PC3). The MTSP4 transcript was also detected in LNCaP and PC-3 prostate cancer cell lines as well as in HT-1080 human fibrosarcoma cell line.

Gene Expression Profile of MTSP6 in Normal and Tumor Tissues

To obtain information regarding the gene expression profile of the MTSP6 transcript, a 495 by DNA fragment obtained from PCR reaction with primers Ch17-NSP-3 and NSP-4AS was used to probe an RNA blot composed of 76 different human tissues (catalog number 7775-1; human multiple tissue expression (MTE) array; CLONTECH). The strongest signal was observed in duodenum. Signal in other tissues were observed in (decreased signal level): Stomach>trachea=mammary gland=thyroid gland=salivary gland=pituitary gland=pancreas>kidney>lung>jejunum=ileum=ilocecum=appendix=fetal kidney>fetal lung. Very weak signals can also be detected in several other tissues.

MTSP6 is also expressed in several tumor cell lines including HeLa S3>colorectal adenocarcinoma (SW480)>leukemia MOLT-4>leukemia K-562. PCR analysis of the MTSP6 transcript from cDNA libraries made from several human primary tumors xenografted in nude mice (human tumor multiple tissue cDNA panel, catalog number K1522-1, CLONTECH) was performed using MTSP6-specific primers (Ch17-NSP-3 and Ch17-NSP2AS). The MTSP6 transcript was strongly detected in lung carcinoma (LX-1), moderately detected in pancreatic adenocarcinoma (GI-103), weakly detected in ovarian carcinoma (GI-102); and very weakly detected in colon adenocarcinoma (GI-112 and CX-1), breast carcinoma (GI-101), lung carcinoma (GI-117) and prostatic adenocarcinoma (PC3). The MTSP6 transcript was also detected in breast cancer cell line MDA-MB-231, prostate cancer cell line PC-3, but not in HT-1080 human fibrosarcoma cell line. MTSP6 is also expressed in mammary gland carcinoma cDNA (Clontech). MTSP6 is also over expressed in ovarian tumor cells.

D. Identification and Isolation of Mtsp Protein Genes

The MTSP proteins, or domains thereof, can be obtained by methods well known in the art for protein purification and recombinant protein expression. Any method known to those of skill in the art for identification of nucleic acids that encode desired genes may be used. Any method available in the art can be used to obtain a full length (i.e., encompassing the entire coding region) cDNA or genomic DNA clone encoding an MTSP protein. In particular, the polymerase chain reaction (PCR) can be used to amplify a sequence identified as being differentially expressed in normal and tumor cells or tissues, e.g., nucleic acids encoding an MTSP protein (SEQ. NOs: 1-12), in a genomic or cDNA library. Oligonucleotide primers that hybridize to sequences at the 3' and 5' termini of the identified sequences can be used as primers to amplify by PCR sequences from a nucleic acid sample (RNA or DNA), preferably a cDNA library, from an appropriate source (e.g., tumor or cancer tissue).

PCR can be carried out, e.g., by use of a Perkin-Elmer Cetus thermal cycler and Taq polymerase (Gene Amp™). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain MTSP protein sequences from species other than humans or to obtain human sequences with homology to MTSP protein) by allowing for greater or lesser degrees of nucleotide sequence similarity between the known nucleotide sequence and the nucleic acid homolog being isolated. For cross species hybridization, low stringency conditions are preferred. For same species hybridization, moderately stringent conditions are preferred. After successful amplification of the nucleic acid containing all or a portion of the identified MTSP protein sequence or of a nucleic acid encoding all or a portion of an MTSP protein homolog, that segment may be molecularly cloned and sequenced, and used as a probe to isolate a complete cDNA or genomic clone. This, in turn, will permit the determination of the gene's complete nucleotide sequence, the analysis of its expression, and the production of its protein product for functional analysis. Once the nucleotide sequence is determined, an open reading frame encoding the MTSP protein gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the nucleotide sequences of the entire MTSP protein genes as well as the amino acid sequences of MTSP protein proteins and analogs may be identified.

Any eukaryotic cell potentially can serve as the nucleic acid source for the molecular cloning of the MTSP protein gene. The nucleic acids can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a portion of the MTSP protein (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments may be screened by nucleic acid hybridization to the labeled probe (Benton and Davis, Science 196:180 (1977); Grunstein and Hogness, Proc. Natl. Acad. Sci. U.S.A. 72:3961 (1975)). Those DNA fragments with substantial homology to the probe will hybridize. It is also possible to identify the appropriate fragment by restriction enzyme digestion(s) and comparison of fragment sizes with those expected according to a known restriction map if such is available or by DNA sequence analysis and comparison to the known nucleotide sequence of MTSP protein. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNA, can be selected which produce a protein that, e.g., has similar or identical electrophoretic migration, isoelectric focusing behavior, proteolytic digestion maps, antigenic properties, serine protease activity. If an anti-MTSP protein antibody is available, the protein may be identified by binding of labeled antibody to the putatively MTSP protein synthesizing clones, in an ELISA (enzyme-linked immunosorbent assay)-type procedure.

Alternatives to isolating the MTSP protein genomic DNA include, but are not limited to, chemically synthesizing the gene sequence from a known sequence or making cDNA to the mRNA that encodes the MTSP protein. For example, RNA for cDNA cloning of the MTSP protein gene can be isolated from cells expressing the protein. The identified and isolated nucleic acids can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. I the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and MTSP protein gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated MTSP protein gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

E. Vectors, Plasmids and Cells that Contain Nucleic Acids Encoding an MTSP Protein or Protease Domain Thereof and Expression of MTSP Proteins Vectors and Cells For recombinant expression of one or more of the MTSP proteins, the nucleic acid containing all or a portion of the nucleotide sequence encoding the MTSP protein can be inserted into an appropriate expression vector, i.e., a vector that contains the necessary elements for the transcription and translation of the inserted protein coding sequence. The necessary transcriptional and translational signals can also be supplied by the native promoter for MTSP genes, and/or their flanking regions.

Also provided are vectors that contain nucleic acid encoding the MTSPs. Cells containing the vectors are also provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells plant cells, insect cells and animal cells. The cells are used to produce an MTSP protein or protease domain thereof by growing the above-described cells under conditions whereby the encoded MTSP protein or protease domain of the MTSP protein is expressed by the cell, and recovering the expressed protease domain protein. For purposes herein, the protease domain is preferably secreted into the medium.

In one embodiment, the vectors include a sequence of nucleotides that encodes a polypeptide that has protease activity and contains all or a portion of only the protease domain, or multiple copies thereof, of an MTSP protein are provided. Also provided are vectors that comprise a sequence of nucleotides that encodes the protease domain and additional portions of an MTSP protein up to and including a full length MTSP protein, as well as multiple copies thereof, are also provided. The vectors may selected for expression of the MTSP protein or protease domain thereof in the cell or such that the MTSP protein is expressed as a transmembrane protein. Alternatively, the vectors may include signals necessary for secretion of encoded proteins. When the protease domain is expressed the nucleic acid is preferably linked to a secretion signal, such as the Saccharomyces cerevisiae a mating factor signal sequence or a portion thereof.

A variety of host-vector systems may be used to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements may be used.

Any methods known to those of skill in the art for the insertion of DNA fragments into a vector may be used to construct expression vectors containing a chimeric gene containing appropriate transcriptional/translational control signals and protein coding sequences. These methods may include in vitro recombinant DNA and synthetic techniques and in vivo recombinants (genetic recombination). Expression of nucleic acid sequences encoding MTSP protein, or domains, derivatives, fragments or homologs thereof, may be regulated by a second nucleic acid sequence so that the genes or fragments thereof are expressed in a host transformed with the recombinant DNA molecule(s). For example, expression of the proteins may be controlled by any promoter/enhancer known in the art. In a specific embodiment, the promoter is not native to the genes for MTSP protein. Promoters which may be used include but are not limited to the SV40 early promoter (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci USA* 78:1441-1445 (1981)), the regulatory sequences of the metallothionein gene (Brinster et al., *Nature* 296:39-42 (1982)); prokaryotic expression vectors such as the β-lactamase promoter (Villa-Kamaroff et al., *Proc. Natl. Acad. Sci. USA* 75:3727-3731 1978)) or the tac promoter (DeBoer et al., *Proc. Natl. Acad. Sci. USA* 80:21-25 (1983)); see also "Useful Proteins from Recombinant Bacteria": in Scientific American 242:79-94 (1980)); plant expression vectors containing the nopaline synthetase promoter (Herrar-Estrella et al., *Nature* 303:209-213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310:115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639-646 (1984); Ornitz et al., *Cold Spring Harbor Symp. Quant. Biol.* 50:399-409 (1986); MacDonald, *Hepatology* 7:425-515 (1987)); insulin gene control region which is active in pancreatic beta cells (Hanahan et al., *Nature* 315:115-122 (1985)), immunoglobulin gene control region which is active in lymphoid cells (Grosschedl et al., *Cell* 38:647-658 (1984); Adams et al., *Nature* 318:533-538 (1985); Alexander et al., *Mol. Cell Biol.* 7:1436-1444 (1987)), mouse mammary tumor virus control region which is active in testicular, breast, lymphoid and mast cells (Leder et al., *Cell* 45:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-1648 (1985); Hammer et al., *Science* 235:53-58 1987)), alpha-1 antitrypsin gene control region which is active in liver (Kelsey et al., *Genes and Devel.* 1:161-171 (1987)), beta globin gene control region which is active in myeloid cells (Mogram et al., *Nature* 315:338-340 (1985); Kollias et al., *Cell* 46:89-94 (1986)), myelin basic protein gene control region which is active in oligodendrocyte cells of the brain (Readhead et al., *Cell* 48:703-712 (1987)), myosin light chain-2 gene control region which is active in skeletal muscle (Sani, *Nature* 314:283-286 (1985)), and gonadotrophic releasing hormone gene control region which is active in gonadotrophs of the hypothalamus (Mason et al., *Science* 234:1372-1378 (1986)).

In a specific embodiment, a vector is used that contains a promoter operably linked to nucleic acids encoding an MTSP protein, or a domain, fragment, derivative or homolog, thereof, one or more origins of replication, and optionally, one or more selectable markers (e.g., an antibiotic resistance gene). Expression vectors containing the coding sequences, or portions thereof, of an MTSP protein, is made, for example, by subcloning the coding portions into the EcoRI restriction site of each of the three pGEX vectors (glutathione S-transferase expression vectors (Smith and Johnson, *Gene* 7:31-40 (1988)). This allows for the expression of products in the correct reading frame. Preferred vectors and systems for expression of the protease domains of the MTSP proteins are well known *Pichia* vectors (available, for example, from Invitrogen, San Diego, Calif.), particularly those designed for secretion of the encoded proteins. One exemplary vector is described in the EXAMPLES.

Plasmids for transformation of *E. coli* cells, include, for example, the pET expression vectors (see, U.S. Pat. No. 4,952,496; available from NOVAGEN, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (NOVAGEN, Madison, Wis.), which contain a His-Tag™ leader sequence for use in purification with a His column and a thrombin cleavage site that permits cleavage following purification over the column; the T7-lac promoter region and the T7 terminator.

The vectors are introduced into host cells, such as Pichia cells and bacterial cells, such as *E. coli*, and the proteins expressed therein. Preferred Pichia strains, include, for example, GS115. Preferred bacterial hosts contain chromosomal copies of DNA encoding T7 RNA polymerase operably linked to an inducible promoter, such as the lacUV promoter (see, U.S. Pat. No. 4,952,496). Such hosts include, but are not limited to, the lysogenic *E. coli* strain BL21(DE3).

Expression and Production of Proteins

The MTSP domains, derivatives and analogs be produced by various methods known in the art. For example, once a recombinant cell expressing an MTSP protein, or a domain, fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product. The MTSP protein proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once an MTSP protein or its domain or derivative is identified, the amino acid sequence of the protein can be deduced from the nucleotide sequence of the gene which encodes it. As a result, the protein or its domain or derivative can be synthesized by standard chemical methods known in the art (e.g. see Hunkapiller et al, *Nature* 310:105-111 (1984)).

Manipulations of MTSP protein sequences may be made at the protein level. Also contemplated herein are MTSP protein proteins, domains thereof, derivatives or analogs or fragments thereof, which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In addition, domains, analogs and derivatives of an MTSP protein can be chemically synthesized. For example, a peptide corresponding to a portion of an MTSP protein, which includes the desired domain or which mediates the desired activity in vitro can be synthesized by use of a peptide synthesizer. Furthermore, if desired, nonclassical amino acids or chemical amino acid analogs can be introduced as a substitution or addition into the MTSP protein sequence. Nonclassical amino acids include but are not limited to the D-isomers of the common amino acids, a-amino isobutyric acid, 4-aminobutyric acid, Abu, 2-aminobutyric acid, ε-Abu, e-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

In cases where natural products are suspected of being mutant or are isolated from new species, the amino acid sequence of the MTSP protein isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

Modifications

A variety of modification of the MTSP proteins and domains are contemplated herein. An MTSP-encoding nucleic acid molecule may be modified by any of numerous strategies known in the art (Sambrook et al., 1990, *Molecular Cloning, A Laboratory Manual,* 2d ed., Cold Spring Harbor Laboratory, Cold Spring Harbor, N.Y.). The sequences can be cleaved at appropriate sites with restriction endonuclease(s), followed by further enzymatic modification if desired, isolated, and ligated in vitro. In the production of the gene encoding a domain, derivative or analog of MTSP, care should be taken to ensure that the modified gene retains the original translational reading frame, uninterrupted by translational stop signals, in the gene region where the desired activity is encoded.

Additionally, the MTSP-encoding nucleic acid molecules can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Also, as described herein muteins with primary sequence alterations, such as replacements of Cys residues and elimination of glycosylation sites are contemplated. Such mutations may be effected by any technique for mutagenesis known in the art, including, but not limited to, chemical mutagenesis and in vitro site-directed mutagenesis (Hutchinson et al., *J. Biol. Chem.* 253:6551-6558 (1978)), use of TAB® linkers (Pharmacia). In one embodiment, for example, an MTSP protein or domain thereof is modified to include a fluorescent label. In other specific embodiments, the MTSP protein is modified to have a heterofunctional reagent, such heterofunctional reagents can be used to crosslink the members of the complex.

The MTSP proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once a MTSP or its domain or derivative is identified, the amino acid sequence of the protein can be deduced from the nucleotide sequence of the gene which encodes it. As a result, the protein or its domain or derivative can be synthesized by standard chemical methods known in the art (e.g., see Hunkapiller et al, *Nature,* 310:105-111 (1984)).

Manipulations of MTSP sequences may be made at the protein level. MTSP domains, derivatives or analogs or fragments, which are differentially modified during or after translation, e.g., by glycosylation, acetylation, phosphorylation, amidation, derivatization by known protecting/blocking groups, proteolytic cleavage, linkage to an antibody molecule and other cellular ligand, are contemplated herein. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc.

In addition, domains, analogs and derivatives of a MTSP can be chemically synthesized. For example, a peptide corresponding to a portion of a MTSP, which comprises the desired domain or which mediates the desired activity in vitro can be synthesized by use of a peptide synthesizer. Furthermore, if desired, nonclassical amino acids or chemical amino acid analogs can be introduced as a substitution or addition into the MTSP sequence. Non-classical amino acids include but are not limited to the D-isomers of the common amino acids, a-amino isobutyric acid, 4-aminobutyric acid, Abu, 2-aminobutyric acid, ε-Abu, e-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

F. Screening Methods

The single chain protease domains, as shown herein, can be used in a variety of methods to identify compounds that modulate the activity thereof For MTSPs that exhibit higher activity or expression in tumor cells, compounds that inhibit the proteolytic activity are of particular interest. For any MTSPs that are active at lower levels in tumor cells, compounds or agents that enhance the activity are potentially of interest. In all instances the identified compounds will include agents that are candidate cancer treatments.

Several types of assays are exemplified and described herein. It is understood that the protease domains may be used in other assays. It is shown here, however, that the single chain protease domains exhibit catalytic activity. As such they are ideal for in vitro screening assays.

They may also be used in binding assays.

The MTSP3, MTSP4 and MTSP6 full length zymogens, activated enzymes, single and double chain protease domains are contemplated for use in any screening assay known to those of skill in the art, including those provided herein. Hence the following description, if directed to proteolytic assays is intended to apply to use of a single chain protease domain or a catalytically active portion thereof of any MTSP, including an MTSP3, MTSP4 or an MTSP6. Other assays, such as binding assays are provided herein, particularly for use with an MTSP3, MTSP4 or MTSP6, including any variants, such as splice variants thereof. MTSP3 and MTSP4 are of most interest in such assays.

1. Catalytic Assays for Identification of Agents that Modulate the Protease Activity of an MTSP Protein Methods for identifying a modulator of the catalytic activity of an MTSP, particularly a single chain protease domain or catalytically active portion thereof, are provided herein. The methods can be practiced by: a) contacting the MTSP, particularly a single-chain domain thereof, with a substrate of the MTSP in the presence of a test substance, and detecting the proteolysis of the substrate, whereby the activity of the MTSP is assessed, and comparing the activity to a control. For example, the control can be the activity of the MTSP assessed by contacting an MTSP, particularly a single-chain domain thereof, with a substrate of the MTSP, and detecting the proteolysis of the substrate, whereby the activity of the MTSP is assessed. The results in the presence and absence of the test compounds are compared. A difference in the activity indicates that the test substance modulates the activity of the MTSP.

In one embodiment a plurality of the test substances are screened simultaneously in the above screening method. In another embodiment, the MTSP is isolated from a target cell as a means for then identifying agents that are potentially specific for the target cell.

In still another embodiment, The test substance is a therapeutic compound, and whereby a difference of the MTSP activity measured in the presence and in the absence of the test substance indicates that the target cell responds to the therapeutic compound.

One method include the steps of (a) contacting the MTSP protein or protease domain thereof with one or a plurality of test compounds under conditions conducive to interaction between the ligand and the compounds; and (b) identifying one or more compounds in the plurality that specifically binds to the ligand.

Another method provided herein includes the steps of a) contacting an MTSP protein or protease domain thereof with a substrate of the MTSP protein, and detecting the proteolysis of the substrate, whereby the activity of the MTSP protein is assessed; b) contacting the MTSP protein with a substrate of the MTSP protein in the presence of a test substance, and detecting the proteolysis of the substrate, whereby the activity of the MTSP protein is assessed; and c) comparing the activity of the MTSP protein assessed in steps a) and b), whereby the activity measured in step a) differs from the activity measured in step b) indicates that the test substance modulates the activity of the MTSP protein.

In another embodiment, a plurality of the test substances are screened simultaneously. In comparing the activity of an MTSP protein in the presence and absence of a test substance to assess whether the test substance is a modulator of the MTSP protein, it is unnecessary to assay the activity in parallel, although such parallel measurement is preferred. It is possible to measure the activity of the MTSP protein at one time point and compare the measured activity to a historical value of the activity of the MTSP protein.

For instance, one can measure the activity of the MTSP protein in the presence of a test substance and compare with historical value of the activity of the MTSP protein measured previously in the absence of the test substance, and vice versa. This can be accomplished, for example, by providing the activity of the MTSP protein on an insert or pamphlet provided with a kit for conducting the assay.

Methods for selecting substrates for a particular MTSP are described in the EXAMPLES, and particular proteolytic assays are exemplified.

Combinations and kits containing the combinations optionally including instructions for performing the assays are provided. The combinations include an MTSP protein and a substrate of the MTSP protein to be assayed; and, optionally reagents for detecting proteolysis of the substrate. The substrates, which are typically proteins subject to proteolysis by a particular MTSP protein, can be identified empirically by testing the ability of the MTSP protein to cleave the test substrate. Substrates that are cleaved most effectively (i.e., at the lowest concentrations and/or fastest rate or under desirable conditions), are identified.

Additionally provided herein is a kit containing the above-described combination. Preferably, the kit further includes instructions for identifying a modulator of the activity of an MTSP protein. Any MTSP protein is contemplated as target for identifying modulators of the activity thereof.

2. Binding Assays

Also provided herein are methods for identification and isolation of agents, particularly compounds that bind to MTSPs. The assays are designed to identify agents that bind to the zymogen form, the single chain isolated protease domain (or a protein, other than an MTSP protein, that contains the protease domain of an MTSP protein), and to the activated form, including the activated form derived from the full length zymogen or from an extended protease domain. The identified compounds are candidates or leads for identification of compounds for treatments of tumors and other disorders and diseases involving aberrant angiogenesis. The MTSP proteins used in the methods include any MTSP protein as defined herein, and preferably use MTSP single chain domain or proteolytically active portion thereof.

A variety of methods are provided herein. These methods may be performed in solution or in solid phase reactions in which the MTSP protein(s) or protease domain(s) thereof are linked, either directly or indirectly via a linker, to a solid support. Screening assays are described in the Examples, and these assays have been used to identify candidate compounds.

For purposes herein, all binding assays described above are provided for MTSP3, MTSP4 and MTSP6. For MTSP1 (including any variant thereof) and other such proteases, binding assays that employ the isolated single chain protease domain or a protein containing such domain (other than the MTSP from which the protease is derived) are provided.

Methods for identifying an agent, such as a compound, that specifically binds to an MTSP single chain protease domain or an MTSP, such as an MTSP3, MTSP4 or an MTSP6, are provided herein. The method can be practiced by (a) contacting the MTSP with one or a plurality of test agents under conditions conducive to binding between the MTSP and an agent; and (b) identifying one or more agents within the plurality that specifically binds to the MTSP.

For example, in practicing such methods the MTSP polypeptide is mixed with a potential binding partner or an extract or fraction of a cell under conditions that allow the association of potential binding partners with the polypeptide. After mixing, peptides, polypeptides, proteins or other molecules that have become associated with an MTSP are separated from the mixture. The binding partner that bound to the MTSP can then be removed and further analyzed. To identify and isolate a binding partner, the entire protein, for instance the entire disclosed protein of SEQ ID Nos. 6, 8 10 or 12 can be used. Alternatively, a fragment of the protein can be used.

A variety of methods can be used to obtain cell extracts. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the MTSP under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be used to separate the mixture. For example, antibodies specific to an MTSP can be used to immunoprecipitate the binding partner complex. Alternatively, standard chemical separation techniques such as chromatography and density/sediment centrifugation can be used.

After removing the non-associated cellular constituents in the extract, the binding partner can be dissociated from the complex using conventional methods. For example, dissociation can be accomplished by altering the salt concentration or pH of the mixture.

To aid in separating associated binding partner pairs from the mixed extract, the MTSP can be immobilized on a solid support. For example, the protein can be attached to a nitrocellulose matrix or acrylic beads. Attachment of the protein or a fragment thereof to a solid support aids in separating peptide/binding partner pairs from other constituents found in the extract. The identified binding partners can be either a single protein or a complex made up of two or more proteins.

Alternatively, the nucleic acid molecules encoding the single chain proteases can be used in a yeast two-hybrid system. The yeast two-hybrid system has been used to identify other protein partner pairs and can readily be adapted to employ the nucleic acid molecules herein described.

Another in vitro binding assay, particularly for an MTSP3, MTSP4 or an MTSP6 uses a mixture of a polypeptide that contains at least the catalytic domain of one of these proteins and one or more candidate binding targets or substrates. After incubating the mixture under appropriate conditions, one determines whether the MTSP or a polypeptide fragment thereof containing the catalytic domain binds with the candidate substrate. For cell-free binding assays, one of the components includes or is coupled to a detectable label. The label may provide for direct detection, such as radioactivity, luminescence, optical or electron density, etc., or indirect detection such as an epitope tag, an enzyme, etc. A variety of methods may be employed to detect the label depending on the nature of the label and other assay components. For example, the label may be detected bound to the solid substrate or a portion of the bound complex containing the label may be separated from the solid substrate, and the label thereafter detected.

3. Detection of Signal Transduction

The cell surface location of the MTSPs suggests a role for some or all of these proteins in signal transduction. Assays for assessing signal transduction are well known to those of skill in the art, and may be adapted for use with the MTSP protein.

Assays for identifying agents that effect or alter signal transduction mediated by an MTSP, particularly the full length or a sufficient portion to anchor the extracellular domain or a function portion thereof of an MTSP on the surface of a cell are provided. Such assays, include, for example, transcription based assays in which modulation of a transduced signal is assessed by detecting an effect on an expression from a reporter gene (see, e.g., U.S. Pat. No. 5,436,128).

4. Methods for Identifying Agents that Modulate the Expression a Nucleic Acid Encoding an MTSP, Particularly an MTSP3, MTSP4 or MTSP6

Another embodiment provides methods for identifying agents that modulate the expression of a nucleic acid encoding an MTSP, particularly an MTSP3, MTSP4 or MTSP. Such assays use any available means of monitoring for changes in the expression level of the nucleic acids encoding an MTSP, such as MTSP3 or MTSP4.

In one assay format, cell lines that contain reporter gene fusions between the open reading frame of MTSP3, MTSP4 or MTSP6 or a domain thereof, particularly the protease domain and any assayable fusion partner may be prepared. Numerous assayable fusion partners are known and readily available including the firefly luciferase gene and the gene encoding chloramphenicol acetyltransferase (Alam et al., Anal. Biochem. 188: 245-54 (1990)). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding an MTSP3, MTSP4 or MTSP6.

Additional assay formats may be used to monitor the ability of the agent to modulate the expression of a nucleic acid encoding an MTSP3, MTSP4 or MTSP6. For instance, mRNA expression may be monitored directly by hybridization to the nucleic acids. Cell lines are exposed to the agent to be tested under appropriate conditions and time and total RNA or mRNA is isolated by standard procedures (see, e.g., Sambrook et al. (1989) MOLECULAR CLONING: A LABORATORY MANUAL, 2nd Ed. Cold Spring Harbor Laboratory Press). Probes to detect differences in RNA expression levels between cells exposed to the agent and control cells may be prepared from the nucleic acids. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids through methods known in the art. For instance, the G+C content of the probe and the probe length can affect probe binding to its target sequence. Methods to optimize probe specificity are commonly available (see, e.g., Sambrook et al. (1989) MOLECULAR CLONING: A LABORATORY MANUAL, 2nd Ed. Cold Spring Harbor Laboratory Press); and Ausubel et al. (1995) CURRENT PROTOCOLS IN MOLECULAR BIOLOGY, Greene Publishing Co., NY).

Hybridization conditions are modified using known methods (see, e.g., Sambrook et al. (1989) MOLECULAR CLONING: A LABORATORY MANUAL, 2nd Ed. Cold Spring Harbor Laboratory Press); and Ausubel et al. (1995) CURRENT PROTOCOLS IN MOLECULAR BIOLOGY, Greene Publishing Co., NY), as required for each probe. Hybridization of total cellular RNA or RNA enriched for polyA RNA can be accomplished in any available format. For instance, total cellular RNA or RNA enriched for polyA RNA can be affixed to a solid support, and the solid support exposed to at least one probe comprising at least one, or part of one of the nucleic acid molecules under conditions in which the probe will specifically hybridize. Alternatively, nucleic acid fragments comprising at least one, or part of one of the sequences can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the protein having the sequence of SEQ ID NO:3 or SEQ ID NO:4 are identified.

5. Methods for Identifying Agents that Modulate at Least One Activity of an MTPS, Such as MTSP3, MTSP4 or MTSP6

Methods for identifying agents that modulate at least one activity of a an MTSP, such as an MTSP3, MTSP4 or MTSP6 are provided. Such methods or assays may use any means of monitoring or detecting the desired activity.

In one format, the relative amounts of a protein between a cell population that has been exposed to the agent to be tested compared to an un-exposed control cell population may be assayed (e.g., a prostate cancer cell line, a lung cancer cell line, a colon cancer cell line or a breast cancer cell line). In this format, probes, such as specific antibodies, are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe.

For example, N- and C-terminal fragments of the MTSP can be expressed in bacteria and used to search for proteins which bind to these fragments. Fusion proteins, such as His-tag or GST fusion to the N- or C-terminal regions of the MTSP, such as an MTSP3, MTSP4 or an MTSP6, can be prepared for use as a substrate. These fusion proteins can be coupled to, for example, Glutathione-Sepharose beads and then probed with cell lysates. Prior to lysis, the cells may be treated with a candidate agent which may modulate an MTSP, such as an MTSP3, MTSP4 or an MTSP6, or proteins that interact with domains thereon. Lysate proteins binding to the fusion proteins can be resolved by SDS-PAGE, isolated and identified by protein sequencing or mass spectroscopy, as is known in the art.

Antibody probes are prepared by immunizing suitable mammalian hosts in appropriate immunization protocols using the peptides, polypeptides or proteins if they are of sufficient length (e.g., 4, 5, 6, 7, 8, 9, 10, 11, 12, 13, 14, 15, 20, 25, 30, 35, 40 or more consecutive amino acids the MTSP protein, such as an MTSP3, an MTSP4 or an MTSP6), or if required to enhance immunogenicity, conjugated to suitable carriers. Methods for preparing immunogenic conjugates with carriers, such as bovine serum albumin (BSA), keyhole limpet hemocyanin (KLH), or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. Hapten peptides can be extended at either the amino or carboxy terminus with a Cys residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

Anti-peptide antibodies can be generated using synthetic peptides corresponding to, for example, the carboxy terminal amino acids of the MTSP. Synthetic peptides can be as small as 1-3 amino acids in length, but are preferably at least 4 or more amino acid residues long. The peptides can be coupled to KLH using standard methods and can be immunized into animals, such as rabbits or ungulate. Polyclonal antibodies can then be purified, for example using Actigel beads containing the covalently bound peptide.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler et al., (*Nature* 256:495-7 (1975)) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in vivo via ascites fluid. Of particular interest, are monoclonal antibodies that recognize the catalytic domain of an MTSP, such as an MTSP3, MTSP4 or an MTSP6.

Additionally, the zymogen or two-chain forms the MTSP can be used to make monoclonal antibodies which recognize conformation epitopes. For peptide-directed monoclonal antibodies, peptides from the C1r/C1s domain can be used to generate anti-C1r/C1s domain monoclonal antibodies which can thereby block activation of the zymogen to the two-chain form of the MTSP. This domain can similarly be the substrate for other non-antibody compounds which bind to these preferred domains on either the single-chain or double-chain forms of the MTSP3, MTSP4 or MTSP6, and thereby modulate the activity of thereof or prevent its activation.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')2 fragments are often preferable, especially in a therapeutic context, as these fragments are generally less immunogenic than the whole immunoglobulin.

The antibodies or fragments may also be produced. Regions that bind specifically to the desired regions of receptor can also be produced in the context of chimeras with multiple species origin.

Agents that are assayed in the above method can be randomly selected or rationally selected or designed.

The agents can be, as examples, peptides, small molecules, and carbohydrates. A skilled artisan can readily recognize that there is no limit as to the structural nature of the agents.

The peptide agents can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems.

The production using solid phase peptide synthesis is necessitated if non-gene-encoded amino acids are to be included.

G. Assay Formats and Selection of Test Substances

A variety of formats and detection protocols are known for performing screening assays. Any such formats and protocols may be adapted for identifying modulators of MTSP protein activities. The following includes a discussion of exemplary protocols.

1. High Throughput Screening Assays

Although the above-described assay can be conducted where a single MTSP protein is screened, and/or a single test substance is screened for in one assay, the assay is preferably conducted in a high throughput screening mode, i.e., a plurality of the MTSP proteins are screened against and/or a plurality of the test substances are screened for simultaneously (See generally, *High Throughput Screening: The Discovery of Bioactive Substances* (Devlin, Ed.) Marcel Dekker, 1997; Sittampalam et al., *Curr. Opin. Chem. Biol.*, 1(3):384-91 (1997); and Silverman et al., *Curr. Opin. Chem. Biol.*, 2(3):397-403 (1998)). For example, the assay can be conducted in a multi-well (e.g., 24-, 48-, 96-, or 384-well), chip or array format.

High-throughput screening (HTS) is the process of testing a large number of diverse chemical structures against disease targets to identify "hits" (Sittampalam et al., *Curr. Opin. Chem. Biol.*, 1(3):384-91 (1997)). Current state-of-the-art HTS operations are highly automated and computerized to handle sample preparation, assay procedures and the subsequent processing of large volumes of data.

Detection technologies employed in high-throughput screens depend on the type of biochemical pathway being investigated (Sittampalam et al., *Curr. Opin. Chem. Biol.*, 1(3):384-91 (1997)). These methods include, radiochemical methods, such as the scintillation proximity assays (SPA), which can be adapted to a variety of enzyme assays (Lerner et al., *J. Biomol. Screening*, 1:135-143 (1996); Baker et al., *Anal. Biochem.*, 239:20-24 (1996); Baum et al., *Anal. Biochem.*, 237:129-134 (1996); and Sullivan et al., *J. Biomol. Screening*, 2:19-23 (1997)) and protein-protein interaction assays (Braunwalder et al., *J. Biomol. Screening*, 1:23-26 (1996); Sonatore et al., *Anal. Biochem.*, 240:289-297 (1996); and Chen et al., *J. Biol. Chem.*, 271:25308-25315 (1996)), and non-isotopic detection methods, including but are not limited to, colorimetric and luminescence detection methods, resonance energy transfer (RET) methods, time-resolved fluorescence (HTRF) methods, cell-based fluorescence assays, such as fluorescence resonance energy transfer (FRET) procedures (see, e.g., Gonzalez et al., *Biophys. J.*, 69:1272-1280 (1995)), fluorescence polarization or anisotropy methods (see, e.g., Jameson et al., *Methods Enzymol.*, 246:283-300 (1995); Jolley, *J. Biomol. Screening*, 1:33-38 (1996); Lynch et al., *Anal. Biochem.*, 247:77-82 (1997)), fluorescence correlation spectroscopy (FCS) and other such methods.

2. Test Substances

Test compounds, including small molecules and libraries and collections thereof can be screened in the above-described assays and assays described below to identify compounds that modulate the activity an MTSP protein. Rational drug design methodologies that rely on computational chemistry may be used to screen and identify candidate compounds.

The compounds identified by the screening methods include inhibitors, including antagonists, and may be agonists Compounds for screening are any compounds and collections of compounds available, know or that can be prepared.

a. Selection of Compounds

Compounds can be selected for their potency and selectivity of inhibition of serine proteases, especially MTSP protein. As described herein, and as generally known, a target serine protease and its substrate are combined under assay conditions permitting reaction of the protease with its substrate. The assay is performed in the absence of test compound, and in the presence of increasing concentrations of the test compound. The concentration of test compound at which 50% of the serine protease activity is inhibited by the test compound is the $IC_{50}$ value (Inhibitory Concentration) or $EC_{50}$ (Effective Concentration) value for that compound. Within a series or group of test compounds, those having lower $IC_{50}$ or $EC_{50}$ values are considered more potent inhibitors of the serine protease than those compounds having higher $IC_{50}$ or $EC_{50}$ values. The $IC_{50}$ measurement is often used for more simplistic assays, whereas the $EC_{50}$ is often used for more complicated assays, such as those employing cells.

Preferred compounds according to this aspect have an $IC_{50}$ value of 100 nM or less as measured in an in vitro assay for inhibition of MTSP protein activity. Especially preferred compounds have an $IC_{50}$ value of less than 100 nM.

The test compounds also are evaluated for selectivity toward a serine protease. As described herein, and as generally known, a test compound is assayed for its potency toward a panel of serine proteases and other enzymes and an $IC_{50}$ value or $EC_{50}$ value is determined for each test compound in each assay system. A compound that demonstrates a low $IC_{50}$ value or $EC_{50}$ value for the target enzyme, e.g., MTSP protein, and a higher $IC_{50}$ value or $EC_{50}$ value for other enzymes within the test panel (e.g., urokinase tissue plasminogen activator, thrombin, Factor Xa), is considered to be selective toward the target enzyme. Generally, a compound is deemed selective if its $IC_{50}$ value or $EC_{50}$ value in the target enzyme assay is at least one order of magnitude less than the next smallest $IC_{50}$ value or $EC_{50}$ value measured in the selectivity panel of enzymes.

Presently preferred compounds have an $IC_{50}$ value of 100 nM or less as measured in an in vitro assay for inhibition of urokinase activity. Especially preferred compounds have an $IC_{50}$ value in the in vitro urokinase inhibition assay that is at least one order of magnitude smaller than the $IC_{50}$ value measured in the in vitro tPA inhibition assay. Compounds having a selectivity ratio of $IC_{50}$ u-PA assay: $IC_{50}$ MTSP protein assay of greater than 100 are especially preferred.

Compounds are also evaluated for their activity in vivo. The type of assay chosen for evaluation of test compounds will depend on the pathological condition to be treated or prevented by use of the compound, as well as the route of administration to be evaluated for the test compound.

For instance, to evaluate the activity of a compound to reduce tumor growth through inhibition of MTSP protein, the procedures described by Jankun et al., *Canc. Res.*, 57:559-563 (1997) to evaluate PAI-1 can be employed. Briefly, the ATCC cell lines DU145 and LnCaP are injected into SCID mice. After tumors are established, the mice are given test compound according to a dosing regime determined from the compound's in vitro characteristics. The Jankun et al. compound was administered in water. Tumor volume measurements are taken twice a week for about five weeks. A compound is deemed active if an animal to which the compound was administered exhibited decreased tumor volume, as compared to animals receiving appropriate control compounds.

Another in vivo experimental model designed to evaluate the effect of p-aminobenzamidine, a swine protease inhibitor, on reducing tumor volume is described by Billström et al., *Int. J. Cancer*, 61:542-547 (1995).

To evaluate the ability of a compound to reduce the occurrence of, or inhibit, metastasis, the procedures described by Kobayashi et al., *Int. J. Canc.*, 57:727-733d (1994) can be employed. Briefly, a murine xenograft selected for high lung colonization potential in injected into C57B1/6 mice i.v. (experimental metastasis) or s.c. into the abdominal wall (spontaneous metastasis). Various concentrations of the compound to be tested can be admixed with the tumor cells in Matrigel prior to injection. Daily i.p. injections of the test compound are made either on days 1-6 or days 7-13 after tumor inoculation. The animals are sacrificed about three or four weeks after tumor inoculation, and the lung tumor colonies are counted. Evaluation of the resulting data permits a determination as to efficacy of the test compound, optimal dosing and route of administration.

The activity of the tested compounds toward decreasing tumor volume and metastasis can be evaluated in model described in Rabbani et al., *Int. J. Cancer* 63:840-845 (1995) to evaluate their inhibitor. There, Mat LyLu tumor cells were injected into the flank of Copenhagen rats. The animals were implanted with osmotic minipumps to continuously administer various doses of test compound for up to three weeks. The tumor mass and volume of experimental and control animals were evaluated during the experiment, as were metastatic growths. Evaluation of the resulting data permits a determination as to efficacy of the test compound, optimal dosing, and route of administration. Some of these authors described a related protocol in Xing et al., *Canc. Res.*, 57:3585-3593 (1997).

To evaluate the inhibitory activity of a compound, a rabbit cornea neovascularization model can be employed. Avery et al., *Arch. Ophthalmol.*, 108:1474-1475 (1990) describe anesthetizing New Zealand albino rabbits and then making a central corneal incision and forming a radial corneal pocket. A slow release prostaglandin pellet was placed in the pocket to induce neovascularization. Test compound was administered i.p. for five days, at which time the animals were sacrificed. The effect of the test compound is evaluated by review of periodic photographs taken of the limbus, which can be used to calculate the area of neovascular response and, therefore, limbal neovascularization. A decreased area of neovascularization as compared with appropriate controls indicates the test compound was effective at decreasing or inhibiting neovascularization.

An angiogenesis model used to evaluate the effect of a test compound in preventing angiogenesis is described by Min et al., *Canc. Res.*, 56:2428-2433 (1996). C57BL6 mice receive subcutaneous injections of a Matrigel mixture containing bFGF, as the angiogenesis-inducing agent, with and without the test compound. After five days, the animals are sacrificed and the Matrigel plugs, in which neovascularization can be visualized, are photographed. An experimental animal receiving Matrigel and an effective dose of test compound will exhibit less vascularization than a control animal or an experimental animal receiving a less- or non-effective does of compound.

An in vivo system designed to test compounds for their ability to limit the spread of primary tumors is described by Crowley et al., *Proc. Natl. Acad. Sci.*, 90:5021-5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. In addition, the level of CAT detected in various organs provides an indication of the ability of the test compound to inhibit metastasis; detection of less CAT in tissues of a treated animal versus a control animal indicates less CAT-expressing cells migrated to that tissue.

In vivo experimental modes designed to evaluate the inhibitory potential of a test serine protease inhibitors, using a tumor cell line F3II, the to be highly invasive, are described by Alonso et al., *Breast Canc. Res. Treat.*, 40:209-223 (1996). This group describes in vivo studies for toxicity determination, tumor growth, invasiveness, spontaneous metastasis, experimental lung metastasis, and an angiogenesis assay.

The CAM model (chick embryo chorioallantoic membrane model), first described by L. Ossowski in 1998 (*J. Cell Biol.*, 107:2437-2445 (1988)), provides another method for evaluating the urokinase inhibitory activity of a test compound. In the CAM model, tumor cells invade through the chorioallantoic membrane containing CAM with tumor cells in the presence of several serine protease inhibitors results in less or no invasion of the tumor cells through the membrane. Thus, the CAM assay is performed with CAM and tumor cells in the presence and absence of various concentrations of test compound. The invasiveness of tumor cells is measured under such conditions to provide an indication of the compound's inhibitory activity. A compound having inhibitory activity correlates with less tumor invasion.

The CAM model is also used in a standard assay of angiogenesis (i.e., effect on formation of new blood vessels (Brooks et al., *Methods in Molecular Biology*, 129:257-269 (1999)). According to this model, a filter disc containing an angiogenesis inducer, such as basic fibroblast growth factor (bFDG) is placed onto the CAM. Diffusion of the cytokine into the CAM induces local angiogenesis, which may be measured in several ways such as by counting the number of blood vessel branch points within the CAM directly below the filter disc. The ability of identified compounds to inhibit cytokine-induced angiogenesis can be tested using this model. A test compound can either be added to the filter disc that contains the angiogenesis inducer, be placed directly on the membrane or be administered systemically. The extent of new blood vessel formation in the presence and/or absence of test compound can be compared using this model. The formation of fewer new blood vessels in the presence of a test compound would be indicative of anti-angiogenesis activity. Demonstration of anti-angiogenesis activity for inhibitors of an MTSP protein indicates a role in angiogenesis for that MTSP protein.

b. Known Serine Protease Inhibitors

Compounds for screening can be serine protease inhibitors, which can be tested for their ability to inhibit the activity of an MTSP, particularly an MTSP3, MTSP4, or MTSP6.

Exemplary, but not limiting serine proteases, include the following known serine protease inhibitors are used in the screening assays: Serine Protease Inhibitor 3 (SPI-3) (Chen, M. C., et al., *Citokine*, 11(11):856-862 (1999)); Aprotinin (Iijima, R., et al., *J. Biochem. (Tokyo)*, 126(5):912-916 (1999)); Kazal-type serine protease inhibitor-like proteins (Niimi, T., et al., *Eur. J. Biochem.*, 266(1):282-292 (1999)); Kunitz-type serine protease inhibitor (Ravichandran, S., et al., *Acta Crystallogr. D. Biol, Crystallogr.*, 55(11):1814-1821 (1999)); Tissue factor pathway inhibitor-2/Matrix-associated serine protease inhibitor (TFPI-2/MSPI), (Liu, Y., et al., *Arch. Biochem. Biophys.*, 370(1):112-8 (1999)); Bukunin, (Yi, C. Y., et al., *J. Invest. Dermatol.*, 113(2):182-8 (1999)); Nafmostat mesilate (Ryo, R., et al., *Vox Sang.*, 76(4):241-6 (1999)); TPCK (Huang, Y., et al., *Oncogene*, 18(23):3431-9 (1999)); A synthetic cotton-bound serine protease inhibitor (Edwards, J. V., et al., *Wound Repair Regen.*, 7(2):106-18 (1999)); FUT- 175 (Sawada, M., et al., *Stroke*, 30(3):644-50 (1999)); Combination of serine protease inhibitor FUT-0175 and thromboxane synthetase inhibitor OKY-046 (Kaminogo, M., et al., *Neurol. Med. Chir. (Tokyo)*, 38(11):704-8; discussion 708-9 (1998)); The rat serine protease inhibitor 2.1 gene (LeCam, A., et al., *Biochem. Biophys. Res. Commun.*, 253(2):311-4 (1998)); A new intracellular serine protease inhibitor expressed in the rat pituitary gland complexes with granzyme B (Hill; R. M., et al., *FEBS Lett.*, 440(3):361-4 (1998)); 3,4-Dichloroisocoumarin (Hammed, A., et al., *Proc. Soc. Exp. Biol. Med.*, 219(2):132-7 (1998)); LEX032 (Bains, A. S., et al., *Eur. J. Pharmacol.*, 356(1):67-72 (1998)); N-tosyl-L-phenylalanine chloromethyl ketone (Dryjanski, M., et al., *Biochemistry*, 37(40):14151-6 (1998)); Mouse gene for the serine protease inhibitor neuroserpin (P112) (Berger, P., et al., *Gene*, 214(1-2):25-33 (1998)); Rat serine protease inhibitor 2.3 gene (Paul, C., et al., *Eur. J. Biochem.*, 254(3):538-46 (1998)); Ecotin (Yang, S. Q., et al., *J. Mol. Biol.*, 279(4):945-57 (1998)); A 14 kDa plant-related serine protease inhibitor (Roch, P., et al., *Dev. Comp. Immunol.*, 22(1):1-12 (1998)); Matrix-associated serine protease inhibitor TFPI-2/33 kDa MSPI (Rao, C. N., et al., *Int. J. Cancer*, 76(5):749-56 (1998)); ONO-3403 (Hiwasa, T., et al., *Cancer Lett.*, 126(2):221-5 (1998)); Bdellastasin (Moser, M., et al., *Eur. J. Biochem.*, 253(1):212-20 (1998)); Bikunin (Xu, Y., et al., *J. Mol. Biol.*, 276(5):955-66 (1998)); Nafamostat mesilate (Mellgren, K., et al., *Thromb. Haemost.*, 79(2):342-7 (1998)); The growth hormone dependent serine protease inhibitor, Spi 2.1 (Maake, C., et al., *Endocrinology*, 138(12):5630-6 (1997)); Growth factor activator inhibitor type 2, a Kunitz-type serine protease inhibitor (Kawaguchi, T., et al., *J. Biol. Chem.*, 272(44):27558-64 (1997)); Heat-stable serine protease inhibitor protein from ovaries of the desert locust, *Schistocerga gregaria* (Hamdaoui, A., et al., *Biochem. Biophys. Res. Commun.*, 238(2):357-60 (1997)); Bikunin, (Delaria, K. A., et al., *J. Biol. Chem.*, 272(18):12209-14 (1997)); Human placental bikunin (Marlor, C. W., et al., *J. Biol. Chem.*, 272(10):12202-8 (1997)); Hepatocyte growth factor activator inhibitor, a novel Kunitz-type serine protease inhibitor (Shimomura, T., et al., *J. Biol. Chem.*, 272(10):6370-6 (1997)); FUT-187, oral serine protease inhibitor, (Shiozaki, H., et al., *Gan To Kagaku Ryoho*, 23(14): 197 1-9 (1996)); Extracellular matrix-associated serine protease inhibitors (Mr 33,000, 31,000, and 27,000 (Rao, C. N., et al., *Arch. Biochem. Biophys.*, 335(1):82-92 (1996)); An irreversible isocoumarin serine protease inhibitor (Palencia, D. D., et al., *Biol. Reprod.*, 55(3):536-42 (1996)); 4-(2-aminoethyl)-benzenesulfonyl fluoride (AEBSF) (Nakabo, Y., et al., *J. Leukoc. Biol.*, 60(3):328-36 (1996)); Neuroserpin (Osterwalder, T., et al., *EMBO J.*, 15(12):2944-53 (1996)); Human serine protease inhibitor alpha-1-antitrypsin (Forney, J. R., et al., *J. Parasitol.*, 82(3):496-502 (1996)); Rat serine protease inhibitor 2.3 (Simar-Blanchet, A. E., et al., *Eur. J. Biochem.*, 236(2):638-48 (1996)); Gebaxate mesilate (parodi, F., et al., *J. Cardiothorac. Vasc. Anesth.*, 10(2):235-7 (1996)); Recombinant serine protease inhibitor, CPTI II (Stankiewicz, M., et al., *(Acta Biochim. Pol.*, 43(3):525-9 (1996)); A cysteine-rich serine protease inhibitor (Guamerin II) (Kim, D. R., et al., *J. Enzym. Inhib.*, 10(2):81-91 (1996)); Diisopropylfluorophosphate (Lundqvist, H., et al., *Inflamm. Res.*, 44(12):510-7 (1995)); Nexin 1 (Yu, D. W., et al., *J. Cell Sci.*, 108(Pt 12):3867-74 (1995)); LEX032 (Scalia, R., et al., *Shock*, 4(4):251-6 (1995)); Protease nexin I (Houenou, L. J., et al., *Proc. Natl. Acad. Sci. U.S.A.*, 92(3):895-9 (1995)); Chymase-directed serine protease inhibitor (Woodard S. L., et al., *J. Immunol.*, 153(11):5016-25 (1994)); N-alpha-tosyl-L-lysyl-chloromethyl ketone (TLCK) (Bourinbaiar, A. S., et al., *Cell Immunol.*, 155(1):230-6 (1994)); Smpi56 (Ghendler, Y., et al., *Exp. Parasitol.*, 78(2):121-31 (1994)); Schistosoma haematobium serine protease inhibitor (Blanton, R. E., et al., *Mol. Biochem. Parasitol.*, 63(1):1-11 (1994)); Spi-1 (Warren, W. C., et al., *Mol. Cell Endocrinol.*, 98(1):27-32 (1993)); TAME (Jessop, J. J., et al., *Inflammation*, 17(5):613-31 (1993)); Antithrombin III (Kalaria, R. N., et al., *Am. J. Pathol.*, 143(3):886-93 (1993)); FOY-305 (Ohkoshi, M., et al., *Anticancer Res.*, 13(4):963-6 (1993)); Camostat mesilate (Senda, S., et al., *Intern. Med.*, 32(4):350-4 (1993)); Pigment epithelium-derived factor (Steele, F. R., et al., *Proc. Natl. Acad. Sci. U.S.A.*, 90(4):1526-30 (1993)); Antistasin (Holstein, T. W., et al., *FEBS Lett.*, 309(3):288-92 (1 92)); The vaccinia virus K2L gene encodes a serine protease inhibitor (Zhou, J., et al., *Virology*, 189(2):678-86 (1992)); Bowman-Birk serine-protease inhibitor (Werner, M. H., et al., *J. Mol. Biol.*, 225(3):873-89 (1992); FUT-175 (Yanamoto, H., et al., *Neurosurgery*, 30(3):358-63 (1992)); FUT-175; (Yanamoto, H., et al., *Neurosurgery*, 30(3):351-6, discussion 356-7 (1992)); PAI-I (Yreadwell, B. V., et al., *J. Orthop. Res.*, 9(3):309-16 (1991)); 3,4-Dichloroisocoumarin (Rusbridge, N. M., et al., *FEBS Lett.*, 268(1):133-6 (1990)); Alpha 1-antichymotrypsin (Lindmark, B. E., et al., *Am. Rev. Respir. Des.*, 141(4 Pt 1):884-8 (1990)); P-toluenesulfonyl-L-arginine methyl ester (TAME) (Scuderi, P., *J. Immunol.*, 143(1):168-73 (1989)); Aprotinin (Seto, S., et al., *Adv. Exp. Med. Biol.*, 247B:49-54 (1989)); Alpha 1-antichymotrypsin (Abraham, C. R., et al., *Cell*, 52(4):487-501 (1988)); Contrapsin (Modha, J., et al., *Parasitology*, 96(Pt 1):99-109 (1988)); (FOY-305) (Yamauchi, Y., et al., *Hiroshima J. Med. Sci.*, 36(1):81-7 No abstract available (1987)); Alpha 2-antiplasmin (Holmes, W. E., et al., *J. Biol. Chem.*, 262(4):1659-64 (1987)); 3,4-dichloroisocoumarin (Harper, J. W., et al., *Biochemistry*, 24(8):1831-41 (1985)); Diisopropylfluorophosphate (Tsutsui, K., et al., *Biochem. Biophys. Res. Commun.*, 123(1):271-7 (1984)); Gabexate mesilate (Hesse, B., et al., *Pharmacol. Res. Commun.*, 16(7):637-45 (1984)); Phenyl methyl sulfonyl fluoride (Dufer, J., et al., *Scand. J. Haematol.*, 32(1):25-32 (1984)); Aprotinin (Seto, S., et al., *Hypertension*, 5(6):893-9 (1983)); Protease inhibitor CI-2 (McPhalen, C. A., et al., *J. Mol. Biol.*, 168(2):445-7 (1983)); Phenylmethylsulfonyl fluoride (Sekar V., et al., *Biochem. Biophys. Res. Commun.*, 89(2):474-8 (1979)); PGE1 (Feinstein, M. D., et al., *Prostaglandine*, 14(6):1075-93 (1977).

c. Combinatorial Libraries and Other Libraries

The source of compounds for the screening assays, can be libraries, including, but are not limited to, combinatorial libraries. Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol.*, 2(3):363-71 (1998); Lam, *Anticancer Drug Des.*, 12(3):145-67 (1997); Blaney and Martin, *Curr. Opin. Chem. Biol.*, 1(1):54-9 (1997); and Schultz and Schultz, *Biotechnol. Prog.*, 12(6):729-43 (1996)).

Methods and strategies for generating diverse libraries, primarily peptide- and nucleotide-based oligomer libraries, have been developed using molecular biology methods and/or simultaneous chemical synthesis methodologies (see, e.g., Dower et al., *Annu. Rep. Med. Chem.*, 26:271-280 (1991); Fodor et al., *Science*, 251:767-773 (1991); Jung et al., *Angew. Chem. Ind. Ed. Engl.*, 31:367-383 (1992); Zuckerman et al., *Proc. Natl. Acad. Sci. USA*, 89:4505-4509 (1992); Scott et al., *Science*, 249:386-390 (1990); Devlin et al., *Science*, 249:404-406 (1990); Cwirla et al., *Proc. Natl. Acad. Sci. USA*, 87:6378-6382 (1990); and Gallop et al., *J. Medicinal Chem-* istry, 37:1233-1251 (1994)). The resulting combinatorial libraries potentially contain millions of compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads (see, e.g., Lam et al., *Nature,* 354:82-84 (1991)) and cotton supports (see, e.g., Eichler et al., *Biochemistry* 32:11035-11041 (1993)); and methods in which the compounds are used in solution (see, e.g., Houghten et al., *Nature,* 354:84-86 (1991); Houghten et al., *BioTechniques,* 313:412-421 (1992); and Scott et al., *Curr. Opin. Biotechnol.,* 5:40-48 (1994)). There are numerous examples of synthetic peptide and oligonucleotide combinatorial libraries and there are many methods for producing libraries that contain non-peptidic small organic molecules. Such libraries can be based on basis set of monomers that are combined to form mixtures of diverse organic molecules or that can be combined to form a library based upon a selected pharmacophore monomer.

Either a random or a deterministic combinatorial library can be screened by the presently disclosed and/or claimed screening methods. In either of these two libraries, each unit of the library is isolated and/or immobilized on a solid support. In the deterministic library, one knows a priori a particular unit's location on each solid support. In a random library, the location of a particular unit is not known a priori although each site still contains a single unique unit. Many methods for preparing libraries are known to those of skill in this art (see, e.g., Geysen et al., *Proc. Natl. Acad. Sci. USA,* 81:3998-4002 (1984), Houghten et al., *Proc. Natl. Acad. Sci. USA,* 81:5131-5135 (1985)). Combinatorial library generated by the any techniques known to those of skill in the art are contemplated (see, e.g., Table 1 of Schultz and Schultz, *Biotechnol. Prog.,* 12(6):729-43 (1996)) for screening; Bartel et al., *Science,* 261:1411-1418 (1993); Baumbach et al. *BioPharm,* (May): 24-35 (1992); Bock et al. *Nature,* 355:564-566 (1992); Borman, S., Combinatorial chemists focus on sam11 molecules molecular recognition, and automation, *Chem. Eng. News,* 2(12):29 (1996); Boublik, et al., Eukaryotic Virus Display: Engineering the Major Surface Glycoproteins of the Autographa California Nuclear Polyhedrosis Virus (ACNPV) for the Presentation of Foreign Proteins on the Virus Surface, *Bio/Technology,* 13:1079-1084 (1995); Brenner, et al., Encoded Combinatorial Chemistry, *Proc. Natl. Acad Sci. U.S.A.,* 89:5381-5383 (1992); Caflisch, et al., Computational Combinatorial Chemistry for De Novo Ligand Design: Review and Assessment, *Perspect. Drug Discovery Des.,* 3:51-84 (1995); Cheng, et al., Sequence-Selective Peptide Binding with a Peptido-A,B-trans-steroidal Receptor Selected from an Encoded Combinatorial Library, *J. Am. Chem. Soc.,* 118:1813-1814 (1996); Chu, et al., Affinity Capillary Electrophoresis to Identify the Peptide in A Peptide Library that Binds Most Tightly to Vancomycin, *J. Org. Chem.,* 58:648-652 (1993); Clackson, et al., Making Antibody Fragments Using Phage Display Libraries, *Nature,* 352: 624-628 (1991); Combs, et al., Protein Structure-Based Combinatorial Chemistry: Discovery of Non-Peptide Binding Elements to Src SH3 Domain, *J. Am. Chem. Soc.,* 118:287-288 (1996); Cwirla, et al., Peptides On Phage: A Vast Library of Peptides for Identifying Ligands, *Proc. Natl. Acad. Sci. U.S.A.,* 87:6378-6382 (1990); Ecker, et al., Combinatorial Drug Discovery: Which Method will Produce the Greatest Value, *Bio/Technology,* 13:351-360 (1995); Ellington, et al., In vitro Selection of RNA Molecules That Bind Specific Ligands, *Nature,* 346:818-822 (1990); Ellman, J. A., Variants of Benzodiazepines, *J. Am. Chem. Soc.,* 114:10997 (1992); Erickson, et al., *The Proteins*; Neurath, H., Hill, R. L., Eds.: Academic: New York, 1976; pp. 255-257; Felici, et al., *J. Mol. Biol.,* 222:301-310 (1991); Fodor, et al., Light-Directed, Spatially Addressable Parallel Chemical Synthesis, *Science,* 251: 767-773 (1991); Francisco, et al., Transport and Anchoring of Beta-Lactamase to the External Surface of *E. Coli., Proc. Natl. Acad. Sci. U.S.A.,* 89:2713-2717 (1992); Georgiou, et al., Practical Applications of Engineering Gram-Negative Bacterial Cell Surfaces, *TIBTECH,* 11:6-10 (1993); Geysen, et al., Use of peptide synthesis to probe viral antigens for epitopes to a resolution of a single amino acid, *Proc. Natl. Acad. Sci. U.S.A.,* 81:3998-4002 (1984); Glaser, et al., Antibody Engineering by Condon-Based Mutagenesis in a Filamentous Phage Vector System, *J. Immunol.,* 149:3903-3913 (1992); Gram, et al., In vitro selection and affinity maturation of antibodies from a naive combinatorial immunoglobulin library, *Proc. Natl. Acad. Sci.,* 89:3576-3580 (1992); Han, et al., Liquid-Phase Combinatorial Synthesis, *Proc. Natl. Acad. Sci. U.S.A.,* 92:6419-6423 (1995); Hoogenboom, et al., Multi-Subunit Proteins on the Surface of Filamentous Phage: Methodologies for Displaying Antibody (Fab) Heavy and Light Chains, *Nucleic Acids Res.,* 19:4133-4137 (1991); Houghten, et al., General Method for the Rapid Solid-Phase Synthesis of Large Numbers of Peptides: Specificity of Antigen-Antibody Interaction at the Level of Individual Amino Acids, *Proc. Natl. Acad. Sci. U.S.A.,* 82:5131-5135 (1985); Houghten, et al., The Use of Synthetic Peptide Combinatorial Libraries for the Determination of Peptide Ligands in Radio-Receptor Assays-Opioid-Peptides, *Bioorg. Med. Chem. Lett.,* 3:405-412 (1993); Houghten, et al., Generation and Use of Synthetic Peptide Combinatorial Libraries for Basic Research and Drug Discovery, *Nature,* 354:84-86 (1991); Huang, et al., Discovery of New Ligand Binding Pathways in Myoglobin by Random Mutagenesis, *Nature Struct. Biol.,* 1:226-229 (1994); Huse, et al., Generation of a Large Combinatorial Library of the Immunoglobulin Repertoire In Phage Lambda, *Science,* 246:1275-1281 (1989); Janda, K. D., New Strategies for the Design of Catalytic Antibodies, *Biotechnol. Prog.,* 6:178-181 (1990); Jung, et al., Multiple Peptide Synthesis Methods and Their Applications, *Angew. Chem. Int. Ed. Engl.,* 31:367-486 (1992); Kang, et al., Linkage of Recognition and Replication Functions By Assembling Combinatorial Antibody Fab Libraries Along Phage Surfaces, *Proc. Natl. Acad. Sci. U.S.A.,* 88:4363-4366 (1991a); Kang, et al., Antibody Redesign by Chain Shuffling from Random Combinatorial Immunoglobulin Libraries, *Proc. Natl. Acad. Sci. U.S.A.,* 88:11120-11123 (1991b); Kay, et al., An M13 Phage Library Displaying Random 38-Amino-Acid-Peptides as a Source of Novel Sequences with Affinity to Selected Targets Genes, *Gene,* 128:59-65 (1993); Lam, et al., A new type of synthetic peptide library for identifying ligand-binding activity, *Nature,* 354:82-84 (1991) (published errata appear in *Nature,* 358:434 (1992) and *Nature,* 360:768 (1992); Lebl, et al., One Bead One Structure Combinatorial Libraries, *Biopolymers (Pept. Sci.),* 37:177-198 (1995); Lerner, et al., Antibodies without Immunization, *Science,* 258:1313-1314 (1992); Li, et al., Minimization of a Polypeptide Hormone, *Science,* 270:1657-1660 (1995); Light, et al., Display of Dimeric Bacterial Alkaline Phosphatase on the Major Coat Protein of Filamentous Bacteriophage, *Bioorg. Med. Chem. Lett.,* 3:1073-1079 (1992); Little, et al., Bacterial Surface Presentation of Proteins and Peptides: An Alternative to Phage Technology, *Trends Biotechnol.,* 11:3-5 (1993); Marks, et al., By-Passing Immunization. Human Antibodies from V-Gene Libraries Displayed on Phage, *J. Mol. Biol.,* 222:581-597 (1991); Matthews, et al., Substrate Phage: Selection of Protease Substrates by Monovalent Phage Display, *Science,* 260:1113-1117 (1993); McCafferty, et al., Phage Enzymes: Expression and Affinity Chromatography of Functional Alkaline Phosphatase on the Surface of Bacteriophage, *Protein Eng.,* 4:955-961 (1991); Menger, et al., Phosphatase Catalysis Developed Via Combinatorial Organic Chemistry, *J. Org. Chem.,* 60:6666-6667 (1995); Nicolaou, et al., *Angew. Chem. Int. Ed. Engl.,* 34:2289-2291 (1995); Oldenburg, et al., Peptide Ligands for A Sugar-Binding Protein Isolated from a Random Peptide Library, *Proc. Natl. Acad. Sci. U.S.A.,* 89:5393-5397 (1992); Parmley, et al., Antibody-Selectable Filamentous fd Phage Vectors: Affinity Purification of Target Genes, *Genes,* 73:305-318 (1988); Pinilla, et al., Synthetic Peptide Combinatorial Libraries (SPCLS)—Identification of the Antigenic Determinant of Beta-Endorphin Recognized by Monoclonal Antibody-3E7, *Gene,* 128: 71-76 (1993); Pinilla, et al., Review of the Utility of Soluble Combinatorial Libraries, *Biopolymers,* 37:221-240 (1995); Pistor, et al., Expression of Viral Hemegglutinan On the Surface of *E. Coli., Klin. Wochenschr.,* 66:110-116 (1989); Pollack, et al., Selective Chemical Catalysis by an Antibody, *Science,* 234:1570-1572 (1986); Rigler, et al., Fluorescence Correlations, Single Molecule Detection and Large Number Screening: Applications in Biotechnology, *J. Biotechnol.,* 41:177-186 (1995); Sarvetnick, et al., Increasing the Chemical Potential of the Germ-Line Antibody Repertoire, *Proc. Natl. Acad. Sci. U.S.A.,* 90:4008-4011 (1993); Sastry, et al., Cloning of the Immunological Repertiore in *Escherichia Coli* for Generation of Monoclonal Catalytic Antibodies: Construction of a Heavy Chain Variable Region-Specific cDNA Library, *Proc. Natl. Acad. Sci. U.S.A.,* 86:5728-5732 (1989); Scott, et al., Searching for Peptide Ligands with an Epitope Library, *Science,* 249:386-390 (1990); Sears, et al., Engineering Enzymes for Bioorganic Synthesis: Peptide Bond Formation, *Biotechnol. Prog.,* 12:423-433 (1996); Simon, et. al., Peptides: A Modular Approach to Drug Discovery, *Proc. Natl. Acad. Sci. U.S.A.,* 89:9367-9371 (1992); Still, et al., Discovery of Sequence-Selective Peptide Binding by Synthetic Receptors Using Encoded Combinatorial Libraries, *Acc. Chem. Res.,* 29:155-163 (1996); Thompson, et al., Synthesis and Applications of Small Molecule Libraries, *Chem. Rev.,* 96:555-600 (1996); Tramontano, et al., Catalytic Antibodies, *Science,* 234:1566-1570 (1986); Wrighton, et al., Small Peptides as Potent Mimetics of the Protein Hormone Erythropoietin, *Science,* 273:458-464 (1996); York, et al., Combinatorial mutagenesis of the reactive site region in plasminogen activator inhibitor I, *J. Biol. Chem.,* 266:8595-8600 (1991); Zebedee, et al., Human Combinatorial Antibody Libraries to Hepatitis B Surface Antigen, *Proc. Natl. Acad. Sci. U.S.A.,* 89:3175-3179 (1992); Zuckerman, et al., Identification of Highest-Affinity Ligands by Affinity Selection from Equimolar Peptide Mixtures Generated by Robotic Synthesis, *Proc. Natl. Acad. Sci. U.S.A.,* 89:4505-4509 (1992).

For example, peptides that bind to an MTSP protein or a protease domain of an MTSP protein can be identified using phage display libraries. In an exemplary embodiment, this method can include a) contacting phage from a phage library with the MTSP protein or a protease domain thereof; (b) isolating phage that bind to the protein; and (c) determining the identity of at least one peptide coded by the isolated phage to identify a peptide that binds to an MTSP protein.

H. Modulators of the Activity of MTSP Proteins

Provided herein are compounds, identified by screening or produced using the MTSP proteins or protease domain in other screening methods, that modulate the activity of an MTSP. These compounds act by directly interacting with the MTSP protein or by altering transcription or translation thereof. Such molecules include, but are not limited to, antibodies that specifically react with an MTSP protein, particularly with the protease domain thereof, antisense nucleic acids that alter expression of the MTSP protein, antibodies, peptide mimetics and other such compounds.

1. Antibodies

Antibodies, including polyclonal and monoclonal antibodies, that specifically bind to the MTSP proteins provided herein, particularly to the single chain protease domains thereof are provided. Preferably, the antibody is a monoclonal antibody, and preferably, the antibody specifically binds to the protease domain of the MTSP protein. In particular embodiments, antibodies to each of the single chain of protease domain of MTSP1, MTSP3, MTSP4 and MTSP6. Also provided are antibodies that specifically bind to any domain of MTSP3 or MTSP4, and to double chain forms thereof.

The MTSP protein and domains, fragments, homologs and derivatives thereof may be used as immunogens to generate antibodies that specifically bind such immunogens. Such antibodies include but are not limited to polyclonal, monoclonal, chimeric, single chain, Fab fragments, and an Fab expression library. In a specific embodiment, antibodies to human MTSP protein are produced. In another embodiment, complexes formed from fragments of MTSP protein, which fragments contain the serine protease domain, are used as immunogens for antibody production.

Various procedures known in the art may be used for the production of polyclonal antibodies to MTSP protein, its domains, derivatives, fragments or analogs. For production of the antibody, various host animals can be immunized by injection with the native MTSP protein or a synthetic version, or a derivative of the foregoing, such as a cross-linked MTSP protein. Such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *corynebacterium parvum.*

For preparation of monoclonal antibodies directed towards an MTSP protein or domains, derivatives, fragments or analogs thereof, any technique that provides for the production of antibody molecules by continuous cell lines in culture may be used. Such techniques include but are not restricted to the hybridoma technique originally developed by Kohler and Milstein (*Nature* 256:495-497 (1975)), the trioma technique, the human B-cell hybridoma technique (Kozbor et al., *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77-96 (1985)). In an additional embodiment, monoclonal antibodies can be produced in germ-free animals utilizing recent technology (PCT/US90/02545). Human antibodies may be used and can be obtained by using human hybridomas (Cote et al., *Proc. Natl. Acad. Sci. USA* 80:2026-

2030 (1983)). Or by transforming human B cells with EBV virus in vitro (Cole et al., in *Monoclonal Antibodies and Cancer Therapy*, Alan R. Liss, Inc., pp. 77-96 (1985)). Techniques developed for the production of "chimeric antibodies" (Morrison et al., *Proc. Natl. Acad. Sci. USA* 81:6851-6855 (1984); Neuberger et al., *Nature* 312:604-608 (1984); Takeda et al., *Nature* 314:452-454 (1985)) by splicing the genes from a mouse antibody molecule specific for the MTSP protein together with genes from a human antibody molecule of appropriate biological activity can be used.

Techniques described for the production of single chain antibodies (U.S. Pat. No. 4,946,778) can be adapted to produce MTSP protein-specific single chain antibodies. An additional embodiment uses the techniques described for the construction of Fab expression libraries (Huse et al., *Science* 246:1275-1281 (1989)) to allow rapid and easy identification of monoclonal Fab fragments with the desired specificity for MTSP protein or MTSP protein, or domains, derivatives, or analogs thereof Non-human antibodies can be "humanized" by known methods (see, e.g., U.S. Pat. No. 5,225,539).

Antibody fragments that contain the idiotypes of MTSP protein can be generated by techniques known in the art. For example, such fragments include but are not limited to: the F(ab')2 fragment which can be produced by pepsin digestion of the antibody molecule; the Fab' fragments that can be generated by reducing the disulfide bridges of the F(ab')2 fragment, the Fab fragments that can be generated by treating the antibody molecular with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the MTSP protein one may assay generated hybridomas for a product that binds to the fragment of the MTSP protein that contains such a domain.

The foregoing antibodies can be used in methods known in the art relating to the localization and/or quantitation of MTSP proteins, e.g., for imaging these proteins, measuring levels thereof in appropriate physiological samples, in diagnostic methods, etc.

In another embodiment, (see infra), anti-MTSP protein antibodies, or fragments thereof, containing the binding domain are used as therapeutic agents.

2. Peptides and Peptide Mimetics

Provided herein are methods for identifying molecules that bind to and modulate the activity of MTSP proteins. Included among molecules that bind to MTSPs, particularly the single chain protease domain or catalytically active fragments thereof, are peptides and peptide mimetics. Peptide mimetics are molecules or compounds that mimic the necessary molecular conformation of a ligand or polypeptide for specific binding to a target molecule such as, e.g., an MTSP protein. In an exemplary embodiment, the peptides or peptide mimetics bind to the protease domain of the MTSP protein. Such peptides and peptide mimetics include those of antibodies that specifically bind an MTSP protein and, preferably, bind to the protease domain of an MTSP protein. The peptides and peptide mimetics identified by methods provided herein can be agonists or antagonists of MTSP proteins.

Such peptides and peptide mimetics are useful for diagnosing, treating, preventing, and screening for a disease or disorder associated with MTSP protein activity in a mammal. In addition, the peptides and peptide mimetics are useful for identifying, isolating, and purifying molecules or compounds that modulate the activity of an MTSP protein, or specifically bind to an MTSP protein, preferably, the protease domain of an MTSP protein. Low molecular weight peptides and peptide mimetics can have strong binding properties to a target molecule, e.g., an MTSP protein or, preferably, to the protease domain of an MTSP protein.

Peptides and peptide mimetics that bind to MTSP proteins as described herein can be administered to mammals, including humans, to modulate MTSP protein activity. Thus, methods for therapeutic treatment and prevention of neoplastic diseases comprise administering a peptide or peptide mimetic compound in an amount sufficient to modulate such activity are provided. Thus, also provided herein are methods for treating a subject having such a disease or disorder in which a peptide or peptide mimetic compound is administered to the subject in a therapeutically effective dose or amount.

Compositions containing the peptides or peptide mimetics can be administered for prophylactic and/or therapeutic treatments. In therapeutic applications, compositions can be administered to a patient already suffering from a disease, as described above, in an amount sufficient to cure or at least partially arrest the symptoms of the disease and its complications. Amounts effective for this use will depend on the severity of the disease and the weight and general state of the patient.

In prophylactic applications, compositions containing the peptides and peptide mimetics are administered to a patient susceptible to or otherwise at risk of a particular disease. Such an amount is defined to be a "prophylactically effective dose". In this use, the precise amounts again depend on the patient's state of health and weight.

Accordingly, the peptides and peptide mimetics that bind to an MTSP protein can be used generating pharmaceutical compositions containing, as an active ingredient, at least one of the peptides or peptide mimetics in association with a pharmaceutical carrier or diluent. The compounds can be administered, for example, by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration (see, e.g., International PCT application Nos. WO 93/25221 and WO 94/17784; and European Patent Application 613,683).

Peptides and peptide mimetics that bind to MTSP proteins are useful in vitro as unique tools for understanding the biological role of MTSP proteins, including the evaluation of the many factors thought to influence, and be influenced by, the production of MTSP protein. Such peptides and peptide mimetics are also useful in the development of other compounds that bind to and modulate the activity of an MTSP protein, because such compounds provide important information on the relationship between structure and activity that should facilitate such development.

The peptides and peptide mimetics are also useful as competitive binders in assays to screen for new MTSP proteins or MTSP protein agonists. In such assay embodiments, the compounds can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as $^{125}$I enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The compounds may also include spacers or linkers in cases where the compounds are to be attached to a solid support.

Moreover, based on their ability to bind to an MTSP protein, the peptides and peptide mimetics can be used as reagents for detecting MTSP proteins in living cells, fixed cells, in biological fluids, in tissue homogenates, in purified, natural biological materials, etc. For example, by labelling such peptides and peptide mimetics, one can identify cells having MTSP proteins. In addition, based on their ability to bind an MTSP protein, the peptides and peptide mimetics can be used in situ staining, FACS (fluorescence-activated cell sorting), Western blotting, ELISA, etc. In addition, based on their ability to bind to an MTSP protein, the peptides and peptide mimetics can be used in purification of MTSP protein polypeptides or in purifying cells expressing the MTSP protein polypeptides, e.g., a polypeptide encoding the protease domain of an MTSP protein.

The peptides and peptide mimetics can also be used as commercial reagents for various medical research and diagnostic uses.

The activity of the peptides and peptide mimetics can be evaluated either in vitro or in vivo in one of the numerous models described in McDonald (1992) *Am. J. of Pediatric Hematology/Oncology,* 14:8-21, which is incorporated herein by reference.

3. Peptide and Peptide Mimetic Therapy

Peptides and peptide mimetics that can bind to MTSP proteins or the protease domain of MTSP proteins and modulate the activity thereof, or have MTSP protein activity, can be used for treatment of neoplastic diseases. The peptides and peptide mimetics may be delivered, in vivo or ex vivo, to the cells of a subject in need of treatment. Further, peptides which have MTSP protein activity can be delivered, in vivo or ex vivo, to cells which carry mutant or missing alleles encoding the MTSP protein gene. Any of the techniques described herein or known to the skilled artisan can be used for preparation and in vivo or ex vivo delivery of such peptides and peptide mimetics that are substantially free of other human proteins. For example, the peptides can be readily prepared by expression in a microorganism or synthesis in vitro.

The peptides or peptide mimetics can be introduced into cells, in vivo or ex vivo, by microinjection or by use of liposomes, for example. Alternatively, the peptides or peptide mimetics may be taken up by cells, in vivo or ex vivo, actively or by diffusion. In addition, extracellular application of the peptide or peptide mimetic may be sufficient to effect treatment of a neoplastic disease. Other molecules, such as drugs or organic compounds, that: 1) bind to an MTSP protein or protease domain thereof; or 2) have a similar function or activity to an MTSP protein or protease domain thereof, may be used in methods for treatment.

4. Rational Drug Design

The goal of rational drug design is to produce structural analogs of biologically active polypeptides or peptides of interest or of small molecules or peptide mimetics with which they interact (e.g., agonists, antagonists, inhibitors) in order to fashion drugs which are, e.g., more active or stable forms thereof; or which, e.g., enhance or interfere with the function of a polypeptide in vivo (e.g., an MTSP protein). In one approach, one first determines the three-dimensional structure of a protein of interest (e.g., an MTSP protein or polypeptide having a protease domain) or, for example, of a MTSP protein-ligand complex, by X-ray crystallography, by computer modeling or most typically, by a combination of approaches (see, e.g., Erickson et al. 1990). Also, useful information regarding the structure of a polypeptide may be gained by modeling based on the structure of homologous proteins. In addition, peptides can be analyzed by an alanine scan. In this technique, an amino acid residue is replaced by Ala, and its effect on the peptide's activity is determined. Each of the amino acid residues of the peptide is analyzed in this manner to determine the important regions of the peptide.

Also, a polypeptide or peptide that binds to an MTSP protein or, preferably, the protease domain of an MTSP protein, can be selected by a functional assay, and then the crystal structure of this polypeptide or peptide can be determined. The polypeptide can be, for example, an antibody specific for an MTSP protein or the protein domain of an MTSP protein. This approach can yield a pharmacore upon which subsequent drug design can be based. Further, it is possible to bypass the crystallography altogether by generating anti-idiotypic polypeptides or peptides, (anti-ids) to a functional, pharmacologically active polypeptide or peptide that binds to an MTSP protein or protease domain of an MTSP protein. As a mirror image of a mirror image, the binding site of the anti-ids is expected to be an analog of the original target molecule, e.g., an MTSP protein or polypeptide having an MTSP protein. The anti-id could then be used to identify and isolate peptides from banks of chemically or biologically produced banks of peptides. Selected peptides would then act as the pharmacore.

Thus, one may design drugs which have, e.g., improved activity or stability or which act as modulators (e.g., inhibitors, agonists, antagonists, etc.) of MTSP protein activity, and are useful in the methods, particularly the methods for diagnosis, treatment, prevention, and screening of a neoplastic disease. By virtue of the availability of cloned MTSP protein sequences, sufficient amounts of the MTSP protein polypeptide may be made available to perform such analytical studies as X-ray crystallography. In addition, the knowledge of the amino acid sequence of an MTSP protein or the protease domain thereof, e.g., the protease domain encoded by the amino acid sequence of SEQ ID NO: 2, can provide guidance on computer modeling techniques in place of, or in addition to, X-ray crystallography.

Methods of Identifying Peptides and Peptide Mimetics that Bind to MTSP Proteins

Peptides having a binding affinity to the MTSP protein polypeptides provided herein (e.g., an MTSP protein or a polypeptide having a protease domain of an MTSP protein) can be readily identified, for example, by random peptide diversity generating systems coupled with an affinity enrichment process. Specifically, random peptide diversity generating systems include the "peptides on plasmids" system (see, e.g., U.S. Pat. Nos. 5,270,170 and 5,338,665); the "peptides on phage" system (see, e.g., U.S. Pat. No. 6,121,238 and Cwirla, et al. (1990) *Proc. Natl. Acad. Sci. U.S.A.* 87:6378-6382); the "polysome system;" the "encoded synthetic library (ESL)" system; and the "very large scale immobilized polymer synthesis" system (see, e.g., U.S. Pat. No. 6,121,238; and Dower et al. (1991) *An. Rep. Med. Chem.* 26:271-280

For example, using the procedures described above, random peptides can generally be designed to have a defined number of amino acid residues in length (e.g., 12). To generate the collection of oligonucleotides encoding the random peptides, the codon motif (NNK)x, where N is nucleotide A, C, G, or T (equimolar; depending on the methodology employed, other nucleotides can be employed), K is G or T (equimolar), and x is an integer corresponding to the number of amino acids in the peptide (e.g., 12) can be used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

The random peptides can be presented, for example, either on the surface of a phage particle, as part of a fusion protein containing either the pIII or the pVIII coat protein of a phage fd derivative (peptides on phage) or as a fusion protein with the LacI peptide fusion protein bound to a plasmid (peptides on plasmids). The phage or plasmids, including the DNA encoding the peptides, can be identified and isolated by an affinity enrichment process using immobilized MTSP protein polypeptide having a protease domain. The affinity enrichment process, sometimes called "panning," typically involves multiple rounds of incubating the phage, plasmids, or polysomes with the immobilized MTSP protein polypeptide, collecting the phage, plasmids, or polysomes that bind to the MTSP protein polypeptide (along with the accompanying DNA or mRNA), and producing more of the phage or plasmids (along with the accompanying LacI-peptide fusion protein) collected.

Characteristics of Peptides and Peptide Mimetics

Typically, the molecular weight of preferred peptides or peptide mimetics is from about 250 to about 8,000 daltons. If the peptides are oligomerized, dimerized and/or derivatized with a hydrophilic polymer (e.g., to increase the affinity and/or activity of the compounds), the molecular weights of such peptides can be substantially greater and can range anywhere from about 500 to about 120,000 daltons, more preferably from about 8,000 to about 80,000 daltons. Such peptides can comprise 9 or more amino acids wherein the amino acids are naturally occurring or synthetic (non-naturally occurring) amino acids. One skilled in the art would know how to determine the affinity and molecular weight of the peptides and peptide mimetics suitable for therapeutic and/or diagnostic purposes (e.g., see Dower et al., U.S. Pat. No. 6,121,238).

The peptides may be covalently attached to one or more of a variety of hydrophilic polymers. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. When the peptide compounds are derivatized with such polymers, their solubility and circulation half-lives can be increased with little, if any, diminishment in their binding activity. The peptide compounds may be dimerized and each of the dimeric subunits can be covalently attached to a hydrophilic polymer. The peptide compounds can be PEGylated, i.e., covalently attached to polyethylene glycol (PEG).

Peptide analogs are commonly used in the pharmaceutical industry as non-peptide drugs with properties analogous to those of the template peptide. These types of non-peptide compounds are termed "peptide mimetics" or "peptidomimetics" (Luthman et al., A Textbook of Drug Design and Development, 14:386-406, 2nd Ed., Harwood Academic Publishers (1996); Joachim Grante (1994) Angew. Chem. Int. Ed. Engl., 33:1699-1720; Fauchere (1986) J. Adv. Drug Res., 15:29; Veber and Freidinger (1985) TINS, p. 392; and Evans et al. (1987) J. Med. Chem. 30:1229). Peptide mimetics that are structurally similar to therapeutically useful peptides may be used to produce an equivalent or enhanced therapeutic or prophylactic effect. Preparation of peptidomimetics and structures thereof are known to those of skill in this art.

Systematic substitution of one or more amino acids of a consensus sequence with a D-amino acid of the same type (e.g., D-lysine in place of L-lysine) may be used to generate more stable peptides. In addition, constrained peptides containing a consensus sequence or a substantially identical consensus sequence variation may be generated by methods known in the art (Rizo et al. (1992) An. Rev. Biochem., 61:387, incorporated herein by reference); for example, by adding internal cysteine residues capable of forming intramolecular disulfide bridges which cyclize the peptide.

Those skilled in the art would appreciate that modifications may be made to the peptides and mimetics without deleteriously effecting the biological or functional activity of the peptide. Further, the skilled artisan would know how to design non-peptide structures in three dimensional terms, that mimic the peptides that bind to a target molecule, e.g., an MTSP protein or, preferably, the protease domain of MTSP proteins (see, e.g., Eck and Sprang (1989) J. Biol. Chem., 26: 17605-18795).

When used for diagnostic purposes, the peptides and peptide mimetics may be labeled with a detectable label and, accordingly, the peptides and peptide mimetics without such a label can serve as intermediates in the preparation of labeled peptides and peptide mimetics. Detectable labels can be molecules or compounds, which when covalently attached to the peptides and peptide mimetics, permit detection of the peptide and peptide mimetics in vivo, for example, in a patient to whom the peptide or peptide mimetic has been administered, or in vitro, e.g., in a sample or cells. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of a detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodinating the peptide (see, e.g., Weaner et al. (1994) Synthesis and Applications of isotopically Labelled Compounds, pp. 137-140). If tyrosine is not present in the peptide or peptide mimetic, incorporation of tyrosine to the N or C terminus of the peptide or peptide mimetic can be achieved by well known chemistry. Likewise, $^{32}$P can be incorporated onto the peptide or peptide mimetic as a phosphate moiety through, for example, a hydroxyl group on the peptide or peptide mimetic using conventional chemistry.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not substantially interfere with the desired biological or pharmacological activity of the peptidomimetic.

6. Methods of Preparing Peptides and Peptide Mimetics

Peptides that bind to MTSP proteins can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology (see, e.g., Merrifield (1963) J. Am. Chem. Soc., 85:2149, incorporated herein by reference.)

Using the "encoded synthetic library" or "very large scale immobilized polymer synthesis" systems (see, e.g., U.S. Pat. Nos. 5,925,525, and 5,902,723); one can not only determine the minimum size of a peptide with the activity of interest, one can also make all of the peptides that form the group of peptides that differ from the preferred motif (or the minimum size of that motif) in one, two, or more residues. This collection of peptides can then be screened for ability to bind to the target molecule, e.g., and MTSP protein or, preferably, the protease domain of an MTSP protein. This immobilized polymer synthesis system or other peptide synthesis methods can also be used to synthesize truncation analogs and deletion analogs and combinations of truncation and deletion analogs of the peptide compounds.

These procedures can also be used to synthesize peptides in which amino acids other than the 20 naturally occurring, genetically encoded amino acids are substituted at one, two, or more positions of the peptide. For instance, naphthylalanine can be substituted for tryptophan, facilitating synthesis. Other synthetic amino acids that can be substituted into the peptides include L-hydroxypropyl, L-3,4-dihydroxy-phenylalanyl, d amino acids such as L-d-hydroxylysyl and D-d-methylalanyl, L-α-methylalanyl, β amino acids, and isoquinolyl. D amino acids and non-naturally occurring synthetic amino acids can also be incorporated into the peptides (see, e.g., Roberts et al. (1983) *Unusual Amino/Acids in Peptide Synthesis*, 5(6):341-449).

The peptides may also be modified by phosphorylation (see, e.g., W. Bannwarth et al. (1996) *Biorganic and Medicinal Chemistry Letters*, 6(17):2141-2146), and other methods for making peptide derivatives (see, e.g., Hruby et al. (1990) *Biochem. J.*, 268(2):249-262). Thus, peptide compounds also serve as a basis to prepare peptide mimetics with similar biological activity.

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis (see, e.g., Morgan et al. (1989) *An. Rep. Med. Chem.*, 24:243-252). Methods for preparing peptide mimetics modified at the N-terminal amino group, the C-terminal carboxyl group, and/or changing one or more of the amido linkages in the peptide to a non-amido linkage are known to those of skill in the art.

Amino terminus modifications include alkylating, acetylating, adding a carbobenzoyl group, forming a succinimide group, etc. (see, e.g., Murray et al. (1995) *Burger's Medicinal Chemistry and Drug Discovery*, 5th ed., Vol. 1, Manfred E. Wolf, ed., John Wiley and Sons, Inc.). C-terminal modifications include mimetics wherein the C-terminal carboxyl group is replaced by an ester, an amide or modifications to form a cyclic peptide.

In addition to N-terminal and C-terminal modifications, the peptide compounds, including peptide mimetics, can advantageously be modified with or covalently coupled to one or more of a variety of hydrophilic polymers. It has been found that when peptide compounds are derivatized with a hydrophilic polymer, their solubility and circulation half-lives may be increased and their immunogenicity is masked, with little, if any, diminishment in their binding activity. Suitable nonproteinaceous polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. The hydrophilic polymers also can have an average molecular weights of about 5,000 daltons, 10,000 daltons and 20,000 daltons.

Methods for derivatizing peptide compounds or for coupling peptides to such polymers have been described (see, e.g., Zallipsky (1995) *Bioconjugate Chem.*, 6:150-165; Monfardini et al. (1995) *Bioconjugate Chem.*, 6:62-69; U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 and WO 95/34326, all of which are incorporated by reference in their entirety herein).

Other methods for making peptide derivatives are described, for example, in Hruby et al. (1990), *Biochem J.*, 268(2):249-262, which is incorporated herein by reference. Thus, the peptide compounds also serve as structural models for non-peptidic compounds with similar biological activity. Those of skill in the art recognize that a variety of techniques are available for constructing compounds with the same or similar desired biological activity as a particular peptide compound but with more favorable activity with respect to solubility, stability, and susceptibility to hydrolysis and proteolysis (see, e.g., Morgan et al. (1989) *An. Rep. Med. Chem.*, 24:243-252, incorporated herein by reference). These techniques include replacing the peptide backbone with a backbone composed of phosphonates, amidates, carbamates, sulfonamides, secondary amines, and N-methylamino acids.

Peptide compounds may exist in a cyclized form with an intramolecular disulfide bond between the thiol groups of the cysteines. Alternatively, an intermolecular disulfide bond between the thiol groups of the cysteines can be produced to yield a dimeric (or higher oligomeric) compound. One or more of the cysteine residues may also be substituted with a homocysteine.

I. Conjugates

A conjugate, containing: a) a single chain protease domain (or proteolytically active portion thereof) of an MTSP protein or an MTSP3, MTSP4 or MTSP6 full length zymogen, activated form thereof, or double or single chain protease domain thereof; and b) a targeting agent linked to the MTSP protein directly or via a linker, wherein the agent facilitates: i) affinity isolation or purification of the conjugate; ii) attachment of the conjugate to a surface; iii) detection of the conjugate; or iv) targeted delivery to a selected tissue or cell, is provided herein. The conjugate can be a chemical conjugate or a fusion protein mixture thereof.

The targeting agent is preferably a protein or peptide fragment, such as a tissue specific or tumor specific monoclonal antibody or growth factor or fragment thereof linked either directly or via a linker to an MTSP protein or a protease domain thereof. The targeting agent may also be a protein or peptide fragment that contains a protein binding sequence, a nucleic acid binding sequence, a lipid binding sequence, a polysaccharide binding sequence, or a metal binding sequence, or a linker for attachment to a solid support. In a particular embodiment, the conjugate contains a) the MTSP or portion thereof, as described herein; and b) a targeting agent linked to the MTSP protein directly or via a linker.

Conjugates, such as fusion proteins and chemical conjugates, of the MTSP protein with a protein or peptide fragment (or plurality thereof) that functions, for example, to facilitate affinity isolation or purification of the MTSP protein domain, attachment of the MTSP protein domain to a surface, or detection of the MTSP protein domain are provided. The conjugates can be produced by chemical conjugation, such as via thiol linkages, but are preferably produced by recombinant means as fusion proteins. In the fusion protein, the peptide or fragment thereof is linked to either the N-terminus or C-terminus of the MTSP protein domain. In chemical conjugates the peptide or fragment thereof may be linked anywhere that conjugation can be effected, and there may be a plurality of such peptides or fragments linked to a single MTSP protein domain or to a plurality thereof.

The targeting agent is preferably for in vitro delivery to a cell or tissue, and includes agents such as cell or tissue-specific antibodies, growth factors and other factors expressed on specific cells; and other cell or tissue specific agents the promote directed delivery of a linked protein.

Most preferably the targeting agent specifically delivers the MTSP protein to selected cells by interaction with a cell surface protein and internalization of conjugate or MTSP protein portion thereof These conjugate are used in a variety of methods and are particularly suited for use in methods of activation of prodrugs, such as prodrugs that upon cleavage by the particular MTSP protein are cytotoxic. The prodrugs are administered prior to simultaneously with or subsequently to the conjugate. Upon delivery to the targeted cells, the protease activates the prodrug, which then exhibits is therapeutic effect, such as a cytotoxic effect.

1. Conjugation

Conjugates with linked MTSP protein domains can be prepared either by chemical conjugation, recombinant DNA technology, or combinations of recombinant expression and chemical conjugation. The MTSP protein domains and the targeting agent may be linked in any orientation and more than one targeting agents and/or MTSP protein domains may be present in a conjugate.

a. Fusion Proteins

Fusion proteins are proved herein. A fusion protein contains: a) one or a plurality of domains of an MTSP proteins and b) a targeting agent. The fusion proteins are preferably produced by recombinant expression of nucleic acids that encode the fusion protein.

b. Chemical Conjugation

To effect chemical conjugation herein, the MTSP protein domain is linked via one or more selected linkers or directly to the targeting agent. Chemical conjugation must be used if the targeted agent is other than a peptide or protein, such a nucleic acid or a non-peptide drug. Any means known to those of skill in the art for chemically conjugating selected moieties may be used.

2. Linkers

Linkers for two purposes are contemplated herein. The conjugates may include one or more linkers between the MTSP protein portion and the targeting agent. Additionally, linkers are used for facilitating or enhancing immobilization of an MTSP protein or portion thereof on a solid support, such as a microtiter plate, silicon or silicon-coated chip, glass or plastic support, such as for high throughput solid phase screening protocols.

Any linker known to those of skill in the art for preparation of conjugates may be used herein. These linkers are typically used in the preparation of chemical conjugates; peptide linkers may be incorporated into fusion proteins.

Linkers can be any moiety suitable to associate a domain of MTSP protein and a targeting agent. Such linkers and linkages include, but are not limited to, peptidic linkages, amino acid and peptide linkages, typically containing between one and about 60 amino acids, more generally between about 10 and 30 amino acids, chemical linkers, such as heterofunctional cleavable cross-linkers, including but are not limited to, N-succinimidyl (4-iodoacetyl)-aminobenzoate, sulfosuccinimidyl (4-iodoacetyl)-aminobenzoate, 4-succinimidyl-oxycarbonyl-a-(2-pyridyldithio)toluene, sulfosuccinimidyl-6-[a-methyl-a-(pyridyldithiol)-toluamido]hexanoate, N-succinimidyl-3-(-2-pyridyldithio)-propionate, succinimidyl 6[3(-(-2-pyridyldithio)-propionamido]hexanoate, sulfosuccinimidyl 6[3(-(-2-pyridyldithio)-propionamido]hexanoate, 3-(2-pyridyldithio)-propionyl hydrazide, Ellman's reagent, dichlorotriazinic acid, and S-(2-thiopyridyl)-L-cysteine. Other linkers include, but are not limited to peptides and other moieties that reduce stearic hindrance between the domain of MTSP protein and the targeting agent, intracellular enzyme substrates, linkers that increase the flexibility of the conjugate, linkers that increase the solubility of the conjugate, linkers that increase the serum stability of the conjugate, photocleavable linkers and acid cleavable linkers.

Other exemplary linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimidoethoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. *Molecular Immunol.*, 30:379-386 (1993)). In some embodiments, several linkers may be included in order to take advantage of desired properties of each linker.

Chemical linkers and peptide linkers may be inserted by covalently coupling the linker to the domain of MTSP protein and the targeting agent. The heterobifunctional agents, described below, may be used to effect such covalent coupling. Peptide linkers may also be linked by expressing DNA encoding the linker and TA, linker and targeted agent, or linker, targeted agent and TA as a fusion protein. Flexible linkers and linkers that increase solubility of the conjugates are contemplated for use, either alone or with other linkers are also contemplated herein.

a) Acid Cleavable, Photocleavable and Heat Sensitive Linkers

Acid cleavable linkers, photocleavable and heat sensitive linkers may also be used, particularly where it may be necessary to cleave the domain of MTSP protein to permit it to be more readily accessible to reaction. Acid cleavable linkers include, but are not limited to, bismaleimidoethoxy propane; and adipic acid dihydrazide linkers (see, e.g., Fattom et al. (1992) *Infection & Immun.* 60:584-589) and acid labile transferrin conjugates that contain a sufficient portion of transferrin to permit entry into the intracellular transferrin cycling pathway (see, e.g., Welhöner et al. (1991) *J. Biol. Chem.* 266:4309-4314).

Photocleavable linkers are linkers that are cleaved upon exposure to light (see, e.g., Goldmacher et al. (1992) *Bioconj. Chem.* 3:104-107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp.*, 16th, Brunfeldt, K (Ed), pp. 105-110, which describes the use of a nitrobenzyl group as a photocleavable protective group for cysteine; Yen et al. (1989) *Makromol. Chem* 190:69-82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104-107, which describes a cross-linker and reagent that undergoes photolytic degradation upon exposure to near UV light (350 nm); and Senter et al. (1985) *Photochem. Photobiol* 42:231-237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are useful in connection with diagnostic protocols in which it is desirable to remove the targeting agent to permit rapid clearance from the body of the animal.

b) Other Linkers for Chemical Conjugation

Other linkers, include trityl linkers, particularly, derivatized trityl groups to generate a genus of conjugates that provide for release of therapeutic agents at various degrees of acidity or alkalinity. The flexibility thus afforded by the ability to preselect the pH range at which the therapeutic agent will be released allows selection of a linker based on the known physiological differences between tissues in need of delivery of a therapeutic agent (see, e.g., U.S. Pat. No. 5,612, 474). For example, the acidity of tumor tissues appears to be lower than that of normal tissues.

c) Peptide Linkers

The linker moieties can be peptides. Peptide linkers can be employed in fusion proteins and also in chemically linked conjugates. The peptide typically has from about 2 to about 60 amino acid residues, for example from about 5 to about 40, or from about 10 to about 30 amino acid residues. The length selected will depend upon factors, such as the use for which the linker is included.

Peptide linkers are advantageous when the targeting agent is proteinaceous. For example, the linker moiety can be a flexible spacer amino acid sequence, such as those known in single-chain antibody research. Examples of such known linker moieties include, but are not limited to, peptides, such as $(Gly_mSer)_n$ and $(Ser_mGly)_n$, in which n is 1 to 6, preferably 1 to 4, more preferably 2 to 4, and m is 1 to 6, preferably 1 to 4, more preferably 2 to 4, enzyme cleavable linkers and others.

Additional linking moieties are described, for example, in Huston et al., *Proc. Natl. Acad. Sci. U.S.A.* 85:5879-5883, 1988; Whitlow, M., et al., *Protein Engineering* 6:989-995, 1993; Newton et al., *Biochemistry* 35:545-553, 1996; A. J. Cumber et al., *Bioconj. Chem.* 3:397-401, 1992; Ladurner et al., *J. Mol. Biol.* 273:330-337, 1997; and U.S. Pat. No. 4,894, 443. In some embodiments, several linkers may be included in order to take advantage of desired properties of each linker.

3. Targeting Agents

Any agent that facilitates detection, immobilization, or purification of the conjugate is contemplated for use herein. For chemical conjugates any moiety that has such properties is contemplated; for fusion proteins, the targeting agent is a protein, peptide or fragment thereof that sufficient to effects the targeting activity. Preferred targeting agents are those that deliver the MTSP protein or portion thereof to selected cells and tissues. Such agents include tumor specific monoclonal antibodies and portions thereof, growth factors, such as FGF, EGF, PDGF, VEGF, cytokines, including chemokines, and other such agents.

4. Nucleic Acids, Plasmids and Cells

Isolated nucleic acid fragments encoding fusion proteins are provided. The nucleic acid fragment that encodes the fusion protein includes: a) nucleic acid encoding a protease domain of an MTSP protein encoded by a nucleic acid that hybridizes to a nucleic acid having the nucleotide sequence set forth in the SEQ. ID NO:1; and b) nucleic acid encoding a protein, peptide or effective fragment thereof that facilitates: i) affinity isolation or purification of the fusion protein; ii) attachment of the fusion protein to a surface; or iii) detection of the fusion protein. Preferably, the nucleic acid is DNA.

Plasmids for replication and vectors for expression that contain the above nucleic acid fragments are also provided. Cells containing the plasmids and vectors are also provided. The cells can be any suitable host including, but are not limited to, bacterial cells, yeast cells, fungal cells, plant cells, insect cell and animal cells. The nucleic acids, plasmids, and cells containing the plasmids can be prepared according to methods known in the art including any described herein.

Also provided are methods for producing the above fusion proteins. An exemplary method includes the steps of growing, i.e. culturing the cells so that the proliferate, cells containing a plasmid encoding the fusion protein under conditions whereby the fusion protein is expressed by the cell, and recovering the expressed fusion protein. Methods for expressing and recovering recombinant proteins are well known in the art (See generally, *Current Protocols in Molecular Biology* (1998) §16, John Wiley & Sons, Inc.) and such methods can be used for expressing and recovering the expressed fusion proteins. Preferably, the recombinant expression and recovery methods disclosed in Section B can be used.

The recovered fusion proteins can be isolated or purified by methods known in the art such as centrifugation, filtration, chromatograph, electrophoresis, immunoprecipitation, etc., or by a combination thereof (See generally, *Current Protocols in Molecular Biology* (1998) §10, John Wiley & Sons, Inc.). Preferably, the recovered fusion protein is isolated or purified through affinity binding between the protein or peptide fragment of the fusion protein and an affinity binding moiety. As discussed in the above sections regarding the construction of the fusion proteins, any affinity binding pairs can be constructed and used in the isolation or purification of the fusion proteins. For example, the affinity binding pairs can be protein binding sequences/protein, DNA binding sequences/ DNA sequences, RNA binding sequences/RNA sequences, lipid binding sequences/lipid, polysaccharide binding sequences/polysaccharide, or metal binding sequences/ metal.

5. Immobilization and Supports or Substrates Therefor

In certain embodiments, where the targeting agents are designed for linkage to surfaces, the MTSP protein can be attached by linkage such as ionic or covalent, non-covalent or other chemical interaction, to a surface of a support or matrix material. Immobilization may be effected directly or via a linker. The MTSP protein may be immobilized on any suitable support, including, but are not limited to, silicon chips, and other supports described herein and known to those of skill in the art. A plurality of MTSP protein or protease domains thereof may be attached to a support, such as an array (i.e., a pattern of two or more) of conjugates on the surface of a silicon chip or other chip for use in high throughput protocols and formats.

It is also noted that the domains of the MTSP protein can be linked directly to the surface or via a linker without a targeting agent linked thereto. Hence chips containing arrays of the domains of the MTSP protein.

The matrix material or solid supports contemplated herein are generally any of the insoluble materials known to those of skill in the art to immobilize ligands and other molecules, and are those that used in many chemical syntheses and separations. Such supports are used, for example, in affinity chromatography, in the immobilization of biologically active materials, and during chemical syntheses of biomolecules, including proteins, amino acids and other organic molecules and polymers. The preparation of and use of supports is well known to those of skill in this art; there are many such materials and preparations thereof known. For example, naturally-occurring support materials, such as agarose and cellulose, may be isolated from their respective sources, and processed according to known protocols, and synthetic materials may be prepared in accord with known protocols.

The supports are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item may be fabricated from the matrix material or combined with it, such as by coating all or part of the surface or impregnating particles.

Typically, when the matrix is particulate, the particles are at least about 10-2000 μM, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use.

If necessary, the support matrix material can be treated to contain an appropriate reactive moiety. In some cases, the support matrix material already containing the reactive moiety may be obtained commercially. The support matrix material containing the reactive moiety may thereby serve as the matrix support upon which molecules are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethoxysilyl)propyl]phthalamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art (e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al., *Peptide Res.*, 7:20-23 (1994); and Kleine et al., *Immunobiol.*, 190:53-66 (1994)).

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene and others (see, Merrifield, *Biochemistry*, 3:1385-1390 (1964)), polyacrylamides, latex gels, polystyrene, dextran, polyacrylamides, rubber, silicon, plastics, nitrocellulose, celluloses, natural sponges. Of particular interest herein, are highly porous glasses (see, e.g., U.S. Pat. No. 4,244,721) and others prepared by mixing a borosilicate, alcohol and water.

Synthetic supports include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers (see, e.g., Merrifield, *Biochemistry*, 3:1385-1390 (1964); Berg et al., in *Innovation Perspect. Solid Phase Synth. Collect. Pap.*, Int. Symp., 1st, Epton, Roger (Ed), pp. 453-459 (1990); Berg et al., *Pept., Proc. Eur. Pept. Symp.*, 20th, Jung, G. et al. (Eds), pp. 196-198 (1989); Berg et al., *J. Am. Chem. Soc.*, 111:8024-8026 (1989); Kent et al., *Isr. J. Chem.*, 17:243-247 (1979); Kent et al., *J. Org. Chem.*, 43:2845-2852 (1978); Mitchell et al., *Tetrahedron Lett.*, 42:3795-3798 (1976); U.S. Pat. No. 4,507,230; U.S. Pat. No. 4,006,117; and U.S. Pat. No. 5,389,449). Such materials include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride and polypropylene-co-maleic anhydride. Liposomes have also been used as solid supports for affinity purifications (Powell et al. *Biotechnol. Bioeng.*, 33:173 (1989)).

Numerous methods have been developed for the immobilization of proteins and other biomolecules onto solid or liquid supports (see, e.g., Mosbach, *Methods in Enzymology*, 44 (1976); Weetall, *Immobilized Enzymes, Antigens, Antibodies, and Peptides*, (1975); Kennedy et al., *Solid Phase Biochemistry, Analytical and Synthetic Aspects*, Scouten, ed., pp. 253-391 (1983); see, generally, Affinity Techniques. Enzyme Purification: Part B. Methods in Enzymology, Vol. 34, ed. W. B. Jakoby, M. Wilchek, Acad. Press, N.Y. (1974); and Immobilized Biochemicals and Affinity Chromatography, *Advances in Experimental Medicine and Biology*, vol. 42, ed. R. Dunlap, Plenum Press, N.Y. (1974)).

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art (see, e.g., the PIERCE CATALOG, ImmunoTechnology Catalog & Handbook, 1992-1993, which describes the preparation of and use of such reagents and provides a commercial source for such reagents; Wong, *Chemistry of Protein Conjugation and Cross Linking*, CRC Press (1993); see also DeWitt et al., *Proc. Natl. Acad. Sci. U.S.A.*, 90:6909 (1993); Zuckermann et al., *J. Am. Chem. Soc.*, 114:10646 (1992); Kurth et al., *J. Am. Chem. Soc.*, 116:2661 (1994); Ellman et al., *Proc. Natl. Acad. Sci. U.S.A.*, 91:4708 (1994); Sucholeiki, *Tetrahedron Lttrs.*, 35:7307 (1994); Su-Sun Wang, *J. Org. Chem.*, 41:3258 (1976); Padwa et al., *J. Org. Chem.*, 41:3550 (1971); and Vedejs et al., *J. Org. Chem.*, 49:575 (1984), which describe photosensitive linkers).

To effect immobilization, a composition containing the protein or other biomolecule is contacted with a support material such as alumina, carbon, an ion-exchange resin, cellulose, glass or a ceramic. Fluorocarbon polymers have been used as supports to which biomolecules have been attached by adsorption (see, U.S. Pat. No. 3,843,443; Published International PCT Application WO/86 03840).

J. Prognosis and Diagnosis

MTSP protein proteins, domains, analogs, and derivatives thereof, and encoding nucleic acids (and sequences complementary thereto), and anti-MTSP protein antibodies, can be used in diagnostics. Such molecules can be used in assays, such as immunoassays, to detect, prognose, diagnose, or monitor various conditions, diseases, and disorders affecting MTSP protein expression, or monitor the treatment thereof For purposes herein, the presence of MTSPs in body fluids or tumor tissues are of particular interest.

In particular, such an immunoassay is carried out by a method including contacting a sample derived from a patient with an anti-MTSP protein antibody under conditions such that specific binding can occur, and detecting or measuring the amount of any specific binding by the antibody. In a specific aspect, such binding of antibody, in tissue sections, can be used to detect aberrant MTSP protein localization or aberrant (e.g., low or absent) levels of MTSP protein. In a specific embodiment, antibody to MTSP protein can be used to assay in a patient tissue or serum sample for the presence of MTSP protein where an aberrant level of MTSP protein is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

MTSP protein genes and related nucleic acid sequences and subsequences, including complementary sequences, can also be used in hybridization assays. MTSP protein nucleic acid sequences, or subsequences thereof containing about at least 8 nucleotides, preferably 14 or 16 or 30 or more contiguous nucleotides, can be used as hybridization probes. Hybridization assays can be used to detect, prognose, diagnose, or monitor conditions, disorders, or disease states associated with aberrant changes in MTSP protein expression and/or activity as described herein. In particular, such a hybridization assay is carried out by a method by contacting a sample containing nucleic acid with a nucleic acid probe capable of hybridizing to MTSP protein encoding DNA or RNA, under conditions such that hybridization can occur, and detecting or measuring any resulting hybridization.

In a specific embodiment, a method of diagnosing a disease or disorder characterized by detecting an aberrant level of an MTSP protein in a subject is provided herein by measuring the level of the DNA, RNA, protein or functional activity of the epithelial MTSP protein at least partially encoded by a nucleic acid that hybridizes to a nucleic acid having the nucleotide sequence set forth in the SEQ. ID NO:1 in a sample derived from the subject, wherein an increase or decrease in the level of the DNA, RNA, protein or functional activity of the MTSP protein, relative to the level of the DNA, RNA, protein or functional activity found in an analogous sample not having the disease or disorder indicates the presence of the disease or disorder in the subject.

Kits for diagnostic use are also provided, that contain in one or more containers an anti-MTSP protein antibody, particularly anti-MTSP3 or anti=MTSP4, and, optionally, a labeled binding partner to the antibody. Alternatively, the anti-MTSP protein antibody can be labeled (with a detectable marker, e.g., a chemiluminescent, enzymatic, fluorescent, or radioactive moiety). A kit is also provided that includes in one or more containers a nucleic acid probe capable of hybridizing to MTSP protein-encoding RNA. In a specific embodiment, a kit can comprise in one or more containers a pair of primers (e.g., each in the size range of 6-30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art under appropriate reaction conditions of at least a portion of an MTSP protein-encoding nucleic acid. A kit can optionally further comprise in a container a predetermined amount of a purified MTSP protein or nucleic acid, e.g., for use as a standard or control.

K. Pharmaceutical Compositions and Modes of Administration

1. Components of the Compositions

Pharmaceutical compositions containing the identified compounds that modulate the activity of an MTSP protein are provided herein. Also provided are combinations of a compound that modulates the activity of an MTSP protein and another treatment or compound for treatment of a neoplastic disorder, such as a chemotherapeutic compound.

The MTSP protein modulator and the anti-tumor agent can be packaged as separate compositions for administration together or sequentially or intermittently. Alternatively, they can provided as a single composition for administration or as two compositions for administration as a single composition. The combinations can be packaged as kits.

a. MTSP Protein Inhibitors

Any MTSP protein inhibitors, including those described herein when used alone or in combination with other compounds, that can alleviate, reduce, ameliorate, prevent, or place or maintain in a state of remission of clinical symptoms or diagnostic markers associated with neoplastic diseases, including undesired and/or uncontrolled angiogenesis, can be used in the present combinations.

In one embodiment, the MTSP protein inhibitor is an antibody or fragment thereof that specifically reacts with an MTSP protein or the protease domain thereof, an inhibitor of the MTSP protein production, an inhibitor of the epithelial MTSP protein membrane-localization, or any inhibitor of the expression of or, especially, the activity of an MTSP protein.

b. Anti-Angiogenic Agents and Anti-Tumor Agents

Any anti-angiogenic agents and anti-tumor agents, including those described herein, when used alone or in combination with other compounds, that can alleviate, reduce, ameliorate, prevent, or place or maintain in a state of remission of clinical symptoms or diagnostic markers associated with undesired and/or uncontrolled angiogenesis and/or tumor growth and metastasis, particularly solid neoplasms, vascular malformations and cardiovascular disorders, chronic inflammatory diseases and aberrant wound repairs, circulatory disorders, crest syndromes, dermatological disorders, or ocular disorders, can be used in the combinations. Also contemplated are anti-tumor agents for use in combination with an inhibitor of an MTSP protein.

c. Anti-Tumor Agents and Anti-Angiogenic Agents

The compounds identified by the methods provided herein or provided herein can be used in combination with anti-tumor agents and/or anti-angiogenesis agents.

2. Formulations and Route of Administration

The compounds herein and agents are preferably formulated as pharmaceutical compositions, preferably for single dosage administration. The concentrations of the compounds in the formulations are effective for delivery of an amount, upon administration, that is effective for the intended treatment. Typically, the compositions are formulated for single dosage administration. To formulate a composition, the weight fraction of a compound or mixture thereof is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems, such as the assays provided herein.

The concentration of active compound in the drug composition will depend on absorption, inactivation and excretion rates of the active compound, the physicochemical characteristics of the compound, the dosage schedule, and amount administered as well as other factors known to those of skill in the art.

Typically a therapeutically effective dosage is contemplated. The amounts administered may be on the order of 0.001 to 1 mg/ml, preferably about 0.005-0.05 mg/ml, more preferably about 0.01 mg/ml, of blood volume. Pharmaceutical dosage unit forms are prepared to provide from about 1 mg to about 1000 mg and preferably from about 10 to about 500 mg, more preferably about 25-75 mg of the essential active ingredient or a combination of essential ingredients per dosage unit form. The precise dosage can be empirically determined.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of the claimed compositions and combinations containing them.

Preferred pharmaceutically acceptable derivatives include acids, salts, esters, hydrates, solvates and prodrug forms. The derivative is typically selected such that its pharmacokinetic properties are superior to the corresponding neutral compound.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the disorder for which treatment is contemplated. The concentration of active compound in the composition will depend on absorption, inactivation, excretion rates of the active compound, the dosage schedule, amount administered, particular formulation as well as other factors known to those of skill in the art.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as prodrugs of the compounds may also be used in formulating effective pharmaceutical compositions. For ophthalmic indications, the compositions are formulated in an ophthalmically acceptable carrier. For the ophthalmic uses herein, local administration, either by topical administration or by injection is preferred. Time release formulations are also desirable. Typically, the compositions are formulated for single dosage administration, so that a single dose administers an effective amount.

Upon mixing or addition of the compound with the vehicle, the resulting mixture may be a solution, suspension, emulsion or other composition. The form of the resulting mixture depends upon a number of factors, including the intended mode of administration and the solubility of the compound in the selected carrier or vehicle. If necessary, pharmaceutically acceptable salts or other derivatives of the compounds are prepared.

The compound is included in the pharmaceutically acceptable carrier in an amount sufficient to exert a therapeutically useful effect in the absence of undesirable side effects on the patient treated. It is understood that number and degree of side effects depends upon the condition for which the compounds are administered. For example, certain toxic and undesirable side effects are tolerated when treating life-threatening illnesses that would not be tolerated when treating disorders of lesser consequence.

The compounds can also be mixed with other active materials, that do not impair the desired action, or with materials that supplement the desired action known to those of skill in the art. The formulations of the compounds and agents for use herein include those suitable for oral, rectal, topical, inhalational, buccal (e.g., sublingual), parenteral (e.g., subcutaneous, intramuscular, intradermal, or intravenous), transdermal administration or any route. The most suitable route in any given case will depend on the nature and severity of the condition being treated and on the nature of the particular active compound which is being used. The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art (see, e.g., Remington's Pharmaceutical Sciences, Mack Publishing Company, Easton, Pa., 15th Edition, 1975). The composition or formulation to be administered will contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, the pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The pharmaceutical preparation may also be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid).

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin or to the eye preferably take the form of an ointment, cream, lotion, paste, gel, spray, aerosol and oil. Carriers which may be used include vaseline, lanoline, polyethylene glycols, alcohols, and combinations of two or more thereof. The topical formulations may further advantageously contain 0.05 to 15 percent by weight of thickeners selected from among hydroxypropyl methyl cellulose, methyl cellulose, polyvinylpyrrolidone, polyvinyl alcohol, poly(alkylene glycols), poly/hydroxyalkyl, (meth)acrylates or poly(meth)acrylamides. A topical formulation is often applied by instillation or as an ointment into the conjunctival sac. It can also be used for irrigation or lubrication of the eye, facial sinuses, and external auditory meatus. It may also be injected into the anterior eye chamber and other places. The topical formulations in the liquid state may be also present in a hydrophilic three-dimensional polymer matrix in the form of a strip, contact lens, and the like from which the active components are released.

For administration by inhalation, the compounds for use herein can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

The compounds may be formulated for parenteral administration by injection, e.g., by bolus injection or continuous infusion. Formulations for injection may be presented in unit dosage form, e.g., in ampules or in multi-dose containers, with an added preservative. The compositions may be suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile pyrogen-free water or other solvents, before use.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 to 0.2 M concentration with respect to the active compound. Formulations suitable for transdermal administration may also be delivered by iontophoresis (see, e.g., Pharmaceutical Research 3(6), 318 (1986)) and typically take the form of an optionally buffered aqueous solution of the active compound.

The pharmaceutical compositions may also be administered by controlled release means and/or delivery devices (see, e.g., in U.S. Pat. Nos. 3,536,809; 3,598,123; 3,630,200; 3,845,770; 3,847,770; 3,916,899; 4,008,719; 4,687,610; 4,769,027; 5,059,595; 5,073,543; 5,120,548; 5,354,566; 5,591,767; 5,639,476; 5,674,533 and 5,733,566).

Desirable blood levels may be maintained by a continuous infusion of the active agent as ascertained by plasma levels. It should be noted that the attending physician would know how to and when to terminate, interrupt or adjust therapy to lower dosage due to toxicity, or bone marrow, liver or kidney dysfunctions. Conversely, the attending physician would also know how to and when to adjust treatment to higher levels if the clinical response is not adequate (precluding toxic side effects).

The efficacy and/or toxicity of the MTSP protein inhibitor (s), alone or in combination with other agents can also be assessed by the methods known in the art (See generally, O'Reilly, *Investigational New Drugs*, 15:5-13 (1997)).

The active compounds or pharmaceutically acceptable derivatives may be prepared with carriers that protect the compound against rapid elimination from the body, such as time release formulations or coatings.

Kits containing the compositions and/or the combinations with instructions for administration thereof are provided. The kit may further include a needle or syringe, preferably packaged in sterile form, for injecting the complex, and/or a packaged alcohol pad. Instructions are optionally included for administration of the active agent by a clinician or by the patient.

Finally, the compounds or MTSP proteins or protease domains thereof or compositions containing any of the preceding agents may be packaged as articles of manufacture containing packaging material, a compound or suitable derivative thereof provided herein, which is effective for treatment of a diseases or disorders contemplated herein, within the packaging material, and a label that indicates that the compound or a suitable derivative thereof is for treating the diseases or disorders contemplated herein. The label can optionally include the disorders for which the therapy is warranted.

L. Methods of Treatment

The compounds identified by the methods herein are used for treating or preventing neoplastic diseases in an animal, particularly a mammal, including a human, is provided herein. In one embodiment, the method includes administering to a mammal an effective amount of an inhibitor of an MTSP protein, whereby the disease or disorder is treated or prevented. In a preferred embodiment, the MTSP protein inhibitor used in the treatment or prevention is administered with a pharmaceutically acceptable carrier or excipient. The mammal treated can be a human.

The inhibitors provided herein are those identified by the screening assays. In addition, antibodies and antisense nucleic acids are contemplated.

The treatment or prevention method can further include administering an anti-angiogenic treatment or agent or anti-tumor agent simultaneously with, prior to or subsequent to the MTSP protein inhibitor, which can be any compound identified that inhibits the activity of an MTSP protein, and includes an antibody or a fragment or derivative thereof containing the binding region thereof against the MTSP protein, an antisense nucleic acid encoding the MTSP protein, and a nucleic acid containing at least a portion of a gene encoding the MTSP protein into which a heterologous nucleotide sequence has been inserted such that the heterologous sequence inactivates the biological activity of at least a portion of the gene encoding the MTSP protein, in which the portion of the gene encoding the MTSP protein flanks the heterologous sequence so as to promote homologous recombination with a genomic gene encoding the MTSP protein.

1. Antisense Treatment

In a specific embodiment, as described hereinabove, MTSP protein function is reduced or inhibited by MTSP protein antisense nucleic acids, to treat or prevent neoplastic disease. The therapeutic or prophylactic use of nucleic acids of at least six nucleotides that are antisense to a gene or cDNA encoding MTSP protein or a portion thereof. An MTSP protein "antisense" nucleic acid as used herein refers to a nucleic acid capable of hybridizing to a portion of an MTSP protein RNA (preferably mRNA) by virtue of some sequence complementarily. The antisense nucleic acid may be complementary to a coding and/or noncoding region of an MTSP protein mRNA. Such antisense nucleic acids have utility as therapeutics that reduce or inhibit MTSP protein function, and can be used in the treatment or prevention of disorders as described supra.

The MTSP protein antisense nucleic acids are of at least six nucleotides and are preferably oligonucleotides (ranging from 6 to about 150 nucleotides, or more preferably 6 to 50 nucleotides). In specific aspects, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci. U.S.A.* 84:648-652 (1987); PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Van Der Krol et al., *BioTechniques* 6:958-976 (1988)) or intercalating agents (see, e.g., Zon, *Pharm. Res.* 5:539-549 (1988)).

The MTSP protein antisense nucleic acid is preferably an oligonucleotide, more preferably of single-stranded DNA. In a preferred aspect, the oligonucleotide includes a sequence antisense to a portion of human MTSP protein. The oligonucleotide may be modified at any position on its structure with substituents generally known in the art.

The MTSP protein antisense oligonucleotide may comprise at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide includes at least one modified sugar moiety selected from the group including but not limited to arabinose, 2-fluoroarabinose, xylulose, and hexose. The oligonucleotide can include at least one modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotide can be an α-anomeric oligonucleotide. An α-anomeric oligonucleotide forms specific double-stranded hybrids with complementary RNA in which the strands run parallel to each other (Gautier et al., *Nucl. Acids Res.* 15:6625-6641 (1987)).

The oligonucleotide may be conjugated to another molecule, e.g., a peptide, hybridization triggered cross-linking agent, transport agent and hybridization-triggered cleavage agent.

The oligonucleotides may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448-7451 (1988)), etc.

In a specific embodiment, the MTSP protein antisense oligonucleotide includes catalytic RNA, or a ribozyme (see, e.g., PCT International Publication WO 90/11364, published Oct. 4, 1990; Sarver et al., *Science* 247:1222-1225 (1990)). In another embodiment, the oligonucleotide is a 2'-O-methylribonucleotide (Inoue et al., *Nucl. Acids Res.* 15:6131-6148 (1987)), or a chimeric RNA-DNA analogue (Inoue et al., *FEBS Lett.* 215:327-330 (1987)).

In an alternative embodiment, the MTSP protein antisense nucleic acid is produced intracellularly by transcription from an exogenous sequence. For example, a vector can be introduced in vivo such that it is taken up by a cell, within which cell the vector or a portion thereof is transcribed, producing an antisense nucleic acid (RNA). Such a vector would contain a sequence encoding the MTSP protein antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the MTSP protein antisense RNA can be by any promoter known in the art to act in mammalian, preferably human, cells. Such promoters can be inducible or constitutive. Such promoters include but are not limited to: the SV40 early promoter region (Bernoist and Chambon, *Nature* 290:304-310 (1981), the promoter contained in the 3' long terminal repeat of Rous sarcoma virus (Yamamoto et al., *Cell* 22:787-797 (1980), the herpes thymidine kinase promoter (Wagner et al., *Proc. Natl. Acad. Sci. U.S.A.* 78:1441-1445 (1981), the regulatory sequences of the metallothionein gene (Brinster et al., *Nature* 296:39-42 (1982), etc.

The antisense nucleic acids include sequence complementary to at least a portion of an RNA transcript of an MTSP protein gene, preferably a human MTSP protein gene. Absolute complementarily, although preferred, is not required.

The amount of MTSP protein antisense nucleic acid that will be effective in the treatment or prevention of neoplastic disease will depend on the nature of the disease, and can be determined empirically by standard clinical techniques. Where possible, it is desirable to determine the antisense cytotoxicity in cells in vitro, and then in useful animal model systems prior to testing and use in humans.

2. Gene Therapy

In an exemplary embodiment, nucleic acids that include a sequence of nucleotides encoding an MTSP protein or functional domains or derivative thereof, are administered to promote MTSP protein function, by way of gene therapy. Gene therapy refers to therapy performed by the administration of a nucleic acid to a subject. In this embodiment, the nucleic acid produces its encoded protein that mediates a therapeutic effect by promoting MTSP protein function. Any of the methods for gene therapy available in the art can be used (see, Goldspiel et al., *Clinical Pharmacy* 12:488-505 (1993); Wu and Wu, *Biotherapy* 3:87-95 (1991); Tolstoshev, *An. Rev. Pharmacol. Toxicol.* 32:573-596 (1993); Mulligan, *Science* 260:926-932 (1993); and Morgan and Anderson, *An. Rev. Biochem.* 62:191-217 (1993); *TIBTECH* 11(5):155-215 (1993). For example, one therapeutic composition for gene therapy includes an MTSP protein-encoding nucleic acid that is part of an expression vector that expresses an MTSP protein or domain, fragment or chimeric protein thereof in a suitable host. In particular, such a nucleic acid has a promoter operably linked to the MTSP protein coding region, the promoter being inducible or constitutive, and, optionally, tissue-specific. In another particular embodiment, a nucleic acid molecule is used in which the MTSP protein coding sequences and any other desired sequences are flanked by regions that promote homologous recombination at a desired site in the genome, thus providing for intrachromosomal expression of the MTSP protein nucleic acid (Koller and Smithies, *Proc. Natl. Acad. Sci. USA* 86:8932-8935 (1989); Zijlstra et al., *Nature* 342:435-438 (1989)).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, *J. Biol. Chem.* 262:4429-4432 (1987)) (which can be used to target cell types specifically expressing the receptors), etc. In another embodiment, a nucleic acid-ligand complex can be formed in which the ligand is a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932-8935 (1989); Zijlstra et al., *Nature* 342:435-438 (1989)).

In a specific embodiment, a viral vector that contains the MTSP protein nucleic acid is used. For example, a retroviral vector can be used (see Miller et al., *Meth. Enzymol.* 217:581-599 (1993)). These retroviral vectors have been modified to delete retroviral sequences that are not necessary for packaging of the viral genome and integration into host cell DNA. The MTSP protein nucleic acid to be used in gene therapy is cloned into the vector, which facilitates delivery of the gene into a patient. More detail about retroviral vectors can be found in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); and Mastrangeli et al., *J. Clin. Invest.* 91:225-234 (1993).

Adeno-associated virus (AAV) has also been proposed for use in gene therapy (Walsh et al., *Proc. Soc. Exp. Biol. Med.* 204:289-300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* 217:599-618 (1993); Cohen et al., *Meth. Enzymol.* 217:618-644 (1993); Cline, *Pharmac. Ther.* 29:69-92 (1985)) and may be used, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient. In an embodiment in which recombinant cells are used in gene therapy, an MTSP protein nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, *Cell* 71:973-985 (1992)).

Epithelial stem cells (ESCs) or keratinocytes can be obtained from tissues such as the skin and the lining of the gut by known procedures (Rheinwald, *Meth. Cell Bio.* 21A:229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, *Meth. Cell Bio.* 21A:229 (1980); Pittelkow and Scott, *Mayo Clinic Proc.* 61:771 (1986)). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment. Techniques by which this may be accomplished include (a) the isolation and establishment of HSC cultures from bone marrow cells isolated from the future host, or a donor, or (b)

the use of previously established long-term HSC cultures, which may be allogeneic or xenogeneic. Non-autologous HSC are used preferably in conjunction with a method of suppressing transplantation immune reactions of the future host/patient. In a particular embodiment, human bone marrow cells can be obtained from the posterior iliac crest by needle aspiration (see, e.g., Kodo et al., *J. Clin. Invest.* 73:1377-1384 (1984)). In a preferred embodiment, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., *J. Cell Physiol.* 91:335 (1977) or Witlock-Witte culture techniques (Witlock and Witte, *Proc. Natl. Acad. Sci. USA* 79:3608-3612 (1982)).

In a specific embodiment, the nucleic acid to be introduced for purposes of gene therapy includes an inducible promoter operably linked to the coding region, such that expression of the nucleic acid is controllable by controlling the presence or absence of the appropriate inducer of transcription.

3. Prodrugs

A method for treating tumors is provided. The method is practiced by administering a prodrug that is specifically cleaved by an MTSP to release an active drug. Upon contact with a cell that expresses MTSP activity, the prodrug is converted into an active drug. The prodrug can be a conjugate that contains the active agent, such as an anti-tumor drug, such as a cytotoxic agent, or other atherapeutic agent, linked, linked to a substrate for the targeted MTSP, such that the drug or agent is inactive or unable to enter a cell, in the conjugate, but is activated upon cleavage. The prodrug, for example, can contain an oligopeptide, preferably a relatively short, less than about 10 amino acids peptide, that is selectively proteolytically cleaved by the targeted MTSP. Cytotoxic agents, include, but are not limited to, alkylating agents, antiproliferative agents and tubulin binding agents. Others include, vinca drugs, mitomycins, bleomycins and taxanes.

M. Animal Models

Transgenic animal models are provided herein. Such an animal can be initially produced by promoting homologous recombination between an MTSP protein gene in its chromosome and an exogenous MTSP protein gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally inactivated MTSP protein gene, such that homologous recombination occurs, followed by injecting the ES cells into a blastocyst, and implanting the blastocyst into a foster mother, followed by the birth of the chimeric animal ("knockout animal") in which an MTSP protein gene has been inactivated (see Capecchi, *Science* 244:1288-1292 (1989)). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing neoplastic diseases and thus can have use as animal models of such diseases e.g., to screen for or test molecules for the ability to treat or prevent such diseases or disorders. Hence, the animal models for are provided. Such an animal can be initially produced by promoting homologous recombination between an MTSP gene in its chromosome and an exogenous MTSP protein gene that would be over-expressed or mis-expressed (preferably by expression under a strong promoter). In a preferred aspect, this homologous recombination is carried out by transforming embryo-derived stem (ES) cells with a vector containing the over-expressed or mis-expressed MTSP protein gene, such that homologous recombination occurs, followed by injecting the ES cells into a blastocyst, and implanting the blastocyst into a foster mother, followed by the birth of the chimeric animal in which an MTSP gene has been over-expressed or mis-expressed (see Capecchi, *Science* 244:1288-1292 (1989)). The chimeric animal can be bred to produce additional animals with over-expressed or mis-expressed MTSP protein. Such animals can be mice, hamsters, sheep, pigs, cattle, etc., and are preferably non-human mammals. In a specific embodiment, a mouse with over-expressed or mis-expressed MTSP protein is produced.

The following examples are included for illustrative purposes only and are not intended to limit the scope of the invention.

Example 1

Cloning of MTSP3, Cloning and Mutagenesis of the Protease Domain of MTSP3

1. Identification and Cloning of MTSP3 a. Identification of EST Clones AI924527 and AI924182 as Part of a Serine Protease MTSP3

DNA encoding the protease domain of the protease designated MTSP1 was independently cloned from the human prostatic adenocarcinoma cell line, PC-3, using degenerate oligonucleotide primers, then sequenced and characterized (see EXAMPLE 6). The sequence of the sense degenerate primer used in cloning MTSP1 was 5'-TGGRT(I)VT(I)WS (I)GC(I)RC(I)CAYTG-3' (SEQ ID No: 13), and that of the anti-sense was 5'-(I)GG(I)CC(I)CC(I)SWRTC(I)CCYT(I) RCA(I)GHRTC-3' (SEQ ID No:14), where R=A,G; V=G,A, C; W=A,T; S=G,C; Y=C,T; H=A,T,C. The primer sequences correspond to two highly conserved regions in all serine proteases and should amplify PCR products ranging from 400 to 500 base pairs. MTSP1 was subsequently found to be identical to matriptase (Genbank accession number AF118224; see also Takeuchi et al., *Proc. Natl. Acad. Sci. USA*, 96(20): 11054-61 (1999); and Lin et al., *J. Biol. Chem.*, 274(26): 18231-6 1999).

Using the protein sequence of the protease domain of the serine protease MTSP1, the EST database (dbEST) at the National Center for Biotechnology Information (Bethesda, Md.; www.ncbi.nlm.nih.gov) was searched for EST clones that contain similar or identical sequences to MTSP1 using the search algorithm tblastn. The tblastn algorithm compares a protein query sequence against a nucleotide sequence database dynamically translated in all six reading frames (both strands). The sequences for two identical EST clones (NCI_CGAP_Lu19 AI924527 and AI924182) derived from human lung tumor tissue showed 43% identity with the MTSP1 protein sequence. Subsequent search of GenBank and SwissProt database for the EST sequence AI924527 and AI924182 did not show any matching sequence to MTSP1, indicating that the sequence contained in these EST clones AI924527 and AI924182 may be portions of a new serine protease.

b. PCR Cloning of a cDNA Fragment of Another Membrane Type Serine Protease MTSP3

The double-stranded Marathon-Ready™ cDNA library derived from human lung carcinoma (LX-1) was obtained from Clontech (Palo Alto, Calif.; catalog #7495-1) and used as a template. Two primers, 5'-TCACCGAGAAGATGAT-GTGTGCAGGCATCC-3' (SEQ ID No:15) (sense primer), and 5'-GGGACAGGGGCTGTAAGGCAGGGAATGAG-3' (SEQ ID No:16) (antisense primer), were used to amplify a ~360 by DNA fragment. The PCR product was separated on a 2% agarose gel and purified using a gel extraction kit (catalog number 28706; QIAquick gel extraction kit; Qiagen). The purified DNA fragment was ligated into TA vectors (catalog number K4500-01; TOPO-TA cloning kit, Invitrogen, Carlsbad, Calif.). After transformation into E. coli cells, plasmids were isolated and analyzed by digestion with EcoRI restriction enzyme. Clones that had inserted DNA were further characterized by sequencing using a fluorescent dye-based DNA sequencing method (catalog number 4303149; BigDye terminator cycle sequencing kit with AmpliTaq DNA polymerase; Perkin Elmer, Lincoln, Calif.).

The DNA sequence obtained was analyzed and has 43% identity with the MTSP1 protein sequence. This indicates that the LX-1 cDNA library contains a desired nucleic acid molecule. It was used to isolate a cDNA clone encompassing a full length protease.

c. 5'- and 3'-Rapid Amplification of cDNA Ends (RACE)

To obtain the full-length cDNA that encoded this serine protease, hereafter called MTSP3, 5'- and 3'-RACE reactions were performed. The Marathon-Ready cDNA library from human lung carcinoma (LX-1) was used to isolate the 5' and 3' ends of the cDNA encoding MTSP3. Marathon-Ready cDNA is specifically made for RACE reactions. Two gene specific primers were used: 5'-CCCGCAGCCATAGC-CCCAGCTAACG-3' (SEQ ID No. 17) for 5'-RACE reaction and 5'-GCAGACGATGCGTACCAGGGGGAAGTC-3' (SEQ ID No. 18) for 3'-RACE reaction. Two fragments, approximately 1.8 kbp and 0.85 kbp, were isolated that correspond to the missing 5' and 3' end sequences, respectively. These fragments were subcloned as described above. They were further confirmed by Southern analysis using an internal cDNA fragment encompassing the 2 primers used in the RACE reactions as probe and by DNA sequence analysis.

d. PCR Amplification of cDNA Encoding Full-Length Protease Domain of MTSP3

To obtain the cDNA fragment encoding the protease domain of MTSP3, an end-to-end PCR amplification using gene-specific primers was used. The two primers used were: 5'-CTCGAGAAAAGA GTGGTGGGTGGGGAGGAGGCCTCTGTG-3' (SEQ ID No. 19) for the 5' end and 5'-GCGGCCGCA TTACAGCTCAGCCTTCCAGAC-3' (SEQ ID No. 20) for the 3' end. The 5' primer contains the sequence (underlined) that encodes the start of the MTSP3 protease domain (VVG-GEEASV). The 3' primer contains the stop codon (underlined) of MTSP3. A ~700-bp fragment was amplified and subcloned into a Pichia pastoris expression vector, pPIC9K.

e. C310S Mutagenesis of MTSP3

To eliminate the free cysteine (at position 310 in SEQ ID No. 4) that exists when the protease domain of the MTSP3 protein is expressed or the zymogen is activated, the free cysteine at position 310 (see SEQ ID No. 3), which is Cys122 if a chymotrypsin numbering scheme is used, was replaced with a serine. The resulting vector was designated pPIC9K: MTSP3C122S.

The gene encoding the protease domain of MTSP3 was mutagenized by PCR SOE (PCR-based splicing by overlap extension) to replace the unpaired cysteine at position 310 (122 chymotrypsin numbering system) with a serine. Two overlapping gene fragments, each containing the TCT codon for serine at position 310 were PCR amplified using the following primers: for the 5' gene fragment, TCTCTC-GAGAAAAGAGTGGTGGGTGGGTGGGGAG-GAGGCCTCTGTG SEQ ID No. 51 and GCTCCTCAT-CAAAGAAGGGCAGAGAGATGGGCCTGACTGTGCC SEQ ID No. 52; for the 3' gene fragment, ATTCGCGGCCG-CATTACAGCTCAGCCTTCCAGAC (SEQ ID No. 53) and GGCACAGTCAGGCCCATCTCTCTGCCCT-TCTTTGATGAGGAGC (SEQ ID No. 54). The amplified gene fragments were purified on a 1% agarose gel, mixed and reamplified by PCR to produce the full length coding sequence for MTSP3 C122S. This sequence was then cut with restriction enzymes NotI and XhoI, and ligated into vector pPic9K.

2. Sequence Analysis

All derived DNA and protein sequences were analyzed using MacVector (version 6.5; Oxford Molecular Ltd., Madison, Wis.). The full-length cDNA encoding MTSP3 is composed of 2,137 base pairs containing the longest open reading frame of 1,314 base pairs which translate to a 437-amino acid protein sequence. The cDNA fragment (nt 873-1,574) encoding the protease domain of MTSP3 is composed of 702 base pairs which translate to a 233-amino acid protein sequence plus the stop codon. The DNA sequence and the translated protein sequence of MTSP3 are shown in SEQ ID Nos. 3 and 4, respectively.

3. Construction of the Expression Vectors

DNA encoding MTSP3 full length protein containing the C310S point mutation (i.e., MTSP3C122S) was cloned from pPIC9K:MTSP3C122S. The primers MTSP3: 5' GAATTC-CATATGCCGCGCTTTAAAGTG-GTGGGTGGGGAGGAGGCC SEQ ID No. 47 (containing a NdeI restriction site) and MTSP3-3' GGGATACCCGTTA-CAGCTCAGCCTTCCAGAC 5' SEQ ID No. 48 (containing a BamHI restriction site) were used to PCR amplify the human MTSP3C122S protease domain utilizing a plasmin recognition sequence (PRFK) for zymogen activation. Amplification was conducted in a total volume of 50 µl containing 10 mM KCl, 20 mM Tris-HCl (pH 8.8 at 25° C.), 10 mM (NH$_4$)$_2$SO$_4$, 2.0 mM MgSO$_4$, 0.1% Triton X-100, 0.3 mM dNTPs, 5.0 units of vent DNA polymerase, and 100 pmol of primers. The reaction mixtures were heated to 95° C. for 5 min, followed by 25-30 cycles of 95, 60, and 75° C. for 30 s each and a final extension at 75° C. for 2 min.

PCR products were purified using a QIAquick PCR purification kit (QIAGEN Inc., Chatsworth, Calif.). Full-length oligonucleotides were doubly digested with 10 units BamHI and 20 units NdeI for 2 h at 37° C. The digested fragments were purified on a 1.3% agarose gel and stained with ethidium bromide. The band containing the MTSP3C122S encoding DNA was excised and purified using a QIAEX II gel extraction kit.

The MTSP3C122S encoding DNA was then cloned into the NdeI and BamHI sites of the pET19b vector (Novagen) using standard methods. This vector allows the fusion of a HIS$_6$ tag for purification by metal affinity chromatography (MAC). Competent XL1 Blue cells (Stratagene) were transformed with the pET19b-MTSP3C122S vector and used to produce plasmid stocks. Proper insertion and DNA sequence were confirmed by fluorescent thermal dye DNA sequencing methods as well as restriction digests.

4. Protein Expression, Purification, and Refolding

Overexpression of the gene product was achieved in E. coli strain BL21 (DE3) (Novagen, Madison Wis.) containing the DNAY plasmid for rare codon optimization (see, e.g., Garcia et al. (1986) Cell 45:453-459). Cells were grown at 37° C. in (2×YT) media supplemented with carbenicillin and kanamycin to a final concentrations of 50 ug/ml and 34 ug/ml, respectively. One liter cultures were inoculated with 10 mL of an overnight culture grown in the same media. Cells were allowed to grow to a density of 0.6-1.0 $OD_{600}$ before the addition of IPTG (final concentration 1.0 mM). Cells were grown an additional 4 hours before harvesting.

The cell pellet was resuspended in 20 mL of lysis buffer (50 mM $Na_2HPO_4$, 300 mM NaCl, pH 7.4). The cell suspension was treated with 10-20 mg lysozyme and incubated at 37° C. for 1 hour. DNaseI was then added (1-2 mg) with mixing until the solution was no longer viscous. The solution was then transferred to a Rosette flask and sonicated, on ice, at high power for 15 min. Inclusion bodies were pelleted by centrifugation at 20K rpm (~48,000 g) at 4° C. for 30 min.

Inclusion bodies were washed by douncing 2 times in 50 mM $Na_2HPO_4$, 300 mM NaCl, 5% LADO, pH 7.4 followed by 2 times in 50 mM $Na_2HPO_4$, 300 mM NaCl, pH 7.4. Inclusion bodies (~500 mg) are solubilized in 25 mL 6 M GuHCl, 100 mM tris-HCl, 20 mM βMe, pH 8.0. This solution was spun at 20K rpm for 30 minutes to pull down any particulate matter. This solution was passed through a 0.2 µM filter and diluted to 100 mL in solubilization buffer.

MTSP3C122S was refolded by slowly adding the inclusion body mixture to 8 L of refolding buffer (100 mM tris-HCl, 150 mM NaCl, 5 mM GSH, 0.05 mM GSSG, 1 M arginine, pH 8.0) using a peristaltic pump. The refolding mixture was allowed to stir at 4° C. for 7 days or until the thiol concentration was below 1 mM as detected by Ellman's reagent. The solution was filtered through a 5 µM filter, concentrated by ultrafiltration and the buffer exchanged into MAC equilibration buffer (50 mM $Na_2HPO_4$, 300 mM NaCl, 10 mM imidazole, pH 8.0) by crossflow filtration. The resulting solution was passed through a 0.2 µM filter and further purified on a FPLC (Amersham-Pharmacia) using Pharmacia chelating sepharose. The solution was loaded onto the nickel loaded MAC at a flow rate of 1.0 mL/min and eluted with a linear gradient of 1.0 mM-1.0 M imidazole in 50 mM $Na_2HPO_4$, 300 mM NaCl, pH 8.0. Protein containing fractions were determined by SDS-PAGE and subsequently pooled and frozen at −80° C.

Small amounts of purified MTSP3C122S were activated using plasmin sepharose for 30 min. at 37° C. The resin was spun down at 14K rpm for 5 min. and the protein solution removed. The resulting solution was screened for activity against of series of protease substrates; spec-tpa, spec-pl, spec-UK, spec-fXIIa (American Diagnostica), S-2238, S-2266 (Kabi Diagnostica), S-2586, S-2366, S-2444, S-2288, S-2251, S-2302, S-2765, S-2222, spec-THE (Chromogenix), spec-fVIIa (Pentapharm). MTSP3C122S cleaved several of these substrates efficiently but was most active towards Spec-fXIIa, Spec-tPA, S-2765, Spec-fVIIa and S-2444.

5. Gene Expression Profile of the Serine Protease MTSP3 in Normal and Tumor Tissues To obtain information regarding the tissue distribution of the MTSP3 transcripts, the DNA insert encoding the MTSP3 protease domain was used to probe a RNA blot composed of 76 different human tissues (catalog number 7775-1; human multiple tissue expression (MTE) array; CLONTECH, Palo Alto, Calif.). The expression pattern observed in decreasing signal level was: trachea=colon (descending) =esophagus>colon (ascending)>colon (transverse) =rectum>ileum>duodenum>jejunum>bladder>ilocecum> stomach>kidney>appendix. It is also expressed less abundantly in fetal kidney, and in two tumor cell lines, HeLa S3 and leukemia, K-562. Northern analysis using RNA blots (catalog numbers 7780-1, 7765-1 & 7782-1; human 12-lane, human muscle and human digestive system multiple tissue northern (MTN) blots; CLONTECH) confirmed that the expression was detected most abundantly in the colon, moderately in the esophagus, small intestine, bladder and kidney, and less abundantly in stomach and rectum. A single transcript of ~2.2 kb was detected.

Amplification of the MTSP3 transcript in several human primary tumors xenografted in mouse was performed using gene-specific primers. The MTSP3 transcript was detected in lung carcinoma (LX-1), colon adenocarcinoma (CX-1), colon adenocarcinoma (GI-112) and ovarian carcinoma (GI-102). No apparent signal was detected in another form of lung carcinoma (GI-117), breast carcinoma (GI-101), pancreatic adenocarcinoma (GI-103) and prostatic adenocarcinoma (PC3).

Example 2

Identification of Genomic Clone of MTSP4

Using the nucleotide sequence encoding the protease domain of the serine protease MTSP1 (also called matriptase), the protein database (SWISSPROT) at the National Center for Biotechnology Information (Bethesda, Md.; <http://www.ncbi.nlm.nih.gov>) was searched for similar or identical sequence to MTSP1 using the search algorithm blastx. The blastx algorithm compares the six-frame conceptual translation products of a nucleotide query sequence (both strands) against a protein sequence database. A protein encoding sequence (CAA18442) that has 37% identity to the MTSP1 protein sequence that was found to include a putative LDL-receptor domain and a trypsin-like serine protease domain was identified. This protein-encoding sequence (hereinafter referred to as MTSP4) was found to be encoded by a genomic clone (AL022314) derived from human chromosome 22 sequenced by the Sanger Centre Chromosome 22 Mapping Group and deposited into the public database as part of the Human Genome Project. Subsequent search of the GenBank database showed that no identical sequence has been deposited. A search of the EST database also did not show any matching human sequence, indicating that no human EST clone exists in the public database. Mouse EST clones (AI391417 and AA208793) are present and showed 88% identity to the serine protease at the nucleotide level.

PCR Cloning of a Genomic DNA Fragment of MTSP4 for Use as Hybridization Probe

In order to obtain tissue distribution profile of MTSP4 as well as to identify a tissue source for subsequent cloning of the cDNA, a genomic fragment was amplified from human genomic DNA using two gene-specific primers, 5'-CCTC-CACGGTGCTGTGGACCGTGTTCC-3' (5' primer) SEQ ID No. 21 and 5'-CCTCGCGCAAGGCGCCCCAGCCCG-3' (3' primer) SEQ ID No. 22. These two primers amplified a 265-base pair fragment within a single exon of MTSP4. The fragment was then used as a hybridization probe on human tissue northern blot (human 12-lane multiple tissue northern (MTN) blot (catalog number 7780-1); CLONTECH, Palo Alto, Calif.). A prominent band (~2.6 kb) was detected in liver. Relatively weaker signals were obtained from the brain, heart, skeletal muscle and kidney. Since human liver showed a very strong signal, this tissue was selected for the amplification of the MTSP4 cDNA.

5'- and 3'-Rapid Amplification of cDNA Ends (RACE)

To obtain a full-length clone encoding MTSP4, 5'- and 3'-RACE reactions were performed. The Marathon-Ready cDNA library from human liver (CLONTECH) was used to isolate the 5' and 3' ends of the cDNA encoding MTSP4. Marathon-Ready cDNA clones are specifically made for RACE reactions. Two gene specific primers were used: 5'-GCGTGGCGTCACCTGGTAGCGATAGACCTCGC-3' (SEQ ID No. 23) for 5'-RACE reaction and 5'-CCTCCACG-GTGCTGTGGACCGTGTTCC-3' (SEQ ID No. 24) for 3'-RACE reaction. No fragment was obtained from the initial 5'-RACE reaction.

The 3'-RACE reaction, however, produced a ~1.5 kbp fragment. A nested PCR reaction was used on the initial 5'-RACE reaction products to obtain part of the 5' end of MTSP4. The nested 5' gene-specific primer used was 5'-CCTCGCG-CAAGGCGCCCCAGCCCG-3' (SEQ ID No. 25) and produced a ~0.8 kbp fragment. The fragments were subcloned into pCR2.1-TOPO TA cloning vector (Invitrogen, Carlsbad, Calif.). The resulting clones were analyzed by Southern analysis using the internal genomic fragment encompassing the primers used in the RACE reactions as probe and by DNA sequence analysis. Sequence analysis of the 5'-RACE product showed that the potential initiation codon was still missing.

To obtain the 5' cDNA end that encodes the N terminus of MTSP4, the publicly available genomic sequence of chromosome 22 was searched for sequence corresponding to the sequence obtained in the 5'-RACE clone. The resulting genomic sequence was translated and the protein sequence was compared to that derived from the translated sequence of the 5'-RACE clone. After determining the overlapping sequences, a gene-specific oligonucleotide primer (5'-TCATCGGCCAGAGGGTGATCAGTGAG-3') SEQ ID No. 26 corresponding to the sequence upstream of the potential initiation codon and another gene-specific oligonucleotide primer (5'-CCTCCTCAGTGCATAGGCATCAAACCAG-3') SEQ ID No. 27 corresponding to a sequence within the overlapping region were used to amplify the missing 5' cDNA of MTSP4 from the human liver cDNA library.

Splice Variants and Domain Organization of MTSP4

At least two cDNA fragments were consistently obtained during PCR amplification, indicating multiple splice variants of MTSP4. Subcloning and sequence analysis revealed that a longer, more abundant form, MTSP4-L and a shorter form, MTSP4-S. The encoded proteins are multi-domain, type II membrane-type serine proteases and include a transmembrane domain at the N terminus followed by a CUB domain, 3 LDLR domains and a trypsin-like serine protease domain at the C terminus. The difference between these two forms of MTSP4 is the absence in MTSP4-S of a 432-bp nucleotide sequence between the transmembrane and the CUB domains (see FIG. 2).

PCR Amplification of cDNA Encoding Full-Length Protease Domain of MTSP4

To obtain a cDNA fragment encoding the protease domain of MTSP4, an end-to-end PCR amplification using gene-specific primers and the Marathon-Ready cDNA library from human liver was used. The two primers used were: 5'-TCTCTCGAGAAAAGAATTGTTGGTG-GAGCTGTGTCCTCCGAG-3' (SEQ ID No. 28) for the 5' end and 5'-AGGTGGGCCTTGCTTTG-CAGGGGGGCAGTTC-3' for the 3' end SEQ ID NO. 29).

The 5' primer contained the sequence that encodes the start of the MTSP4 protease domain (IVGGAVSSE). The 3' primer corresponds to the sequence just downstream of the stop codon. A ~740-bp fragment was amplified, subcloned into pCR2.1-TOPO TA cloning vector and sequenced.

Gene Expression Profile of MTSP4 in Normal and Tumor Tissues

To obtain information regarding the gene expression profile of the MTSP4 transcript, a DNA fragment encoding part of the LDL receptor domain and the protease domain was used to probe an RNA blot composed of 76 different human tissues (catalog number 7775-1; human multiple tissue expression (MTE) array; CLONTECH). As in the northern analysis of gel blot, a very strong signal was observed in the liver. Signals in other tissues were observed in (decreasing signal level): fetal liver>heart=kidney=adrenal gland=testis=fetal heart and kidney=skeletal muscle=bladder=placenta>brain=spinal cord=colon=stomach=spleen=lymph node=bone marrow=trachea=uterus=pancreas=salivary gland=mammary gland=lung. MTSP4 is also expressed less abundantly in several tumor cell lines including HeLa S3=leukemia K-562=Burkitt's lymphomas (Raji and Daudi) =colorectal adenocarcinoma (SW480)>lung carcinoma (A549)=leukemia MOLT-4=leukemia HL-60. PCR of the MTSP4 transcript from cDNA libraries made from several human primary tumors xenografted in nude mice (human tumor multiple tissue cDNA panel, catalog number K1522-1, CLONTECH) was performed using MTSP4-specific primers. The MTSP4 transcript was detected in breast carcinoma (GI-101), lung carcinoma (LX-1), colon adenocarcinoma (GI-112) and pancreatic adenocarcinoma (GI-103). No apparent signal was detected in another form of lung carcinoma (GI-117), colon adenocarcinoma (CX-1), ovarian carcinoma (GI-102). and prostatic adenocarcinoma (PC3). The MTSP4 transcript was also detected in LNCaP and PC-3 prostate cancer cell lines as well as in HT-1080 human fibrosarcoma cell line.

Sequence Analysis

MTSP4 DNA and protein sequences were analyzed using MacVector (version 6.5; Oxford Molecular Ltd., Madison, Wis.). The ORF of MTSP4-L includes 2,409 bp, which translate to a 802-amino acid protein, while the ORF of MTSP4-S is composed of 1,977 by which translate to a 658-amino acid protein. The cDNA encoding the protease domain in both forms is composed of 708 by which translate to a 235-amino acid protein sequence (see, SEQ ID No. 6) The DNA sequences and the translated protein sequences of MTSP4-L and MTSP4-S, and of the protease domain of MTSP4 are set forth in SEQ ID Nos. 8, 10 and 6, respectively.

Example 3

Cloning of MTSP6

Identification of Genomic Clone of MTSP6

Using the protein sequence of the protease domain of the serine protease MTSP4 (see EXAMPLE 2), the non-redundant database (all non-redundant GenBank CDS translations+PDB+SwissProt+PIR+PRF) at the National Center for Biotechnology Information (Bethesda, Md.; <http://www.ncbi.nlm.nih.gov>) was searched for sequences that were similar or identical to MTSP4 using the search algorithm tblastn. The tblastn algorithm compares a protein query sequence against a nucleotide sequence database dynamically translated in all reading frames. A protein (55 amino acids), which has 60% identity with the query MTSP4 sequence (55 amino acids), was obtained from the translation of genomic sequence of AC015555 (nucleotide #15553 to 15717). This protein hereafter is referred to as MTSP6. Subsequent search of the GenBank database showed that no cDNA encoding MTSP6 has been deposited.

The gene exhibiting highest homology to MTSP6 was human transmembrane serine protease 2 (GenBank accession number U75329; Swissprot accession number O15393), which showed 66% identity to MTSP6 within the 45 amino acid regions compared. Consequently, the nucleotide sequence encoding the MTSP6 protease domain was obtained by comparing the protein sequence of human transmembrane serine protease 2 protease domain with the nucleotide sequence of AC015555 translated in six reading frames. The protein sequence obtained from the translated nucleotide sequence of MTSP6 revealed an overall 50% identity with human transmembrane serine protease 2. A search of the EST database indicated the presence of seven MTSP6 EST clones (AA883068, AW591433, AI978874, AI469095, AI935487, AA534591 and AI758271).

Cloning of Human MTSP6 Full-Length cDNA

To obtain cDNA encoding the region of the MTSP6 protease domain identified by database searches described above, two gene-specific primers, Ch17-NSP-1, 5'-TCACG-CATCGTGGGTGGAACATGTCC-3' (5' primer) SEQ ID NO. 30 nd Ch17-NSP-2AS, 5'-ACCCACCTCCATCT-GCTCGTGGATCC-3' SEQ ID NO. 31 (3' primer), were used for PCR. These two primers amplified a 708-base pair fragment from human mammary gland carcinoma cDNA (Clontech Marathon-Ready cDNA, Cat. No. 7493-1).

To obtain the remaining, unknown cDNA of MTSP6, 5'- and 3'-RACE reactions were performed on the human mammary gland carcinoma. Marathon-Ready cDNA is specifically made for RACE reactions. The first RACE reactions were performed by PCR using Marathon cDNA adaptor primer 1 (AP1) with gene specific primers, Ch17-NSP-2AS, 5'-ACCCACCTCCATCTGCTCGTGGATCC-3' SEQ ID NO. 31 for 5'-RACE reaction and Ch17-NSP-1, 5'-TCACG-CATCGTGGGTGGAACATGTCC-3' SEQ ID NO. 30 for 3'-RACE reaction. The PCR products were purified from agarose gel. A second nested PCR was then performed using Marathon cDNA adaptor primer 2 (AP2) with gene specific primer Ch17-NSP-3AS, 5'-CCACAGCCTCCTCTCTTGA-CACACCAG-3' SEQ ID No. 32 for 5'-RACE reaction (using first 5'-RACE product as template) and Ch17-NSP-3 5'-ACGCCCTGTGGATCATCACTGCTGC-3' SEQ ID No. 33 for 3'-RACE reaction (using first 3'-RACE product as template). First 5'- and 3'-RACE products were also used as template for PCR reactions using primers Ch17-NSP-3 and Ch17-NSP-4AS to obtain a cDNA fragment for use as a probe. PCR products from RACE reactions which were larger than 700 by were cut out and purified from agarose gel and subcloned into pCR2.1-TOPO cloning vector (Invitrogen, Carlsbad, Calif.). Colony hybridization was then performed to identify positive colonies containing MTSP6 sequence. Positive clones were identified by colony hybridization using the 495 by DNA fragment obtained from PCR reaction (with primers Ch17-NSP-3 and Ch17-NSP-4AS) and by DNA sequencing.

Sequence analysis of the 5'-RACE products indicated that an additional 420 by of upstream sequence were obtained. The potential initial codon was not present in the 5'-RACE sequence. Another round of nested 5'-RACE reaction was performed using AP2 and a gene specific primer (designed based on the new RACE sequence) Ch17-NSP-5AS 5'-TC-CCTCCCTCACATATACTGAGTGGTG-3' SEQ ID No. 34, using the PCR products obtained from the first 5'-RACE as template. A PCR product of 367 by using Ch17-NSP-6 5'-CGACTGCTCAGGGAAGTCAGATGTCG-3' SEQ ID NO. 35 (designed based on the new 5'-RACE sequence) and Ch17-NSP-5AS was used to identify the positive clones. An additional sequence of 480 by was obtained from the second 5'-RACE products. A potential ATG start codon was observed within a sequence of GTCACCATGG (nucleotides 262-272 of SEQ ID No. 12, which appears to be a Kozak sequence (GCC (A/G) CCAUGG), indicating that this ATG is likely the initiation codon for MTSP6.

The 3'-RACE reaction to obtain the rest of the 3' end of MTSP6 was not successful using Marathon Ready human mammary gland carcinoma cDNA. The sequence of the 3'-RACE products obtained was exclusively that of an MTSP6 cDNA truncated with the Marathon AP2 primer sequence within the coding region.

The 3'-end sequence of MTSP6 was obtained by PCR using Ch17-NSP-3 (5'-ACGCCCCTGTGGATCATCACT-GCTGC-3'; SEQ ID NO. 33) and Ch17-NSP-4 (5'-CTGGT-GTGTCAAGAGAGGAGGCTGTGG-3'; SEQ ID NO. 37) with an antisense primer Ch17-NSP-7AS (5'-ACTCAG-GTGGCTACTTATCCCCTTCCTC-3; SEQ ID NO. 38) designed based on the sequence of an EST clone AA883068, which apparently covers the 3'-end of MTSP6 sequence, and human small intestine cDNA (Clontech) as template. Two PCR products (650 by and 182 bp, respectively) were obtained and DNA sequence analysis indicated that both PCR products contained a stop codon.

Sequence Analysis and Domain Organization of MTSP6

The MTSP6 DNA and protein sequences were analyzed using DNA Strider (version 1.2). The ORF of MTSP6 is composed of 1,362 bp, which translate into a 453-amino acid protein. Protein sequence analysis using the SMART (Simple Modular Architecture Research Tool) program at http://smart.embl-heidelberg.de predicts that MTSP6 is a multi-domain, type-II membrane-type serine protease containing of a transmembrane domain (amino acids 48-68) at the N terminus followed by a LDLRa domain (LDL receptor domain class a) (amino acids 72-108), a SR domain (Scavenger receptor Cys-rich domain)(amino acids 109-205), and a trypsin-like serine protease domain (amino acids 216-443) (see FIG. 3).

Gene Expression Profile of MTSP6 in Normal and Tumor Tissues

To obtain information regarding the gene expression profile of the MTSP6 transcript, a 495 by DNA fragment obtained from PCR reaction with primers Ch17-NSP-3 and NSP-4AS was used to probe an RNA blot composed of 76 different human tissues (catalog number 7775-1; human multiple tissue expression (MTE) array; CLONTECH). The strongest signal was observed in duodenum. Signal in other tissues were observed in (decreased signal level): Stomach>trachea=mammary gland=thyroid gland=salivary gland=pituitary gland=pancreas>kidney>lung>jejunum=ileum=ilocecum= appendix=fetal kidney>fetal lung. Very weak signals can also be detected in several other tissues. MTSP6 is also expressed in several tumor cell lines including HeLa S3>colorectal adenocarcinoma (SW480)>leukemia MOLT-4>leukemia K-562. PCR analysis of the MTSP6 transcript from cDNA libraries made from several human primary tumors xenografted in nude mice (human tumor multiple tissue cDNA panel, catalog number K1522-1, CLONTECH) was performed using MTSP6-specific primers (Ch17-NSP-3 and Ch17-NSP2AS). The MTSP6 transcript was strongly detected in lung carcinoma (LX-1), moderately detected in pancreatic adenocarcinoma (GI-103), weakly detected in ovarian carcinoma (GI-102); and very weakly detected in colon adenocarcinoma (GI-112 and CX-1), breast carcinoma (GI-101), lung carcinoma (GI-117) and prostatic adenocarcinoma (PC3). The MTSP6 transcript was also detected in breast cancer cell line MDA-MB-231, prostate cancer cell line PC-3, but not in HT-1080 human fibrosarcoma cell line. MTSP6 is also expressed in mammary gland carcinoma cDNA (Clontech).

Example 4

Expression of the Protease MTSP Domains

The DNA encoding each of the MTSP 3 and 4 protease domains was cloned into a derivative of the *Pichia pastoris* vector pPIC9K (available from Invitrogen; see SEQ ID NO. 45). Plasmid pPIC9k features include the 5' AOX1 promoter fragment at 1-948; 5' AOX1 primer site at 855-875; alpha-factor secretion signal(s) at 949-1218; alpha-factor primer site at 1152-1172; multiple cloning site at 1192-1241; 3' AOX1 primer site at 1327-1347; 3' AOX1 transcription termination region at 1253-1586; HIS4 ORF at 4514-1980; kanamycin resistance gene at 5743-4928; 3' AOX1 fragment at 6122-6879; ColE1 origin at 7961-7288; and the ampicillin resistance gene at 8966-8106. The plasmid used herein is derived from pPIC9K by eliminating the XhoI site in the kanamycin resistance gene and the resulting vector is herein designated pPIC9KX.

Primers Used for PCR Amplification of Protease Domain and Subcloning into the XhoI/NotI Sites of *Pichia* Vector MTSP3

```
5' primer (with XhoI site [underlined])
                                    SEQ ID No. 39
5' TCTCTCGAGAAAAGAGTGGTGGGTGGGGAGGAGGCCTCTGTG 3'

3' primer (with NotI site [underlined])
                                    SEQ ID No. 40
5' ATTCGCGGCCGCATTACAGCTCAGCCTTCCAGAC 3'
```

MTSP4-S and MTSP4-L

```
5' primer (with XhoI site [underlined])
                                    SEQ ID No. 41
5' TCTCTCGAGAAAAGAATTGTTGGTGGAGCTGTGTCCTCCGAG 3' primer with NotI site
                                    SEQ ID No. 42
5' ATTCGCGGCCGCTCAGGTCACCACTTGCTGGATCCAG 3'
```

MTSP6

MTSP6 was cloned into the *E. coli* TOPO vector (pcR® 2.1 TOPO™, SEQ ID No. 46, Invitrogen, Carlsbad, Calif.; the TOPO® TA Cloning® Kit is designed form cloning Taq-amplified PRCR products).

```
5' primer (with XhoI site [underlined])
                                    SEQ ID No. 43
5' CTCGAGAAACGCATCGTGGGTGGAAACATGTCCTTG 3'

3' primer NotI site comes from E. coli TOPO
vector:
                                    SEQ ID No. 44
5' ACTCAGGTGGCTACTTATCCCCTTCCTC 3'
```

Example 5

Assays for Identification of Candidate Compounds that Modulate that Activity of an MTSP Assay for Identifying Inhibitors The ability of test compounds to act as inhibitors of catalytic activity of an MTSP, including MTSP1, MTSP3, MTSP4, MTSP6 can be assessed in an amidolytic assay. The inhibitor-induced inhibition of amidolytic activity by a recombinant MTSP or the protease domain portions thereof, can be measured by IC50 values in such an assay.

An exemplary assay buffer is HBSA (10 mM Hepes, 150 mM sodium chloride, pH 7.4, 0.1% bovine serum albumin). All reagents were from Sigma Chemical Co. (St. Louis, Mo.), unless otherwise indicated. Two IC50 assays at 30-minute (a 30-minute preincubation of test compound and enzyme) and at 0-minutes (no preincubation of test compound and enzyme) are conducted. For the IC50 assay at 30-minute, the following reagents are combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the MTSP or protease domain thereof diluted in buffer, yielding a final enzyme concentration of about 100-500 pM. Following a 30-minute incubation at ambient temperature, the assay is initiated by the addition of 50 microliters of a substrate for the particular MTSP (see, e.g., table and discussion below) and reconstituted in deionized water, followed by dilution in HBSA prior to the assay) were added to the wells, yielding a final volume of 200 microliters and a final substrate concentration of 300 μM (about 1.5-times Kin).

For an 1050 assay at 0-minute, the same reagents are combined: 50 microliters of HBSA, 50 microliters of the test compound, diluted (covering the identical concentration range) in HBSA (or HBSA alone for uninhibited velocity measurement), and 50 microliters of the substrate, such as a chromogenic substrate. The assay is initiated by the addition of 50 microliters of MTSP. The final concentrations of all components are identical in both 1050 assays (at 30- and 0-minute incubations).

The initial velocity of the substrate hydrolysis is measured in both assays by, for example for a chromogenic substrate, as the change of absorbance at a particular wavelength, using a Thermo Max Kinetic Microplate Reader (Molecular Devices) over a 5 minute period, in which less than 5% of the added substrate was used. The concentration of added inhibitor, which caused a 50% decrease in the initial rate of hydrolysis was defined as the respective 1050 value in each of the two assays (30- and 0-minute).

Another Assay for Identifying Inhibitors

Test compounds for inhibition of the protease activity of the protease domain of is assayed in Costar 96 well tissue culture plates (Corning N.Y.). Approximately 2-3 nM the MTSP or protease domain thereof is mixed with varying concentrations of inhibitor in 29.2 mM Tris, pH 8.4, 29.2 mM imidazole, 217 mM NaCl (100 mL final volume), and allowed to incubate at room temperature for 30 minutes. 400 mM substrate is added, and the reaction monitored in a SpectraMAX Plus microplate reader (Molecular Devices, Sunnyvale Calif.) by following the change in a parameter correlated with hydrolysis, such as absorbance for a chromogenic substrate for 1 hour at 37° C.

Assay for Screening MTSP6

The protease domain of MTSP6 expressed in *Pichia pastoris* is assayed for inhibition by various compounds in Costar 96 well tissue culture plates (Corning N.Y.). Approximately 1-20 nM MTSP6 is mixed with varying concentrations of inhibitor in 29.2 mM Tris, pH 8.4, 29.2 mM Imidazole, 217 mM NaCl (100 µL final volume), and allowed to incubate at room temperature for 30 minutes. 500 µM substrate Spectrozyme t-PA (American Diagnostica, Greenwich, Conn.) is added, and the reaction is monitored in a SpectraMAX Plus microplate reader (Molecular Devices, Sunnyvale Calif.) by measuring the change in absorbance at 405 nm for 30 minutes at 37° C.

Identification of Substrates

Particular substrates for use in the assays can be identified empirically by testing substrates. The following list of substrates are exemplary of those that can be tested.

| Substrate name | Structure |
|---|---|
| S 2366 | pyroGlu-Pro-Arg-pNA•HCl |
| spectrozyme t-PA | $CH_3SO_2$-D-HHT-Gly-Arg-pNA•AcOH |
| N-p-tosyl-Gly-Pro-Arg-pNA | N-p-tosyl-Gly-Pro-Arg-pNA |
| Benzoyl-Val-Gly-Arg-pNA | Benzoyl-Val-Gly-Arg-pNA |
| Pefachrome t-PA | $CH_3SO_2$-D-HHT-Gly-Arg-pNA |
| S 2765 | N-α-Z-D-Arg-Gly-Arg-pNA•2HCl |
| S 2444 | pyroGlu-Gly-Arg-pNA•HCl |
| S 2288 | H-D-Ile-Pro-Arg-pNA•2HCl |
| spectrozyme UK | Cbo-L-(γ)Glu(α-t-BuO)-Gly-Arg-pNA•2AcOH |
| S 2302 | H-D-Pro-Phe-Arg-pNA•2HCl |
| S 2266 | H-D-Val-Leu-Arg-pNA•2HCl |
| S 2222 | Bz-Ile-Glu(g-OR)-Gly-Arg-pNA•HCl R = H(50%) and R = $CH_3$(50%) |
| Chromozyme PK | Benzoyl-Pro-Phe-Arg-pNA |
| S 2238 | H-D-Phe-Pip-Arg-pNA•2HCl |
| S 2251 | H-D-Val-Leu-Lys-pNA•2HCl |
| Spectrozyme Pl | H-D-Nle-HHT-Lys-pNA•2AcOH |
| | Pyr-Arg-Thr-Lys-Arg-AMC |
| | H-Arg-Gln-Arg-Arg-AMC |
| | Boc-Gln-Gly-Arg-AMC |
| | Z-Arg-Arg-AMC |
| Spectrozyme THE | H-D-HHT-Ala-Arg-pNA•2AcOH |
| Spectrozyme fXIIa | H-D-CHT-Gly-Arg-pNA•2AcOH |
| | CVS 2081-6 ($MeSO_2$-dPhe-Pro-Arg-pNA) |
| | Pefachrome fVIIa ($CH_3SO_2$-D-CHA-But-Arg-pNA) | pNA = para-nitranilide (chromogenic)
AMC = amino methyl coumarin (fluorescent)

If none of the above substrates are cleaved, a coupled assay, described above, can be used. Briefly, test the ability of the protease to activate and enzyme, such as plasminogen and trypsinogen. To perform these assays, the single chain protease is incubated with a zymogen, such as plasminogen or trypsinogen, in the presence of the a known substrate, such, lys-plasminogen, for the zymogen. If the single chain activates the zymogen, the activated enzyme, such as plasmin and trypsin, will degrade the substrate therefor.

Example 6

Isolation and Cloning of Matriptase

A. Cell Type and Growth of Cells

Human prostate adenocarcinoma cell line, PC-3, was purchased from ATCC (catalog number CRL-1435; Manassas, Va.). The cells were cultured at 37° C., 5% $CO_2$ in Ham's F-12K growth medium (catalog number 9077; Irvine) supplemented with 2 mM L-glutamine and 10% fetal bovine serum. All subsequent cell manipulations were carried out according to the manufacturer's instructions. PC-3 cells were allowed to grow to about 90% confluence, and were then washed briefly with 1× phosphate buffered saline.

B. Isolation of Total RNA, and Purification and Enrichment of polyA+ RNA

PC-3 cells were lysed in Trizol reagent (catalog number 15596; Life Technologies, Rockville, Md.) and total RNA was isolated according to the manufacturer's protocol. The concentration of total RNA was estimated from absorbance reading at 260 nm. PolyA$^+$ RNA was purified and enriched using oligo-dT beads (catalog number 70061; Oligotex, Qiagen, Valencia, Calif.).

C. Reverse-Transcription and Polymerase Chain Reaction (PCR)

PC-3-derived polyA$^+$ RNA was converted to single-stranded cDNA (sscDNA) by reverse transcription using ProSTAR first-strand RT-PCR kit (catalog number 200420; Stratagene, La Jolla, Calif.) and SuperScript II RNase H-reverse transcriptase (catalog number 18064-022; Life Technologies). After reverse transcription, an aliquot of PC-3 sscDNA (4 µL) was subjected to PCR using 2 mM each of the sense and anti-sense degenerate oligonucleotide primers and Taq polymerase (catalog number 201203; Qiagen). Total reaction volume was 100 µL. The sequence of the sense primer was 5'TGGRT(I)VT(I)WS(I)GC(I)RC(I)CAYTG-3' (SEQ ID No. 13) and that of the anti-sense was 5'(I)GG(I)CC(I)CC(I)SWRTC(I)CCYT(I)RCA(I)GHRTC-3' (SEQ ID No. 14), where R=A,G; V=G,A,C; W=A,T; S=G,C; Y=C,T; H=A,T,C. The primer sequences correspond to two highly conserved regions in all chymotrypsin-like serine proteases and amplify PCR products ranging from approximately 400 to 500 base pairs.

D. Clone Screening and Sequencing

The PCR products were separated on a 2% agarose gel and purified using a gel extraction kit (catalog number 28706; QIAquick gel extraction kit; Qiagen). The purified DNA fragments were ligated into pCR2.1-TOPO (catalog number K4500-01; Invitrogen, Carlsbad, Calif.). After transformation into *E. coli* cells, plasmid DNA was isolated and analyzed by digestion with EcoRI restriction enzyme. Clones that had inserted nucleic acid were further characterized by sequencing using a fluorescent dye-based DNA sequencing method (catalog number 4303149; BigDye terminator cycle sequencing kit with AmpliTaq DNA polymerase; Perkin Elmer, Lincoln, Calif.). A total of 31 clones were sequenced and analyzed. All sequences were analyzed by a multiple nucleotide sequence alignment algorithm (blastn) (www.ncbi.nlm.nih.gov/blast) to identify identical or closely related DNA deposited in GenBank (NCBI, Bethesda, Md.). Those that did not show significant homology were further analyzed using blastx, which compares the six-frame conceptual translation products of a nucleotide sequence (both strands) against a protein sequence database (SwissProt). Eight clones yielded identical cDNA fragments that encode MTSP1. MTSP1 was subsequently found to be identical to matriptase (GenBank accession number AF 118224).

E. Rapid Amplification of cDNA Ends (RACE) and Gene-Specific Amplification of MTSP1

To obtain DNA encoding the complete protease domain of MTSP1, RACE and gene-specific amplification reactions were performed. A human prostate Marathon-Ready cDNA (catalog #7418-1; Clontech) was used to isolate part of the cDNA encoding MTSP1. Marathon-Ready cDNA is prepared to contain a known hybridization sequence at the 5' and 3' ends of the sscDNA. The 3' region of MTSP1 cDNA was obtained by a 3'-RACE reaction using a gene specific primer, 5'-CACCCCTTCTTCAATGACTTCACCTTCG-3' (SEQ ID No. 55). The 5' end of the MTSP 1 protease domain was obtained by gene-specific amplification reaction using two MTSP1-specific primers, 5'-TACCTCTCCTACGACTCC-3' (SEQ ID No. 56) for the sense primer and 5'-GAGGT-TCTCGCAGGTGGTCTGGTTG-3' (SEQ ID No. 57) for the antisense primer. The sequences for these two primers were obtained from the human SNC19 mRNA sequence. The 3'-RACE reaction and gene-specific PCR produced DNA fragments that were >1 kbp in size. These fragments were subcloned into pCR2.1-TOPO (Invitrogen, San Diego, Calif.). After transformation into *E. coli* cells, plasmid DNA was isolated and analyzed by digestion with EcoRI restriction enzyme. Clones that had inserts were characterized by Southern blot analysis (using the internal cDNA fragment as probe) and by DNA sequence analysis.

F. PCR Amplification of cDNA Encoding the Protease Domain of MTSP1

To obtain a cDNA fragment encoding the entire protease domain of MTSP 1, an end-to-end PCR amplification using gene-specific primers was used. The two primers used were: 5'-CTCGAGAAAAGAGTTGTTGGGGGCACG-GATGCGGATGAG-3' (SEQ ID No. 58) for the 5' end and 5'-GCGGCCGCACTATACCCCAGTGT-TCTCTTTGATCCA-3' (SEQ ID No. 36 for the 3' end. The 5' primer contained the sequence that encodes the start of the MTSP1 protease domain (VVGGTDADE) (SEQ. ID. NO. 10). The 3' primer contained the stop codon of MTSP 1. A ~800-bp fragment was amplified, purified and subcloned into the *Pichia pastoris* expression vector, pPIC9K, resulting in pPIC9K-MTSP 1.

G. Gene Expression Profile of MTSP1 in Normal Tissues, Cancer Cells and Cancer Tissues To obtain information regarding the tissue distribution and gene expression level of MTSP1, the DNA insert from pPIC9K-MTSP1 was used to probe a blot containing RNA from 76 different human tissues (catalog number 7775-1; human multiple tissue expression (MTE) array; CLON-TECH, Palo Alto, Calif.). Significant expression was observed in the colon (ascending, transverse and descending), rectum, trachea, esophagus and duodenum. Moderate expression levels were observed in the jejunum, ileum, ilocecum, stomach, prostate, pituitary gland, appendix, kidney, lung, placenta, pancreas, thyroid gland, salivary gland, mammary gland, fetal kidney, and fetal lung. Lower expression levels were seen in the spleen, thymus, peripheral blood leukocyte, lymph node, bone marrow, bladder, uterus, liver, adrenal gland, fetal heart, fetal liver, fetal spleen, and fetal thymus. A significant amount of the MTSP1 transcript was also detected in colorectal adenocarcinoma cell line (SW480), Burkitt's lymphoma cell line (Daudi), and leukemia cell line (HL-60). RT-PCR of the MTSP1 transcript in several human primary tumors xenografted in athymic nude mice was performed using gene-specific primers. A high level of MTSP1 transcript was detected in colon adenocarcinoma (CX-1) and pancreatic adenocarcinoma (GI-103). Moderate levels were observed in another colon adenocarcinoma (GI-112), ovarian carcinoma (GI-102), lung carcinoma (LX-1), and breast carcinoma (GI-101). Another lung carcinoma (GI-117) expressed a low level of the MTSP1 transcript. A similar RT-PCR was performed to detect the presence of the MTSP1 transcript in PC-3 and LNCaP cell lines. Both cell lines expressed significant amounts of MTSP1 transcript.

H. Sequence Analysis

All derived DNA and protein sequences were analyzed using MacVector (version 6.5; Oxford Molecular Ltd., Madison, Wis.). The cDNA encoding the protease domain of MTSP1 is composed of 726 base pairs which translate into a 241-amino acid protein sequence (rMAP) (see SEQ ID No. 1, 2, 49 and 50).

Example 7

Production of Recombinant Serine Protease Domain of Matriptase or MTSP1 (rMAP)

A. Fermentation

The production of multi-milligram amounts of rMAP was carried out by fermentation in a BioFlo 3000 fermentor (New Brunswick Scientific, N.J.) equipped with a 3.3 L capacity bioreactor using a SMD1168/pPIC9K:MTSP1 Sac SC1 clone. ZA001 complex media (10 g/L yeast extract, 20 g/L peptone, 40 g/L glycerol, 5 g/L ammonium sulfate, 0.2 g/L calcium sulfate dihydrate, 2 g/L magnesium sulfate heptahydrate, 2 g/L potassium sulfate, 25 g/L sodium hexametaphosphate, 4.35 ml/L PTM1) was inoculated with 100 ml of an overnight culture of the *P. pastoris* transformant. The culture was supplemented with 50% glycerol by fed-batch phase and induced for 18-24 hours with methanol controlled at 0.025%.

B. Purification of Recombinant Serine Protease Domain of Matriptase or MTSP1 (rMAP)

The rMAP was secreted into the culture medium, so the first step of the purification involved the removal of cells and cell debris by centrifugation at 5000 g for 30 minutes. The resulting supernatant was decanted, adjusted to pH 8.0 with 10 N NaOH, and filtered through a SartoBran 300 0.45+0.2 μM capsule. This supernatant was concentrated to 1 L by ultrafiltration using a 10 kDa ultrafiltration cartridge (NC SRT UF system with AG/Technologies UFP-10-C-5A filter), and the buffer was exchanged by crossflow filtration into 50 mM tris-HCl, 50 mM NaCl, 0.05% tween-80, pH 8.0 (buffer A). The filtration unit was rinsed once with 1 L buffer A which was combined with the concentrate.

The concentrated rMAP-containing solution was passed over a 150 ml benzamidine column that had been equilibrated with buffer A, at a flow rate of 8 ml/min. The column was washed with 3 column volumes of 50 mM tris-HCl, 1.0 M NaCl, 0.05% tween-80, pH 8.0 (buffer B) and eluted with 3 column volumes of 50 mM tris-HCl, 1.0 M L-arginine, 0.05% tween-80, pH 8.0 (buffer C). Fractions containing rMAP were identified by activity assay and pooled. This pooled material was concentrated to 10 ml using a JumboSep concentrator (Pall Gelman) and a 10 kDa cutoff membrane. Once concentrated to 10 ml, the buffer was exchanged into 50 mM $Na_2HPO_4$, 125 mM NaCl, pH 5.5 (buffer D) and the volume adjusted to 5-10 ml. The retentate was removed and the concentrator washed with buffer D which was added to the concentrate. The total sample volume was adjusted 15 ml.

The partially purified rMAP was passed through a 5 ml Q-sepharose Fast Flow HiTrap column (Amersham-Pharmacia Biotech) pre-equilibrated with 15 ml of buffer D. The flow through was collected. The HiTrap column was washed with an additional 10 ml of buffer D. Both flow throughs were pooled, and the protein concentration was determined by measurement of $OD_{280}$ (using an extinction coefficient of 2.012 mg/$OD_{280}$). Purified rMAP was then deglycosylated by the addition 0.1 μl of Endoglycosidase H (ProZyme, 5 U/ml) per mg of protein and incubating overnight at 4° C. with gentle swirling.

The conductivity of the deglycosylated pool was adjusted to 2.0-3.0 mS/cm with Nanopure $H_2O$ and the pH adjusted to 6.5 (~200-300 mL final volume). The rMAP was then further purified by anion exchange chromatography by loading directly onto a Pharmacia Akta Explorer system using a 7 mL Source 15Q anion exchange column (Amersham-Pharmacia Biotech). The protein was eluted in a buffer containing 50 mM HEPES, pH 6.5 with a 0-0.33 M NaCl gradient over 10 column volumes at a flow rate of 6 ml/min. Fractions containing protein were pooled, and benzamidine was added to a final concentration of 10 mM. Protein purity was examined by SDS-PAGE and protein concentration determined by measurement of $OD_{280}$ and use of a theoretical extinction coefficient of 2.012 mg/$OD_{280}$.

Example 8

Assays

Amidolytic Assay for Determining Inhibition of Serine Protease Activity of Matriptase or MTSP1

The ability of test compounds to act as inhibitors of rMAP catalytic activity was assessed by determining the inhibitor-induced inhibition of amidolytic activity by the MAP, as measured by $IC_{50}$ values. The assay buffer was HBSA (10 mM Hepes, 150 mM sodium chloride, pH 7.4, 0.1% bovine serum albumin). All reagents were from Sigma Chemical Co. (St. Louis, Mo.), unless otherwise indicated.

Two $IC_{50}$ assays (a) one at either 30-minutes or 60-minutes (a 30-minute or a 60-minute preincubation of test compound and enzyme) and (b) one at 0-minutes (no preincubation of test compound and enzyme) were conducted. For the $IC_{50}$ assay at either 30-minutes or 60-minutes, the following reagents were combined in appropriate wells of a Corning microtiter plate: 50 microliters of HBSA, 50 microliters of the test compound, diluted (covering a broad concentration range) in HBSA (or HBSA alone for uninhibited velocity measurement), and 50 microliters of the rMAP (Corvas International) diluted in buffer, yielding a final enzyme concentration of 250 pM as determined by active site filtration. Following either a 30-minute or a 60-minute incubation at ambient temperature, the assay was initiated by the addition of 50 microliters of the substrate S-2765 (N-α-Benzyloxy-carbonyl-D-arginyl-L-glycyl-L-arginine-p-nitroaniline dihydrochloride; DiaPharma Group, Inc.; Franklin, Ohio) to each well, yielding a final assay volume of 200 microliters and a final substrate concentration of 100 µM (about 4-times $K_m$). Before addition to the assay mixture, S-2765 was reconstituted in deionized water and diluted in HBSA. For the $IC_{50}$ assay at 0 minutes; the same reagents were combined: 50 microliters of HBSA, 50 microliters of the test compound, diluted (covering the identical concentration range) in HBSA (or HBSA alone for uninhibited velocity measurement), and 50 microliters of the substrate S-2765. The assay was initiated by the addition of 50 microliters of rMAP. The final concentrations of all components were identical in both $IC_{50}$ assays (at 30- or 60- and 0-minute).

The initial velocity of chromogenic substrate hydrolysis was measured in both assays by the change of absorbance at 405 nM using a Thermo Max® Kinetic Microplate Reader (Molecular Devices) over a 5 minute period, in which less than 5% of the added substrate was used. The concentration of added inhibitor, which caused a 50% decrease in the initial rate of hydrolysis was defined as the respective $IC_{50}$ value in each of the two assays (30- or 60-minutes and 0-minute).

In vitro Enzyme Assays for Specificity Determination

The ability of compounds to act as a selective inhibitor of matriptase activity was assessed by determining the concentration of test compound that inhibits the activity of matriptase by 50%, ($IC_{50}$) as described in the above Example, and comparing $IC_{50}$ value for matriptase to that determined for all or some of the following serine proteases: thrombin, recombinant tissue plasminogen activator (rt-PA), plasmin, activated protein C, chymotrypsin, factor Xa and trypsin.

The buffer used for all assays was HBSA (10 mM HEPES, pH 7.5, 150 mM sodium chloride, 0.1% bovine serum albumin). The assay for $IC_{50}$ determinations was conducted by combining in appropriate wells of a Corning microtiter plate, 50 microliters of HBSA, 50 microliters of the test compound at a specified concentration (covering a broad concentration range) diluted in HBSA (or HBSA alone for $V_0$ (uninhibited velocity) measurement), and 50 microliters of the enzyme diluted in HBSA. Following a 30 minute incubation at ambient temperature, 50 microliters of the substrate at the concentrations specified below were added to the wells, yielding a final total volume of 200 microliters. The initial velocity of chromogenic substrate hydrolysis was measured by the change in absorbance at 405 nm using a Thermo Max® Kinetic Microplate Reader over a 5 minute period in which less than 5% of the added substrate was used. The concentration of added inhibitor which caused a 50% decrease in the initial rate of hydrolysis was defined as the $IC_{50}$ value.

Thrombin (fIIa) Assay

Enzyme activity was determined using the chromogenic substrate, Pefachrome t-PA ($CH_3SO_2$-D-hexahydrotyrosine-glycyl-L-Arginine-p-nitroaniline, obtained from Pentapharm Ltd.). The substrate was reconstituted in deionized water prior to use. Purified human α-thrombin was obtained from Enzyme Research Laboratories, Inc. The buffer used for all assays was HBSA (10 mM HEPES, pH 7.5, 150 mM sodium chloride, 0.1% bovine serum albumin).

$IC_{50}$ determinations were conducted where HBSA (50 µL), α-thrombin (50 µl) (the final enzyme concentration is 0.5 nM) and inhibitor (50 µl) (covering a broad concentration range), were combined in appropriate wells and incubated for 30 minutes at room temperature prior to the addition of substrate Pefachrome-t-PA (50 µl) (the final substrate concentration is 250 µM, about 5 times Km). The initial velocity of Pefachrome t-PA hydrolysis was measured by the change in absorbance at 405 nm using a Thermo Max® Kinetic Microplate Reader over a 5 minute period in which less than 5% of the added substrate was used. The concentration of added inhibitor which caused a 50% decrease in the initial rate of hydrolysis was defined as the $IC_{50}$ value.

Factor Xa

Factor Xa catalytic activity was determined using the chromogenic substrate S-2765 (N-benzyloxycarbonyl-D-arginine-L-glycine-L-arginine-p-nitroaniline), obtained from DiaPharma Group (Franklin, Ohio). All substrates were reconstituted in deionized water prior to use. The final concentration of S-2765 was 250 µM (about 5-times Km). Purified human Factor X was obtained from Enzyme Research Laboratories, Inc. (South Bend, Ind.) and Factor Xa (FXa) was activated and prepared from it as described [Bock, P. E., Craig, P. A., Olson, S. T., and Singh, P. *Arch. Biochem. Biophys.* 273:375-388 (1989)]. The enzyme was diluted into HBSA prior to assay in which the final concentration was 0.25 nM.

Recombinant Tissue Plasminogen Activator (rt-PA) Assay rt-PA catalytic activity was determined using the substrate, Pefachrome t-PA ($CH_3SO_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2366 [L-pyroglutamyl-L-prolyl-L-arginine-p-nitroaniline hydrochloride], which was obtained from DiaPharma group. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC) Assay aPC catalytic activity was determined using the chromogenic substrate, Pefachrome PC (delta-carbobenzyloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 400 micromolar (about 3-times Km). Purified human aPC was obtained from Hematologic Technologies, Inc. The enzyme was diluted into HBSA prior to assay in which the final concentration was 1.0 nM.

Chymotrypsin Assay

Chymotrypsin catalytic activity was determined using the chromogenic substrate, S-2586 (methoxy-succinyl-L-arginine-L-prolyl-L-tyrosyl-p-nitroanilide), which was obtained from DiaPharma Group. The substrate was made up in deionized water followed by dilution in HBSA prior to the assay in which the final concentration was 100 micromolar (about 9-times Km). Purified (3x-crystallized; CDI) bovine pancreatic alpha-chymotrypsin was obtained from Worthington Biochemical Corp. The enzyme was reconstituted in deionized water and diluted into HBSA prior to assay in which the final concentration was 0.5 nM.

Trypsin Assay

Trypsin catalytic activity was determined using the chromogenic substrate, S-2222 (benzoyl-L-isoleucine-L-glutamic acid-[gamma-methyl ester]-L-arginine-p-nitroanilide), which was obtained from DiaPharma Group. The substrate was made up in deionized water followed by dilution in HBSA prior to the assay in which the final concentration was 250 micromolar (about 4-times Km). Purified (3x-crystallized; TRL3) bovine pancreatic trypsin was obtained from Worthington Biochemical Corp. The enzyme was reconstituted in deionized water and diluted into HBSA prior to assay in which the final concentration was 0.5 nM.

Since modifications will be apparent to those of skill in this art, it is intended that this invention be limited only by the scope of the appended claims.

What is claimed is:

1. A nucleic acid molecule, comprising a sequence of nucleic acids encoding a single chain polypeptide that consists only of a protease domain of a type-II membrane-type serine protease (MTSP), or a proteolytically active fragment thereof, as a single chain, wherein:
   a free Cys in the protease domain, which is normally disulfide bonded to a Cys in the pro-domain of the full length MTSP, is replaced with another amino acid;
   the nucleic acid molecule contains a stop codon so that only the single chain MTSP protease domain, or proteolytically active fragment thereof, can be expressed; and
   the MTSP protease domain, or proteolytically active fragment thereof, has serine protease activity as a single chain.

2. The nucleic acid molecule of claim 1, wherein the MTSP portion has an N-terminus that comprises IVNG, ILGG, VGLL or ILGG.

3. The nucleic acid molecule of claim 1, wherein the MTSP is selected from among MTSP1, MTSP3, MTSP4 and MTSP6.

4. The nucleic acid molecule of claim 1, wherein the MTSP protease domain consists of a sequence of amino acid residues selected from among amino acids 615-855 of SEQ ID NO: 2, amino acids 205-437 of SEQ ID NO: 4, the amino acids set forth as SEQ ID NO: 6 or as amino acids 217-443 in SEQ ID NO: 12.

5. The nucleic acid molecule of claim 1, wherein the encoded polypeptide has at least about 95% sequence identity with a protease domain consisting of a sequence of amino acid residues selected from among amino acids 615-855 of SEQ ID NO: 2, amino acids 205-437 of SEQ ID NO: 4, the amino acids set forth as SEQ ID NO: 6 and amino acids 217-443 in SEQ ID NO: 12.

6. The nucleic acid molecule of claim 1, wherein the MTSP protease domain is encoded by a sequence of nucleic acid residues selected from among nucleotides 1865-2585 of SEQ ID NO: 1, nucleotides 873-1571 of SEQ ID NO: 3, the nucleotides set forth as SEQ ID NO: 5 and nucleotides 916-1596 of SEQ ID NO: 11.

7. The nucleic acid molecule of claim 1, wherein a free Cys in the protease domain of the polypeptide is replaced with a serine.

8. The nucleic acid molecule of claim 1, wherein the MTSP is selected from among corin, MTSP1, enteropeptidase, human airway trypsin-like protease (HAT), TMPRSS2, and TMPRSS4.

9. The nucleic acid molecule of claim 1, wherein:
   the encoded MTSP protease domain is linked directly or via a polypeptide linker to a targeting agent; and
   the encoded conjugate has serine protease activity.

10. The nucleic acid molecule of claim 1, wherein the nucleic acid encoding the MTSP protease domain is operatively linked to a nucleic acid encoding a signal sequence.

11. The nucleic acid molecule of claim 9, wherein the targeting agent permits:
    i) affinity isolation or purification of the conjugate;
    ii) attachment of the conjugate to a surface;
    iii) detection of the conjugate; or
    iv) targeted delivery to a selected tissue or cell.

12. A vector, comprising the nucleic acid molecule of claim 1.

13. A cell, comprising the vector of claim 12.

14. The cell of claim 13 that is a eukaryotic cell.

15. The cell of claim 13 that is a yeast cell.

16. The cell of claim 15 that is a *Pichia* species cell.

17. A method for production of a single chain polypeptide that consists only of a protease domain of a type-II membrane-type serine protease (MTSP), or a proteolytically active fragment thereof, as a single chain, the method comprising:

growing a cell of claim 13 under conditions, whereby the single chain MTSP polypeptide is expressed; and isolating the single chain MTSP polypeptide.

18. The method of claim 17, wherein the nucleic acid encoding the MTSP polypeptide is operatively linked to a nucleic acid encoding a signal sequence, whereby the encoded MTSP polypeptide is secreted into the cell culture medium.

19. The method of claim 17, wherein the cell is a eukaryotic cell.

20. The method of claim 17, wherein the cell is a yeast cell.

21. The method of claim 20, wherein the cell is a *Pichia* species cell.

* * * * *